United States Patent
Streeter, Jr. et al.

(10) Patent No.: US 10,434,022 B2
(45) Date of Patent: Oct. 8, 2019

(54) DYNAMIC SUPPORT APPARATUS

(71) Applicant: DEKA Products Limited Partnership, Manchester, NH (US)

(72) Inventors: Alexander D. Streeter, Jr., Concord, NH (US); N. Christopher Perry, Manchester, NH (US); Matthew A. Norris, Londonderry, NH (US); Stewart M. Coulter, Bedford, NH (US); Jake S. Urman, Portsmouth, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 16/102,074

(22) Filed: Aug. 13, 2018

(65) Prior Publication Data

US 2019/0000701 A1 Jan. 3, 2019

Related U.S. Application Data

(63) Continuation of application No. 14/811,215, filed on Jul. 28, 2015, now Pat. No. 10,045,897.

(60) Provisional application No. 62/029,826, filed on Jul. 28, 2014, provisional application No. 62/029,813, filed on Jul. 28, 2014.

(51) Int. Cl.
| | |
|---|---|
| *A47C 27/08* | (2006.01) |
| *A61G 7/057* | (2006.01) |
| *F16K 11/076* | (2006.01) |
| *F16K 31/12* | (2006.01) |
| *F16K 31/04* | (2006.01) |
| *A61G 5/10* | (2006.01) |
| *A61B 5/103* | (2006.01) |
| *A61B 5/11* | (2006.01) |

(52) U.S. Cl.
CPC ........ *A61G 7/05769* (2013.01); *A47C 27/082* (2013.01); *A61B 5/1036* (2013.01); *A61B 5/1115* (2013.01); *A61G 5/1043* (2013.01); *A61G 5/1045* (2016.11); *A61G 7/05715* (2013.01); *F16K 11/076* (2013.01); *F16K 31/041* (2013.01); *F16K 31/12* (2013.01); *A61G 2203/12* (2013.01); *A61G 2203/30* (2013.01)

(58) Field of Classification Search
CPC ..................................................... A47C 27/082
USPC ......................................... 5/710, 713, 655.3
See application file for complete search history.

(56) References Cited

U.S. PATENT DOCUMENTS

| | | | |
|---|---|---|---|
| 6,671,911 B1 * | 1/2004 | Hill ...................... | A61G 5/1043 5/655.3 |
| 2008/0105842 A1 * | 5/2008 | Webster ................ | F16K 11/074 251/180 |
| 2009/0064418 A1 * | 3/2009 | Genaro .............. | A61G 7/05776 5/713 |

\* cited by examiner

*Primary Examiner* — Fredrick C Conley

(74) *Attorney, Agent, or Firm* — Michelle Saquet Temple

(57) ABSTRACT

A dynamic support apparatus. The dynamic support apparatus includes a cushion, at least one actuator wherein the at least one actuator defines an interior volume and wherein the interior volume may be configured to be at least partially filled with a fluid, and a support disposed in the interior volume wherein the support configured to support an occupant when the interior volume is not filled with the fluid such that the support is sufficient to support the occupant.

14 Claims, 69 Drawing Sheets

Relief Regimen Summary

Client ID: [ ]  Configuration Date:

Client Type: [ ] ← 1774

Notes: [ ]

Channel Settings:

| | Channel 1 | Channel 2 | Channel 3 | Channel 4 |
|---|---|---|---|---|
| Name: | Parameter Value | Parameter Value | Parameter Value | Parameter Value |
| Type: | Parameter Value | Parameter Value | Parameter Value | Parameter Value |
| Order: | Parameter Value | Parameter Value | Parameter Value | Parameter Value |
| System High Pressure Limit [mmHg]: | Parameter Value | Parameter Value | Parameter Value | Parameter Value |
| System Low Pressure Limit [mmHg]: | Parameter Value | Parameter Value | Parameter Value | Parameter Value |
| Actuator Set Point [mmHg]: | Parameter Value | Parameter Value | Parameter Value | Parameter Value |

1770 ↙    1772 ←

Relief Schedule:

| Repeat Interval: | Parameter Value | |
|---|---|---|
| | Deflation (mm:ss) | Inflation (mm:ss) |
| Channel1 | Parameter Value | Parameter Value |
| Channel2 | Parameter Value | Parameter Value |
| Channel3 | Parameter Value | Parameter Value |
| Channel4 | Parameter Value | Parameter Value |

DYNAMIC SUPPORT APPARATUS

CROSS REFERENCE TO RELATED APPLICATION(S)

This application is a Continuation of U.S. patent application Ser. No. 14/811,215, filed Jul. 28, 2015 and entitled Dynamic Support Apparatus, now U.S. Pat. No. 10,045,897, issued Aug. 14, 2018, which claims priority to and the benefit of the following: U.S. Provisional Application No. 62/029,813, filed on Jul. 28, 2014 and entitled Dynamic Support Apparatus; and U.S. Provisional Application No. 62/029,826, filed on Jul. 28, 2014 and entitled Rotary Valve, each of which are hereby incorporated herein by reference in their entirety.

TECHNICAL FIELD

The present disclosure relates to supporting a load. More specifically, the present disclosure relates to dynamically supporting a load.

BACKGROUND

Decubitus ulcers or pressure sores are areas of damaged soft tissue caused by staying in a single position for a prolonged period of time. They often develop where bones within the body are close to the skin and pressure, or pressure in combination with shear and/or friction, is high. When sufficiently high, these contact forces inhibit blood flow to the contact area. Over time, this obstructed or partially obstructed blood flow can lead to pain, ulceration, osteomyelitis, local infection, and in extreme cases sepsis or death. Other factors, such as malnutrition, skin wetness, and conditions which reduce blood flow or sensation may also play a role.

Compounded on top of this, pressure sore treatment can prove to be very expensive. The average cost associated with a pressure ulcer in the United States was reported to be $48,000 in 2006. This accounts for approximately an 11 billion dollar annual expenditure on pressure ulcer treatment. The severest of pressure sores, categorized as stage IV pressure ulcers, can be even more costly. One study estimated the average cost of such an ulcer to be on average $127,185. Risk of re-injury is also quite high after a previously developed pressure sore has healed or in the process of healing.

Decubitus ulcers are particularly common among populations which have limited mobility. Specifically, according to one study, nearly 40% of those with spinal cord injuries develop pressure ulcers. The true occurrence of pressure ulceration is, however, likely higher because pressure ulcers may be seen as signs of negligent care and are therefore under reported. Additionally, various studies have attributed about 5% of deaths of paraplegics and quadriplegics to complications from pressure sores.

Some methods and strategies for preventing pressure ulcers do exist. Traditional methods of mitigating the risk of pressure sores unfortunately tend to be demanding and disruptive. Generally, traditional methods involve manual repositioning of an individual. This may not be an option for populations with limited or impaired mobility. Another approach for mitigating pressure sore risk is through the use of passive seat cushions which attempt to more evenly distribute pressure across the contacted area of a supported person. Such seat cushions, however, are often still not adequate to prevent pressure sores on their own. Consequentially, such systems may, for example, require a supported person to tilt or recline their seat at predefined intervals to relieve pressure. As such, they are still relatively disruptive. Active cushions also exist which mechanically or pneumatically redistribute or relieve pressure from a desired area. Such cushions are also not without a number of shortcomings. Among these shortcomings, many such pneumatic cushions include interconnected bladders. If one such bladder is compromised, all of the interconnected bladders are compromised as well, and consequentially a person is left uncushioned. In the example of a wheelchair, this may lead to a person being supported only by the hard seat pan which can be injurious to the person, especially as they ride over bumps and are jostled about. The bladders of such seat cushions are not easy or cost effective to replace. These systems also tend to be bulky and may rely on a mobile source of power with limited life.

SUMMARY

In accordance with an embodiment of the present disclosure, a dynamic support apparatus is disclosed. The dynamic support apparatus includes a cushion, at least one actuator wherein the at least one actuator defines an interior volume and wherein the interior volume may be configured to be at least partially filled with a fluid, and a support disposed in the interior volume wherein the support configured to support an occupant when the interior volume is not filled with fluid sufficient to support the occupant.

Some embodiments of this implementation include one or more of the following. Wherein the support is a foam support. Wherein the support includes a plurality of foam strata. Wherein each of the plurality of strata includes foam with a different indentation force deflection value. Wherein the plurality of strata configured wherein they have progressively increasing indentation force deflection values. Wherein the at least one actuator comprising a clamshell. Wherein the actuator includes a first face and an opposing bottom second face connected by a plurality of sides and the actuator includes a seam on at least one of the plurality of sides. Wherein the seam is located substantially at a midpoint between the first face and the second face. Wherein the at least one actuator is constructed of polyurethane. Wherein the dynamic support apparatus comprising two actuators. Wherein the dynamic support apparatus comprising a first actuator and second actuator separated by a divider. Wherein the cushion comprising a void adjacent the two actuators. Wherein the void is disposed along a plane of the divider. Wherein the at least one actuator comprising pleated walls. Wherein the at least one actuator comprising a baffle attached to an interior first face of the at least one actuator and an opposing interior second face of the at least one actuator. Wherein the at least one actuator includes a pressure relief valve. Wherein the at least one actuator includes a first side and opposing second side connected by a side wall, wherein the first side is thicker than the side wall.

In accordance with an embodiment of the present disclosure, a dynamic support is disclosed. The dynamic support apparatus includes a cushion, at least one actuator wherein the at least one actuator defines an interior volume and wherein the interior volume may be configured to be at least partially filled with a fluid and the at least one actuator includes an orifice in a wall of the at least one actuator, and a sensor assembly, the sensor assembly including a housing portion in which a sensor is disposed, and a plug portion, wherein the housing portion disposed within the interior of the at least one actuator and wherein the plug portion is coupled to the housing portion through the orifice whereby an airtight seal is formed.

Some embodiments of this implementation include one or more of the following. Wherein the housing includes a housing flange and the plug portion comprising a plug flange and wherein when the housing and plug portion are coupled together the wall of the actuator is compressed between the housing flange and plug flange. Wherein at least one of the housing flange and plug flange comprising a channel, the channel sized for an o-ring to be seated therein.

Wherein one of the housing and plug portion includes a groove and the other of the housing and plug portion includes a protuberance configured to pressure the wall of the at least one actuator into the groove. Wherein the sensor is a pressure sensor. Wherein the housing and plug portion are coupled together via a threaded coupling. Wherein the sensor is configured to sense the distance from a face of the at least one actuator to the sensor.

In accordance with an embodiment of the present disclosure, a dynamic support apparatus is discloses. The dynamic support apparatus includes a cushion, at least one actuator wherein the at least one actuator defines an interior volume and wherein the interior volume may be configured to be at least partially filled with a fluid, and a manifold including a plurality of fluid pathways leading to a manifold port for each of the at least one actuators, and at least one valve, at least one sensor for each manifold port, a pump in fluid communication with the manifold, and a controller comprising a processor, the processor configured to monitor data samples from the at least one sensor and determine a pulse density modulation command for the pump based at least in part on the data samples from the at least one sensor for each of the at least one actuators, wherein the processor determines the pulse density modulation command by starting a pulse timer during a first pulse, computing a pulse time interval for each data sample, and commanding the pump to pump fluid when the pulse timer time is less than or equal to the pulse time interval.

Some embodiments of this implementation include one or more of the following. Wherein the at least one sensor is a pressure sensor. Wherein the at least one actuator includes an internal support for supporting a load when the interior volume is not filled with fluid sufficient to support the load. Wherein the data samples are subjected to a low pass filter. Wherein the data samples are subjected to a low pass filter having a band width of less than or equal to 0.1 Hz. Wherein the processor computing the pulse time interval comprises determining an error value based on a predetermined set point range and the data samples. Wherein the processor computing the pulse time interval comprises determining if the error value is above a predetermined maximum allowable error value and setting the pulse time interval to a predetermined minimum time value if the error value is above the maximum allowable error value. Wherein the processor computing the pulse time interval comprises increasing the pulse time interval as the error value decreases. Wherein if the error value is negative, the processor commands one of the at least one actuator to be vented. Wherein if the error value is negative, the processor suspends pumping of fluid until the error value is positive. Wherein if the error value is negative, the processor sets the pulse time interval to a predetermined maximum time value. Wherein if the predetermined set point range is a negative pressure range and the error value is negative, the processor sets the pulse time interval to a predetermined maximum time value. Wherein if the predetermined set point range is a positive pressure range and the error value is negative, the processor suspends pumping of fluid until the error value becomes positive.

In accordance with an embodiment of the present disclosure, a dynamic support apparatus is disclosed. The dynamic support apparatus includes at least one actuator wherein the at least one actuator defines an interior volume and wherein the interior volume may be configured to be at least partially filled with a fluid, a fluid pump, a manifold in fluid communication with the fluid pump, the manifold having at least one fluid flow path, at least one flow path valve associated with each of the at least one fluid flow paths, the manifold comprising a manifold port for each of the at least one actuators, a pressure sensor configured to monitor pressure at each of the manifold ports and generate pressure data signals, a processor, the processor configured to: generate a pump command causing the pump to pump fluid; generate a manifold command governing the position of the at least one valve such that fluid communication is established between the fluid pump and a desired manifold port connected to a desired actuator of the at least one actuator; monitor the pressure data signals to determine if the pressure at the desired manifold port is above an over inflation target pressure; generate, upon determination that the pressure is above the over inflation pressure target, a deflation command governing the position of the at least one valve in the manifold wherein the desired manifold port is in fluid communication with atmosphere; and monitor the pressure data signals while the desired manifold port is in communication with the atmosphere to determine if the pressure at the desired manifold port is within a range of a target pressure.

Some embodiments of this implementation include one or more of the following. Wherein the over inflation target pressure is equal to a sum of the target pressure, plus an overshoot margin, plus an additional margin. Wherein the addition margin is in the range of 2 mmHg-4 mmHg. Wherein the processor is further configured to start a minimum on-time timer upon generation of the pump command and the processor is configured to prevent stopping of pumping until the minimum on-time timer reaches a predetermined minimum on-time value.

Wherein the minimum on-time value is 0.5 seconds. Wherein the processor is further configured to start a wait timer upon determining the pressure is above the over inflation target pressure and after a predetermined wait period has elapsed, the processor is configured to collect a post wait pressure data sample from the pressure sensor. Wherein the processor is further configured to compare the post wait pressure data sample to a sum of the target pressure plus the overshoot margin. Wherein the processor is further configured to generate a re-inflation command if the post wait pressure data sample indicates the pressure is less than the target pressure plus the overshoot margin. Wherein the processor is further configured to collect a vented pressure data sample after generation of the deflation command and compare the vented pressure data sample to a sum of the target pressure, plus a dead band pressure range, less the additional margin. Wherein the processor is further configured to start a post-vent wait timer if the vented pressure sample is less than or equal to the target pressure, plus a dead band pressure range, less the additional margin. Wherein the method further comprising generating a second deflation command with the processor if the pressure is greater than a sum of target pressure plus the deadband pressure range after a post-vent wait period has elapsed, the second deflation command governing the position of the at least one valve in the manifold wherein the desired manifold port is in fluid communication with atmosphere. Wherein the processor determining the pressure is within the target pressure range comprising comparing a post-vent wait period pressure data sample taken after the post-vent wait period has elapsed to a first pressure threshold and a second pressure threshold lower than the first pressure threshold and determining the pressure is within the target pressure range if the a post-vent wait period pressure data sample indicates the pressure is below the first threshold, but above the second threshold.

In accordance with an embodiment of the present disclosure, a method for inflating an actuator of a dynamic support apparatus is disclosed. The method includes generating, with a processor, a pump command, the pump command causing a pump to pump fluid; generating, with the processor, a manifold command, the manifold command governing the position of at least one valve in a manifold such that fluid communication is established between the pump and a manifold port connected to the actuator; monitoring pressure data samples from a sensor at the manifold port with the processor; determining the pressure is above an over inflation target pressure; generating, with the processor, a deflation command, the deflation command governing the position of the at least one valve in the manifold wherein the manifold port connected to the actuator is in fluid communication with the atmosphere; monitoring pressure data samples from a sensor at the manifold port with the processor while the manifold port connected to the actuator is in fluid communication with the atmosphere; and determining the pressure is within a range of a target pressure.

Some embodiments of this implementation include one or more of the following. Wherein the over inflation target pressure is equal to a sum of the target pressure, plus an overshoot margin, plus an additional margin. Wherein the addition margin is in the range of 2 mmHg-4 mmHg. Wherein the method further comprising: starting, with the processor, a minimum on-time timer upon generation of the pump command; and preventing stopping of pumping until the minimum on-time timer reaches a predetermined minimum on-time value.

Wherein the minimum on-time value is 0.5 seconds. Wherein the method further comprising: starting, with the processor, a wait timer upon determining the pressure is above the over inflation target pressure; and after a predetermined wait period has elapsed, collecting a post wait pressure data sample from the pressure sensor. Wherein the method further comprising comparing the post wait pressure data sample to a sum of the target pressure plus the overshoot margin. Wherein the method further comprising generating a re-inflation command if the post wait pressure data sample indicates the pressure is less than the target pressure plus the overshoot margin. Wherein the method further comprising: collecting a vented pressure data sample after generation of the deflation command; and comparing the vented pressure data sample to a sum of the target pressure, plus a dead band pressure range, less the additional margin. Wherein the method further comprising starting a post-vent wait timer if the vented pressure sample is less than or equal to a sum of the target pressure and a dead band pressure range, less the additional margin. Wherein the method further comprising generating a second deflation command with the processor if the pressure is greater than a sum of the target pressure plus the deadband pressure range after a post-vent wait period has elapsed, the second deflation command governing the position of the at least one valve in the manifold such the manifold port connected to the actuator is in fluid communication with the atmosphere. Wherein determining the pressure is within the target pressure range comprising: comparing a post-vent wait period pressure data sample taken after the post-vent wait period has elapsed to a first pressure threshold and a second pressure threshold lower than the first pressure threshold; and determining the pressure is within the target pressure range if the a post-vent wait period pressure data sample indicates the pressure is below the first threshold, but above the second threshold.

In accordance with an embodiment of the present disclosure, a method for maintaining the pressure of an actuator of a dynamic support apparatus is disclosed. The method includes monitoring, with a processor, pressure data samples from at least one sensor associated with a manifold port of a manifold, the manifold port connected to the actuator; and determining, with the processor, a pulse density modulation command for a pump in communication with the manifold, the pulse density modulation command determined by starting a pulse timer during a first pump pulse, computing a pulse time interval for each data sample, and commanding the pump to pump fluid when the pulse time is less than or equal to the pulse time interval.

Some embodiments of this implementation include one or more of the following. Wherein the actuator includes an internal support for supporting a load when an interior volume of the actuator is not filled with fluid sufficient to support the load. Wherein the method further comprising subjecting the data samples to a low pass filter. Wherein the method further comprising subjecting the data samples to a low pass filter having a band width of less than or equal to 0.1 Hz. Wherein computing the pulse time interval comprising determining an error value based on a predetermined set point range and the data samples. Wherein computing the pulse time interval comprising: determining if the error value is above a predetermined maximum allowable error value; and setting the pulse time interval to a predetermined minimum time value if the error value is above the maximum allowable error value. Wherein computing the pulse time interval comprising increasing the pulse time interval as the error value decreases.

Wherein the method further comprising commanding the actuator to be vented. Wherein the method further comprising suspending pumping of fluid if the error value is negative until the error value becomes positive. Wherein the method further comprising setting the pulse time interval to a predetermined maximum time value if the error value is negative. Wherein the method further comprising setting the pulse time interval to a predetermined maximum value if the predetermined set point range is a negative pressure range and the error value is negative.

Wherein the method further comprising suspending pumping of fluid if the predetermined set point range is a positive pressure range and the error value is negative until the error value becomes positive.

In accordance with an embodiment of the present disclosure, a dynamic support apparatus is disclosed. The dynamic support apparatus includes a cushion; at least one actuator wherein the at least one actuator defines an interior volume and wherein the interior volume configured to be at least partially filled with a fluid and the at least one actuator attached to an actuator fluid conduit in communication with the interior volume; a fluid pump having a pump inlet and a pump outlet; a rotary valve including a stationary portion and a rotor, the rotor being a planar body having transversely disposed flow paths recessed into each of a first face and a second face of the rotor, wherein the first face is oppositely situated with respect to the second face, the flow paths terminating in valve fluid ports; and a processor for commanding a motor to rotate the rotor to at least a first position in which the pump inlet is in fluid communication with the atmosphere through the valve and the pump outlet is in fluid communication with the actuator fluid conduit through the valve, a second position in which the pump inlet is in communication with the actuator fluid conduit via the valve and the pump outlet is in communication with the atmosphere via the valve, and a third position in which the actuator fluid conduit is in communication with the atmosphere via the valve.

Some embodiments of this implementation include one or more of the following. Wherein the first, second, and third positions are spaced equal angular intervals apart. Wherein the motor drives the rotor in a single direction to align the rotor in the first position, second position, and third position. Wherein the motor drives the rotor in a first direction to align the rotor first with the first position, the motor drives the rotor in the first direction to rotate the rotor from the first position to the second position, and the motor rotates the rotor in the first direction to rotate the rotor from the second position to the third position. Wherein the motor may rotate the rotor clockwise to the first position, the second position, and the third position, and wherein the motor may rotate the rotor counterclockwise to the first position, the second position, and the third position. Wherein the rotary valve is a multi-stable valve which maintains its position when power to the rotary valve is lost. Wherein the motor is a stepper motor. Wherein the rotary valve is part of a manifold. Wherein an outer edge of the rotor is teethed. Wherein the processor is configured to rotate the valve in equal angular increments. Wherein the rotor includes eight fluid ports. Wherein the rotor is held between a first part of the stationary portion and a second part of the stationary portion. Wherein at least one of the first and second face include a recessed portion which does not contact the stationary portion. Wherein the stationary portion includes a valve interface.

In accordance with an embodiment of the present disclosure, a multi-stable rotary valve is disclosed. The rotary valve includes a stationary portion including a pump inlet port, a pump outlet port, an atmosphere port, and an actuator port; a rotor having a planar body with transversely disposed flow paths recessed into each of q first face and a second face of the rotor, wherein the second face is oppositely situated with respect to the first face, the rotor captured between a first part of the stationary portion and a second part of the stationary portion, the rotor having at least one recessed portion which does not contact the stationary portion; and a motor arranged to impart rotary motion to the rotor to rotate the rotor to at least a first position in which the pump inlet port is in fluid communication with the atmosphere port through the valve and the pump outlet port is in fluid communication with the actuator port through the valve, a second position in which the pump inlet port is in communication with the actuator port via the valve and the pump outlet port is in communication with the atmosphere port via the valve, and a third position in which the actuator port is in communication with the atmosphere port via the valve.

Some embodiments of this implementation include one or more of the following. Wherein an outer edge of the motor is teethed. Wherein the motor is a stepper motor. Wherein a fastener extend through the first part of the stationary portion and through the rotor to the second part of the stationary portion such that the rotor is held between the first part and second part of the stationary portion. Wherein the rotor includes four fluid pathways. Wherein the first face of the rotor includes a plurality of fluid pathways and the second face of the rotor includes a single fluid pathway. Wherein the first face of the rotor includes three fluid pathways and the second face of the rotor includes a single fluid path way. Wherein the motor is arranged to impart rotary motion to the rotor in only a single rotational direction. Wherein the rotary valve is a pneumatic valve. Wherein the rotor comprising a plurality of flow paths on the first face and at least one flow path on the second face extending in a direction perpendicular to at least one of the plurality of flow paths on the first face. Wherein the rotor comprising: at least one flow path on the first face; at least one flow path on the second face; and two pass throughs extending from the first face to the second face for each of the at least one flow path on the second face, wherein the pass throughs being in fluid communication with an associated flow path of the at least one flow path on the second face.

In accordance with an embodiment of the present disclosure, a dynamic support apparatus is disclosed. The dynamic support apparatus includes a cushion; at least one actuator wherein the at least one actuator defines an interior volume and wherein the interior volume may be configured to be at least partially filled with a fluid; and a support disposed in the interior volume wherein the support configured to support an occupant when the interior volume is not filled with the fluid such that the support is sufficient to support the occupant.

In accordance with an embodiment of the present disclosure, a dynamic support apparatus may comprise a cushion. The dynamic support apparatus may comprise at least one actuator. The at least one actuator may define an interior volume. The interior volume may be configured to be at least partially filled with a fluid such that said fluid is sufficient to support an occupant. The dynamic support apparatus may comprise a support disposed in the interior volume. The support may be configured to support said occupant when the interior volume is not filled with said fluid such that said support is sufficient to support said occupant.

In accordance with another embodiment of the present disclosure, a dynamic support apparatus may comprise a cushion. The dynamic support apparatus may comprise at least one actuator. The at least one actuator may have an interior volume. The interior volume may be configured to be at least partially filled with a fluid such that said fluid is sufficient to support an occupant. The dynamic support apparatus may comprise a stratified foam support disposed in the interior volume. The strata of said stratified foam support may be defined by foams of differing support characteristics. The support characteristics may be indentation load deflections. The stratified foam support may have a total volume less than that of the interior volume. The stratified foam support may be configured to support the occupant when said interior volume is not filled with said fluid such that said fluid is sufficient to support said occupant.

In accordance with another embodiment of the present disclosure a dynamic support apparatus may comprise a cushion. The dynamic support apparatus may comprise at least one actuator. The at least one actuator may define an interior volume. The interior volume may be configured to be at least partially filled with a fluid such that said fluid is sufficient to support an occupant. The dynamic support apparatus may comprise a foam support inside said interior volume. The foam support may have a volume less than that of the interior volume. The foam support may be configured to support the occupant when said interior volume is not filled with said fluid such that said fluid is sufficient to support said occupant. The dynamic support apparatus may comprise a baffle disposed inside said interior volume. The baffle may be configured to constrain the shape of said actuator in at least one direction.

In accordance with an embodiment of the present disclosure; a dynamic support apparatus may comprise a cushion. The cushion may be a foam cushion. The dynamic support apparatus may comprise at least one bladder. The at least one bladder may be disposed in at least one void in said cushion. The at least one bladder may have an interior volume. The interior volume may be configured to be at least partially filled with fluid such that said fluid is sufficient to support an occupant. The dynamic support apparatus may comprise a stratified foam support in the interior volume. The strata of the stratified foam support may be defined by foams of differing indentation force deflections. The stratified foam support may have a volume less than that of the interior volume. The stratified foam support may be configured to support the occupant when said interior volume is not filled with said fluid such that said fluid is sufficient to support said occupant. The dynamic support apparatus may comprise a baffle disposed inside the interior volume. The baffle may be configured to constrain the shape of said at least one bladder in at least one direction. The dynamic support apparatus may comprise at least one sensor. The sensor may be configured to measure at least one characteristic of said fluid.

In accordance with an embodiment of the present disclosure, a method of constructing an actuator for a dynamic support apparatus for an occupant may comprise coupling at least two pieces of material together to form said actuator such that said at least two pieces of material define an interior volume. The two pieces of material may also be coupled together such that the surface of the actuator proximal to a contact surface for the occupant is free of seams which create a surface discontinuity in the contact surface. The method may also comprise providing a foam support disposed inside said interior volume. The foam support may have a volume less than said interior volume. The foam support may be stratified. The strata of the foam support may each be a foam with different support characteristics. The support characteristics may be indentation load deflection values.

The details of one or more embodiments are set forth in the accompanying drawings and the description below. Other features and advantages will become apparent from the description, the drawings, and the claims.

BRIEF DESCRIPTION OF THE DRAWINGS

These and other aspects will become more apparent from the following detailed description of the various embodiments of the present disclosure with reference to the drawings wherein:

FIG. 82 depicts a screen which may be displayed on a remote interface for a dynamic support apparatus in accordance with one embodiment.

DETAILED DESCRIPTION OF THE EXEMPLARY EMBODIMENTS

Figure 1:
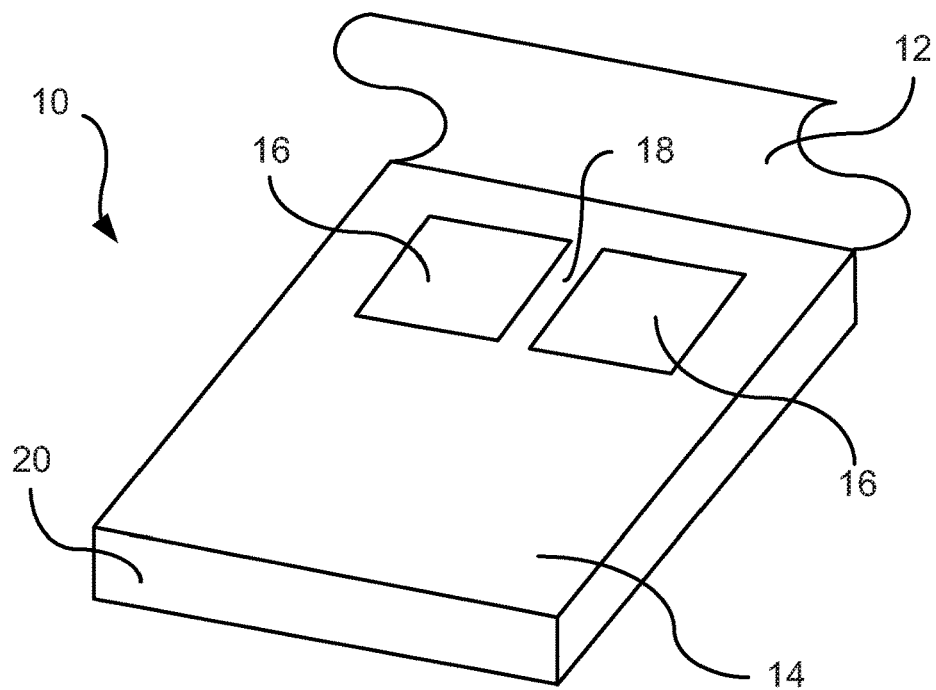
FIG. 1 shows a perspective, representational view of one embodiment of a person support apparatus with the top cover of the person support apparatus pulled away to expose the interior of the person support apparatus in accordance with an embodiment.

FIG. 1 shows a perspective view of one embodiment of a dynamic support apparatus 10 with the top cover 12 of the dynamic support apparatus 10 pulled away to expose the interior of the dynamic support apparatus 10. The dynamic support apparatus 10 may be a person support apparatus utilized to provide support with more uniform pressure distribution and greater comfort to a seated or supine individual. For example, the dynamic support apparatus 10 may be or may be placed on a person support structure such as a chair, couch, bench, automotive seat, aircraft seat, bed, wheelchair or the like. The dynamic support apparatus 10 may also be used to help prevent the formation of decubitus ulcers or pressure sores and speed the recovery thereof.

Though the shown dynamic support apparatus 10 has a roughly square footprint, the dynamic support apparatus 10 may have any suitable footprint. In some embodiments, the dynamic support apparatus 10 may be roughly rectangular in embodiments where the dynamic support apparatus 10 is a bed. In one embodiment shown in FIG. 1 the dynamic support apparatus 10 is sized to be used as the support surface of a wheelchair. Additionally, the contact face or surface of the dynamic support apparatus 10 may be substantially planar as shown or may be contoured.

In various embodiments, the dynamic support apparatus 10 may include a cushion or a number of cushions. One of the cushions may be a foam cushion 14. The foam cushion 14 may be made of any suitable type or types of foam. In other embodiments, the foam cushion 14 need not necessarily be made of foam. In some embodiments the foam cushion 14 may alternatively be made of wool, feathers, cotton batting, etc. In some embodiments, dynamic support apparatus 10 additionally includes two actuators 16. Various embodiments may include any other suitable number of actuator 16.

As shown, the actuators 16 may be disposed in voids in the foam cushion 14 and are roughly level with the top of the foam cushion 14 in some embodiments. In some embodiments the top of the actuators 16 may be proud of the foam cushion 14. In some embodiments, foam or another padding material may be included over top of the actuators 16. The actuators 16 may be located near the back of the dynamic support apparatus 10. In various embodiments, the actuators 16 are disposed laterally of the midline of the dynamic support apparatus 10; one actuator 16 on the left and the other on the right. The actuators 16 in some embodiments are also generally symmetric about the midline. Some embodiments may include a different number of actuators 16. For example, in some embodiments, a third actuator 16 may be situated on the midline of the dynamic support apparatus 10. Such an actuator 16 may be situated between the left and right actuators 16 or may be positioned anteriorly or posteriorly to the left and right actuators 16.

The arrangement of the actuators 16 may allow the actuators 16 to support high contact pressure areas of an occupant in the dynamic support apparatus 10. Specifically, in some embodiments where the dynamic support apparatus 10 is the support surface of a wheelchair, the bony prominences of the ischial tuberosities, sacrum, and/or greater trochanters may be supported by the actuators 16. Other regions or areas may also be actuator 16 supported. Some embodiments may also or instead support the coccyx/sacrum region of an occupant with an actuator 16.

Figure 2:
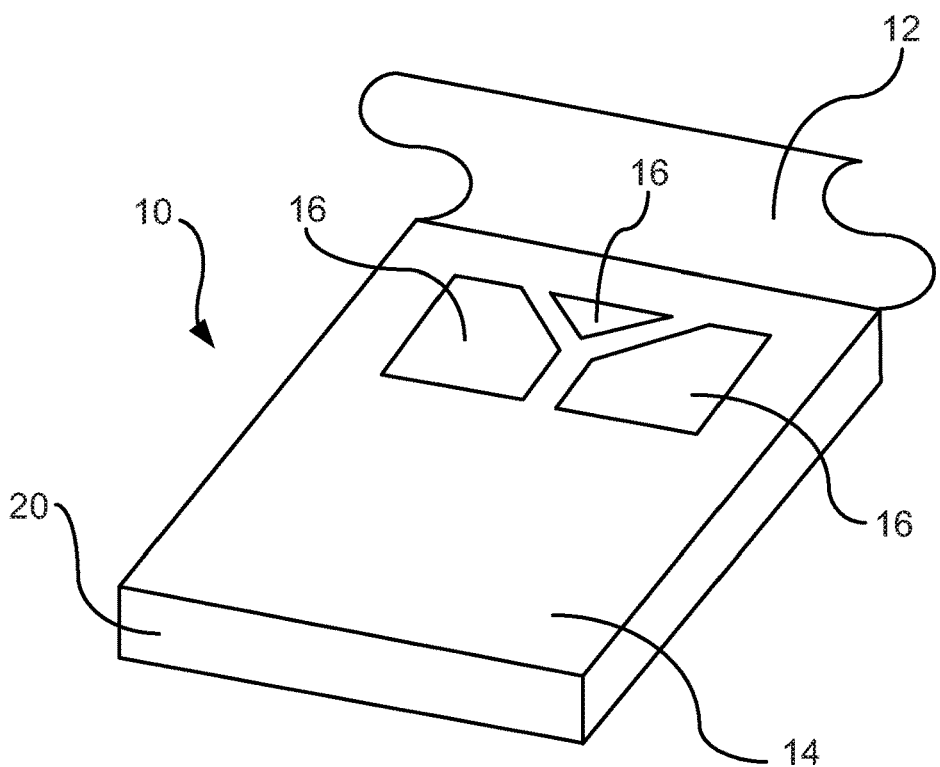
FIG. 2 shows a perspective view of one embodiment of a dynamic support apparatus with the top cover of the dynamic support apparatus pulled away to expose the interior of the dynamic support apparatus.

In some embodiments, the dynamic support apparatus 10 may include three actuators 16. FIG. 2 shows a representational perspective view of one embodiment of a dynamic support apparatus 10 with the top cover 12 of the dynamic support apparatus 10 pulled away to expose the interior of the dynamic support apparatus 10. In some embodiments, two of the actuators 16 may be rectangular. In some embodiments, one of the actuators 16 may be generally triangular in shape. In some embodiments, a triangularly-shaped actuator 16 may be utilized to provide support for a user's coccyx/sacrum region. In some embodiments, as shown in FIG. 2, the dynamic support apparatus 10 may include two substantially rectangular-shaped actuators 16 and one substantially triangularly-shaped actuator 16. In some embodiments, the posteriorly disposed portion of the rectangular actuators 16 may deviate from a rectangular shape to accommodate the triangular actuator 16. In some embodiments, instead of including the third actuator 16 shown in FIG. 2, the cushion 14 may include a void in its place.

In some embodiments, the actuators 16 may be strategically placed to support the user's bony prominences of the ischial tuberosities, coccyx, sacrum, greater trochanters, or a combination thereof. The rectangular actuators 16 may be disposed laterally of the midline of the dynamic support apparatus 10, with one actuator 16 on the left and the other on the right. The third, triangular actuator 16 may be situated on the midline of the dynamic support apparatus 16. The third triangular actuator 16 may be situated between the left and right actuators 16, as shown in FIG. 2 or may be otherwise positioned in some embodiments. The actuators 16 may differ depending on the occupant. In some embodiments, actuators 16 may come in a number of different sizes, including, but not limited to, a bariatric adult size, average adult size, etc. In some embodiments, the actuators 16 may come in a standard size. This may desirable/beneficial for many reasons, including but not limited to, the anatomical location of bony prominences such as the ischial tuberosities does not have a wide variance from person to person. Thus, though heavier occupants may have a larger footprint, the high contact pressure areas which would benefit most from the actuators 16 described herein would be located in the same general location as they would for a lighter occupant. The actuators 16 may be incorporated into foam cushions 14 of different sizes and/or shapes.

The medial edges of the actuators 16 may be separated by a divider 18 which may prevent the actuators 16 from contacting and rubbing against each other. In some embodiments, the divider 18 is a portion of the foam cushion 14. In some embodiments, the divider 18 may be another material such as a material with a low coefficient of friction. In some embodiments, the divider 18 may not be included.

The actuators 16 and foam cushion 14 may be encased by a cover 20. The cover 20 may help to protect the cushion 14 and actuators 16 inside the dynamic support apparatus 10. In some embodiments, the cover 20 may provide and/or may be made of a material which provides protection for the actuators 16 making damage of the actuators 16 less likely. In some embodiments, the cover 20 may also protect the foam cushion 14 from moisture (perspiration, urine, spills, etc.) which may reduce the lifespan of the foam cushion 14. The cover 20 may be made from a low-friction material which aids in transferring on and off the dynamic support apparatus 10. Such a material may also be useful in reducing the shear forces between an occupant and actuators 16 and/or a foam cushion 14. The cover 20 in some embodiments, may be made from a high friction material that helps to prevent slouching and sliding. The cover 20 may also be made from a coarse woven mesh material that helps wick moisture from the occupant's skin surface and promotes ventilation. In some embodiments, the cover 20 material may differ depending on the specific needs of a user.

In some embodiments, a dynamic support apparatus 10 may include a number of covers 20. In some embodiments, there may be a cover 20 for the cushion 14 and a separate cover 20 for the actuators 16 or a separate cover 20 for each actuator 16. This may help to prevent a "hammocking" effect where an occupant may be supported by a cover 20 when one or more of the actuators is deflated or drawn away from the occupant.

Figure 3:
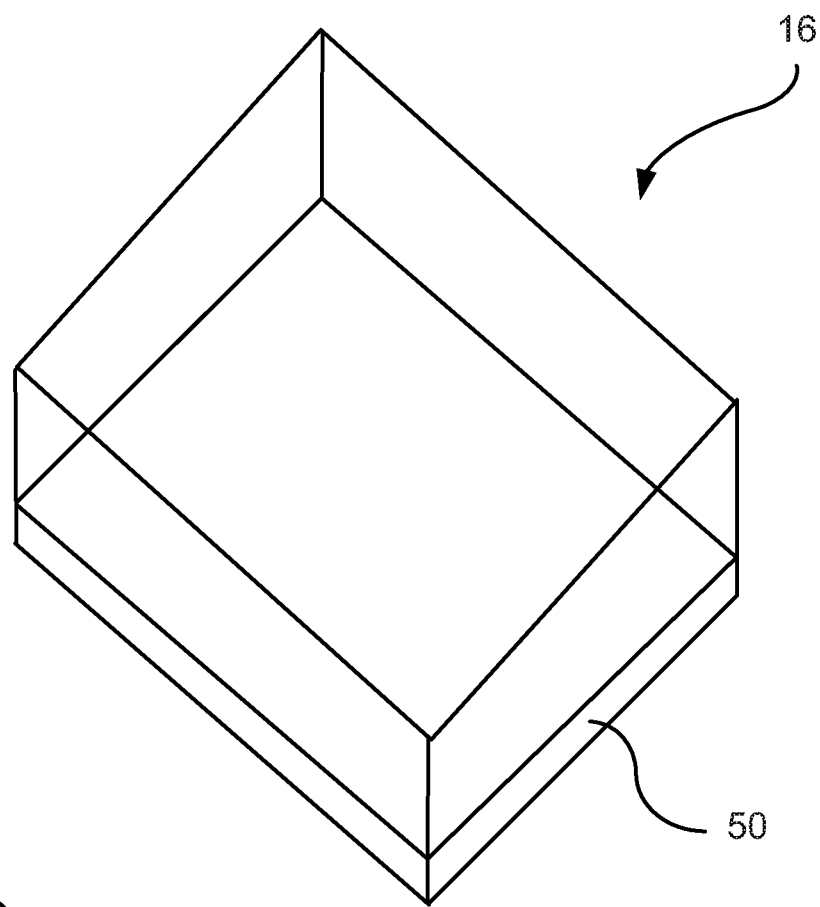
FIG. 3 shows a perspective view of an actuator in accordance with one embodiment.

FIG. 3 shows one embodiment of an actuator 16. The actuator 16 in some embodiments is roughly rectangular. In other embodiments, the shape of the actuators 16 may differ and may be any shape. In some embodiments, the actuator 16, as shown in in FIG. 3, is a bladder. The actuator 16 has an interior volume which may be filled with a fluid. Any suitable fluid, such as water, other liquid, gas, or atmospheric air, may be used. Some embodiments utilize air as the fluid. In some embodiments, the actuator 16 may be constructed of a material which is impervious or nearly imperious to the fluid selected to fill the actuator 16. This may minimize or prevent fluid leakage from the actuators 16. In some embodiments the actuator 16 is made of polyurethane. However, in various other embodiments, the actuator may be made from any material.

As shown, the actuator 16 in FIG. 3 additionally includes a supplementary support 50. The supplementary support 50 is disposed inside the interior volume of the actuator 16. In some embodiments the supplementary support 50 is located at the bottom of the actuator 16. The supplementary support 50 may function as a back-up support. In some embodiments, the supplementary support 50 may support an occupant in the event of a failure of the actuator 16. The supplementary support 50 may also keep the occupant from bottoming out on, for example, a seat pan of a wheelchair if the wheelchair rides off a curb or over a large bump. The supplementary support 50 may be constructed of a material such as foam or any other material.

Figure 4:
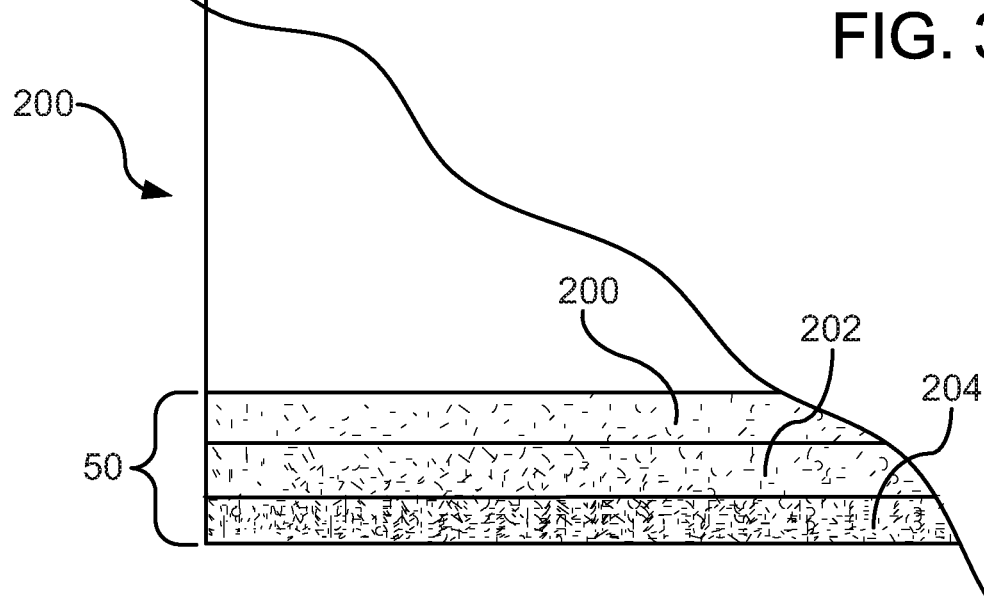
FIG. 4 shows a partial side view of an actuator including a supplementary support in accordance with an embodiment.

Referring now also to FIG. 4, a partial side view of an actuator 16 is shown. The actuator 16 includes a supplementary support 50 similar to the supplementary support 50 depicted in FIG. 3. The supplementary support 50 shown in FIG. 4 is stratified and includes a first stratum 200, a second stratum 202, and a third stratum 204. In other embodiments, such as the embodiment shown in FIG. 3 the supplementary support 50 may not be stratified. In embodiments including a stratified supplementary support 50, the supplementary support 50 may have any number of strata. Additionally, in some embodiments, the foam cushion 14 (see FIG. 1) may also be stratified in a manner similar to that shown and described in relation to FIG. 4. Alternatively, in some embodiments, a supplementary support 50 may be included as a part of the cushion 14. In some embodiments the supplementary support 50 may be a portion of the cushion 14 upon which each actuator 16 is placed. In some embodiments, the supplementary support 50 may be an overlay which is placed on top of each actuator 16 once installed in the cushion 14. In such embodiments, the supplementary support 50 may be stratified.

Each stratum of a supplementary support 50 may be a material having differing properties. In some embodiment the supplementary support 50 may include strata of foams with differing properties or characteristics. In some embodiments of the dynamic support apparatus 10, different actuators 16 may have different supplementary supports 50. In some embodiments, some supplementary supports 50 in some actuators 16 may be stratified while others are not. Some actuators 16 within the dynamic support apparatus 10 may not include supplementary supports 50. Some actuators 16 within a dynamic support apparatus 10 may have supplementary supports 50 with a greater number of strata than other supplementary supports 50 in other actuators 16. The types of foam used to create the strata in one supplementary support 50 may be different than those used to create the strata in other supplementary supports 50. In some embodiments, a slit or number of slits may be cut into a supplementary support 50 to allow a baffle 150 (see FIG. 13) or number of baffles 150 to pass through the supplementary support 50. In some embodiments, foam strata may not be substantially flat, but rather contoured to better suit the anatomy of the supported area of an occupant.

In some embodiments, including those shown in FIG. 4, the first stratum 200 of the supplementary support 50 is a foam with a relatively small indentation force deflection (hereafter "IFD") value as indicated by the low density of the stippling of the first stratum 200. The second stratum 202 of the supplementary support 50 has an IFD higher than that of the first stratum 200 as indicated by the greater density of the stippling of the second stratum 202. The third stratum 204 of the supplementary support 50 has an IFD higher than that of the second stratum 202 as indicated by the high density stippling of the third stratum 204. In some embodiments the strata of foams in the stratified supplementary support 50 are roughly the same thickness. In some embodiments, the strata may have differing thicknesses. In some embodiments the first stratum 200 may be thicker than both the second stratum 202 and third stratum 204.

A stratified supplementary support 50, such as the supplementary support 50 shown in FIG. 4, may be desirable/beneficial for many reasons, including but not limited to, it creates an appealing balance between occupant comfort, proper support, and bottom out protection when the occupant is being supported by the supplementary support 50. Using the example of a wheelchair, when not supported by an inflated actuator 16, the occupant may be substantially supported by the first stratum 200 of the supplementary support 50 during periods of inactivity or low activity. Since the first stratum 200 of the supplementary support 50 has a relatively small IFD value in the example embodiment, the first stratum 200 easily conforms to the contours of an occupant thus affording the occupant an appropriate pressure distributing support surface and large degree of comfort. During periods of increased activity, jostling, riding over rough or uneven surfaces, etc. the higher IFD value strata of the supplementary support 50 prevent a user from bottoming out on the seat pan. This is so because the higher IFD foam strata require a higher amount of force to fully compress to the point of densification (the point where their cushioning capabilities are compromised).

Figure 5:
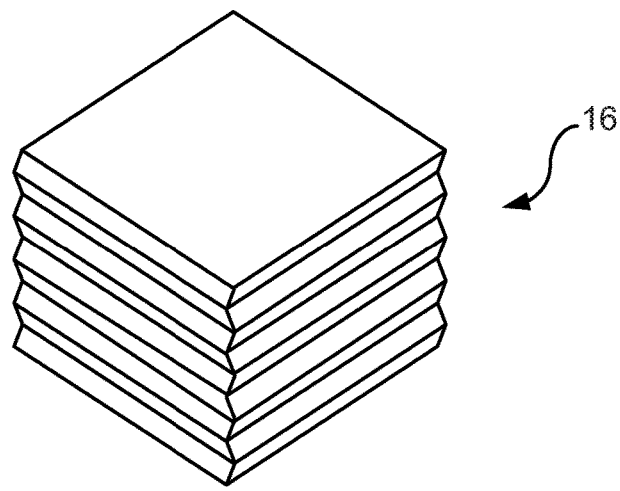
FIG. 5 shows a partial side view of an actuator in accordance with an embodiment.

In some embodiments, the actuators 16 may be structured to be easily collapsible or expandable. In some embodiments, an actuator 16 may have pleated walls as shown in FIG. 5 and resemble an accordion or bellows. Such a configuration may help to increase the linearity of travel as the actuator is inflated or deflated. In some embodiments, an actuator 16 with such pleat features may have a rectangular, a square, circular, etc. type footprint. Other appropriate shapes or combinations of appropriate shapes may be used.

In some embodiments where the actuator 16 is a bladder, the amount of fluid and/or pressure of fluid in the actuator 16 may be varied. In some embodiments, the pressure set point of the actuator 16 may be set such that it substantially mimics the support characteristics of the cushion 14 (see, for example, FIG. 1). Referring back to FIG. 1, the left and right actuator 16 may be inflated and deflated in a manner so as to periodically relieve pressure from a portion of the occupant and shift it to another part of the occupant. The initial set point as well as variation in the actuator 16 pressure can be customized to accommodate the specific support and positioning needs of a person and minimize localized high pressure areas.

This customization may not only increase comfort, but may also aid in the prevention of debucitus ulcers or pressure sores, by allowing sufficient perfusion to the relieved area. When one actuator 16 is deflated, the supplementary support 50 shown in FIG. 3 may prevent the occupant from bottoming out on, for example, the seat pan of a wheelchair. In some embodiments, negative pressure may be applied to the actuators 16 to compress the supplementary support 50 such that the actuator 16 is completely out of contact with the occupant and even greater pressure relief is achieved. In some embodiments, when an actuator 16 is not supporting an occupant, the weight of the occupant may be borne by the a cushion and/or a supplementary support 50 of that actuator 16.

Though some embodiments may use one or more pressure set point to control actuators 16, other embodiments may control actuators 16 with alternative set points. For example, a control set point may be based around the volume, mass, or mols of gas in an actuator 16. Depending on the set point, a dynamic support apparatus 10 may include sensors which can provide feedback related to the set point. For example, a pressure sensor or mass air flow sensor may be included.

In some embodiments, a sensor such as pressure mapping mat may be utilized to determine a specific user's support and positioning needs. After determining the individual user's needs, a customized pressure relief user profile may be created to best meet the individual user's support and positioning needs. In some embodiments, the size of the actuators 16 may be chosen to achieve optimal support. The size and arrangement of the actuators 16 may have an effect on occupant stability. If an actuator 16 is too large, the user may slump into the actuator 16 and become less stable. If an actuator 16 is too small, the user may not receive the most optimal pressure relief. In some instances, it may be desirable to substantially support a user's thigh with a surrounding cushion 14 (see, for example, FIG. 1) instead of the actuator 16. In some embodiments, an actuator 16 spanning 7-inches in the anterior to posterior direction may be desirable. Additionally, in some embodiments, the type of user may be considered in determining the size and or other characteristics of an actuator 16.

In some embodiments, the actuator 16 shown in FIG. 3 may be constructed of a number of different pieces of material. In some embodiments, the actuators 16 may be formed from a number of pieces of polyurethane. In other embodiments, a different material such as neoprene rubber may be used. In some embodiments, the actuators 16 or a portion of the actuators 16 may be constructed out of a piece or pieces of injection molded material. Any other suitable material may also be used. The polyurethane pieces may be sheets of polyurethane of any suitable thickness. For example, in specific embodiments, the polyurethane pieces may be sheets of 0.030" thick polyurethane. Other embodiments may use thinner (e.g. 0.015" thick), more flexible sheets of polyurethane to provide greater comfort for an occupant of the dynamic support apparatus 10. Other embodiments may use thicker (e.g. 0.060" thick), more durable sheets of polyurethane to form more durable actuators 16. The pieces of material may be seamed together to form an actuator 16 such as the actuator 16 shown in FIG. 3. In some embodiments, the thickness of the actuator 16 may not be uniform. For example, it may be desirable that the top face of an actuator 16 be made thicker than the side walls of the actuator 16.

Figure 6:
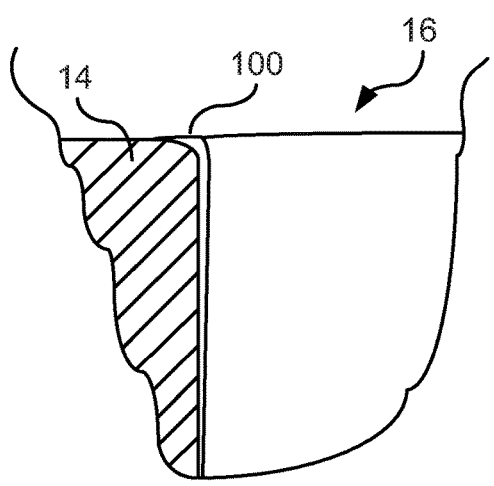
FIG. 6 shows a partial side view of a seam of an actuator in accordance with one embodiment.

Referring now also to FIG. 6, a partial view of an actuator 16 is shown. The seam 100 for two polyurethane pieces of the actuator 16 is also shown. In FIG. 6 the polyurethane pieces are heat seamed together. In other embodiments, other suitable ways of coupling the actuator 16 material together, such as RF welding, laser welding, solvent bonding, adhesive bonding, or any other coupling/bonding method which would be obvious to one skilled in the art may be used.

As shown in FIG. 6, the seam 100 of the two polyurethane pieces is on the outside of the actuator 16. When such a seam 100 is on an exterior surface of the actuator 16 proximal to an occupant, the seam 100 may create a surface discontinuity between the actuator 16 and the foam cushion 14. Such a discontinuity may be felt by the occupant during periods of prolonged occupation of the dynamic support apparatus 10 making the seam 100 a source of discomfort. Moreover, such a discontinuity may create a stress concentration which can inhibit perfusion and lead to the development of a pressure sore. This problem may be reduced by turning the actuator 16 inside out after seams 100 have been created.

Figure 7:
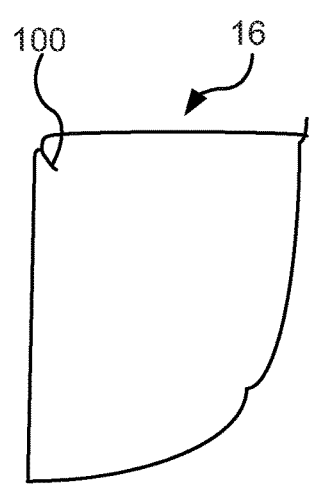
FIG. 7 shows a partial side view of a seam of an actuator in accordance with one embodiment.

Referring now also to FIG. 7 a partial view of an actuator 16 which has been turned inside out is shown. As shown, the seam 100 extends into the interior volume of the actuator 16. As such, the seam 100 would not present such a surface discontinuity and resultant increased ulceration risk and discomfort for an occupant during periods of prolonged occupation of the dynamic support apparatus 10. The actuator 16 may, for example, be turned inside out after the top piece and side piece or pieces of the actuator 16 have been coupled together. The bottom piece of the actuator 16 may then be coupled to the side piece or pieces. Since seams 100 on the bottom of the actuator 16 should not be felt by or project into an occupant, their presence on the exterior of the actuator 16 should not present a comfort or injury concern for the occupant.

Figure 8:
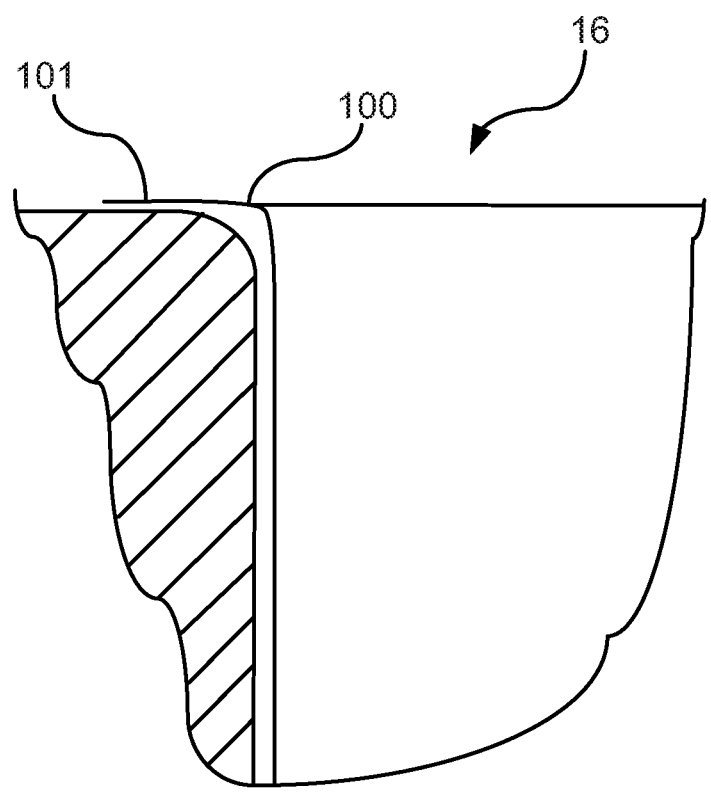
FIG. 8 shows a partial side view of a seam of an actuator in accordance with one embodiment.

Other embodiments may couple the pieces of material with an exaggerated seam 100 as shown in FIG. 8. The seam 100 shown in FIG. 8 is similar to the seam 100 shown in FIG. 6, but there is an extra flange 101 of material from the top sheet of the actuator 16 which rests on the foam cushion 14. The extra flange 101 of material is substantially thinner than the seam 100 of the actuator 16 since it is only a single piece of material and not two seamed together. Though the seam 100 is on the exterior of the actuator 16, surface discontinuity between the foam cushion 14 and the actuator 16 is minimized by the extra flange 101. Thus the seam 100 and extra flange 101 in FIG. 8 creates more negligible discomfort and ulceration risk to an occupant during prolonged periods of occupation of the dynamic support apparatus 10.

Figure 9:
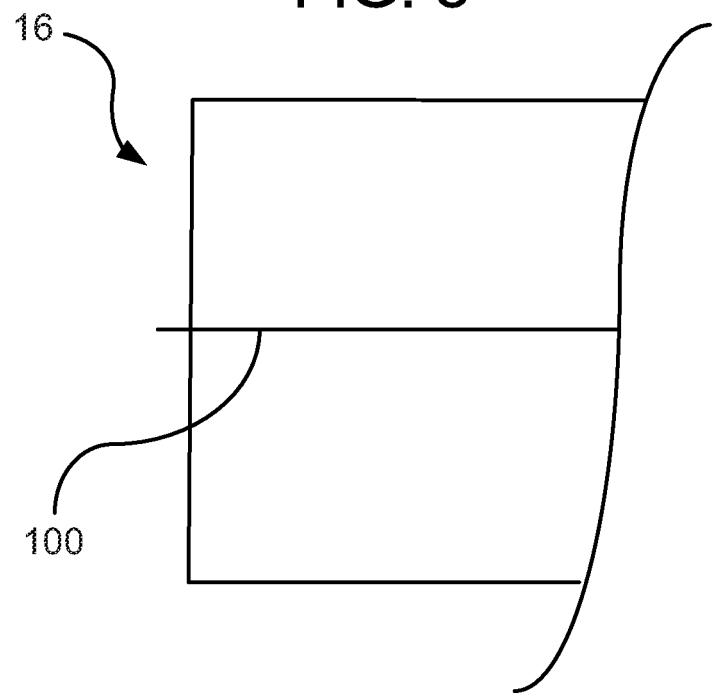
FIG. 9 shows a partial side view of a seam of an actuator in accordance with one embodiment.

In some embodiments, the actuator 16 may only be made of two pieces of material. One such embodiment is shown in FIG. 9. In the embodiment shown in FIG. 9, the actuator 16 is constructed of two pieces of material which have been coupled together. The two pieces of material may be vacuum formed, thermoformed, injection molded, etc. polyurethane in some embodiments. In the embodiment in FIG. 9, the two pieces are of the same dimensions and may be formed from the same mold. The two pieces are coupled together along a central seam 100. The location of the seam 100 ensures that the seam 100 may not be felt by or present a problematic surface discontinuity to an occupant.

Figure 9A:
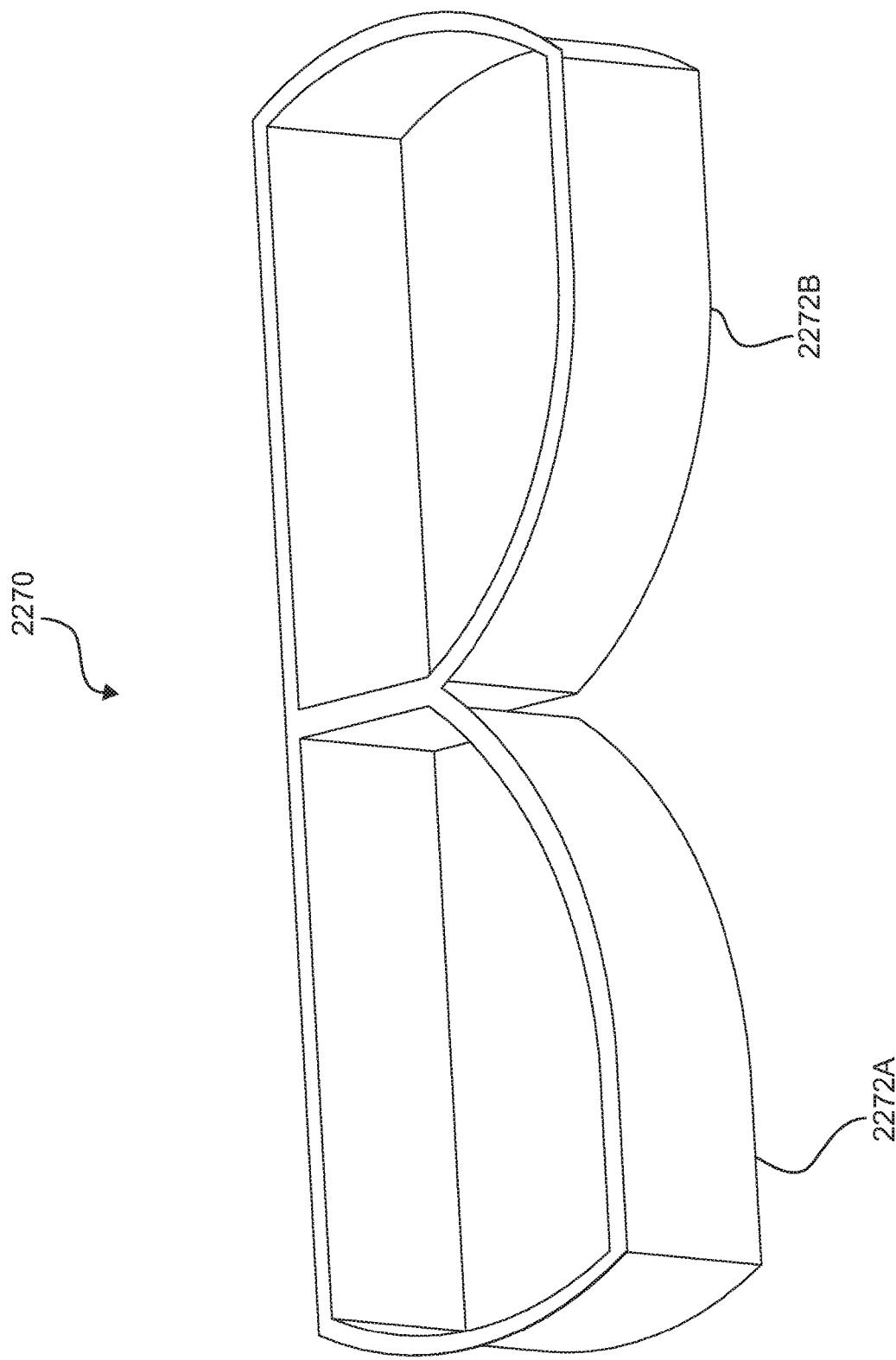
FIGS. 9A-9B show views of an actuator having two halves which may be formed in the same piece of material as a clamshell.
Figure 9B:
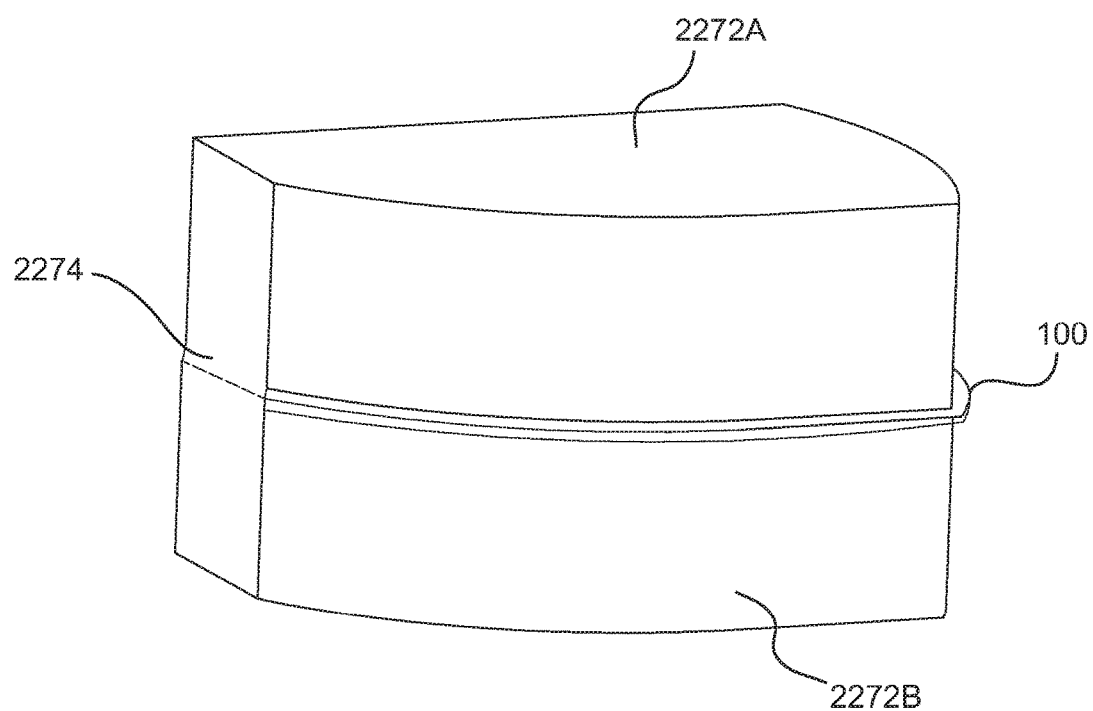

Alternatively, and referring to FIGS. 9A and 9B, the two halves 2272A, 2272B may be formed in the same piece of material as a clamshell 2270. That is, the two halves 2272A, 2272B may be formed adjacent to one another in the same piece of material (FIG. 9A). After forming, the material may then be folded to close the clamshell such that the two halves 2272A, 2272B meet to form the actuator 16 (FIG. 9B). The material may then be seamed to complete the actuator 16. Such an actuator may have a central seam 100 similar to that depicted in FIG. 9. Due to the folding of a continuous piece of material, however, one side 2274 of the actuator 16 would not be required to be seamed.

In embodiments where the actuator 16 or part of the actuator 16 is vacuum or thermoformed from polyurethane, it may be desirable to use a thicker sheet of polyurethane (e.g. 0.060"). This is so because as the actuator 16 is formed some of the polyurethane material is caused to thin as it is stretched. Using a thicker sheet of polyurethane during vacuum or thermoforming may be desirable for other reasons as well. For example, if used in conjunction with a positive form as opposed to a negative, cavity form, it allows the top surface of the actuator 16 to have a relatively greater thickness than the side walls. This may be desirable because the top surface, which is most prone to puncture, is made to be more durable while the thinner side walls still allow for a fairly large amount of flexibility.

In some embodiments, one or more faces of an actuator 16 or actuators 16 may be contoured. Such contours may help to better support a user. Additionally, such contours may be useful in ensuring surface discontinuities and pressure points do not arise when the actuator 16 is in a collapsed, deflated, or otherwise retracted state. In some specific embodiments, the adjacent faces of the actuators 16 may be contoured. Contouring the adjacent faces of the actuators 16, may aid in optimizing pressure distribution.

Figure 10:
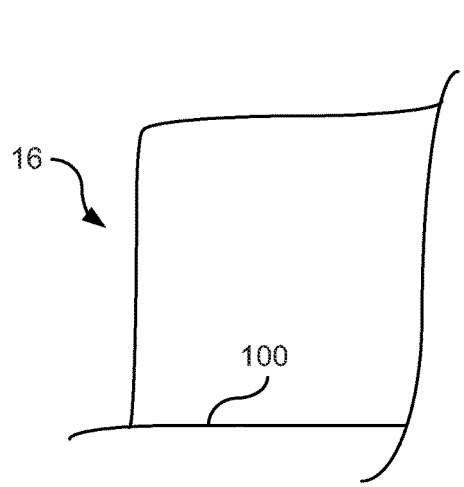
FIG. 10 shows a partial side view of a seam of an actuator in accordance with one embodiment.

FIG. 10 shows another embodiment of an actuator 16 where the actuator 16 is a bladder formed from only two sheets of material. In the embodiment in FIG. 10 the top and sides of the actuator 16 may, for example, be a single piece of vacuum, molded, or thermoformed material such as polyurethane.

The bottom piece may be a sheet of polyurethane which is substantially planar in some embodiments. As shown, the bottom piece is coupled to the bottom edges of the sides of the actuator 16. By locating the seam 100 along the bottom of the actuator 16 it is ensured that the seam 100 may not be felt by the occupant. Additionally, disposing the seam 100 as shown ensures the seam 100 does not raise an ulceration risk to the occupant.

Figure 11:
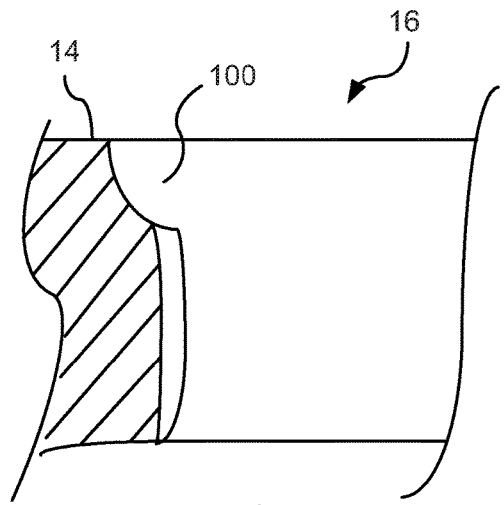
FIG. 11 shows a partial side view of a seam of an actuator in accordance with one embodiment.

FIG. 11 shows an embodiment of an actuator 16 similar to the actuator 16 shown in FIG. 10. The actuator 16 shown in FIG. 11 includes an expanded portion 110 along its top edge such that the actuator 16 vaguely resembles a mushroom or muffin. The expanded portion 110 may bridge any gap which may exist between the actuator 16 and the foam cushion 14 and/or divider 18 (see FIG. 1 for example). The expanded portion 110 may overlap a piece of the foam cushion 14 and/or divider 18. Alternatively, and as shown, a portion of the cushion 14 may be recessed such that it may accept the expanded portion 110. The expanded portion 110 along the top edge of the actuator 16 may be desirable because it helps smooth the transition from the actuator 16 the rest of the dynamic support apparatus 10 by minimizing surface discontinuities. In alternate embodiments, the foam cushion 14 and/or divider 18 may include a portion which overlaps the edges of the actuator 16. The actuators 16 may be contoured to allow such a portion of the foam cushion 14 and/or divider 18 to overlap the actuator 16 edges in a manner which creates minimal surface discontinuity.

Figure 12:
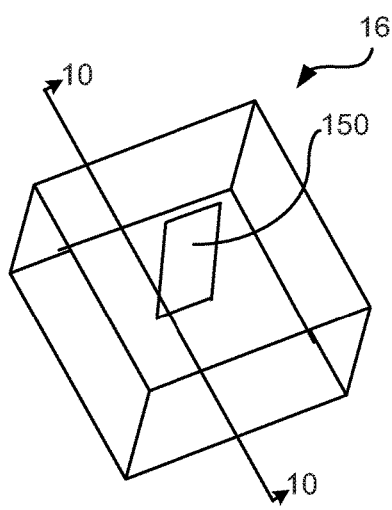
FIG. 12 shows a perspective view of an actuator including a baffle in accordance with one embodiment.

FIG. 12 shows another embodiment of an actuator 16. As shown, the actuator 16 in FIG. 12 is roughly rectangular. As mentioned above, actuators 16 need not be rectangular but may take any suitable shape. The actuator 16 may additionally include a baffle 150 within the interior volume of the actuator 16. In alternate embodiments, multiple baffles 150 may be included in the actuator 16. In the embodiment, the baffle 150 is a band. In other embodiments, the baffle 150 may not be a band, but rather a string, strand, or the like. The baffle 150 may, depending on the embodiment, be located in roughly the center of the actuator 16. The baffle 150 extends from the interior bottom surface of the actuator 16 to the interior top surface of the actuator 16. In the embodiment, the baffle 150 is a relatively thin strip of material. In other embodiments, the baffle 150 may take any suitable width. In embodiments where the actuator 16 is made of polyurethane sheets, the baffle 150 may also be made of polyurethane. The baffle 150 may be coupled to the top and bottom interior surfaces of the actuator 16 by any suitable means. In some embodiments, the baffle 150 may be located off-center of the actuator 16.

The baffle 150 serves to constrain the actuator 16 from expanding in a top-bottom direction when inflated. Without the baffle 150, the actuator 16 would, when inflated, demonstrate a tendency to balloon such that the top surface of the actuator 16 would display a rounded bulge as shown by the dashed line 152 in FIG. 13. Such a bulge would be undesirable because the bulge of the bladder cushion 16 may unevenly push into an occupant. This would create an uneven surface and pressure distribution for an occupant occupying the dynamic support apparatus 10. Such a scenario may cause discomfort and may frustrate ulcer prevention objectives of the dynamic support apparatus 10.

In addition or alternatively, an actuator 16 may include one or more baffle 150 which is oriented horizontally. This may serve to constrain the sides of an actuator 16 from ballooning or bulging out under the weight of an occupant. In embodiments including a horizontal baffle 150, the baffle 150 may be placed between two parts of the actuator 16 when it is seamed together such that edges of the baffle 150 will become a part of the seam. Thus, the baffle 150 may be attached to the actuator 16 in the proper orientation when the actuator 16 is formed.

Figure 13:
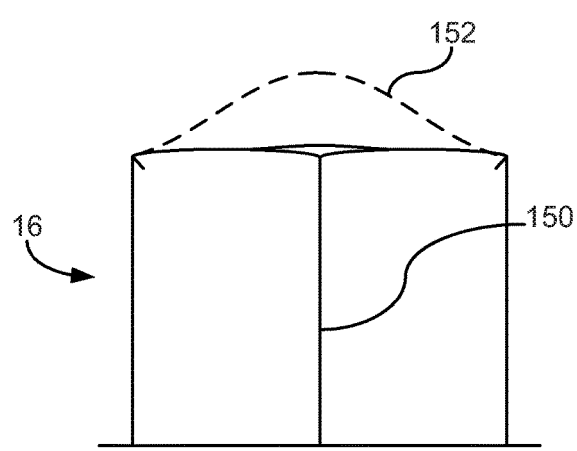
FIG. 13 shows a cross sectional view of an actuator including a baffle taken at 10-10 of FIG. 12 in accordance with one embodiment.

FIG. 13 shows a cross-sectional view of an actuator 16 including a baffle 150 taken at line 10-10 of FIG. 12. The actuator 16 in FIG. 13 is seamed like the actuator 16 shown in FIG. 7. As shown, the actuator 16 is in an inflated condition. The baffle 150 is taught and constraining the top surface of the bladder cushion 16 from bulging up into an occupant. Also shown in FIG. 13 is a dashed line 152 indicating the bulge which would be present in absence of the baffle 150. As indicated above, the baffle 150 may help to ensure a more even pressure distribution across the area of the occupant supported by the actuator 16.

In embodiments of the dynamic support apparatus 10 where the actuators 16 are bladders, the bladders may be filled with a fluid such as air. Preferably, the actuator 16 bladders are not filled with fluid to the point of turgidity, but rather are somewhat flaccid. In the example of a wheelchair, as an occupant sits on the actuators 16, the fluid in the actuators 16 may compress until the pressure of the fluid within the actuators 16 equals the contact pressure of the occupant. Pressure may also be substantially evenly distributed over the occupant contact area. The resulting pneumatic pressure of air in an actuator 16 for an average occupant may be in the range of 0-150 mm Hg.

As mentioned above, in some embodiments where the actuator 16 is a bladder, the volume of fluid in the interior volume of the bladder may be variable. In such embodiments, a pump 500 (see, for example, FIG. 25) may be used to vary the volume of fluid in the actuator 16. In a preferred embodiment, a pump 500 may use the ambient atmosphere as its fluid reservoir 502 (see, for example, FIG. 25). The pump 500 and/or pneumatic system may be capable of applying both positive and negative pressure to respectively inflate or deflate a selected actuator 16. Some embodiments may include a manifold 518 (see, for example, FIG. 25) which may enable fluid to be directed to a specific actuator 16. Thus, by controlling the type of pressure applied and to which actuator 16 it is applied, the actuators 16 may be selectively inflated and deflated to relieve pressure from various anatomical areas and to help prevent the formation of pressure sores by improving perfusion in the blood vessels of the relieved area.

Figure 14:
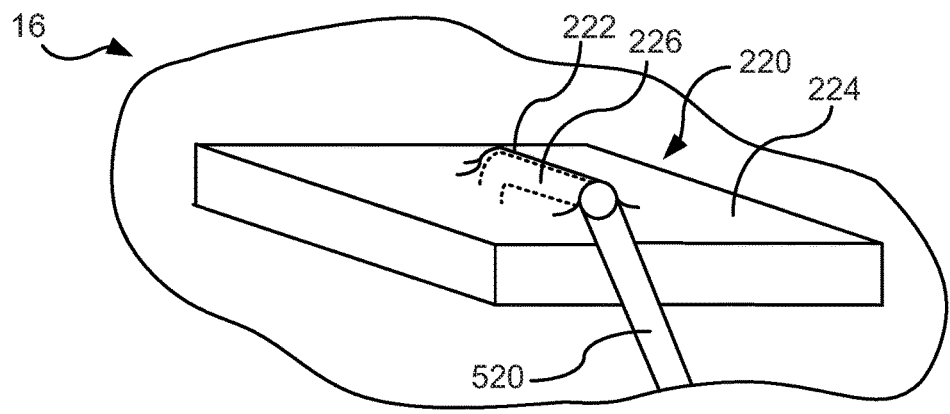
FIG. 14 shows a close up view of a fluid port in accordance with one embodiment.

In order to add or remove fluid from an actuator 16, actuators 16 may include a fluid port 220 such as the embodiment of the fluid port 220 shown in FIG. 14. The fluid port 220 may include an actuator channel attachment feature 222 and a base 224 as shown in FIG. 14. The fluid port 220 may be formed by any suitable manufacturing process, for example, injection molding. As shown, the base 224 in some embodiments is roughly rectangular. In some embodiments, the base 224 may take a different shape. For example, the base 224 may be puck-like. The base 224 may be coupled to the actuator 16 by any of a variety of means. The base 224 may, for example, be heat bonded onto the actuator 16. In some embodiments, the base 224 may be attached differently. For example, the base 224 may be coupled to the actuator 16 by laser welding, RF welding, or any other technique. In some embodiments, the base 224 may not be made an integral part of the actuator 16. In such embodiments, the base 224 may include two parts which are coupled together after one has been passed through a stoma 258 (see, for example, FIG. 16).

As shown in some embodiments, the actuator channel attachment feature 222 rises off roughly the center of the base 224 toward the top of the page. The actuator channel attachment feature 222 in some embodiments extends in a direction substantially parallel to two of the sides of the base 224. In some embodiments, the actuator channel attachment feature 222 includes a passage 226 which is shown in outline form in FIG. 14. As shown, the actuator channel 520 may be coupled into the passage 226 of the actuator channel attachment feature 222. This may be accomplished by any suitable coupling method. The passage 226 provides a pathway for fluid to be communicated into and/or out of the interior volume of the actuator 16 via the actuator channel 520.

Figure 15:
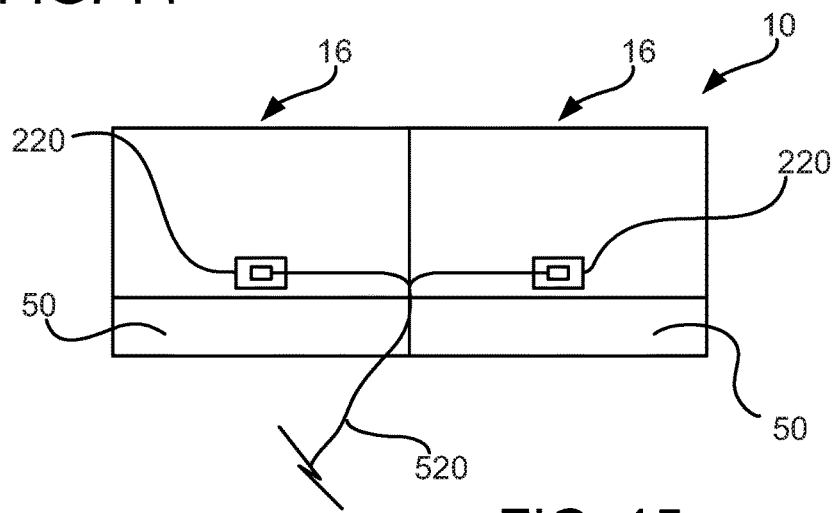
FIG. 15 shows a side view of two actuators including fluid ports and actuator channels in accordance with one embodiment.

FIG. 15 shows two actuators 16 of a dynamic support apparatus 10 which include fluid ports 220 similar to those shown in FIG. 14. As shown, the actuators 16 in FIG. 15 include a supplementary support 50. The fluid ports 220 are disposed on the side walls of the actuators 16 slightly above the supplementary support 50. Such a placement of the fluid ports 220 allows them to have unrestricted fluid communication with the interior volume of the actuators 16. Additionally, by disposing the fluid ports 220 as shown in the embodiment shown in FIG. 15, the fluid ports 220 are kept out of contact with an occupant. Preferably, the fluid ports 220 are disposed on the actuators 16 in a location where they are not likely to be felt by or project into the occupant even when the actuator 16 is deflated.

Some embodiments may include a similarly disposed pressure relief valve (not shown). The pressure relief valve (not shown) may help to prevent actuator 16 damage from impact loading (e.g. riding off a curb in a wheelchair). The pressure relief valve (not shown) may also reduce effects to an occupant by relieving some of the peak loads generated during such scenarios. Any suitable pressure relief valve may be used.

As shown in FIG. 15, the actuator channels 520 do not couple to the fluid ports 220 at an angle substantially perpendicular to the side wall of the actuators 16. The actuator channels 520 instead couple to the fluid ports 220 in a fashion substantially parallel to the side walls of the actuators 16. This may be done to avoid kinking the actuator channels 520 when the actuators 16 are placed in the voids of the foam cushion 14 (see FIG. 1). In some embodiments, the foam cushion 14 (see FIG. 1) may include pathways which allow the actuator channels 520 to pass through at least a part of the foam cushion 14 (see FIG. 1).

As indicated in FIG. 15, the actuator channels 520 are bundled together for a substantial portion of their extent. In some embodiments, the actuator channels 520 may be bundled together by any suitable fastener such as a cable tie, hook and loop tape, or the like. In some embodiments, the actuator channels 520 may be incorporated into a ribbon. In some embodiments, the actuator channels 520 may be braided together. Any other means of achieving the same may also be used. Bundling the actuator channels 520 together is desirable because it minimizes the opportunity for a snag to occur. In some embodiments, the actuator channels 520 may be coupled to their respective fluid ports 220 or to a manifold 518 (see, for example, FIG. 25) in a manner which would facilitate a graceful breakaway should a snag occur.

Figure 16:
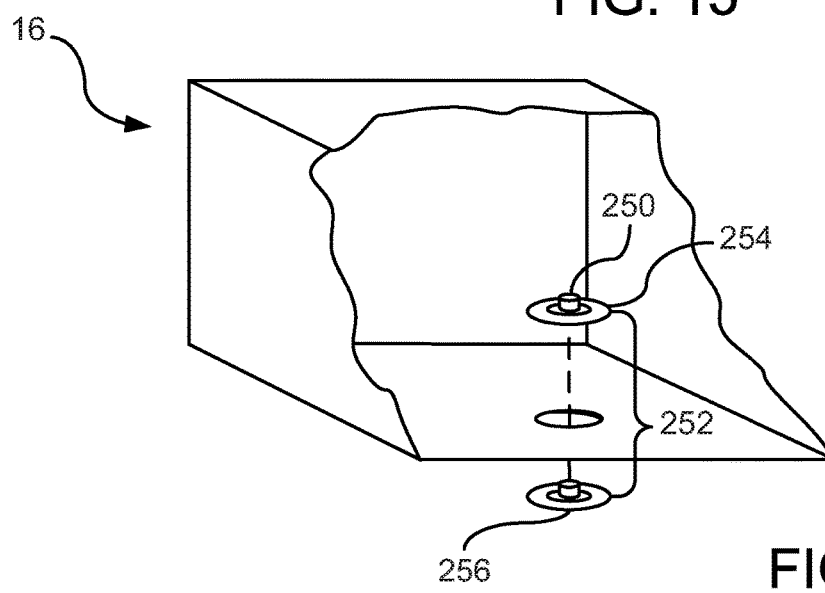
FIG. 16 shows a cutaway view of an actuator including a stoma and an exploded sensor assembly in accordance with one embodiment.

FIG. 16 shows a cutaway view of one embodiment of an actuator 16 which includes a sensor 250. Some embodiments of actuators 16 may include a number of sensors 250. The sensor 250 may be used for gathering information about conditions in the interior volume of the actuators 16. For example, the sensor 250 may sense the pressure of fluid in the interior volume of the actuator 16. The sensor 250 may also be used to sense, for example, the distance between the sensor 250 and a surface of actuator 16. In some embodiments the sensor 250 may detect a bottom out or over inflation of an actuator 16. In some embodiments a sensor 250 may be a mass air flow sensor monitoring air in and out of the actuator 16. Actuators 16 may also include other sensors 250 which may sense other characteristics. For example, an actuator 16 may include a sensor 250 measuring a physiological characteristic such as a pulse-oximeter. Other sensors 250 such as temperature sensors or moisture sensors may also be included. In a preferred embodiment, the sensor 250 or sensors 250 are not made as an integral part of the actuator 16. In some embodiments, a sensor 250 or sensors 250 which are not disposed on or in the actuators 16 may also be included. In some embodiments, a sensor 250 may be included in the fluid pathways to and from the actuator 16.

In some embodiments, the sensor 250 is part of a sensor assembly 252 which is shown exploded apart in FIG. 16. FIG. 16 shows one embodiments of a sensor assembly 252 that is not an integral part of the actuator 16. In some embodiments, the sensor assembly 252 includes a sensor housing 254 which houses the sensor 250 and a plug portion 256. Other embodiments of sensor assemblies 252 may differ. As shown, the actuator 16 includes an orifice or stoma 258 through which the sensor housing 254 and sensor 250 may be passed through. Once the sensor housing 254 and sensor 250 have been passed into the actuator 16, the plug portion 256 may be coupled to the sensor housing 254 so that an airtight seal is formed.

The stoma 258 may be a suitably sized hole cut into the bottom sheet of the actuator 16 as shown in FIG. 16. The stoma 258 may be cut into a different portion of the actuator 16 which may be desirable in embodiments with a supplementary support 50 (see FIG. 5). In embodiments including a stoma 258, it may be desirable that the stoma 258 is not cut into the top of the actuator 16 so that plug portion 256 of the sensor assembly 252 does not contact or press against an occupant when an occupant is occupying the dynamic support apparatus 10. As previously mentioned, a similar arrangement may also be used to couple a fluid port 220 into an actuator 16.

Figure 17:
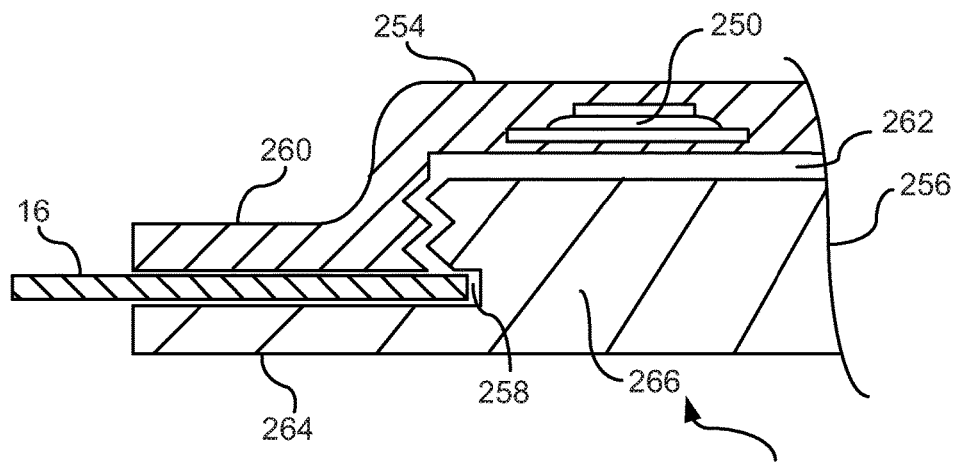
FIG. 17 shows a cross sectional view of a sensor assembly in accordance with one embodiment.

FIG. 17 shows one embodiment of a sensor assembly 252 integrated into an actuator 16 through a stoma 258. As shown, the sensor 250 is disposed inside the sensor housing 254 of the sensor assembly 252. The sensor housing 254 includes a sensor housing flange 262 which projects outwardly from the sensor housing 254 along the same plane as the bottom surface of the sensor housing 254. A cylindrical void 262 is recessed into the bottom of the sensor housing 254. The sides of the cylindrical void 262 may be threaded as shown.

In some embodiments, a plug portion 256 of a sensor assembly 252 is also shown in FIG. 17. As shown, the plug portion 256 includes a plug portion flange 264. The plug portion flange 264 projects outwardly from the plug portion 264 along the same plane as the bottom surface of the plug portion 256. The plug portion 256 also includes a cylindrical protuberance 266 which protrudes toward the top of the page. As shown, the cylindrical protuberance 266 is threaded such that the plug portion 256 may be screwed into the threads of the cylindrical void 262 of the sensor housing 254.

When the sensor housing 254 and plug portion 256 are screwed together, the sensor housing flange 260 and plug portion flange 264 form a flange seal against the material of the actuator 16. This seal ensures that fluid may not exit the actuator 16 via the stoma 258. Other means of creating a fluid or airtight seal may also be used.

Figure 18:
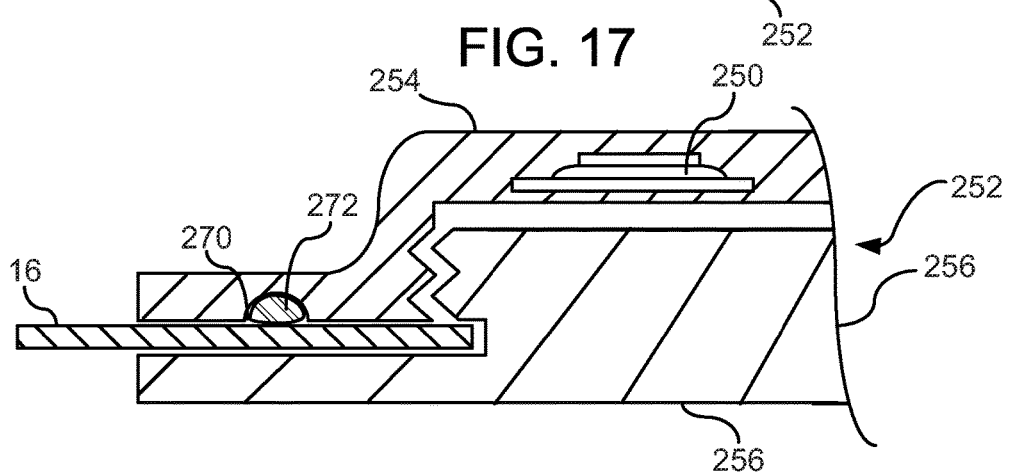
FIG. 18 shows a cross sectional view of a sensor assembly including an O-ring seal in accordance with one embodiment.

FIG. 18 shows another embodiment of a sensor assembly 252 in place within the stoma 258 of an actuator 16. As shown, the plug portion 256 of the sensor assembly 252 is substantially the same as the plug portion 256 shown in FIG. 17. The sensor housing flange 260 includes an O-ring channel 270 which is recessed into the sensor housing flange 260 from the bottom surface of the sensor housing flange 260. As shown, an O-ring 272 is disposed in the O-ring channel 270 of the sensor housing flange 260. As the plug portion 256 and sensor housing 254 of the sensor assembly 250 are screwed together, the O-ring 272 becomes compressed against the material of the actuator 16 forming a fluid or airtight O-ring seal. In alternate embodiments, the O-ring channel 270 and O-ring 272 may be disposed on the top surface of the plug portion flange 264.

Figure 19:
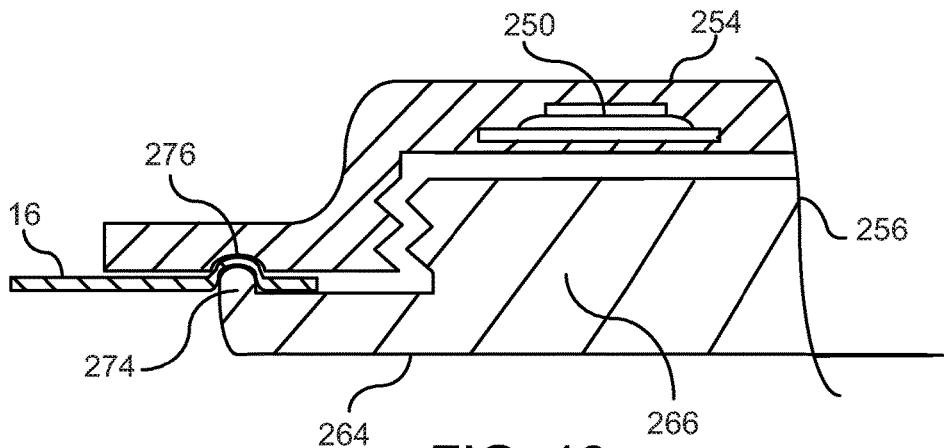
FIG. 19 shows a cross sectional view of a sensor assembly including a groove seal in accordance with one embodiment.

FIG. 19 shows another embodiment of the sensor assembly 252 in place within the stoma 258 of an actuator 16. As shown, the plug portion 256 is different than those shown in FIG. 17 and FIG. 18. The edge of the plug portion flange 264 most distal to the cylindrical protuberance 266 includes a plug portion flange projection 274. As shown, the plug portion flange projection 274 extends from the top surface of the plug portion flange 264 toward the top of the page at an angle substantially perpendicular to the top surface of the plug portion flange 264.

The sensor housing 254 in FIG. 19 is also different than those shown in FIG. 17 and FIG. 18. As shown, the sensor housing flange 260 includes a sensor housing flange groove 276 which is recessed into the bottom surface of the sensor housing flange 260. When the sensor housing 254 and plug portion 256 are married together, a fluid or airtight groove seal is formed as the material of the actuator 16 is pressed into the sensor housing flange groove 276 by the plug portion flange projection 274. In alternate embodiments, the groove of the groove seal may be disposed on the top surface of the plug portion flange 264 while the projection may be disposed on the bottom surface of the sensor housing flange 254.

In some embodiments, the sensor housing 254 and plug portion 256 may not be coupled together via a threaded coupling. In alternate embodiments, the sensor housing 254 and plug portion 256 may be snap fit, friction fit, magnetically coupled, etc. In a preferred embodiment, the sensor housing 254 and plug portion 256 are releasably coupled together. They may also be standardized across actuators 16. This may be desirable because it would allow a user to transplant the sensor assembly 252 to another actuator 16 in the event that the sensor assembly's 252 original actuator 16 is compromised. This would lower the cost of a replacement actuator 16 in the event of an actuator 16 failure.

Figure 20:
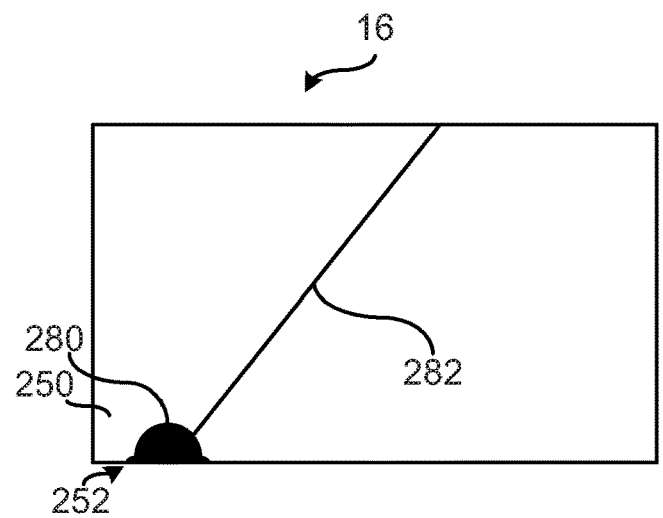
FIG. 20 shows a side view of an actuator with a sensor in accordance with one embodiment.

FIG. 20 shows a side view of an embodiment of an actuator 16. As shown, the actuator 16 is a bladder with a variable interior volume which includes a sensor 250. The sensor 250 may be part of a sensor assembly 252 which is coupled into the actuator 16 as described above. The sensor 250 shown in FIG. 20 includes a potentiometer 280 and an arm 282. As shown, the potentiometer 280 is located on the bottom of the actuator 16. The arm 282 is coupled into the potentiometer 280 such that movement of the arm 282 causes the wiper of the potentiometer 280 to slide across the resistive element of the potentiometer 280. The arm 282 extends from the potentiometer 280 to an attachment point 284 on the top interior surface of the actuator 16.

The sensor 250 may be used to measure the height of the actuator 16. As the actuator 16 inflates or deflates, the arm 282 is caused to move as the angle between the arm 282 and the bottom of the actuator 16 changes. This may be measured by the change in resistance of the potentiometer 280. Measurements from the potentiometer 280 may be used to ensure that the amount of fluid in the actuator 16 is sufficient to support the occupant at a desired height from the bottom of the actuator 16. In some embodiments, if the height of the actuator 16 as measured by the potentiometer 280 suggests the occupant is riding high on a turgid actuator 16, air may be bled off or pumped from the actuator 16 until a more desirable height is measured. Likewise, if the height measurement suggests the occupant is riding too low, more fluid may be added to the actuator 16 to better support the occupant and prevent a bottom out under dynamic loading conditions.

Though the embodiment shown in FIG. 20 depicts a sensor 250 which employs only a single arm 282, other embodiments may be configured with a linkage or scissor jack type mechanism. This may be advantageous, in that the potentiometer 280 may easily be located in the center of the bottom panel of the actuator 16 measure the height of the center of the top of the actuator 16. As would be appreciated by one skilled in the art, the sensitivity of the height measurement could be increased through use of a linkage constructed to create relatively large angular changes in the potentiometer 280 per unit height displacement.

Figure 21:
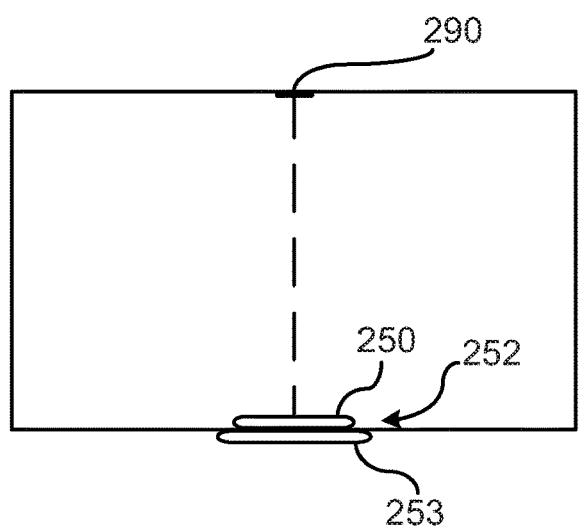
FIG. 21 shows a side view of an actuator with a sensor in accordance with one embodiment of the present disclosure.

FIG. 21 shows another side view of another embodiment of an actuator 16. Again, as shown, the actuator 16 is a bladder with a variable interior volume which includes a sensor 250. In the embodiment shown in FIG. 21, the sensor 250 may be part of a sensor assembly 252 which is coupled into the actuator 16 through a stoma 258 as described above. In the embodiment, the sensor 250 is a non-contact sensor. Specifically, the sensor depicted in FIG. 21 is an optical range finder. As shown, a reflective surface 290 is disposed about the top interior surface of the actuator 16. In alternate embodiments, the actuator may not include a reflective surface 290 but rather another suitable indicator. As the actuator 16 in the embodiment shown in FIG. 21 inflates or deflates, the strength of the reflected signal respectively decreases and increases. The strength of the signal may be used to determine the height of the actuator 16. As mentioned above, the height measurement may be used to determine if an occupant is riding high or low and adjust the height of the actuator 16 by adding or removing fluid accordingly.

A number of other non-contact sensors 250 may be used to achieve the same end. In some embodiments, the sensor or sensors 250 may be an optical or infrared camera chip. The top of the actuator 16 may then be marked with a fiducial marker, grid of fiducial markers, or other pattern of fiducial markers. Such markers may, in some embodiments, be target circles, crosshairs, or any other suitable marker. In some embodiments of a single fiducial marker, the sensor 250 may capture the apparent size of the marker and this apparent size may be fed to an algorithm to divine the approximate height of the actuator 16. Similarly, in the case of a grid or pattern of fiducial markers, the apparent size of the markers, as sensed by one or more sensors 250, may be used to approximate the height and shape of the top of the actuator 16 when fed to an algorithm.

Alternatively, the sensor or sensors 250 may be hall-effect sensors. A magnet or magnets may be embedded or coupled to the top surface of the actuator 16. As the magnet or magnets displace with the top surface of the actuator 16, the output of the sensor or sensors 250 will vary accordingly. The sensor's or sensors' 250 output may then be used to determine the approximate height of the actuator 16.

In some embodiments including a non-contact sensor, the sensor 250 may measure capacitance of the actuator 16. In such embodiments, the top of the actuator 16 may be metalized. As the actuator 16 height changes, the capacitance of the actuator 16 should change in kind. The capacitance of the actuator, as measured by the sensor 250 may be used to determine the approximate height of the actuator 16.

Figure 22:
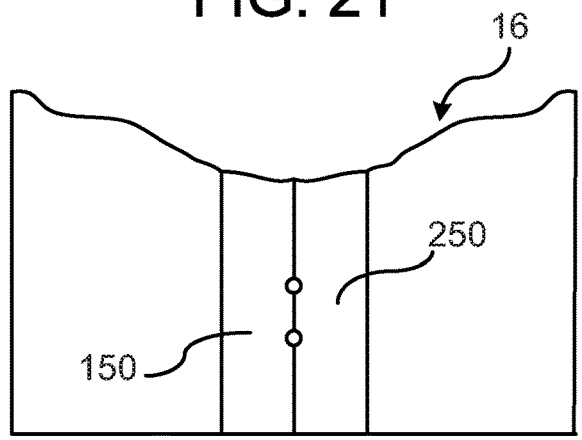
FIG. 22 shows a side view of an actuator including a baffle and a sensor in accordance with one embodiment.
Figure 23:
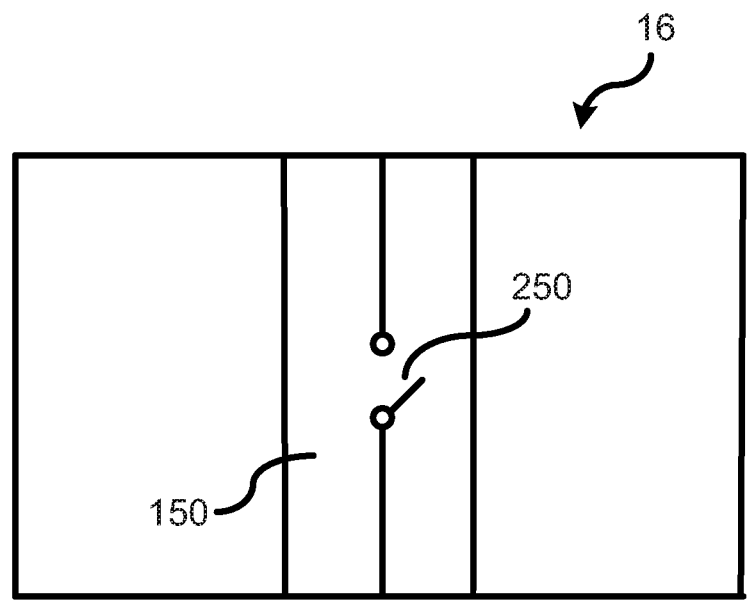
FIG. 23 shows a side view of an actuator including a baffle and a sensor in accordance with one embodiment.

FIG. 22 and FIG. 23 show another side view of an embodiment of an actuator 16. The actuator 16 is a bladder with a variable interior volume which includes a sensor 250. As shown, the actuator 16 includes a baffle 150 similar to the baffle 150 shown in FIG. 12 and FIG. 13. The baffle 150 in FIG. 22 and FIG. 23 is elastically deformable by tensile force. The baffle 150 may include a sensor 250 which functions as a contact sensor. Depending on the amount of deformation of the baffle 150, the circuit formed by the sensor 250 may be partially or fully closed or broken.

As shown in FIG. 22, the actuator 16 is not inflated to the point of turgidity. The baffle 150 is not in a deformed state and the circuit made by the sensor 250 is closed. As the baffle 150 is stretched beyond a certain amount, the circuit made by the sensor 250 may be broken. The baffle 150, in some embodiments, may be configured such that the circuit made by the sensor 250 is broken slightly before the actuator 16 becomes turgid as shown in FIG. 23. A controller 506 (see, for example, FIG. 25) may not allow fluid to be pumped to an actuator 16 if the circuit formed by the sensor 250 is broken. This may be done to help prevent discomfort and high contact pressure areas from over inflation of the actuator 16.

In other embodiments, the sensor 250 in the baffle 150 may not be a contact sensor. In some embodiments, the baffle 150 may include an integrated strain gauge. Any deformation of the baffle 150 due to tensile forces generated from an inflated actuator 16 may be measured by the strain gauge. As mentioned above, this measurement may be used to determine if an occupant is riding at an undesirable level so that the amount of fluid in the actuator 16 may be adjusted accordingly.

Figure 24:
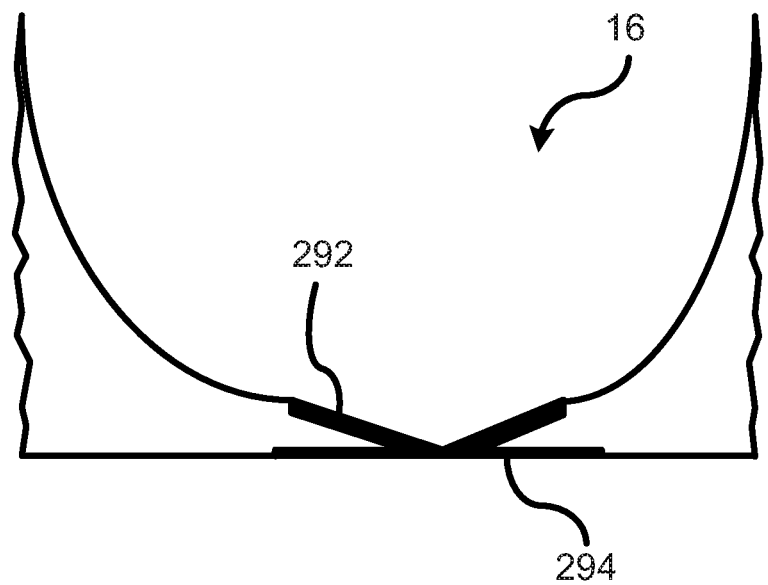
FIG. 24 shows a side view of an actuator and a sensor in accordance with one embodiment.

FIG. 24 shows another side view of one embodiment of an actuator 16 which is largely deflated. The actuator 16 includes a sensor 250 which may sense a "bottom out" condition of the actuator 16. As shown, a portion of the top surface of the actuator 16 is bottomed out on the bottom of the actuator 16. The top interior surface of the actuator 16 may include a metalized patch 292. The bottom interior surface of the actuator 16 may include contacts 294 such as, in some embodiments, an arrangement of thin wires. When a bottom out condition is present, as in the embodiment shown in FIG. 24, the bottom out condition may be registered as a switch closure. When a bottom out condition is detected, the controller may attempt to inflate the actuator 16 such that the occupant is supported by the fluid within the actuator 16. In some embodiments, when a bottom out condition is detected, an alarm may be sounded. In some embodiments, the contact between the top and bottom of the actuator 16 may be made to have a relatively large resistance. By observing the amount of resistance, a controller 506 (see FIG. 25) may be able to distinguish between an incidental contact and a broad bottom out.

Other embodiments may use other varieties of suitable sensors 250 to sense various conditions or characteristics of the actuator 16 or the fluid in the interior volume of the actuator 16. Some embodiments may use multiple sensors 250 in each actuator 16, such as but not limited to those described above. In some embodiments, each actuator 16 may include sensors 250 to sense a number of characteristics of each actuator 16 or the fluid in the interior volume of each actuator 16. In some embodiments, data from the sensor 250 may be used in conjunction with data from other sensors 250 not included on or within the actuator 16. In some embodiments, a bottom out sensor may be used in conjunction with a mass air flow sensor in an actuator channel 520 (see FIG. 15) to determine if a gross leak (e.g. a ruptured or punctured actuator 16) condition exists.

In some embodiments, a sensor 250 may be used to provide automated pressure relief. In some embodiments, information from a sensor 250 may be utilized to determine whether positive or negative pressure should be applied and for how long. In some embodiments, a motor, for example the motor 504 shown in FIG. 25, may be automatically turned on by a controller (which may be or include a microprocessor) using data gathered by a sensor 250, to provide positive or negative pressure as is necessary or dictated by a pressure relief scheme. In some embodiments, a controller may make such determinations based on trends of the data received from a sensor 250. In some embodiments, a controller may utilize data from the sensor 250 as feedback when running the motor 504. Based upon sensor 250 data the controller may determine when an actuator 16 has been sufficiently inflated or deflated. In some embodiments, the motor 504 may be turned off by the controller when sensor 250 data indicates that a step in a pressure relief regimen has been completed. In some embodiments, such a step may be completed passively, without the use of a pump (e.g. by connecting an actuator 16 to the atmosphere and allowing the weight of an occupant to drive fluid out).

Figure 25:
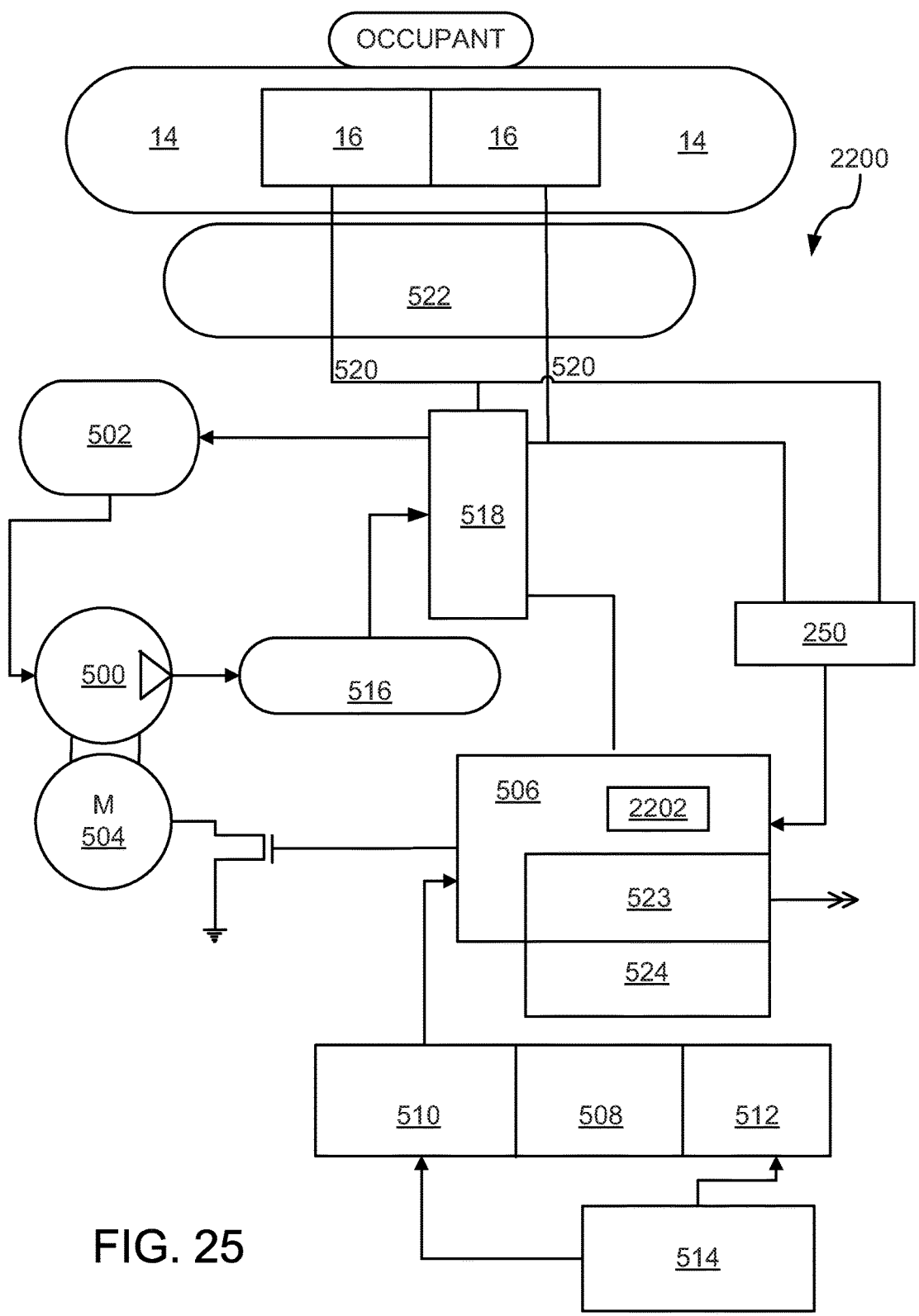
FIG. 25 shows a block diagram of a person support apparatus in accordance with one embodiment.

A block diagram for an embodiment of a dynamic support system 2200 having a dynamic support apparatus 10 with variable fluid volume actuator 16 bladders is shown in FIG. 25. As shown, the pump 500 draws in fluid from a reservoir 502. The pump 500 is powered by a motor 504 which may be turned on or off by a controller 506. In some embodiments, the controller 506 may be, but is not limited to, a smartphone, tablet, Bluetooth, ZIGbee, RF connected device, IR connected device, wirelessly connected device, or any combination thereof. In some specific embodiments, the motor 504 may be a 5-W rated motor 504. An onboard power source 508 and power conditioning 510 are included to provide power to the necessary components. In some embodiments, the onboard power source 508 may be rechargeable by means of a charger 512. In some embodiments, the onboard power source 508 may be a battery or number of batteries such as lithium-ion cells. Some other embodiments may be capable of operation off of an external power source 514 or a variety of different external power sources 514. In some embodiments, power may be provided by an external power source 514 during times of inactivity when such a source is available. During periods of activity the dynamic support apparatus 10 may be run off of an onboard power source 508.

In specific embodiments where the dynamic support apparatus 10 is being used as the seat of a powered wheelchair, the battery bank of the powered wheelchair may also be used as a power source. In some embodiments, the battery bank of the powered wheelchair may be used as the primary power source, or may in some instances be considered an external power source, such as the external power source 514 in FIG. 25. In some embodiments, the battery bank of a powered wheelchair may not be the primary power source used. Instead such a battery bank may be used to ensure that the onboard power source 508 for the dynamic support apparatus 10 is at an acceptable state of charge.

Still referring to FIG. 25, as fluid exits the pump 500, fluid may travel to an accumulator 516. This fluid may then pass into a manifold 518 which directs the fluid to the actuators 16. The manifold 518 may be made using a variety of methods. The manifold 518 may be made from machined solid material such as a plastic or metal. Alternatively, the manifold 518 may be injection molded as one or more parts. In still other embodiments, the manifold 518 may be grown using an additive manufacturing process such as a selective laser sintering process. The manifold 518 and each actuator 16 may be connected via an actuator channel 520 which may, for example, be tubing. In some embodiments, the valves associated with the manifold 518 may be controlled by a controller 506 to selectively direct fluid to specific actuators 16.

In some embodiments, as mentioned above, the actuator channels 520 may be bundled together or arranged in a ribbon-like formation. This may be desirable to reduce the likelihood of the tubing tangling, snagging, or getting caught on various objects. The actuator channels 520 may interface with the actuators 16 and/or controller 506 through a detachable interface 522. The detachable interface 522 may easily allow the actuator channels 520 to be uncoupled from the actuators 16 or controller 506 if needed. In some embodiments, the detachable interface 522 may allow actuator channels 522 which becomes snagged or caught on an object to uncouple from the actuators 16 or controller 506. This breakaway feature may minimize the possibility for damage to the actuators 16, actuator channels 520, etc. In some embodiments, the detachable interface 522 may be magnetically retained. Alternatively or additionally, mechanical retaining structures may be included. For example, latches, snaps, clasps, or similar arrangements may be used.

In some embodiments, fluid which exits the manifold 518 may be subjected to sensing. For example, in some embodiments, the pressure of the fluid may be sensed by a sensor 250 such as a pressure transducer in communication with the actuator channels 520. In other embodiments, a sensor 250 such as a mass air flow sensor may be used to measure fluid in or out of each actuator 16. Other embodiments may use other fluid management systems that meter fluid in discrete amounts. In some embodiments, multiple characteristics of fluid may be sensed. In some embodiments, the fluid may be sensed for the same characteristic at a number of locations. In various embodiments, a pressure transducer may be included in the manifold 518 in addition to a pressure transducer for each actuator channel 520. This arrangement permits the sensors to be cross-checked to ensure accurate measurement. In some embodiments, fluid characteristics may not be sensed in the actuator channels 520. Some embodiments may include a sensor 250, such as a mass air flow sensor 250 disposed at the pump 500 or the manifold 518. Some embodiments may include any of a variety of sensors 250 on or inside the actuators 16 such as, but not limited to those described above. Information from the sensors 250 may be used by the controller 506 for control of the dynamic support apparatus 10. In some embodiments, information from the sensors 250 may be used to determine when the motor 504 should be turned on and which actuator channel 520 fluid should be directed to or from via the manifold 518. In some embodiments, this information may also be used in determining whether positive or negative pressure should be applied and for how long. In some embodiments, the motor 504 may be utilized, in conjunction with the manifold 518, to draw a negative pressure. In some embodiments, a negative pressure may be drawn on an actuator 16 to collapse a supplementary support within the actuator 16. In some embodiments, a negative pressure may be drawn to move a contacting surface of the actuator 16 away from the user. In some embodiments, this may be accomplished passively, without the use of a motor 504. In some embodiments, the user's weight may be utilized, in conjunction with the manifold 518, to collapse a supplementary support, or move the contacting surface of the actuator 16 away from the user, or a combination of both. By utilizing information from the sensors 250, the controller 506 may ensure that the occupant is properly supported by the actuators 16. In some embodiments, sensing may not be necessary. In such embodiments, pump 500 runtime may be used to track the amount of fluid and/or pressure of fluid in each actuator 16.

In some embodiments, the sensors 250 may be used to detect if the dynamic support apparatus 10 is occupied. As such, they may be used in lieu of an on/off switch. In some embodiments, the controller 506 may be programmed to recognize that a user has occupied a dynamic support apparatus 10. In some embodiments, the controller 506 may turn on a dynamic support apparatus 10 upon determination that the dynamic support apparatus 10 is occupied. In some embodiments, a pressure relief regimen may begin upon determination that a dynamic support apparatus 10 is occupied. In some embodiments, the controller 506 may be programmed to recognize that the dynamic support apparatus 10 is empty or unoccupied. In some embodiments, the recognition of the absence of a user may prompt the controller 506 to turn off the dynamic support apparatus 10. In some embodiments, the controller 506 may use signals from a variety of sensors, including, but not limited to, pressure sensors or bladder height sensors, to determine if the dynamic support apparatus 10 is occupied or unoccupied. In some embodiments, the controller 506 may enter a maintenance state in which it causes fluid to be pumped into an actuator 16 to replace fluid lost over time. In some embodiments, the controller 506 may beep, buzz, light, or otherwise indicate (or any combination thereof) to the user that the dynamic support apparatus 10 is on and should be turned off if not in use. In some embodiments, the controller 506 may notify the user that the dynamic support apparatus 10 is on and not in use upon determination that the dynamic support apparatus 10 is empty.

In some embodiments, the controller 506 may be programmed to recognize dynamic loading conditions (e.g. the user is riding over bumps, off road, jostling about, etc.). In some embodiments, the controller 506 may use signals from a variety of sensors, including, but not limited to, pressure sensors or bladder height sensors, to determine if a dynamic loading condition exists. In some embodiments, the controller 506 may enter a power conservation state upon determination that such a state exists. Such a state, may in some embodiments, be a maintenance state in which fluid is pumped into the actuators 16 to replace fluid lost over time. In some embodiments, the controller 506 may equalize pressure in the actuators 16 before entering the maintenance state. In some embodiments, a user may manually inform the controller 506 that he or she is in a dynamic loading condition. In some embodiments, a user may manually inform the controller 506 that he or she is not in a dynamic loading condition. In some embodiments, the controller 506 may momentarily pause or abort the relief regimen when dynamic loading conditions exist.

In some embodiments, the controller 506 may have at least one stored relief regimen. In some embodiments, the controller 506 may have stored relief regimens including, but not limited to, regimens for sedentary activity, semi-active, active, dynamic loading, user-specified modes, etc. In some embodiments, a user may select a stored relief program before the relief regimen may begin or may change to a relief regimen suitable for anticipated activity.

In some embodiments, the controller 506 may be programmed to enter a transfer aid mode. In some embodiments, a transfer aid mode may require affirmative user interaction with the controller 506. In some embodiments, a user may need to press a series of buttons, navigate a series of menus, enter a particular intermediary mode, or any combination thereof. It may be desirable that affirmative user interaction be required to ensure that a user desires to enter the aided transfer mode and to ensure that a user does not enter the aided transfer mode by accident. In some embodiments, the actuators 16 may be inflated to lift and assist a user in transferring to another surface, such as, for example, a bed.

As shown, the controller 506 may include an on-board interface 523. In some embodiments, the on-board interface 523 may be a panel 402 (see, for example, FIG. 26) of buttons 404 (see, for example, FIG. 26) and/or indicators 406 (see, for example, FIG. 26). The indicators 406 may be lights such as LEDs. The on-board interface 523 may include indicators 406 such as a power-on indicator, alert indicators, a charging indicator, a battery remaining indicator, etc. The on-board interface 523 may include a speaker for providing audible feedback for commands and alerts. Additionally, the on-board interface 523 may include a decal or other graphic which displays operating pressures of each actuator 16. The decal or graphic may approximate the shape of the person support apparatus 10 in visual appearance. The decal or graphic may have tri-color LED indicators 406 which visually convey actuator 16 pressure to the occupant by lighting in specific colors (e.g. green for positive pressure, yellow for negative pressure, red for alert). The lights may be arranged on the decal such that their placement reflects the location of the actuators 16 in the person support apparatus 10. The on-board interface 523 may include a pressure up button, a pressure down button, toggle buttons to switch between different operation modes, and/or any number of other user input buttons.

An external or remote interface 524 may be included. The external interface 524 may be, in some embodiments, a wireless pendant or other suitable remote. In such embodiments, the external interface may have buttons 404 and indicators 406 similar to the on-board interface 523. The external interface 524 may be a touch screen, LCD screen, or the like which is mounted on, for example, a wheelchair. In such embodiments, the screen may or may not be dedicated to the dynamic support apparatus 10. In some embodiments, the external interface 524 may be, but is not limited to, an occupant's smartphone, computer, or occupant support (e.g. bed, wheelchair, seat, etc.) control interface. In some embodiments the external interface 524 may include various additional controls such as, though not limited to, bump switches or sip and puff controls. In some embodiments, a dynamic support apparatus 10 may be configured to interface with a number of different external interfaces 524. The external interface 524 provided may be selected such that it best meets an individual user's needs.

In embodiments including an external or remote interface 524, the remote interface 524 may be configured for attachment onto a convenient portion of the occupant support. The external interface 524 may communicate with the controller 506 wirelessly or via a wired connection. In some embodiments, such an interface may communicate over CANbus. Such a bus could also be used for configuration and programming of a dynamic support apparatus 10 via a PC or the like (or a dedicated programming interface). Use of CANbus may be desirable as it may allow for simplified integration with an occupant support (e.g. wheelchair) controller. In other words, the joystick, buttons, sensor inputs, display, etc that are used for control of the occupant support could then also be used to interface with the dynamic support apparatus 10 controller 506 and/or external interface 524.

In some embodiments the external interface 524 may display detailed information, diagnostics, and/or allow a user to alter settings or program customized operational modes. The external interface 524 may have expanded functionality when accessed by a clinician, technician, manufacturing, etc. The external interface 524 may be in cabled communication to the controller 506 via USB, RS-232, CANbus, etc. The external interface 524 may be in wireless communication to the controller 506 (see, for example, FIG. 25).

Figure 26:
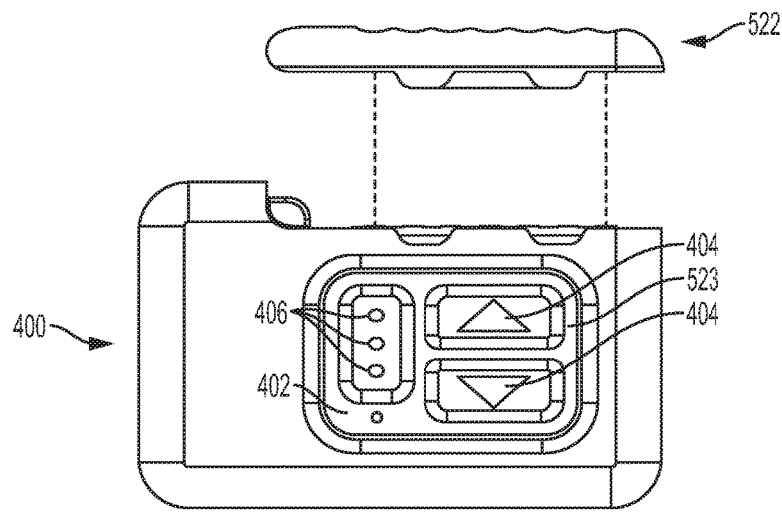
FIG. 26 shows a front view of an embodiment of a housing including an on-board interface and a detachable interface in accordance with one embodiment.

An embodiment of an on-board interface 523 is shown in FIG. 26. The on-board interface 523 is disposed about a panel 402 of a housing 400. The pump 500 (see, for example, FIG. 25), motor 504 (see, for example, FIG. 25), manifold 518 (see, for example, FIG. 25), controller 506 (see, for example, FIG. 25), on-board power 508 (see, for example, FIG. 25), etc. may be disposed inside the housing 400. As shown, the on-board interface 523 includes number indicators 406. The indicators 406 may indicate, in some embodiments, characteristics such as those described above. The on-board interface 523 also includes two buttons 404. In some embodiments, the buttons 404 are for pressure up and pressure down. Other embodiments may include any number of buttons 404 with any number of other functions.

An embodiment of a detachable interface 522 is also shown in FIG. 26. As shown, the detachable interface 522 is detached in FIG. 26. The actuator channels 520 (see, for example, FIG. 15) may couple into the detachable interface 522. When the detachable interface 522 is detached, fluid communication between the manifold 518 and actuators 16 may be broken. As mentioned above, in some specific embodiments, the detachable interface 522 may magnetically or mechanically couple to the housing 400.

Figure 27:
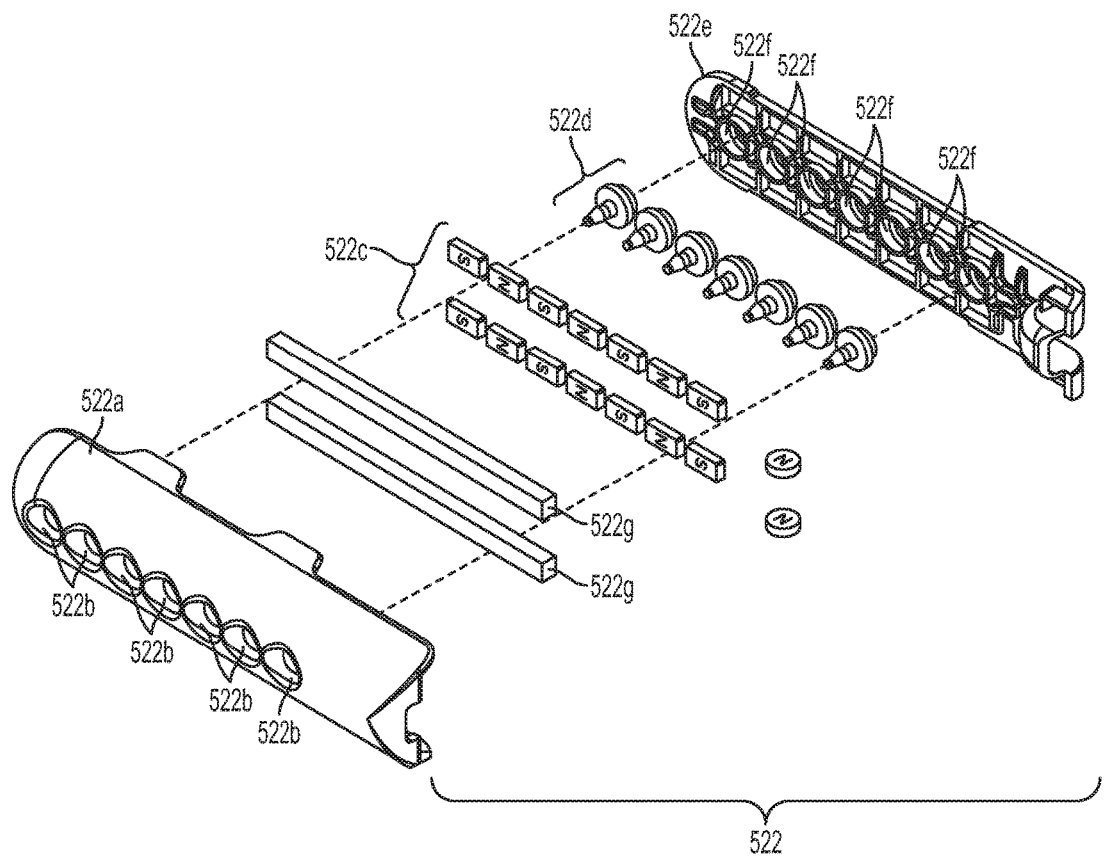
FIG. 27 shows and exploded view of an example detachable interface in accordance with an embodiment of the present disclosure.

FIG. 27 shows one embodiment of a detachable interface 522 in an exploded view. As shown, the detachable interface 522 includes a cover 522a. The cover 522a includes a number of orifices 522b into which the actuator channels 520 (see, for example, FIG. 15) may be inserted. The detachable interface 522 also includes a number of magnets 522c. The detachable interface 522 may include a number of fittings 522d. The fittings 522d may include a barbed portion onto which the actuator channels 520 may be coupled. As shown, the detachable interface 522 also includes a base plate 522e with a number of base plate holes 522f. When assembled, the fittings 522d may be coupled into the base plate holes 522f. When assembled, the fittings 522d may be fixedly coupled into place by any suitable method, such as but not limited to, solvent bonding, ultra-sonic welding, glue or other adhesive, etc. Some embodiments may also include a back iron 522g for the magnets.

When the detachable interface 522 is attached to the housing 400, magnets in the housing 400 may attract the magnets 522c in the detachable interface 522 such that the detachable interface 522 is magnetically and detachably coupled to the housing 400. Alternatively, the detachable interface 522 may be attracted to a ferromagnetic plate included on the housing 400. In such embodiments, the plate may be 400-series stainless steel, however, in various other embodiments, the plate may be made from any material. The base plate holes 522f may line up with the outlets of the various channels of the manifold 518 (see, for example, FIG. 25). The base plate holes 522f may include a feature which creates a seal between the base plate holes 522f and the outlets of the various channels of the manifold 518 when subjected to the compressive force generated by the magnetic coupling. Though the embodiment in FIG. 27 may support up to seven actuators 16, other embodiments may include a different number of orifices 522b, fittings 522d, and base plate holes 522f to support any number of actuators 16.

Figure 28:
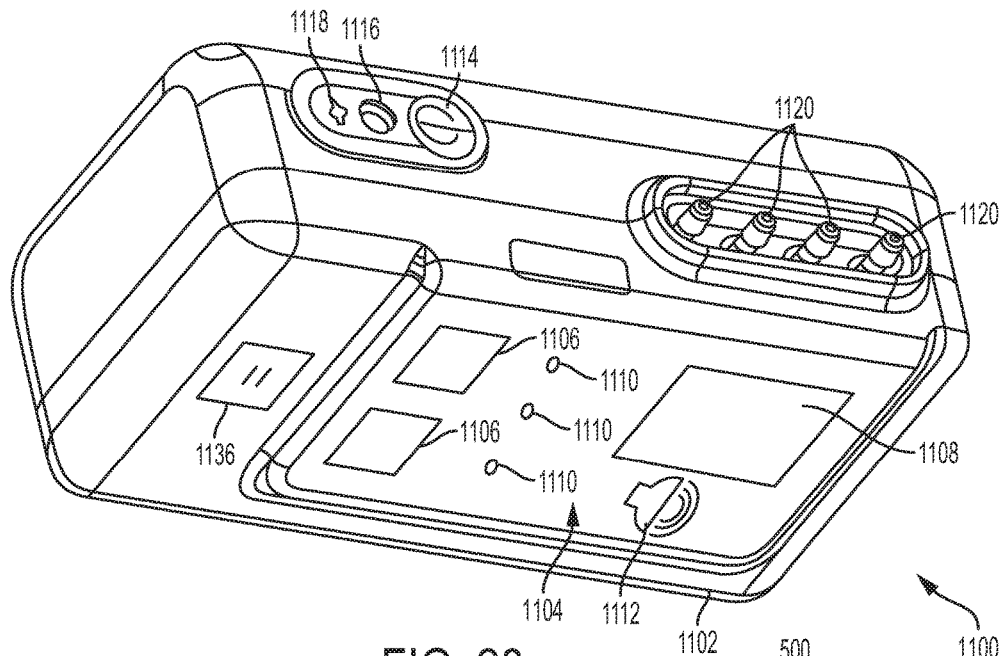
FIG. 28 depicts a perspective view of a controller in accordance with one embodiment.

FIG. 28 depicts an embodiment of a controller 1100 which may be used with a dynamic support apparatus 10. As shown, the controller 1100 includes a housing 1102. The housing 1102 may be shaped and sized such that it may easily be attached to a support structure such as a portion of a wheelchair or placed into a holster. In some embodiments, at least a portion of the housing 1102 (or holster) may include brackets, adhesive, hook and loop tape, etc. (none shown) which facilitate attachment of the controller 1100 to a support structure. The controller may also include a processor.

The controller 1100 shown in FIG. 28 includes a control panel 1104 which may include a user interface for a dynamic support apparatus 10. As shown, the control panel 1104 includes a number of buttons 1106. In some embodiments, only two buttons 1106 are shown, however, other embodiments may include a greater or lesser number of buttons 1106. The buttons 1106 may be assigned any number of various functions. In some embodiments, the buttons 1106 may control which operational mode the controller 1100 is operating under. The buttons 1106 may be used to actuate an actuator 16. In some embodiments, the buttons 1100 may be used to select an actuator 16 or actuators 16 to be controlled. The buttons 1100 may also be used to navigate through and/or select information and settings displayed on a graphic display 1108.

The control panel 1104 may also include a number of illuminated indicators 1110. In various embodiments, the illuminated indicators 1110 may be backlit by one or more LEDs. Though the embodiment depicts three illuminated indicators 1110, other embodiments may include any suitable number of illuminated indicators 1110. The illuminated indicators 1110 may be used to convey various operational states of the controller 1100. They may also be used to provide feedback or other information to a user. In some embodiments, the illuminated indicators 1110 may be used to convey alarm states or other conditions of interest related to a dynamic support apparatus 10.

A display 1108 is also present on the control panel 1104 of the exemplary controller 1100 shown in FIG. 28. The display 1108 may be used to convey information to the user. In some embodiments, the display 1108 may present a number of menus and options to a user which may be respectively navigated and selected to control the operation of a dynamic support apparatus 10. The display 1108 may also be used to program operational modes for a dynamic support apparatus 10. The display 1108 may be any suitable variety of display. In some embodiments, the display 1108 may be a touch screen display. In such embodiments, buttons 1106 may not be included and control of a dynamic support apparatus 10 may be conducted primarily through touch gestures on the touch screen.

The control panel 1104 of the controller 1100 also includes a speaker 1112. The speaker 1112 may be used to provide auditory feedback or other information to a user. In some embodiments, the speaker 1112 may create auditory noise in response to various user inputs such as button 1106 presses. The speaker 1112 may also be used to provide an auditory alarm for a dynamic support apparatus 10 in the event that an issue requiring attention of the user exists.

The controller 1100 shown in FIG. 28 includes a power button 1114. The power button 1114 may be used to turn the controller of a dynamic support apparatus 10 off or on. In some embodiments, the controller 506 may include a pause button 1136. In some embodiments, the pause button 1136 may be utilized to pause a pressure relief scheme. This may be desirable/beneficial, for many reasons, including, but not limited to, when noise from a pneumatic component of a dynamic support apparatus 10 may be disruptive or inconvenient. In some circumstances, such as during conversation, a user may desire to pause the pressure relief regimen. In some embodiments, the pause button 1136 may pause the pressure relief scheme until a later user interaction with the controller, for example, a second depression of the pause button 1136. In some embodiments, the pressure relief scheme may only be suspended for a predetermined period of time. Limiting a pause to a predetermined period of time may prevent a user from forgetting that the relief scheme had been suspended. In some embodiments, after the predetermined period has elapsed, the controller 506 may enter a minimally disruptive mode. In such a mode, the controller 506 may, for example, lengthen the period of time between relief cycles or may otherwise alter its control logic to minimize disruption.

In some embodiments, a user may utilize an interface to turn desired features on or off. In such embodiments, the interface may comprise checkboxes, radio buttons, parameter fields, or other selectors/fields (or any combination thereof) which may be used to toggle features on or off and/or set parameter values. In some embodiments, a user may select numerical values for certain features. For example, a user may define a number of pressure relief cycles per a user defined period of time. In some embodiments, some features may be under headings of other features or categories and/or be arranged in a hierarchy. In some embodiments, selecting one feature may enable user selection of a number of sub-features. In some embodiments, features may be disabled depending on the individual user's needs. For example, a seat transfer feature may be disabled for a user recovering from a recent ulcer.

In some embodiments, a user may utilize a controller 506, on-board interface 523, external interface 524, detachable interface 522, or combination thereof to manually initiate pressure relief as desired. In some embodiments, a user may override automated pressure relief. In some embodiments, pressure relief may be entirely controlled by user intervention. In some embodiments, pressure relief may be entirely controlled by automatic processes. In some embodiments, pressure relief may be controlled by a combination of user intervention and automated processes.

In some embodiments, a power port 1116 may be included. The power port 1116 may allow a user to plug an external power source (not shown) into the controller 1100 of a dynamic support apparatus 10. Such a power source may be used to charge an on board power source of a controller 1100. Additionally, in some embodiments, the controller 1100 may be run directly off of an external power source. A power indicator 1118 may illuminate when an external power source is in communication with the controller 1100.

A serial port 1111 or communications port is also included in some embodiments. The serial port 1111 may be any suitable variety of serial port, for example USB, RS232, etc. The serial port 1111 may be used for charging an on board power source or powering the controller. The serial port 1111 may also be used for interfacing with a computer, laptop or the like. The serial port 1111 may be used to download data (e.g. logs) from the controller 1100. Additionally, the serial port 1111 may be used during programming of the controller 1100.

A number of tubing connectors 1120 are also accessible through the housing of the controller 1100. Tubing (not shown) may be placed onto the tubing connectors 1120 to connect the controller 1100 to other components of a dynamic support apparatus 10. The controller 1100 may control fluid flow through tubing connected to the controller 1100 via an internal manifold associated with the tubing connectors 1120.

The housing 1102 of the controller 1100 may include various control circuitry and fluid system components for a dynamic support apparatus 10. In some embodiments, a fluid pump may be housed in a controller 1100. A manifold and valving for directing fluid flow may also be included. The control circuitry may be included on a PCB housed in a controller 1100. Control circuitry may include any of a variety of sensors (e.g. pressure, temperature, mass air flow), computer-readable memory, one or more microprocessor, etc. An on board power supply may also be included inside the housing 1102 of a controller 1100.

Figure 29:
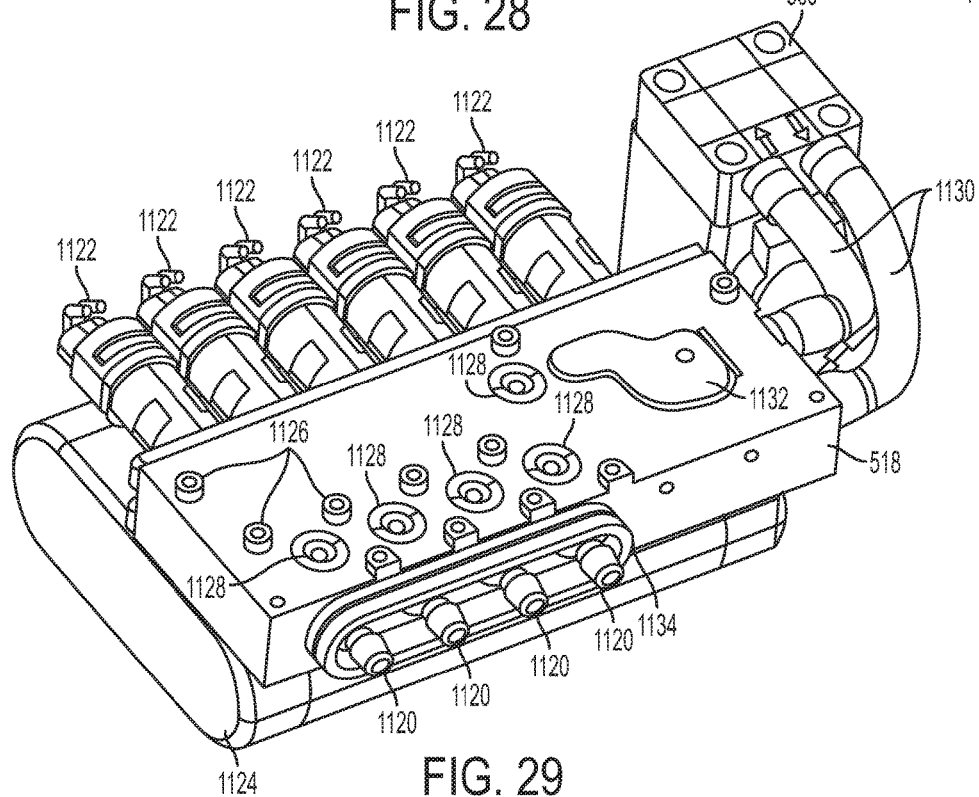
FIG. 29 depicts a perspective view of a number of components which may be included in a controller in accordance with one embodiment.

FIG. 29 depicts embodiments of a number of components which may be included in a controller 1100 such as that shown in FIG. 28. In other embodiments, additional or different components may be included. As shown, the embodiment in FIG. 29 includes a pump 500, manifold 518, a number of valves 1122, and an onboard power source 1124. The pump 500 is in communication with the manifold 518 via tubing 1130. The pump 500 and valves 1122 may draw power from the onboard power source 1124. In some embodiments, the onboard power source 1124 is a battery. The valves 1122 may be actuated in a manner which allows them to direct fluid flow within the manifold 518. The valves 1122 shown in FIG. 29 are solenoid valves. In other embodiments, any suitable type of valve may be used.

The manifold 518 shown in FIG. 29 includes a number of features. As shown, the manifold 518 includes a number of standoffs 1126. A PCB (not shown) with the control circuitry for a controller 1100 (see, for example, FIG. 28) may be coupled to the manifold 518 via fasteners which couple into the standoffs 1126. A number of sensor wells 1128 are also included in the manifold 518. The sensor wells 1128 may be in fluid communication with the interior passages of the manifold 518. As shown, the sensor wells 1128 also each include an o-ring. When assembled, the o-rings of the sensor wells 1128 may be compressed between the manifold 518 and a PCB forming a fluid tight seal. This may allow sensors located on the PCB to sense various conditions within the manifold 518. By orienting the o-ring around the sensors located on the PCB, the compressed o-ring may provide a fluid tight seal. This seal may allow the sensors to accurately measure manifold pressures. Sensor wells 1128 and accompanying sensors may be included for any of the interior passages of the manifold 518. Such an on board pressure sensor arrangement is further described later in the specification.

It may be desirable to have some of the passageways of the manifold 518 cut or recessed into one or more of the faces of the manifold 518. This may contribute to the making of a more compact or easily manufactured manifold 518. Such passageways may then be sealed from the surrounding environment such that fluid may be conducted through the manifold 518 in a desirable fashion. In some embodiments, the manifold 518 includes a plate 1132 which is coupled thereto to seal one such passageway of the manifold 518. In various embodiments, a plate 1132 may be coupled to the manifold 518 via any suitable means, including but not limited to sonic welding, laser welding, solvent bonding, adhesive, etc.

The embodiment of the manifold 518 shown in FIG. 29 also includes a sealing structure 1134 which surrounds the tubing connectors 1120. As shown, the sealing structure 1134 is a stadium shaped projection. Recessed into the outer wall of the sealing structure 1134 is an o-ring groove in which an o-ring may be disposed. Referring now also to FIG. 28, when placed in a housing 1102, such an o-ring may create a fluid tight seal which prohibits fluid ingress into the interior volume of the housing 1102. This may be useful to prevent spills, urine, etc. from fouling the interior components of a controller 1100.

Figure 30:
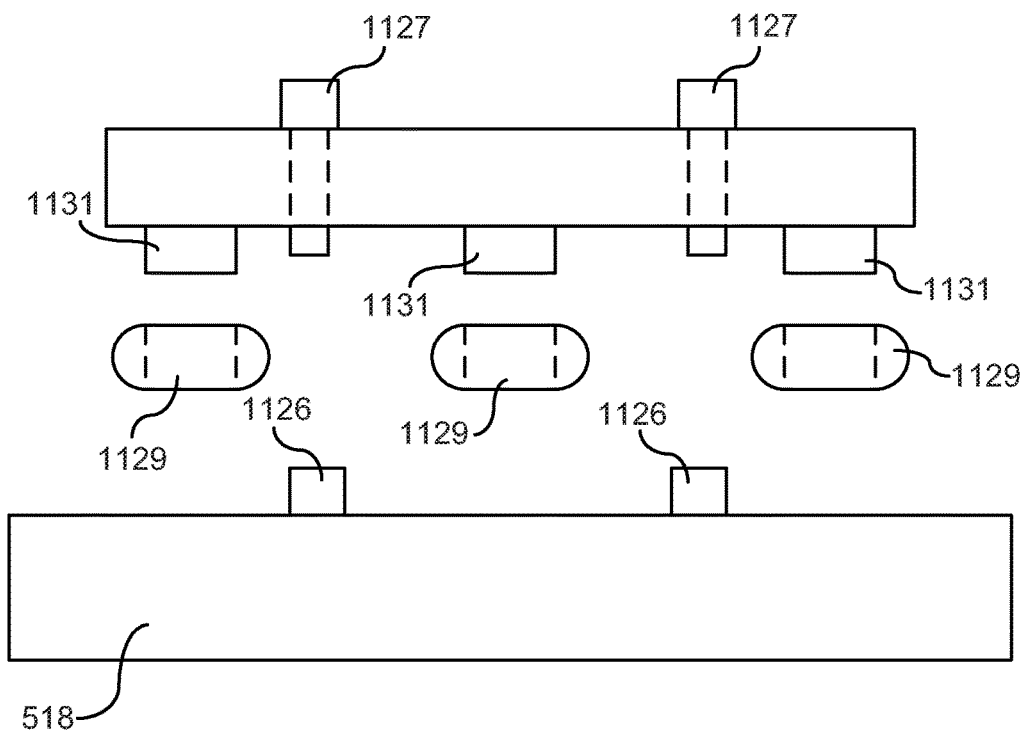
FIG. 30 depicts a representational exploded view of an example manifold and PCB in accordance with an embodiment of the present disclosure.
Figure 31:
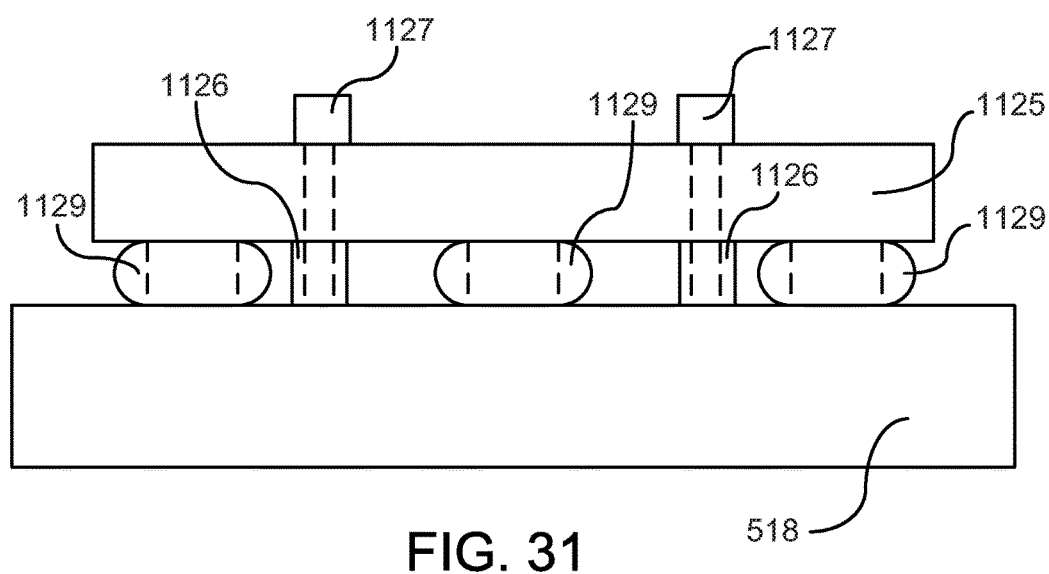
FIG. 31 depicts a representational assembled view of the example manifold and PCB shown in FIG. 30 in accordance with an embodiment of the present disclosure.

FIG. 30 depicts a representational, disassembled view of various components which may be included in a controller such as the controller 1100 shown in FIG. 29. As shown, a manifold 518 and a main PCB 1125 are depicted. Referring now also to FIG. 31, when assembled, fasteners 1127 may pass through the main PCB 1125 and thread into the standoffs 1126 included in the manifold 518.

There are a number of sensors 1131 located on the main PCB 1125. These sensors 1131 may be any type of sensor or sensors. In some embodiments, the sensors 1131 are pressure sensors. These sensors 1131 may be positioned on the main PCB 1125 such that when the main PCB 1125 is attached to the manifold 518, the sensors 1131 may align with or are disposed over holes or voids (see, for example the sensor wells 1128 in FIG. 29) in the manifold 518. These holes may be in communication with various fluid pathways or portions of the manifold 518.

As shown, the sensors 1131 may fit within the interior void of the o-rings 1129 depicted in FIGS. 30 and 31. When assembled, the o-rings 1129 may become compressed between the main PCB 1125 and the manifold 518. Thus a fluid tight seal may be created, isolating the sensors 1131 from the surrounding environment. This may allow the sensors 1131 to accurately measure conditions in the manifold 518. The standoffs 1126 may be suitably sized to ensure that the o-rings 1129 will become sufficiently compressed it create an adequate fluid tight seal. Such an on board pressure sensor arrangement may be an inexpensive and easily assembled means of measuring pressures for a dynamic support apparatus 10.

Figure 32:
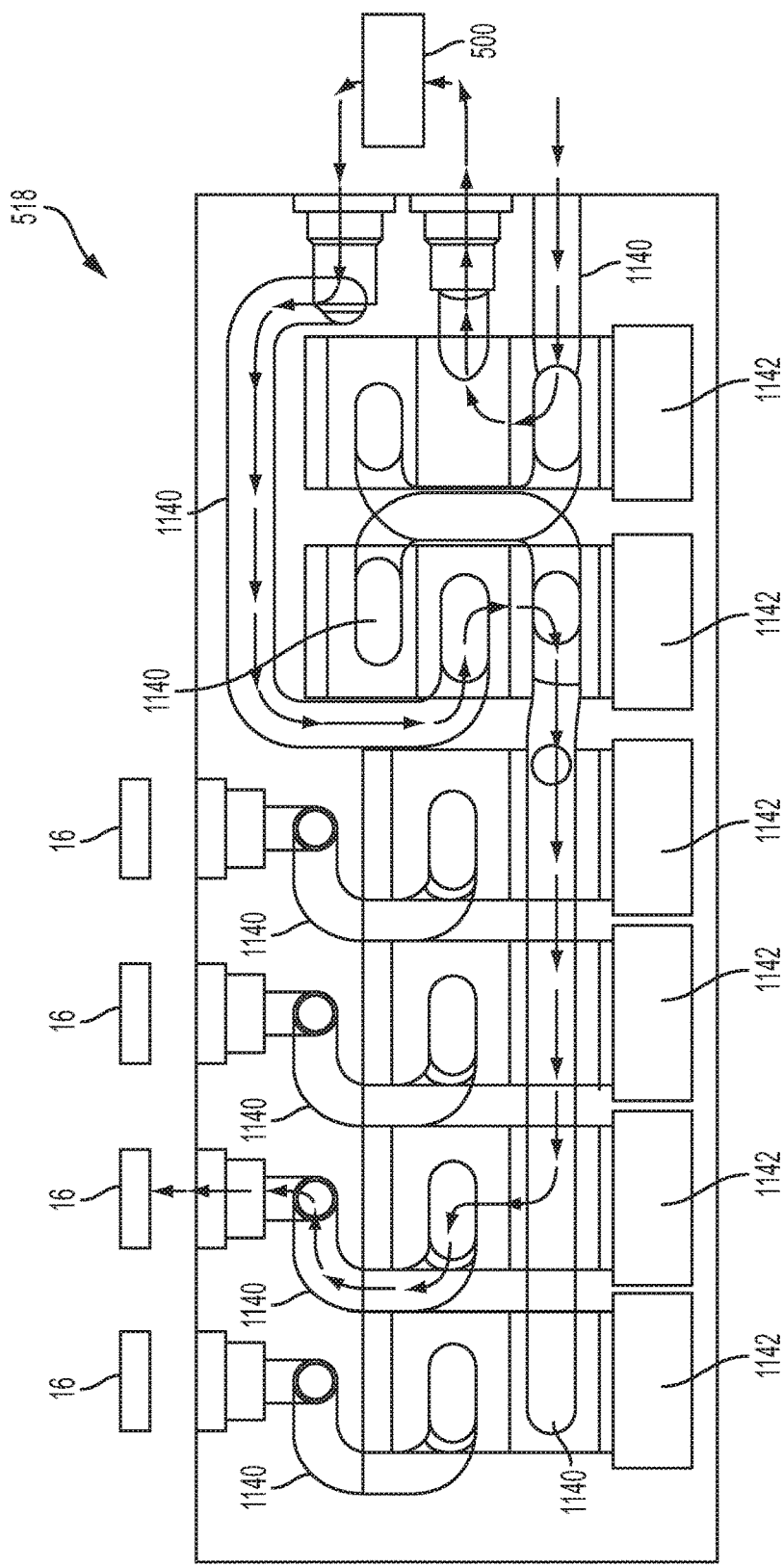
FIG. 32 depicts a view of a manifold in which various fluid pathways of the manifold are shown in accordance with one embodiment.

FIG. 32 depicts an embodiment of a manifold 518 in which the various fluid pathways 1140 within the manifold 518 are shown. For the sake of this illustration, overlapping fluid pathways should be understood to lie in different planes of the manifold 518. Additionally, for sake of illustration, the valves 1142 and the pump 500 are shown representationally in FIG. 32. Arrows are included within the fluid pathways 1140 to delineate the path of fluid flow when the manifold 518 and pump 500 are configured to deliver positive pressure to part of a pneumatic system such as an actuator 16. Though the embodiment in FIG. 32 depicts fluid being delivered to only a single actuator 16, it would be apparent to one skilled in the art that fluid may be delivered to multiple actuators 16 or different actuators 16 by energizing and de-energizing appropriate valves 1142.

Figure 33:
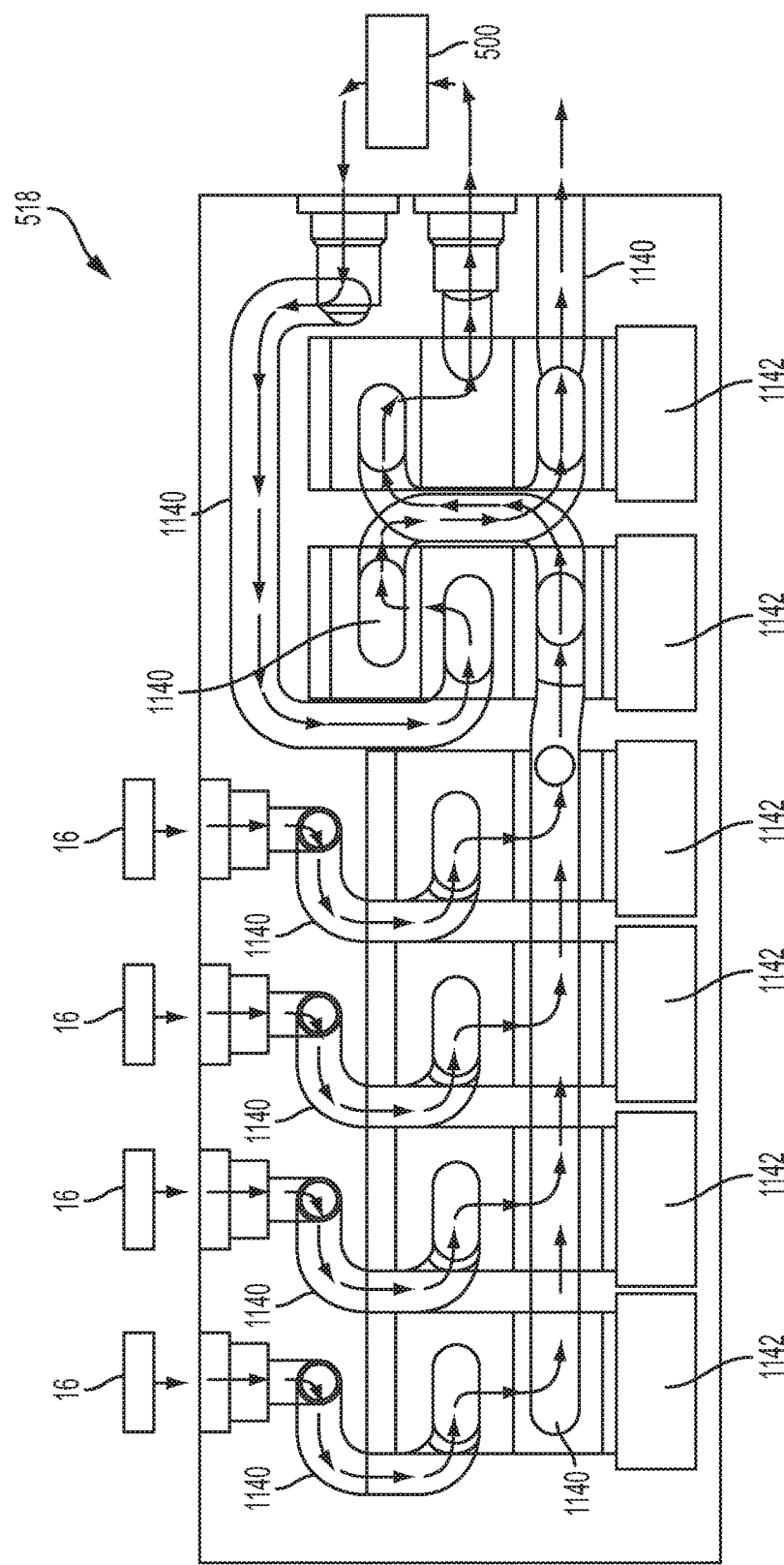
FIG. 33 depicts a view of a manifold in which various fluid pathways of the manifold are shown in accordance with one embodiment.

FIG. 33 depicts an embodiment of a manifold 518 in which the various fluid pathways 1140 within the manifold 518 are shown. For the sake of this illustration, overlapping fluid pathways should be understood to lie in different planes of the manifold 518. The valves 1142 of the manifold 518 and a pump 500 are also shown representationally in FIG. 33. Arrows are included within the fluid pathways 1140 to delineate the path of fluid flow when the manifold 518 and pump 500 are configured to vent another part of a pneumatic system such as an actuator 16. Though the in FIG. 33 depicts fluid being vented from all actuators 16 associated with the manifold 518, it would be apparent to one skilled in the art that fluid may be vented from a selected actuator 16 or actuators 16 by energizing and de-energizing appropriate valves 1142.

Figure 34:
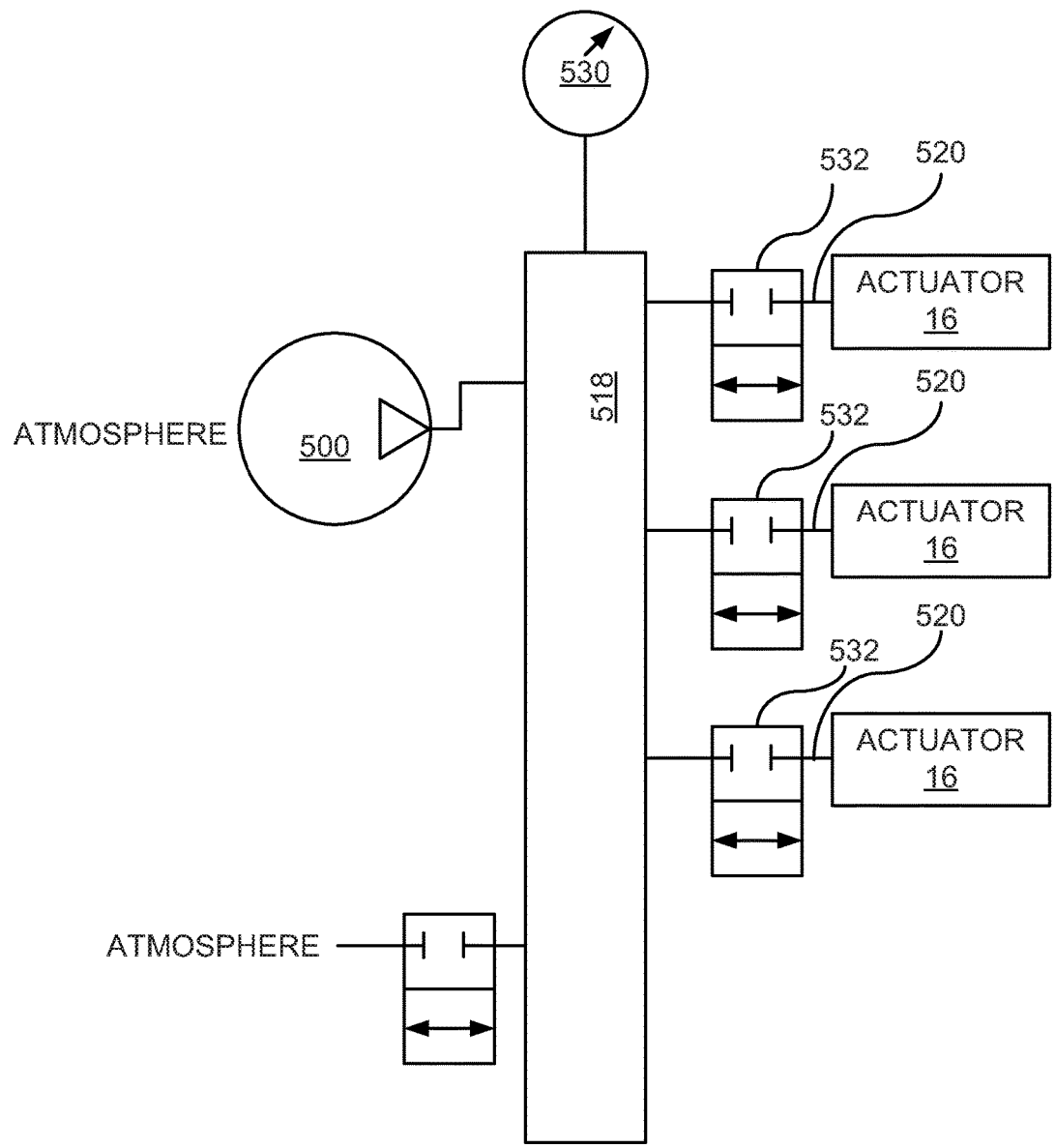
FIG. 34 shows an example pneumatic diagram of an example dynamic support apparatus in accordance with an embodiment of the present disclosure.

FIG. 34 shows a pneumatic diagram for an embodiment of a dynamic support apparatus 10. As shown, three actuators 16 are included in the embodiment shown in FIG. 34. A pump 500 is included. A pump 500 may include a filter (not shown) to prevent debris or liquid such as urine from being drawn into the pump 500. As shown, the pump 500 uses the atmosphere as its fluid reservoir 502. In some embodiments, the pump 500 may be a pump 500 capable of generating both positive and negative pressures. In the embodiment shown in FIG. 34 the pump 500 only generates positive pressures. In some embodiments, the pump 500 may be associated with one or more valve which allows the pump 500 to use different volumes which the pump 500 is in communication with as a reservoir. In some embodiments, a valve or valves may be configured to allow the pump 500 to draw fluid from an actuator 16 and pump this fluid to the atmosphere and vice versa. In some embodiments, the pump 500 may only be configured to displace fluid in one direction. Vavling may be supplied to allow both of the inlet and outlet to be connected to the atmosphere, for example. Depending on which port—the inlet or outlet—or the pump is connected to atmosphere, a vacuum or positive pressure may be supplied. Any of a number of varieties of pumps 500 may be used. For example, the pump 500 may be a diaphragm pump or a rotary vane pump.

In alternate embodiments, a pump 500 may not be included. In such embodiments, a high pressure source (not shown) may replace the pump 500. The high pressure source (not shown) may, in some embodiments, be a canister of pressurized air or gas. The pressurized air or gas canister may be removed and refilled after use. A manual pump such as a squeeze bulb pump may be included in some embodiments. Additionally, some embodiments may include manual relief valves.

As shown in FIG. 34 the pump 500 is in fluid communication with a manifold 518. A pressure transducer 530 is included at the manifold 518 to sense the pressure of fluid at the manifold 518. In other embodiments, there may be multiple pressure transducers 530. In some embodiments, pressure transducers 530 may additionally be included on each of the actuator channels 520. In such embodiments, pressures sensed in the pressure transducers 530 may be required to agree with each other within a tolerance. If the pressure transducers 530 gather conflicting readings, an alarm may be generated.

A number of valves 532 are also included in the pneumatic diagram shown in FIG. 34. The valves 532 may control fluid communication to the actuators 16. The valves 532 may be actuated by a controller 506. In the some embodiments, the valves 532 may be actuated to allow fluid flow into the actuators 16 or a selected actuator 16 to inflate the actuator 16 or actuators 16. The valves 532 may also be actuated to allow fluid to exit the actuators 16 to be bled off back into the atmosphere as shown. In some embodiments, a vacuum may be applied to the actuators 16 or a selected actuator 16 in order to fully deflate the actuators 16 or actuator 16. In some embodiments, a second pump (not shown) may be included to generate a vacuum.

In some embodiments, one or more over-pressure valve or relief valve (not shown) may be included in association with one or more actuator 16. Such an over-pressure valves may allow fluid to escape the actuators 16 in the event that an excess of fluid or an undesirably high pressure exists within one of more of the actuators 16. Allowing such fluid to escape may increase comfort and aid in the prevention of pressure ulceration.

Figure 35:
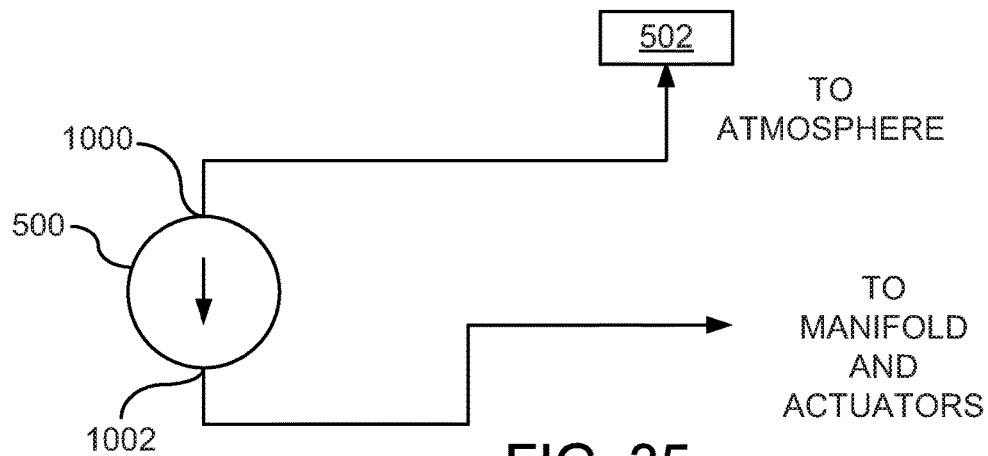
FIG. 35 depicts a pneumatic diagram of a pneumatic system including a single pump capable of delivering fluid from a reservoir to a destination in accordance with one embodiment.

FIG. 35 depicts a basic pneumatic diagram of a pneumatic system including a single pump 500 capable of delivering fluid from a reservoir 502 to a destination. As indicated, this destination may be a manifold 518 (see, for example, FIG. 25) and various actuators 16 (see, for example, FIG. 1) downstream from the manifold 518. As shown, the pump 500 is only capable of drawing fluid from a reservoir 502 to its inlet 1000 to create a positive pressure at its outlet 1002. It may, however, be desirable to also apply a vacuum to the destination. In some embodiments, this may be accomplished by a pump 500 capable of generating both positive and negative pressures or by incorporation of an additional pump (not shown). Both of these approaches tend to increase cost and may increase the form factor of the overall pneumatic system.

Figure 36:
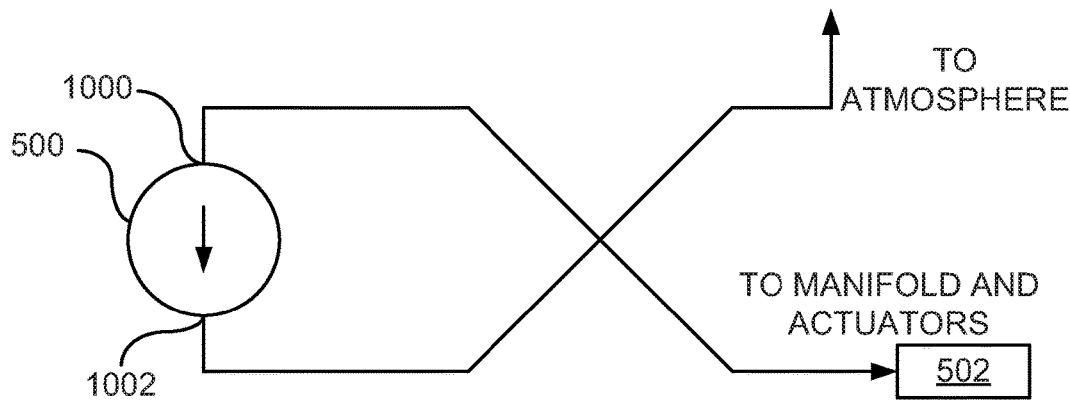
FIG. 36 depicts a pneumatic diagram of a pneumatic system including a single pump capable of delivering fluid from a reservoir to a destination in accordance with one embodiment.

Alternatively, and referring now to FIG. 36, it may therefore be desirable to have the capability to swap which flow paths are connected to the inlet 1000 and outlet 1002 of the pump 500. These flow paths are shown swapped from their position in FIG. 35 in the pneumatic diagram shown in FIG. 36. As shown, this may allow the pump 500 to use the actuators 16 as the reservoir 502 such that the pump 500 may apply a vacuum to the actuators 16.

Figure 37:
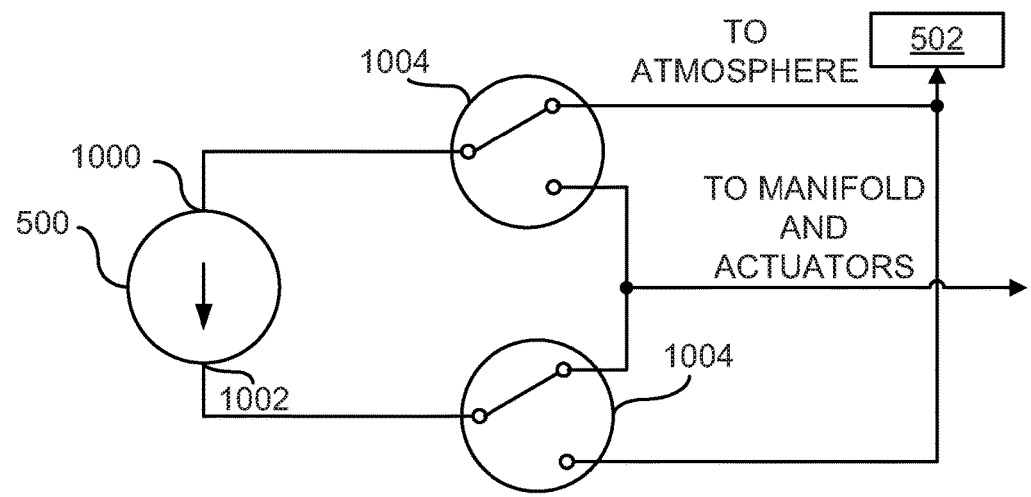
FIG. 37 depicts a pneumatic diagram configured such that the flow paths in communication with the inlet and outlet of the pump may be swapped in accordance with one embodiment.

FIG. 37 depicts another pneumatic diagram. The pneumatic diagram in FIG. 37 is configured such that the flow paths in communication with the inlet 1000 and outlet 1002 of the pump 500 may be swapped as detailed above. In FIG. 37, this is accomplished through the use of two valves 1004. The valves 1004 form the equivalent of a pneumatic H-bridge. In the specific implementation depicted in FIG. 37, the valves 1004 are three port, two position valves. The position of the valves 1004 may be changed in order to swap which flow path is in communication with the inlet 1000 and outlet 1002 of the pump 500. As shown, the valves 1004 are actuated such that the reservoir 502 in FIG. 37 is the atmosphere. The valves 1004 may generally be driven together to avoid a situation where the inlet 1000 and outlet 1002 of the pump 500 are connected to the same fluid path way. In some embodiments, it may be desirable to drive one valve 1004 briefly before the other to limit peak power draw or improve pneumatic performance.

In some embodiments, other valve 1004 arrangements may also be used. In some embodiments, a single four port, two position valve may be used in place of the two valves 1004 shown in FIG. 37. A single five port, two position valve may also be used in place of the two valves 1004 shown in FIG. 37. Any other suitable arrangement may also be used. The valve arrangement chosen for an embodiment may be dependent upon form factor, cost, and power concerns related to the pneumatic system.

Figure 38:
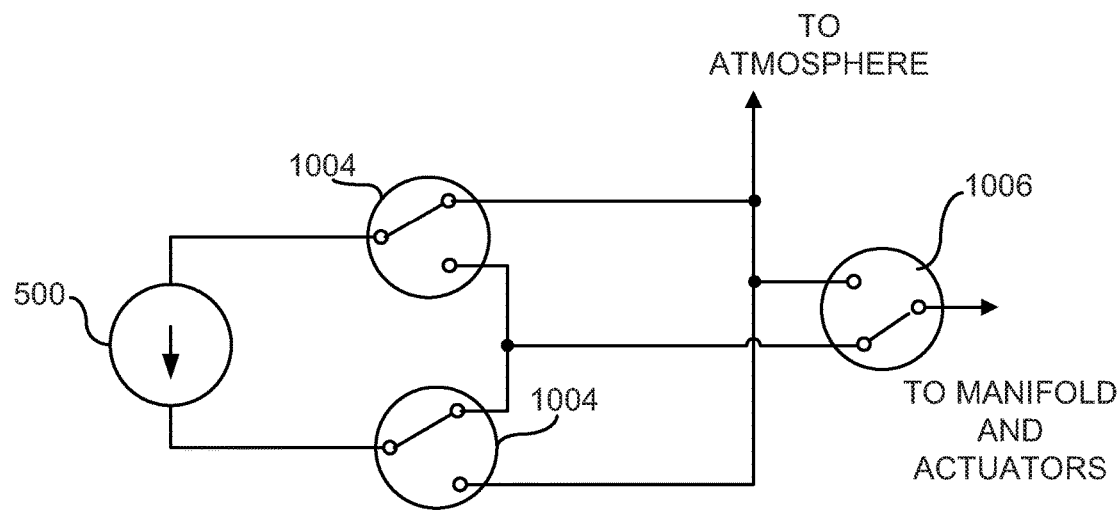
FIG. 38 depicts a pneumatic diagram in which a bypass valve is included in accordance with one embodiment.

Referring now to FIG. 38, another pneumatic diagram is shown. The pneumatic diagram shown in FIG. 38 is similar to the pneumatic diagram shown in FIG. 37, however, it includes an added functionality. The pneumatic diagram shown in FIG. 38, includes a bypass valve 1006 which allows the manifold to be directly connected to the atmosphere. In some embodiments, the bypass valve 1006 is shown as a three port, two position valve. Other valve arrangements serving the same end may also be used. A bypass valve 1006 may allow a pneumatic system to save power and extend the life of the pump 500. This may be so because, without using a pump 500, a desired actuator 16 may be vented by letting the occupant's weight drive a portion of the fluid out of the actuator 16. If needed, the valves 1004 may be positioned such that the pump 500 may then be turned on to draw a vacuum.

The capability of connecting the manifold to the atmosphere may provide an assortment of other advantages as well. If the manifold's pneumatic pressure is measured using an absolute pressure sensor, connecting the manifold to the atmosphere periodically allows the ambient pressure to be measured using the same sensor thus making a dedicated ambient sensor unnecessary. Further, it may be desirable to have the ability to connect the manifold to the atmosphere in a failsafe mode of the pneumatic system.

Figure 39:
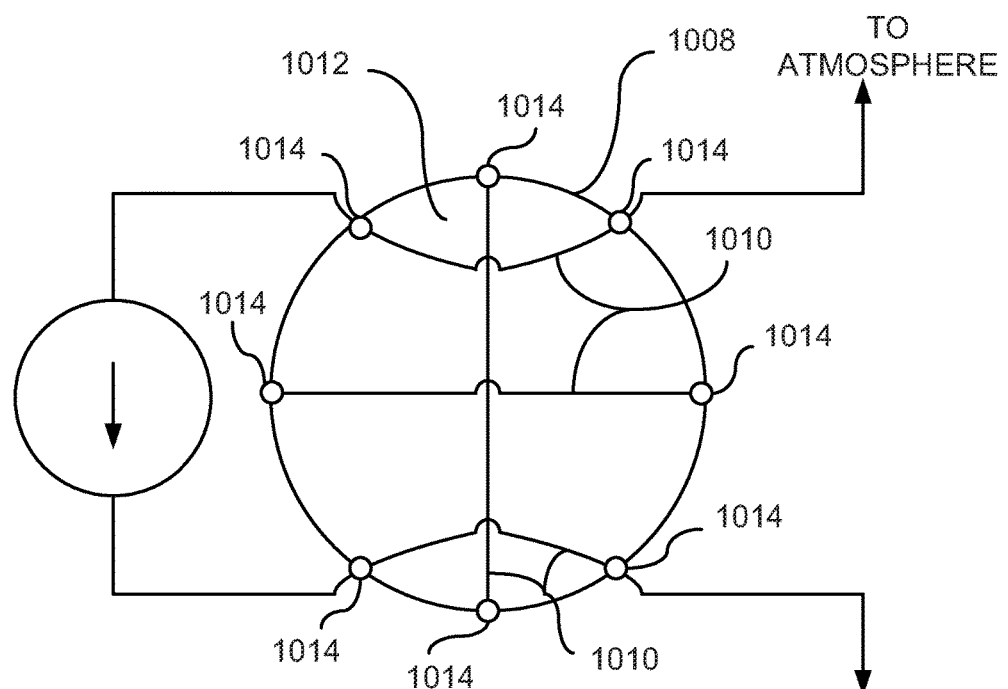
FIG. 39 depicts a pneumatic diagram including a rotary valve in accordance with one embodiment.

FIG. 39 depicts a pneumatic diagram. The pneumatic diagram shown in FIG. 39 includes only a single rotary valve 1008. For purposes of description, the rotary valve 1008 is described in relation to a pneumatic system, however, in various embodiments, the valve may be used in non-pneumatic systems such as hydraulic systems. Likewise, though the valve 1008 is generally described in relation to a dynamic support apparatus 10, the valve 1008 may be used in any number of other suitable applications or systems requiring valves. The embodiments of the valve 1008 and applications for the valve 1008 described herein are merely exemplary and in no way limiting. Additionally, a plurality of such valves 1008 may be used for some applications and the valve 1008 may be included in a manifold 518 (FIG. 25) with any number of other valves.

The rotary valve 1008 depicted in FIG. 39 retains the functionalities of other valve arrangements which use solenoids or other valves, however, may have a smaller form factor, reduced part count, and lower cost. In some embodiments, the rotary valve 1008 depicted in FIG. 39 retains all of the functionalities of the valve arrangement in FIG. 38, however, has a smaller form factor and lower cost. Moreover, such a valve may be made to be multi-stable and thus lower valve related power demands of pneumatic system.

As shown, the rotary valve 1008 depicted includes a number of valve flow paths 1010. Each of the valve flow paths 1010 extend across the body 1012 of the rotary valve 1008 transversely in the some embodiments. So as not to be in communication with one another, the flow paths 1010 may extend across the body 1012 of the rotary valve 1008 in more than one transverse plane. As shown in some embodiments, the fluid ports 1014 for each flow path 1010 may be disposed on the outer circumference of the body 1012 of the valve 1008. In other embodiments, this need not be the case. The fluid ports 1014 may be disposed at regular angular intervals. This may allow the rotary valve 1008 to be rotated a standard amount to make and break connections with any of the flow paths 1010 of the rotary valve 1008. As is shown in FIG. 39, the fluid ports 1014 are located approximately 45° from adjacent fluid ports 1014.

Referring now to the progression of FIGS. 40-43, the rotary valve 1008 is shown in a number of rotational positions. In the embodiments shown in FIGS. 40-43, the fluid ports of the rotary valve 1008 are individually assigned reference numbers 1-8. Each rotational position of the rotary valve 1008 places a different fluid port 1-8 in communication with the fixed pathways of the pneumatic system. Each of these positions enables a specific functionality of the pneumatic system. For sake of this description, rotational stops of the rotary valve 1008 depicted in FIGS. 40-43 will be referred to by the fluid port number which is located at the twelve o'clock position.

Figure 40:
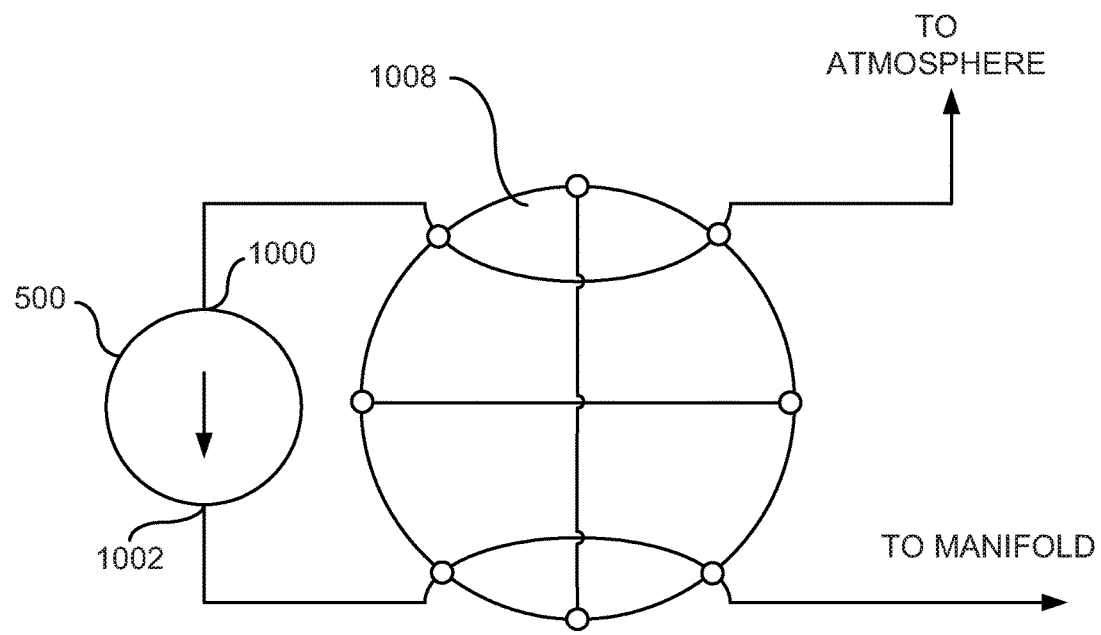
FIG. 40 depicts a pneumatic diagram including a rotary valve in accordance with one embodiment.

FIG. 40 depicts the rotary valve 1008 in position 1. In this position, the inlet 1000 of the pump 500 is in communication with the atmosphere. The outlet 1002 of the pump 500 is in communication with the manifold. This position of the rotary valve 1008 allows the pump 500 to generate positive pressure at the manifold while drawing fluid from the atmosphere. This position may be used to inflate or provide fluid to a destination. The destination may, in some embodiments, be actuators 16 (see, for example, FIG. 25) of a dynamic support apparatus 10 (see, for example, FIG. 25).

Figure 41:
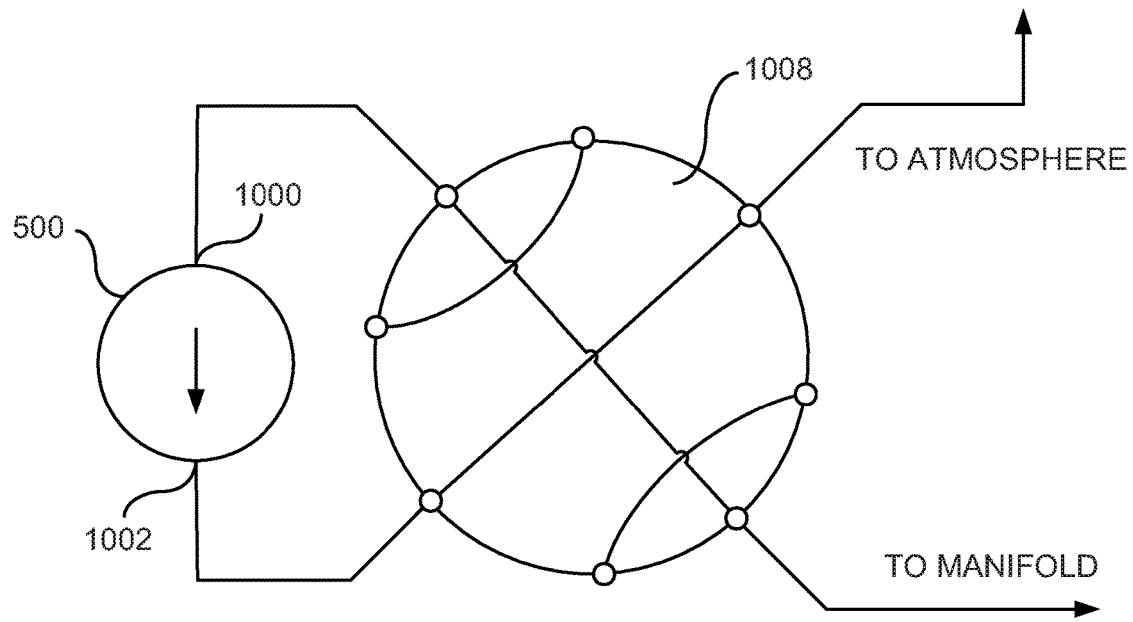
FIG. 41 depicts a pneumatic diagram including a rotary valve in accordance with one embodiment.

FIG. 41 depicts the rotary valve 1008 rotated approximately 45° counterclockwise from its location in FIG. 40 into position 2. In this position, the inlet 1000 of the pump 500 is in communication with the manifold. The outlet 1002 of the pump 500 is in communication with the atmosphere. Rotating the rotary valve 1008 to position 2 allows the pump 500 to draw a vacuum through the manifold. This position may be used to deflate or draw fluid from the destination. The destination may, in some embodiments, be actuators 16 (see, for example, FIG. 25) of a dynamic support apparatus 10 (see, for example, FIG. 25).

Figure 42:
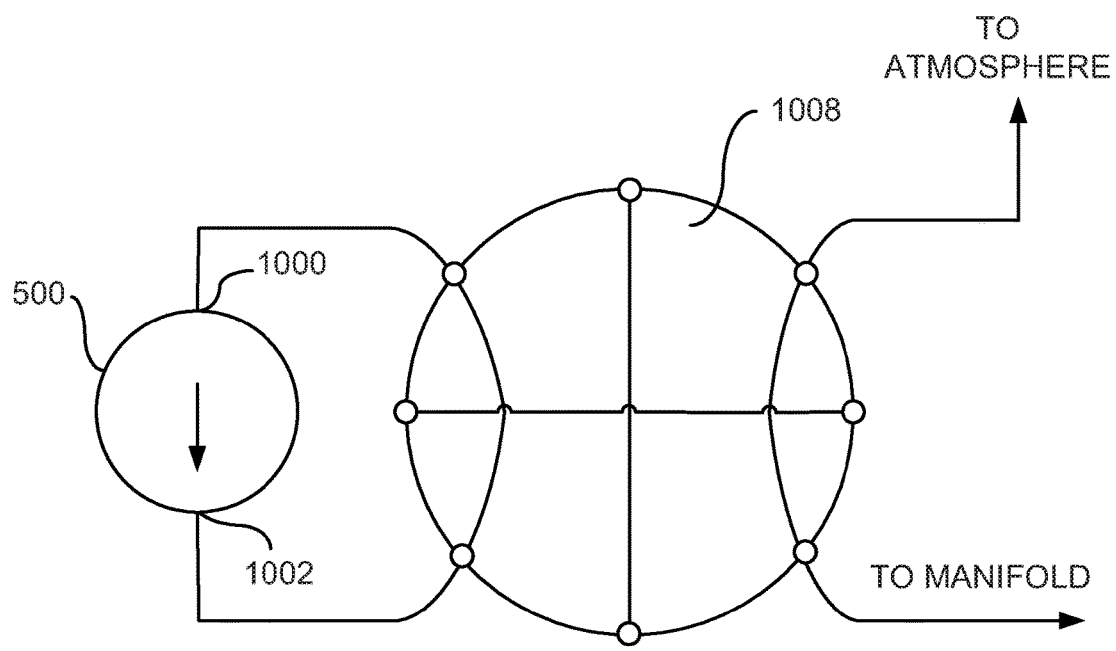
FIG. 42 depicts a pneumatic diagram including a rotary valve in accordance with one embodiment.

FIG. 42 depicts the rotary valve 1008 rotated approximately 45° counterclockwise from its location in FIG. 41 into position 3. In this position, the pump 500 is isolated from the manifold. Additionally, the manifold is directly connected to the atmosphere. Rotating the rotary valve 1008 to position 2 allows the rotary valve 1008 to act as a bypass valve similar to the bypass valve 1006 depicted in FIG. 38. This position may be used to deflate or bleed fluid from a destination. The destination may, in some embodiments, be actuators 16 (see, for example, FIG. 25) of a dynamic support apparatus 10 (see, for example, FIG. 25) without using the pump 500. It may also serve as a failsafe position or allow a pressure sensor in the manifold to measure ambient atmospheric pressure as described above.

Figure 43:
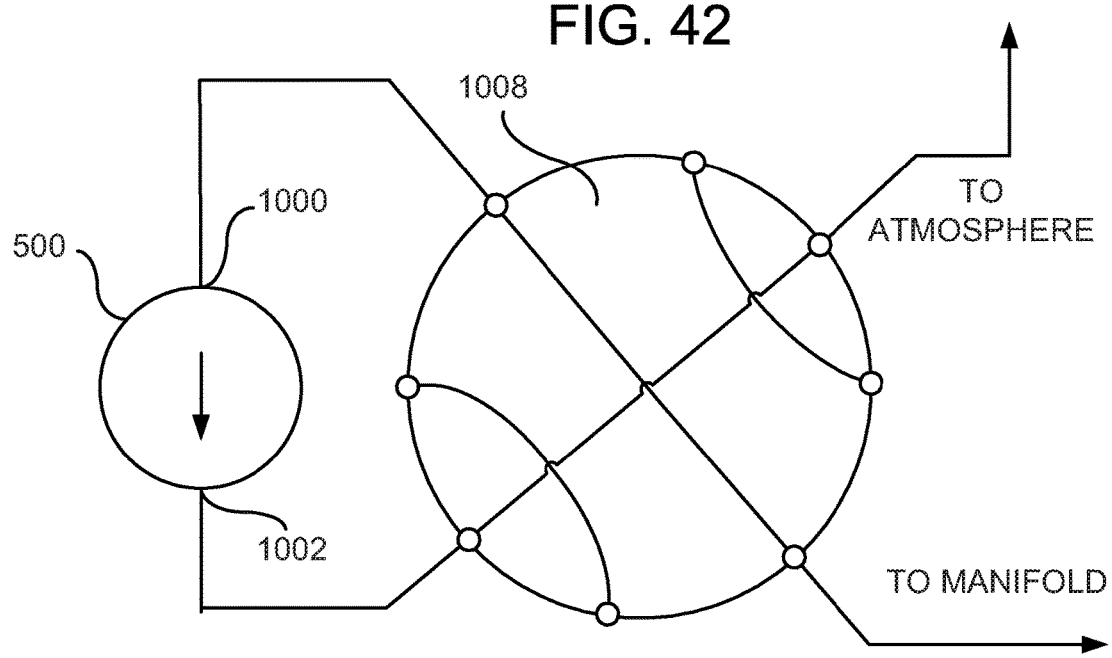
FIG. 43 depicts a pneumatic diagram including a rotary valve in accordance with one embodiment.

FIG. 43 depicts the rotary valve 1008 rotated approximately 45° counterclockwise from its location in FIG. 42 into position 4. Position 4 is pneumatically equivalent to position 2. As would be apparent to one skilled in the art, positions 5-8 are also pneumatic equivalents of the various depicted rotary valve 1008 positions shown in FIGS. 40-43. In some embodiments depicted, position 1 and position 5 are pneumatically equivalent, positions 2, 4, 6, and 8 are pneumatically equivalent, and position 3 and position 7 are pneumatically equivalent.

Embodiments of the rotary valve 1008 depicted in FIGS. 40-43 places the fluid ports 1-8 in a sequential order that generally reflect the sequential order of the pneumatic arrangements which would be desirable for a particular application of the valve. In some embodiments, the arrangement may be desirable when the valve 1008 is used to provide fluid to a pneumatically controlled dynamic support apparatus 10 (see, for example, FIG. 25). Such an arrangement of fluid ports 1-8 ensures that any desired state is at most approximately a quarter rotation of the rotary valve 1008 from any other position. In some embodiments, it may be desirable to have a greater or lesser number of rotary valve 1008 positions which are equivalents of a particular pneumatic arrangement (e.g. a greater number of arrangements which supply positive pressure to the manifold). This may, for example, be accomplished by installing the pump 500 into the pneumatic system such that its inlet 1000 and outlet 1002 are reversed from what is shown in FIG. 40-43. Such an arrangement would cause positions 2, 4, 6, and 8 to allow the pump 500 to supply positive pressure to the manifold. Alternatively, the parts of the pneumatic system communicating with various fixed fluid pathways in the pneumatic system may also be swapped. In some embodiments, the manifold and atmosphere may be swapped. Such an arrangement would again cause positions 2, 4, 6, and 8 to allow the pump 500 to supply positive pressure to the manifold. Additionally, the routing of the valve flow paths 1010 may be altered to any suitable configuration. It should also be noted that a rotary valve 1008 may be rotated to an intermediary position, which may include a position between two adjacent fluid ports, so as to isolate the components of a pneumatic system from one another.

In some embodiments, a manifold may not be needed. In some embodiments, if there are not multiple destinations which are included in a pneumatic system, a rotary valve 1008 may be connected directly to the destination. Additionally, in some embodiments, there may be multiple rotary valves 1008 which may each be connected directly to respective destinations. In such embodiments, the rotary valves 1008 themselves may act as a manifold. In such embodiments, the rotary valves 1008 may be rotated in a cooperative fashion to allow fluid to be communicated to the various destinations as desired. For instance, when it is desired to provide fluid to a single destination, the rotary valve 1008 associated with that destination may be rotated into the appropriate position. The rotary valves 1008 leading to other destinations in the system may be rotated to an intermediary or isolated position while fluid is provided to the desired destination.

Figure 44:
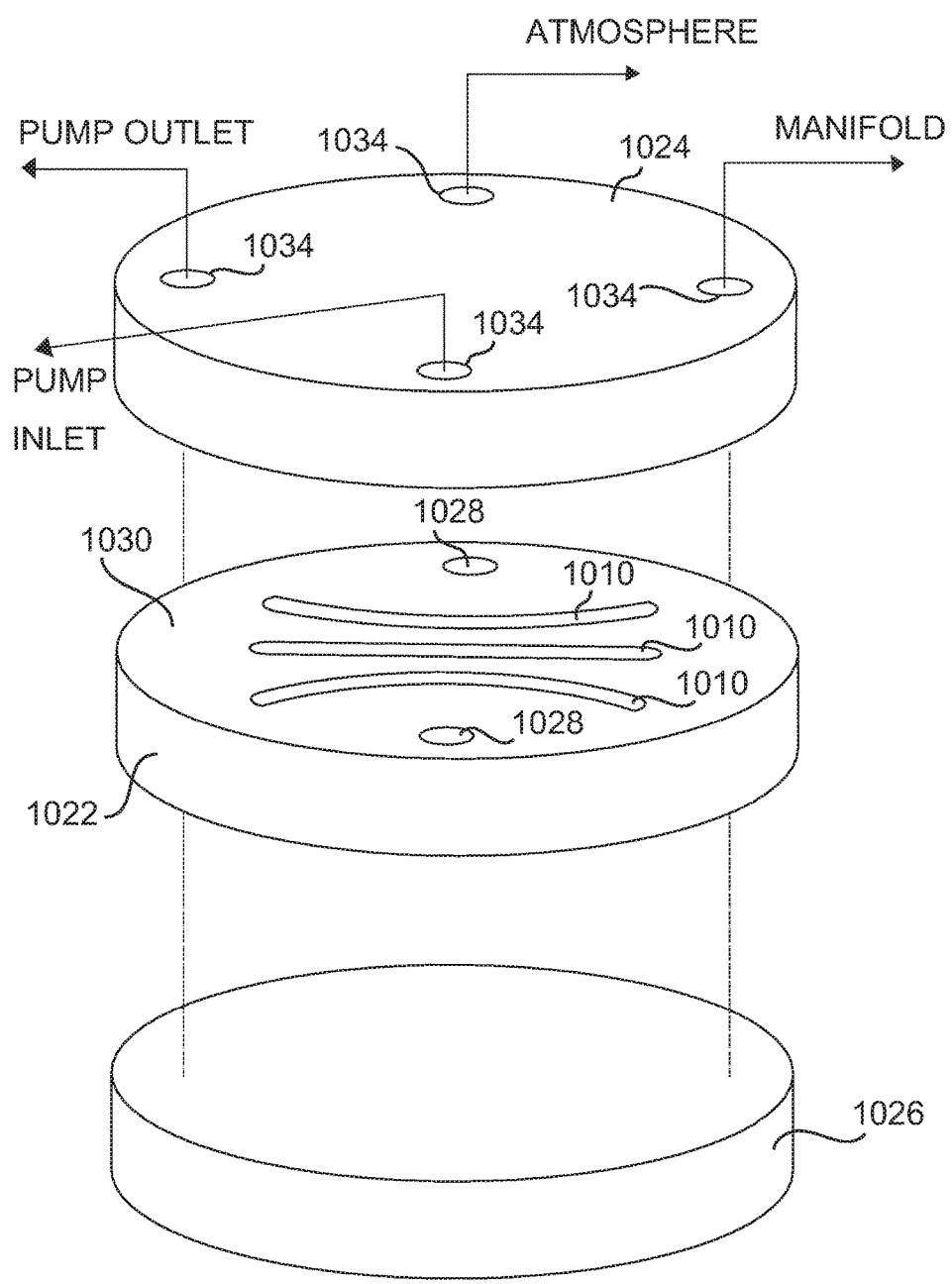
FIG. 44 depicts an exploded view of one embodiment of a rotary valve assembly.

FIG. 44 depicts an embodiment of a rotary valve assembly 1020. The rotary valve assembly 1020 in FIG. 44 is shown in an exploded view. The rotary valve assembly 1020 includes a rotor 1022, stator 1024, and back plate 1026. The rotor 1022 and stator 1024 in some embodiments are disc shaped. In alternate embodiments, the rotor 1022 and stator 1024 may be any suitable shape. In some embodiments, the rotor 1022 may be conical, while the stator 1024 may include a conical cavity therein. When assembled, the pieces of the rotary valve assembly 1020 may be held together by a clamping force sufficient to prevent any fluid leakage during operation.

As shown in FIG. 44, the top face 1030 of the rotor 1022 includes a number of flow paths 1010. These flow paths 1010 allow fluid to pass through the rotary valve assembly 1020. The flow paths 1010 may be selectively rotated into communication with a number of stator ports 1034 which extend through the stator 1024. Each of the stator ports 1034 may connect the rotary valve assembly 1020 to fluid pathways leading to other components of a pneumatic system (e.g. pump inlet, pump outlet, manifold, reservoir, etc.). In some embodiments the stator ports 1034 extend through the stator 1022 in a direction which is substantially perpendicular to the plane of the disc-like stator 1022.

Figure 45:
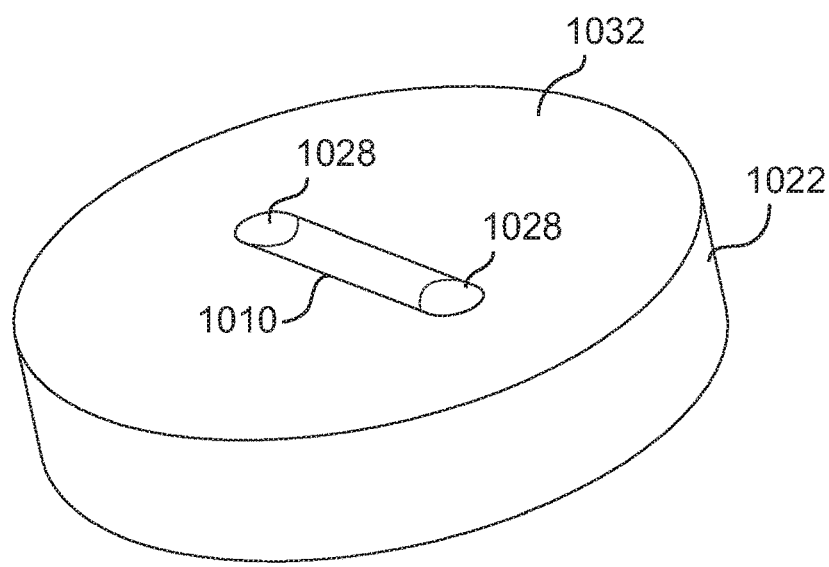
FIG. 45 depicts a perspective view of one embodiment of rotor of a rotary valve assembly.

Referring now also to FIG. 45, the bottom face 1032 of the rotor 1022 is depicted. The bottom face 1032 also includes a flow path 1010. The flow path 1010 in the bottom face 1032 of the rotor 1022 includes two pass-throughs 1028 which are oriented substantially perpendicular to the top face 1030 and bottom face 1032 of the rotor 1022. These pass-throughs 1028 allow the flow path 1010 in the bottom face 1032 of the rotor 1022 to be selectively rotated into communication with the various stator ports 1034 of the stator 1024. This may allow the flow path 1010 in the bottom face 1032 of the rotor 1022 to conduct fluid to and from the other components of a pneumatic system.

The stator 1024 and back plate 1026 may be made from a material such as metal, though any other suitable material may also be used. In some embodiments, the stator 1024 and the back plate 1026 may be identical parts. This may increase ease of manufacturing for a rotary valve assembly 1020. In such embodiments, the back plate 1026 may, for example, be clocked 45° with respect to the stator 1024. In some embodiments, the back plate 1026 is not identical to the stator 1024.

The rotor 1022 may be made from a material such as plastic, though any other suitable material may also be used. In some specific embodiments, the rotor 1022 may be made from Delrin. In other embodiments, the rotor 1022 may be made from a different material such as Rulon or polytetrafluoroethylene. The materials selected for the rotor 1022, stator 1024, and back plate 1026 may be selected such that the coefficient of friction between the moving parts of the rotary valve assembly 1020 is low. Additionally, in some embodiments, a surface treatment may be applied to the contacting surfaces of parts in the rotary valve assembly 1020 in order to reduce friction between the parts. Other surface treatments, such as those that increase the durability or corrosion resistance of the various parts may also be advantageous.

Friction between the two parts may also be reduced by recessing various portions of one or more mating surface in the rotary valve assembly 1022. In some embodiments, areas of the top face 1030 of the rotor 1022 where there are no flow paths 1010 in the vicinity may be recessed such that they contribute no friction. Alternatively or additionally, the flow paths 1010 may be enlarged such that the area of the top face 1030 of the rotor 1032 which contacts the stator 1022 is reduced and therefore contributes less friction. Any other friction reduction scheme which would be obvious to one skilled in the art may also be used.

In some embodiments, one or more parts of the rotary valve assembly 1020 may be stamped or water-jet cut to help minimize the cost of a rotary valve assembly 1020. A finishing process (e.g. lapping) may then be used on these parts to ensure that the contact surfaces between the mating faces of the valve assembly 1020 are flat and smooth.

Figure 46:
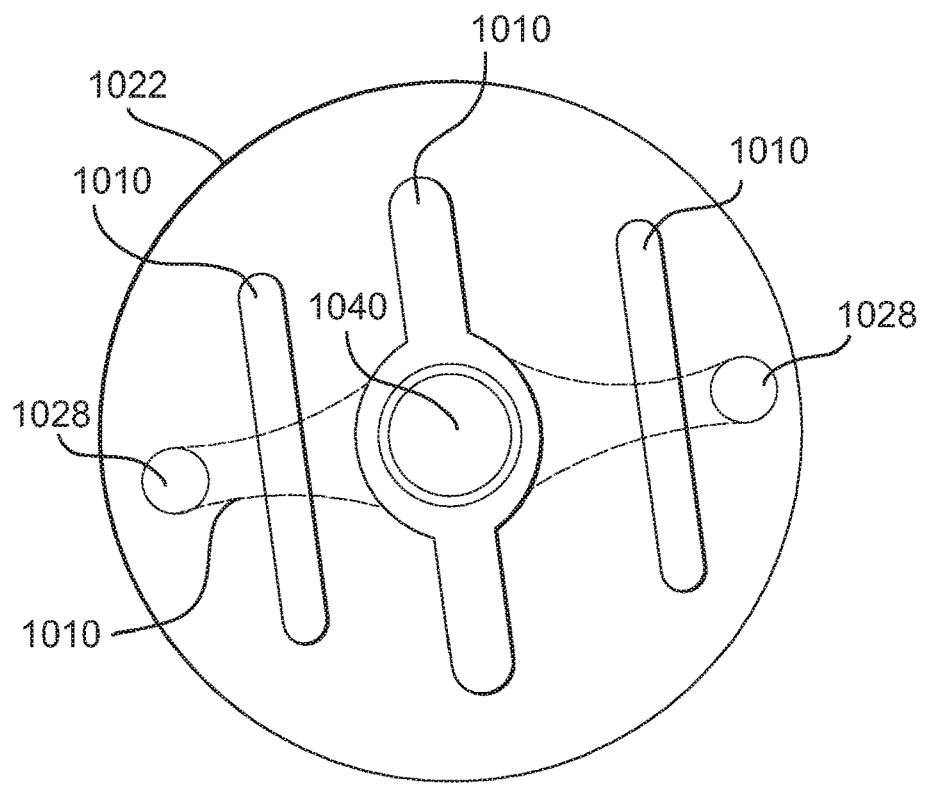
FIG. 46 depicts a top-down view of one embodiment of a rotor of a rotary valve assembly.
Figure 50:
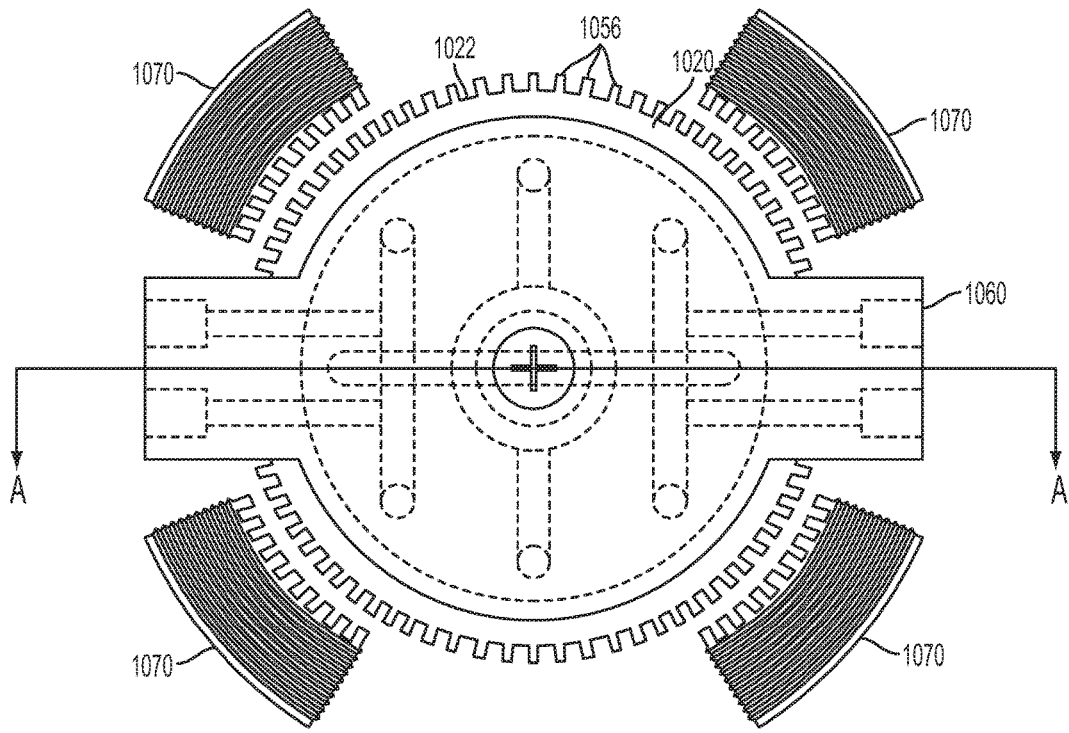
FIG. 50 depicts a top-down view of one example embodiment of a rotary valve and valve interface.
Figure 51:
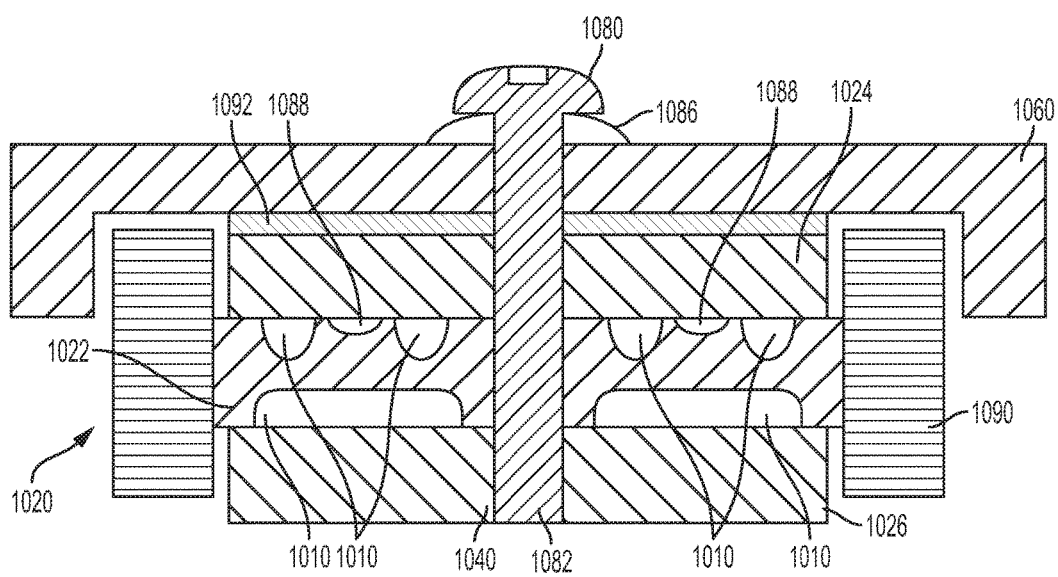
FIG. 51 depicts a cross-sectional view of an embodiment of a rotary valve and valve interface taken at line A-A of FIG. 50.

FIG. 46 depicts an embodiment of a rotor 1022 which may be included in a rotary valve assembly similar to the rotary valve assembly 1022 depicted in FIG. 44. As shown, the rotor 1022 in FIG. 46 includes a number of flow paths 1010. The rotor 1022 in FIG. 46 also includes pass-throughs 1028 which allow all of the flow paths 1010 of the rotor 1022 to be accessed via the same face of the rotor 1022. The rotor 1022 in FIG. 46 includes a central through-hole 1040. A through-hole 1040 may extend through other portions of a rotary valve assembly 1020 as well. A through-hole 1040 may aid in assembly of a rotary valve assembly 1020 by allotting for a fastener to pass through the assembly and aid in clamping the assembly together. An embodiment using such a fastener is depicted in FIGS. 50 and 51.

In some embodiments, a through-hole 1040 in the rotor 1022 may be keyed. This may allow a keyed shaft (not shown) to be inserted into the through-hole such that the rotor 1022 may be driven via the keyed shaft. The keyed shaft may be rotated by a motor. Some such embodiments may use a planetary gear head (not shown) to drive rotation of the keyed shaft.

Figure 47:
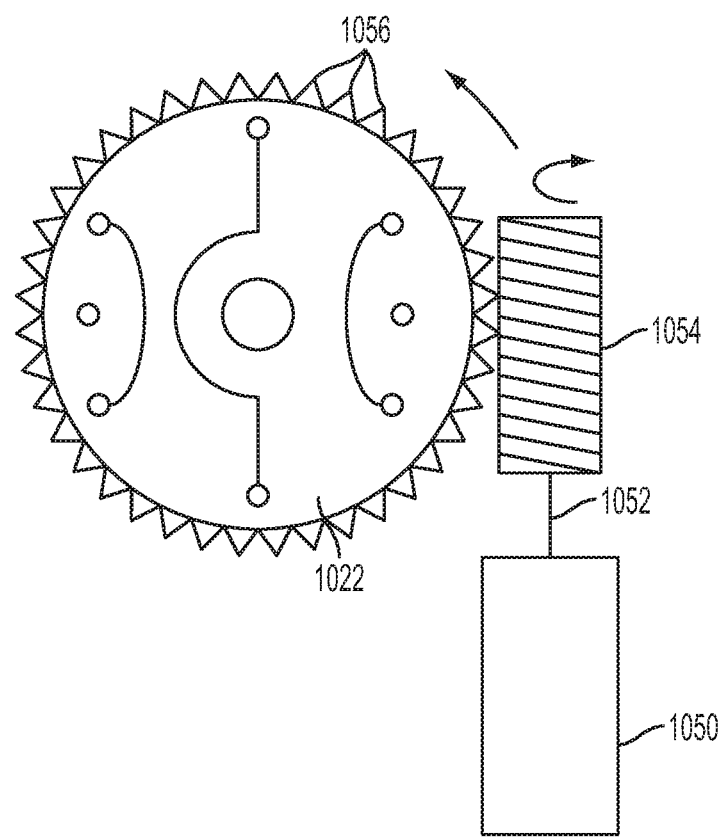
FIG. 47 depicts one embodiment of an arrangement for imparting rotary motion to a rotor of a rotary valve assembly.

FIG. 47 depicts an arrangement for imparting rotary motion to a rotor 1022. As shown in FIG. 47 a motor 1050, which lies substantially in the same plane as the rotor 1022, is included. The motor 1050 rotates a shaft 1052 which is coupled to a worm gear 1054. The worm gear 1054 interdigitates with teeth 1056 disposed about the circumference of the rotor 1022. As the motor 1050 rotates the worm gear 1054, this rotation is imparted to the rotor 1022 thus causing rotation of the rotor 1022.

The motor 1050 used could be any variety of suitable motor 1050. In some embodiments the motor 1050 may be a brushed DC motor, brushless DC motor, or any variety of stepper motor. It may be desirable to use a stepper motor because a stepper motor allows for deterministic motion of the motor (i.e. X pulses creates Y degrees of rotor 1022 movement). Some embodiments may include a rotary encoder (not shown) which may track rotor 1022 rotation. Some embodiments may include a magnetic rotary encoder which senses rotor rotation 1022 via the position of a magnet rotating with the rotor 1022. Other embodiments may include an optical rotary encoder which may, for instance, optically count the gear teeth 1056 of the rotor 1022 as they pass the field of view of the encoder. Other types of rotary encoders or suitable rotation sensing schemes may also be used. In some embodiments, a gray encoder may be built into the rotor 1022. This could be accomplished by means of decal placed on a surface of the rotor 1022. In other embodiments, this may be accomplished electrically with tracks on the rotor 1022. In such embodiments, a thin PCB may also be included as a part of the rotary valve assembly 1020. One or more potentiometers may also be used to track rotation of the rotor 1022. In such embodiments, the one or more potentiometers may be keyed to a rotor shaft such that the wipers of the potentiometers rotate, changing the measured resistance, as the rotor 1022 shaft rotates. The measured resistance may then be used to determine the rotational position of the rotor 1022.

Figure 48:
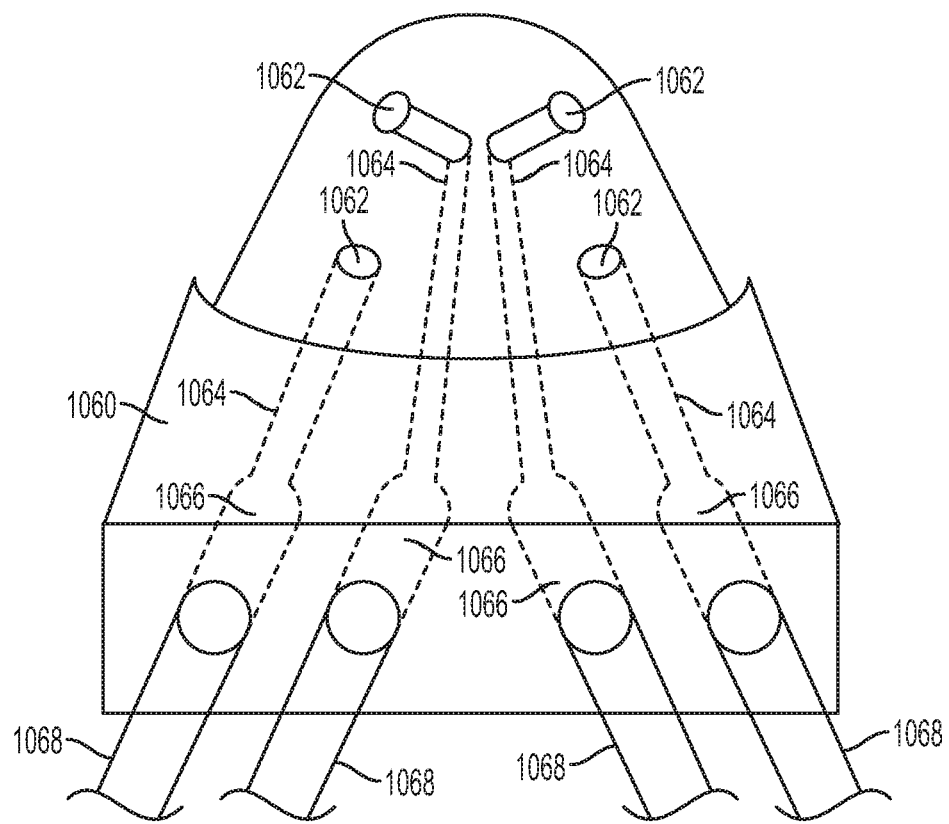
FIG. 48 depicts a perspective view of one embodiment of a valve interface.

FIG. 48 depicts an embodiment of a valve interface 1060. In some embodiments, the valve interface 1060 may double as a valve stator. A valve interface 1060 may be used to interface a valve, such as any of the rotary valves or rotary valve assemblies described herein, to the rest of a pneumatic system. The embodiment valve interface 1060 depicted in FIG. 48 may, in some embodiments, be used in conjunction with the rotary valve assembly 1020 depicted in FIG. 44. As shown, the valve interface 1060 includes a number of interface ports 1062. The interface ports 1062 are each in communication with a respective interface fluid channel 1064. The valve interface 1060 includes a number of connection ports 1066 which are also in communication with respective interface fluid channels 1064. Tubing 1068 may be plumbed into the connection ports 1066 in order to connect various components of a pneumatic system to the valve interface 1060. Such tubing 1068 may connect the valve interface 1060 to components such as a pump, manifold, reservoir, etc.

When assembled, a stator such as the stator 1024 shown in FIG. 44, may be joined to the valve interface 1060 such that the stator ports 1034 (see FIG. 44) are in line with the interface ports 1062. In some embodiments, the valve interface 1060 may be clamped in with a valve assembly (best shown in FIG. 51). The valve interface 1060 may also include a planar or form-in-place gasket (planar gasket 1092 shown in FIG. 51) between the mating faces of the valve interface 1060 and the stator 1024. Thus, rotation of a rotor 1022 (see, for example, FIG. 44) of a valve assembly 1020 (see, for example, FIG. 44) which has been joined to a valve interface 1060 may allow various pneumatic arrangements to be broken and made.

Figure 49:
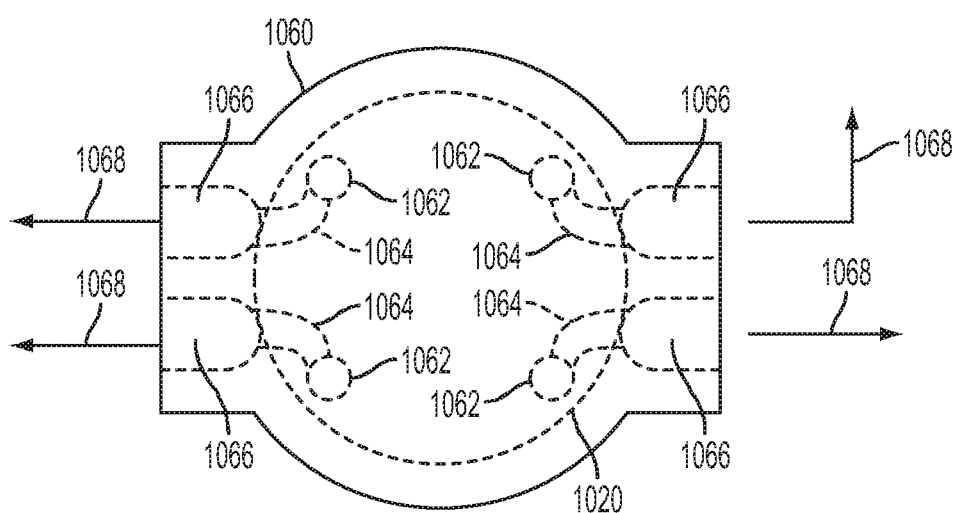
FIG. 49 depicts a top-down view of one embodiment of a valve interface.

FIG. 49 depicts an embodiment of a valve interface 1060. As shown, the valve interface 1060 is similar to that shown in FIG. 48. The valve interface 1060 shown in FIG. 49 includes a number of interface ports 1062, interface fluid channels 1064, and connection ports 1066 all of which serving the same function as those described in relation to FIG. 48. Tubing 1068 is plumbed into the connection ports 1066 of the valve interface 1060 in FIG. 49. A rotary valve assembly 1020 is shown in outline form in place on the valve interface 1060 as well.

In contrast to FIG. 48, the connection ports 1066 in FIG. 49 are not all located on the same side of the valve interface 1060. In the specific embodiment shown in FIG. 49, the connection ports 1066 are in pairs which are disposed 180° from one another. This may be desirable/beneficial for many reasons, including, but not limited to, such an arrangement may allow for the tubing 1068 to be more easily routed for the pneumatic system. The connection ports 1066 may also be disposed in any other suitable configuration.

FIG. 50 depicts an assembled embodiment of a valve interface 1060 and rotary valve assembly 1020. As shown, the valve interface 1060 is similar to the valve interface 1060 illustrated and described in relation to FIG. 49. The rotary valve assembly 1020 is also similar to other rotary valve assemblies shown and described herein. The rotary valve assembly 1020 in FIG. 50 includes a rotor 1022 which has a diameter larger than the footprint of the valve interface 1060. The rotor 1022 also includes teeth 1056 which are disposed about its circumference. In some embodiments, as depicted in FIG. 50, rotation may be imparted to the rotor 1022 of the rotary valve assembly 1020 by means of a number of stepper coils 1070 disposed around the rotor 1022. By selectively energizing the stepper coils 1070 in a suitable sequence, the rotor 1022 may be made to rotate to a desired location. As mentioned above, such an arrangement allows for deterministic motion of the rotor 1022.

FIG. 51 depicts a cross-sectional view of the assembled embodiment of the valve interface 1060 and rotary valve assembly 1020 in FIG. 50 taken at line A-A. As shown, the rotary valve assembly 1022 and valve interface 1060 are coupled together with a fastener 1080. In some embodiments, the fastener 1080 is a bolt, though other embodiments may use any other suitable type fasteners. The fastener 1080 couples the rotary valve assembly 1022 and valve interface 1060 through a through-hole 1040 which passes through the valve assembly 1022 and valve interface 1060. In some embodiments, the portion of the through-hole 1040 in the back plate 1026 of the rotary valve assembly 1040 is threaded to accept a complimentarily threaded portion 1082 of the fastener 1080. To control the clamping force, a bias member 1086 may also be included. In the embodiment in FIG. 51, the bias member 1086 is a Belleville washer which is compressed between the head of the fastener 1080 and the top face of the valve interface 1060. A planar gasket 1092 is included between the valve interface 1060 and the rotary valve assembly 1020.

The mating faces of the rotor 1022 of the rotary valve assembly 1020 have been formed such that they provide a minimal amount of friction which needs to be overcome during rotation. In some embodiments the flow path 1010 present on the bottom face of the rotor 1022 is enlarged such that unnecessary friction producing areas of the mating face are substantially minimized. Additionally, the top face of the rotor 1022 includes recessed portions 1088. These recessed portions 1088 are not in contact with the stator 1024 and therefore do not create friction during rotation. In some embodiments, the rotor 1022 of the rotary valve assembly 1020 may only be rotated in a direction which would cause any friction between the rotor 1022 and back plate 1026 to tend to drive the back plate 1026 in a direction in which it cinches up on the fastener 1080.

As shown in FIG. 51, in some embodiments the rotor 1022 includes a stepper rotor 1090 about its circumference. The stepper rotor 1090 may be a separate piece mated to the rotor 1022 in some embodiments. In some cases, the stepper rotor 1090 may be a multiple piece rotor lamination. As shown in FIG. 50, stepper coils 1070 may be arrayed around the stepper rotor 1090 to drive rotation of the rotor 1022.

Figure 52:
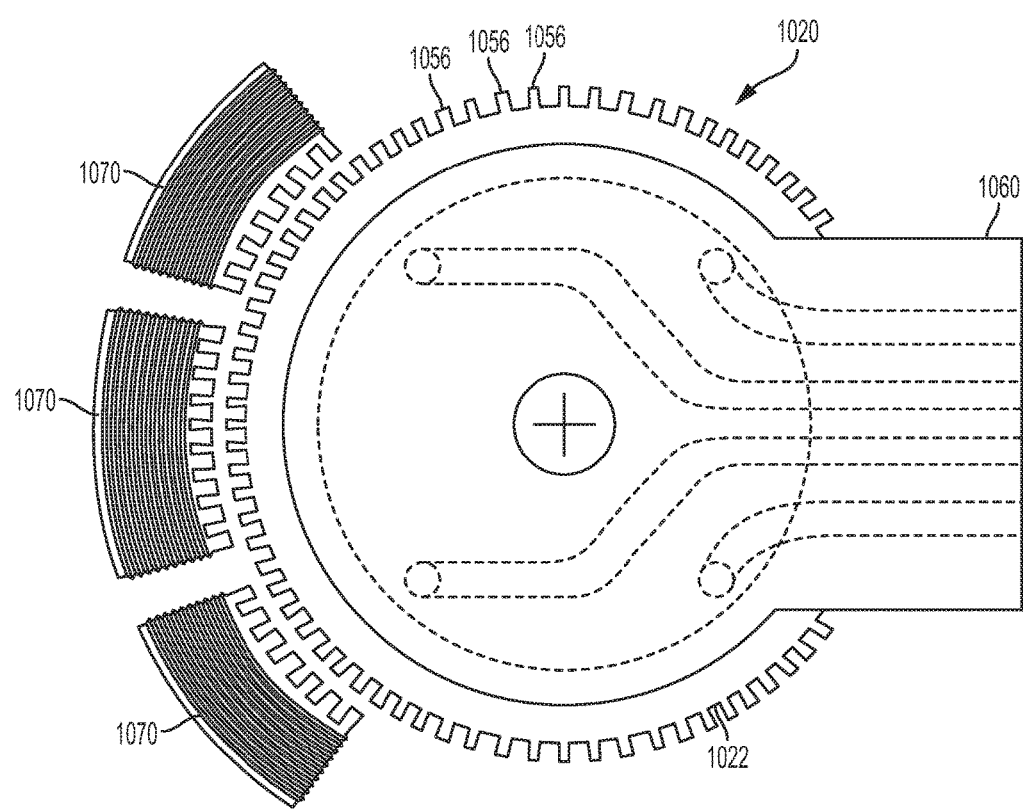
FIG. 52 depicts a top-down view of one embodiment of a rotary valve and valve interface.

FIG. 52 depicts an embodiment of a valve interface 1060 and rotary valve assembly 1020. As shown, the valve interface 1060 is similar to the valve interface 1060 illustrated and described in relation to FIG. 48. The rotary valve assembly 1020 is also similar to other rotary valve assemblies shown and described herein. The rotary valve assembly 1020 in FIG. 52 includes a rotor 1022 which has a diameter which is larger than the footprint of the valve interface 1060. The rotor 1022 also includes teeth 1056 which are disposed about its circumference. In the embodiment depicted in FIG. 50, rotation may be imparted to the rotor 1022 of the rotary valve assembly 1020 by means of a number of stepper coils 1070 disposed around the rotor 1022. By selectively energizing the stepper coils 1070 in a suitable sequence, the rotor 1022 may be made to rotate to a desired location. As mentioned above, such an arrangement allows for deterministic motion of the rotor 1022.

Figure 53:
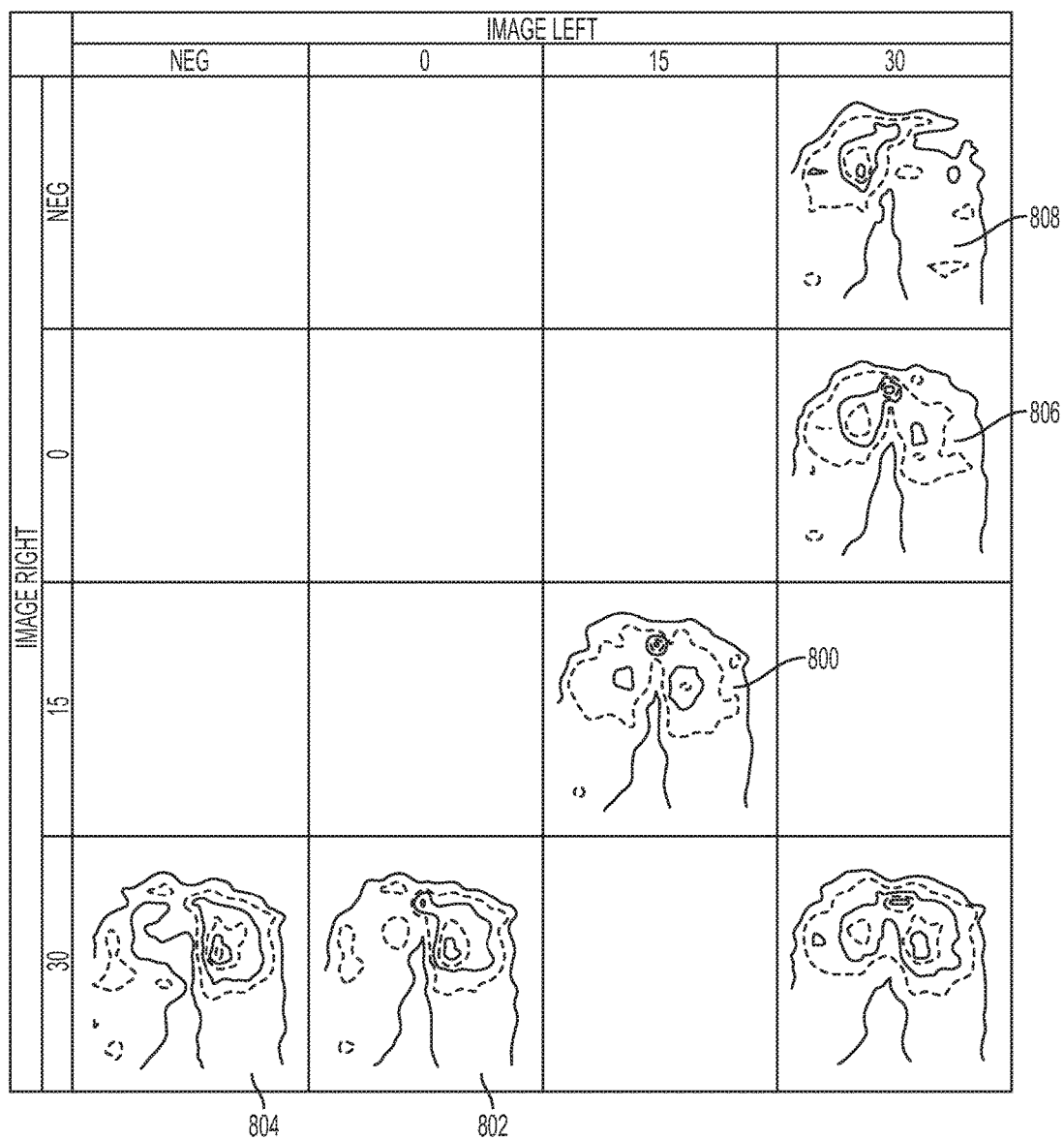
FIG. 53 shows a chart of isopleth maps detailing the contact pressure of a buttock against a person support apparatus in accordance with one embodiment.

FIG. 53 shows a pressure map chart generated from an embodiment of the present disclosure. The chart is only partially populated with pressure maps such that it facilitates conceptual understanding. As shown, the columns of the chart correspond to various inflation pressures of the left actuator 16 of the dynamic support apparatus 10. The far left column displays pressure maps where a vacuum was applied to the left actuator 16. The second column from the left displays pressure maps where the inflation pressure of the left actuator 16 was 0 mmHg. The second column from the right displays pressure maps taken where the inflation pressure of the left actuator 16 was 15 mmHg. The far right column displays pressure maps where the inflation pressure of the left actuator 16 was 30 mmHg.

The rows of the chart correspond to various inflation pressures of the right actuator 16. The top row of the chart displays pressure maps where a vacuum was drawn on the right actuator 16. The second row from the top displays pressure maps where the right actuator 16 was inflated to a pressure of 0 mmHg. The second row from the bottom of the chart displays pressure maps where the right actuator 16 was inflated to a pressure of 15 mmHg. The bottom row of the chart displays pressure maps where the right actuator 16 was inflated to a pressure of 30 mmHg.

The pressure maps shown depict the contact pressures of a sample human buttock and thighs against a dynamic support apparatus 10 which is functioning as a seat cushion for a wheelchair. In some embodiments, the dynamic support apparatus 10 includes two actuators 16 disposed similarly to those shown in FIG. 1. The pressure maps shown are isopleth maps. Each isopleth of the pressure maps represents a particular contact pressure.

Map 800 depicts a pressure map where the right and left actuators 16 were inflated to the same positive pressure of 15 mmHg. As shown the pressure distributions on the pressure map were substantially similar on both the right and left side of the buttock. Three high pressure areas are visible. The highest pressure corresponds generally to the contact point of the sacrum on the dynamic support apparatus 10. Additionally, two high pressure areas are depicted which correspond generally to contact points of the ischial tuberosities. As described above, high pressure areas such as these may become problematic over periods of prolonged occupation. Such high pressure areas may make prolonged occupation uncomfortable. Additionally, inhibited blood flow to high pressure areas such as those shown may foster the formation of pressure sores. For this reason, the actuators 16 may be inflated and deflated in a manner which may provide pressure relief to contact areas of the occupant. This may stimulate perfusion to the area thus helping to prevent formation of pressure ulcers.

Map 802 depicts a pressure map taken when the inflation pressure of the left actuator 16 was dropped to 0 mmHg while the inflation pressure of the right actuator 16 was increased to 30 mmHg. As shown, contact pressure, was consequentially substantially relieved from the left side of the buttock. Contact pressure of the right side of the buttock increased.

Contact pressure may be further relieved from the left side of the buttock by applying a negative pressure to the left actuator 16 as shown in map 804 of FIG. 53. As mentioned above, this relief of the contact pressure shown in maps 802 and 804 may allow for relatively uninhibited perfusion to take place in the relieved region. Contact pressure may be relieved from the left buttock for a period of time which allows sufficient perfusion to necessary areas in order to prevent the formation of decubitus ulcers in the region.

After such a period of relief, the pressures may, in some embodiments, be brought back to the pressures used to generate map 800. After a period of time, the right buttock may then undergo a relief period. Map 806 depicts a contact pressure map taken where the pressure of the right actuator 16 was dropped to 0 mmHg while the inflation pressure of the left actuator 16 has been increased to 30 mmHg. Consequently, contact pressure was substantially relieved from the right side of the buttock and contact pressure of the left side of the buttock increased moderately.

Contact pressure may be further relieved from the right side of the buttock by applying a negative pressure to the right actuator 16 as shown in map 808 of FIG. 53. Contact pressure may be relieved from the right buttock for a period of time to allow sufficient perfusion to necessary areas in order to prevent the formation of pressure sores in the region. This pattern may then repeat. Repetition of such a pattern of shifting and relieving contact forces may help ensure no one area is subjected to conditions favoring the development of pressure ulcers for a hazardously long duration of time.

The above described relief pattern is only one of many embodiments of relief regimens which may be employed with the above described dynamic support apparatus 10 embodiments. Various relief patterns other than the embodiments of the pattern described above may be used to help inhibit the formation of pressure sores. The pressures or sequence may differ from embodiment to embodiment. The pressures or sequence may also differ from user to user and be determined on an individual basis by a care giver or other.

Additionally, pressure need not be adjusted on or solely on the basis of elapsed time. For instance, the occupant may manually enter a voluntary relief mode by, in some embodiments, pushing a button 404 (see FIG. 26) on the onboard interface 523 of the controller 506 (see FIG. 25). The controller 506 may, in some embodiments, also use sensor data to determine whether or not to add or remove fluid to an actuator 16. Users may also be able to program in a customized relief pattern to be used by the dynamic support apparatus 10. In still other embodiments, the pattern may not be a preprogrammed pattern. Instead, a dynamic support apparatus may rely on an occupant or caretaker to manually adjust actuator pressures to provide pressure relief during occupation.

In some embodiments, the pressure relief periods may be based upon physiological data from an occupant. Physiological data may be gathered by a sensor which monitors perfusion such as a pulse oximeter. In such embodiments, when it is sensed that perfusion has fallen below a predefined level or has been below such a level for a predetermined period of time, a relief mode for that area may be initiated. Pressure may then be reapplied after it has been determined sufficient perfusion has occurred.

Figure 54:
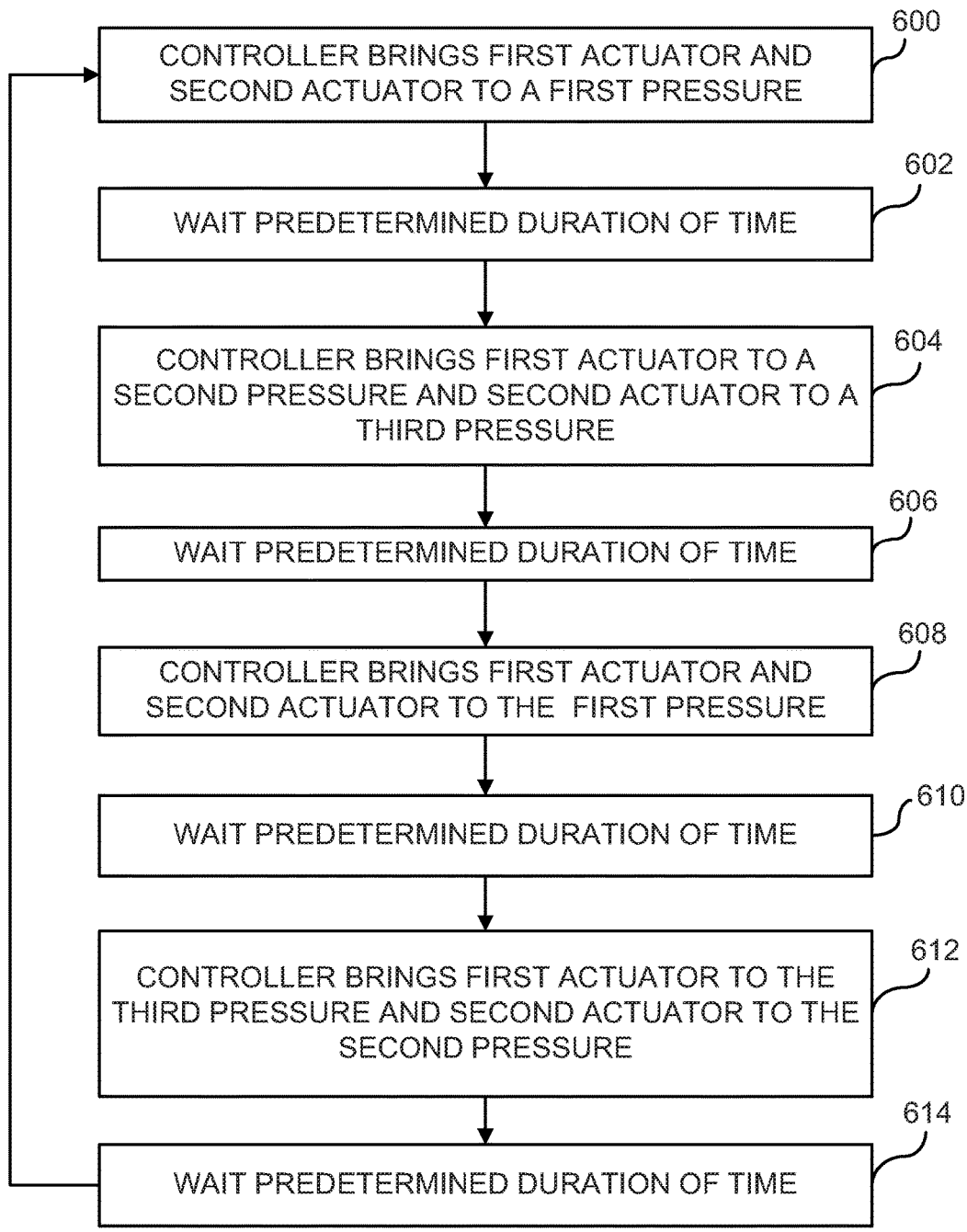
FIG. 54 depicts a flowchart detailing a number of steps which may be used to actuate actuators of a dynamic support apparatus in a pressure relief mode or pattern in accordance with one embodiment.

FIG. 54 depicts a flowchart detailing a number of steps which may be used to actuate actuators of a dynamic support apparatus in a pressure relief mode or pattern. As mentioned, such a pattern may be used to combat the formation of pressure sores and/or increase occupant comfort. The flowchart details a pressure relief pattern for a dynamic support apparatus including only two actuators for sake of simplicity. As would be appreciated by one of ordinary skill in the art, the steps called out in the flowchart depicted in FIG. 54 may be modified for use with a dynamic support apparatus including a different number of actuators. Though the flowchart depicted in FIG. 54 and many other flowcharts depicted herein use pressure set points for their relief pattern, other types of set points may be used to define a desired inflation level for any embodiments described herein. In some embodiments, a set point may be an amount of fluid (e.g. mass or moles) communicated to or from an actuator. In such embodiments, a mass airflow sensor may monitor moles of air communicated into and out of the actuator. In other embodiments, a set point may be an actuator height set point. In such embodiments, a sensor may monitor how distant a face of the actuator is from a reference point inside the actuator. Any other suitable set point may also be used.

In step 600 a controller for a dynamic support apparatus may bring both the first and second actuator to a first pressure. Bringing the actuators to a desired pressure may involve pumping air into or out of the first or second actuator with a pump. The controller may wait a predetermined amount of time in step 602 allowing actuators to remain at the first pressure. In some embodiments, the controller may monitor the pressure in the first and second actuator to ensure it is within a predetermined range of the first pressure. If the pressure in the first and second actuators falls outside of the predetermined range (e.g. due to slow leakage of fluid filling the actuators over time), the controller may act to bring the pressure of the first and second actuator back to the first pressure or within the predetermined range. In some embodiments, if attempts by the controller to bring the first and/or second actuator to the first pressure fail (e.g. due to a compromised actuator), the controller may generate an error, alert, alarm, or enter a failsafe.

After the predetermined period of time has elapsed, the controller may, in step 604, bring the first actuator to a second pressure and bring the second actuator to a third pressure. The third pressure may be the same as or differ from the first pressure. In some embodiments, the second pressure may be a pressure lower than the first pressure and the third pressure may be a pressure higher than the first pressure. In such embodiments, in step 604 the area of an occupant supported by the first actuator may experience pressure relief while the area supported by the second actuator bears more of the load. The controller may wait a predetermined amount of time in step 606 allowing the first and second actuator to respectively remain at the second and third pressures. In some embodiments, the controller may monitor the pressure in the first and second actuator to ensure it is within a predetermined range of the respective target pressures. If the pressure in the first and second actuators falls outside of the predetermined range (e.g. due to slow leakage of fluid filling the actuators over time), the controller may act to bring the pressure of the first and second actuator back to the target pressure or within the predetermined range of that pressure. In some embodiments, if attempts by the controller to bring the first and/or second actuator to the target pressure fail (e.g. due to a compromised actuator), the controller may generate an error, alert, alarm, or enter a failsafe.

After the predetermined period of time has elapsed, in step 608, the controller may bring the first and second actuators back to the first pressure. The controller may wait a predetermined amount of time in step 610 allowing actuators to remain at the first pressure. In some embodiments, the controller may monitor the pressure in the first and second actuator to ensure it is within a predetermined range of the first pressure. If the pressure in the first and second actuators falls outside of the predetermined range (e.g. due to slow leakage of fluid filling the actuators over time), the controller may act to bring the pressure of the first and second actuator back to the first pressure or within the predetermined range. In some embodiments, if attempts by the controller to bring the first and/or second actuator to the first pressure fail (e.g. due to a compromised actuator), the controller may generate an error, alert, alarm, or enter a failsafe.

After the predetermined period of time has elapsed, the controller may, in step 612, bring the first actuator to the third pressure and bring the second actuator to the second pressure. As mentioned above, in some embodiments, the second pressure may be a pressure lower than the first pressure and the third pressure may be a pressure higher than the first pressure. In such embodiments, in step 612 the area of an occupant supported by the second actuator may experience pressure relief while the area supported by the first actuator bears more of the load. The controller may wait a predetermined amount of time in step 614 allowing the first and second actuator to respectively remain at the third and second pressures. In some embodiments, the controller may monitor the pressure in the first and second actuator to ensure it is within a predetermined range of the respective target pressures. If the pressure in the first and second actuators falls outside of the predetermined range (e.g. due to slow leakage of fluid filling the actuators over time), the controller may act to bring the pressure of the first and second actuator back to the target pressure or within the predetermined range of that pressure. In some embodiments, if attempts by the controller to bring the first and/or second actuator to the target pressure fail (e.g. due to a compromised actuator), the controller may generate an error, alert, alarm, or enter a failsafe.

In some embodiments, and as shown in FIG. 54, the process may then return back to step 600 and repeat. Thus the controller may perform pressure relief cycles to help prevent the formation of decubitus ulcers and/or increase occupant comfort. As mentioned above, other pressure relief patterns or schemes may also be used. Various embodiments may not use time based pressure adjustment. Some embodiments may be manually adjusted or allow for manual adjustment. Some embodiments may also be adjusted based on physiological data from an occupant.

Figure 55:
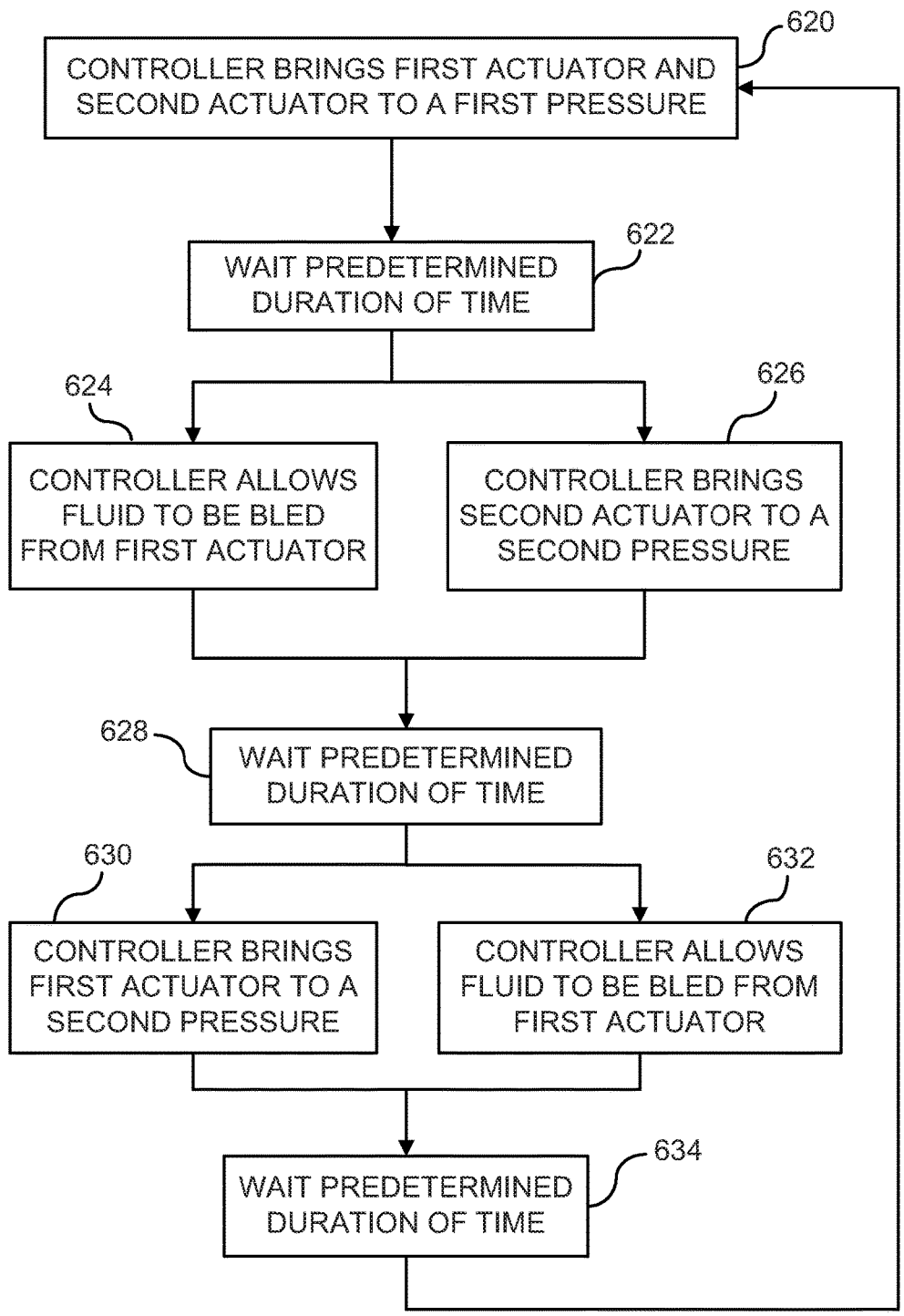
FIG. 55 depicts a flowchart detailing a number of example steps which may be used to actuate actuators of a dynamic support apparatus in a pressure relief mode or pattern in accordance with one embodiment.

FIG. 55 depicts another flowchart detailing a number of steps which may be used to actuate actuators of a dynamic support apparatus in a pressure relief mode or pattern in various embodiments. As mentioned, such a pattern may be used to combat the formation of pressure sores and/or increase occupant comfort. The flowchart details a pressure relief pattern for a dynamic support apparatus including only two actuators for sake of simplicity. As would be appreciated by one of ordinary skill in the art, the steps called out in the flowchart depicted in FIG. 55 may be modified for use with a dynamic support apparatus including a different number of actuators. Though the flowchart uses pressure set points, as described above, any other suitable type of set point may also be used in various embodiments.

In step 620 a controller for a dynamic support apparatus may bring both the first and second actuator to a first pressure. Bringing the actuators to a desired pressure may involve pumping air into or out of the first or second actuator with a pump. In FIG. 55, a pump is only used in order to increase the pressure in an actuator. To decrease pressure in an actuator, the controller may open a valve putting the interior volume of the actuator in communication with the atmosphere and allow fluid within the interior volume of the actuator to be bled out. This may be more efficient from a power consumption standpoint because lowering pressure in the actuators is accomplished passively. That is, the weight of the occupant may drive fluid out of the actuator instead of an actively powered pump.

The controller may wait a predetermined amount of time in step 622 allowing actuators to remain at the first pressure. In some embodiments, the controller may monitor the pressure in the first and second actuator to ensure it is within a predetermined range of the first pressure. If the pressure in the first and second actuators falls outside of the predetermined range (e.g. due to slow leakage of fluid filling the actuators over time), the controller may act to bring the pressure of the first and second actuator back to the first pressure or within the predetermined range. In some embodiments, if attempts by the controller to bring the first and/or second actuator to the first pressure fail (e.g. due to a compromised actuator), the controller may generate an error, alert, alarm, or enter a failsafe.

After the predetermined period of time has elapsed, the controller may proceed to steps 624 and 626. These steps may be performed in simultaneous manner or at points temporally close to one another. In other embodiments, steps 624 and 626 may be performed in a more spaced temporal relation to one another. In step 624, the controller may allow fluid to be bled from the first actuator. As mentioned above, this may involve opening a valve which puts the interior volume of the first actuator into communication with the atmosphere. In step 626, the controller may bring the second actuator to a second pressure. After these steps have been performed, the area of an occupant supported by the first actuator may experience pressure relief (after sufficient fluid has been bled out of the actuator) while the area supported by the second actuator bears more of the load. The controller may wait a predetermined amount of time in step 628 allowing the first actuator to remain in communication with the atmosphere and for the second actuator to remain at the second pressure. In some embodiments, the controller may monitor the pressure in the second actuator to ensure it is within a predetermined range of the target pressure. If the pressure in the second actuators falls outside of the predetermined range (e.g. due to slow leakage of fluid filling the actuators over time), the controller may act to bring the pressure of the second actuator back to the target pressure or within the predetermined range of that pressure. The controller may also monitor to ensure that the pressure decays in the first actuator to indicate that fluid in the actuator is indeed being bled out from the actuator. In some embodiments, if attempts by the controller to bring the second actuator to the target pressure fail (e.g. due to a compromised actuator), the controller may generate an error, alert, alarm, or enter a failsafe. Additionally, if pressure decay is not observed in the first actuator, the controller may behave similarly.

After the predetermined period of time has elapsed the controller may proceed to steps 630 and 632. These steps may be performed in simultaneous manner or at points temporally close to one another. In other embodiments, steps 630 and 632 may be performed in a more spaced temporal relation to one another. In step 630, the controller may bring the first actuator to the second pressure. In step 632, the controller may allow fluid to be bled from the second actuator. As mentioned above, this may involve opening a valve which puts the interior volume of the second actuator into communication with the atmosphere. After these steps have been performed, the area of an occupant supported by the second actuator may experience pressure relief (after sufficient fluid has been bled out of the actuator) while the area supported by the first actuator bears more of the load. The controller may wait a predetermined amount of time in step 634 allowing the second actuator to remain in communication with the atmosphere and for the first actuator to remain at the second pressure. In some embodiments, the controller may monitor the pressure in the first actuator to ensure it is within a predetermined range of the target pressure. If the pressure in the first actuators falls outside of the predetermined range (e.g. due to slow leakage of fluid filling the actuators over time), the controller may act to bring the pressure of the first actuator back to the target pressure or within the predetermined range of that pressure. The controller may also monitor to ensure that the pressure decays in the second actuator to indicate that fluid in the actuator is indeed being bled out from the actuator. In some embodiments, if attempts by the controller to bring the first actuator to the target pressure fail (e.g. due to a compromised actuator), the controller may generate an error, alert, alarm, or enter a failsafe. Additionally, if a pressure decay is not observed in the second actuator, the controller may behave similarly.

In some embodiments, and as shown in FIG. 55, the process may then return back to step 620 and repeat. Thus the controller may perform pressure relief cycles to help prevent the formation of decubitus ulcers and/or increase occupant comfort. As mentioned above, other pressure relief patterns or schemes may also be used. Various embodiments may not use time based pressure adjustment. Some embodiments may be manually adjusted or allow for manual adjustment. Some embodiments may also be adjusted based on physiological data from an occupant.

Figure 56:
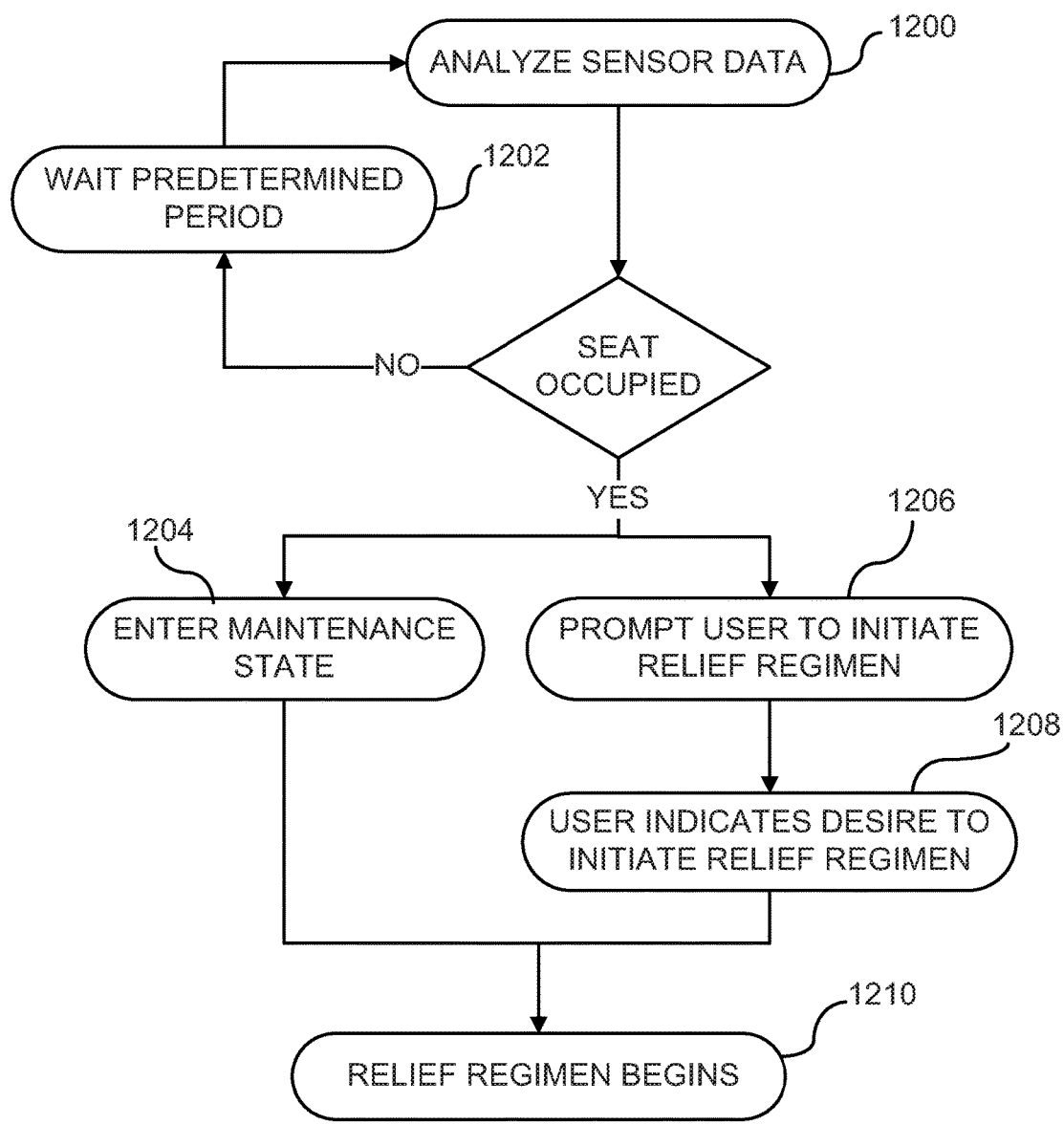
FIG. 56 depicts a flowchart detailing a number of steps which may be used to begin a relief regimen upon a determination that a dynamic support apparatus is occupied in accordance with one embodiment.

FIG. 56 depicts a flowchart detailing a number of steps which may be used by a dynamic support apparatus to determine if it is occupied and begin a relief regimen. As shown, in step 1200 the controller of the dynamic support apparatus may analyze data from one or more sensors. These sensors may, in some embodiments, be pressure sensors or bladder/actuator height sensors. Other varieties of sensors may also be used. Using the pressure sensors, the controller may monitor for a pressure increase which would be indicative of a user sitting down to occupy the dynamic support apparatus.

In some embodiments, in step 1200, the controller may compare sensor data to previously gathered sensor data in order to determine the dynamic support apparatus is occupied. Additionally, in some embodiments, the controller may compare data from a number of different sensors included in a dynamic support apparatus. In some embodiments, the controller may compare data from a pressure sensor associated with each actuator in a dynamic support apparatus. This may help to ensure that an occupant is fully seated in a dynamic support apparatus and may also serve as a cross check for sensor functionality.

In the event that the sensor data analyzed in step 1200 does not indicate that a dynamic support apparatus is occupied, a predetermined wait period may elapse in step 1202. After this predetermined wait period elapses, the controller may return to step 1200 and analyze new sensor data. Upon determination that the seat is occupied, the controller may proceed to both of steps 1204 and 1206 in some embodiments. In alternative embodiments, the controller may wait a predetermine period of time and analyze new sensor data. The controller may then check to ensure that the sensor data is still indicative that the dynamic support apparatus is occupied. This may help to ensure that the user is fully situated before proceeding to later steps.

In step 1204, the controller may enter a maintenance state. In the maintenance state, the controller may periodically replace any fluid which leaks out of actuators in a dynamic support apparatus. This may involve, in some embodiments, taking pressure readings of the actuators on a predetermined schedule and pumping in fluid as is necessary to maintain a predetermined pressure set point.

In step 1206, the controller may prompt the user to initiate a relief regimen. This prompt may be visual, auditory, tactile, or a combination thereof. In one specific embodiment, the controller may beep, lighting one or more indicator light, and/or display a prompt asking if the user would like to being a pressure relief regimen. In step 1208, a user may indicate their desire to begin a pressure relief regimen. This may involve a button press, touch gesture on a touch screen, or the like. In embodiments where multiple pressure relief regimens are stored by the controller, there may be an additional step in which the user selects which pressure relief regimen that they would like to initiate. In step 1210, the controller may start the relief regimen.

In an alternative embodiment, steps 1204, 1206, and 1208 may not be included. Instead, in such embodiments, the controller may automatically proceed to step 1210 upon determination that a dynamic support apparatus has been occupied by the user.

Figure 57:
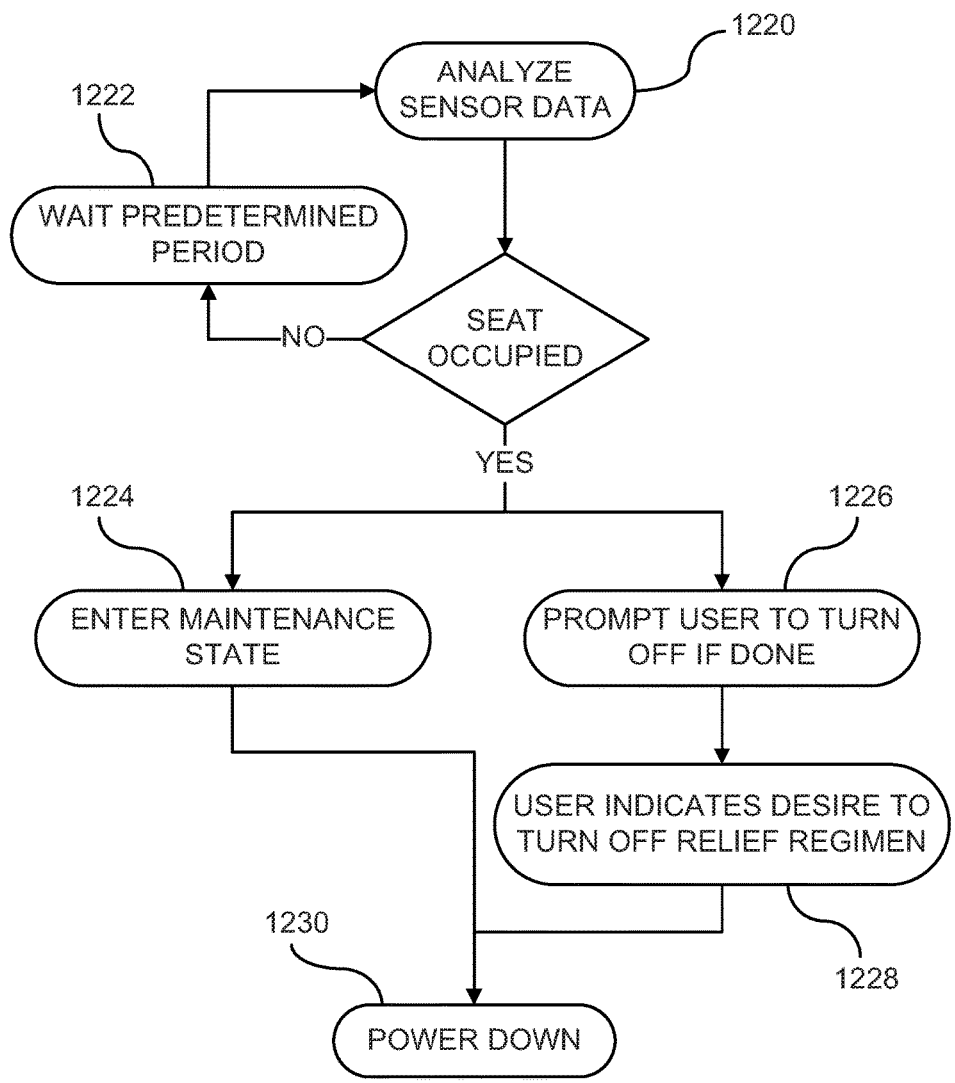
FIG. 57 depicts a flowchart detailing a number of steps which may be used to power down a dynamic support apparatus upon a determination that a dynamic support apparatus is no longer occupied in accordance with one embodiment.

FIG. 57 depicts a flowchart detailing a number of steps which may be used by a dynamic support apparatus to determine if it is unoccupied and power down. The flowchart depicted may begin after a pressure relief regimen has been initiated. As shown, in step 1220 the controller of the dynamic support apparatus may analyze data from one or more sensors. In various embodiments, these sensors may be any of the sensors described herein. Using the example of pressure sensors, the controller may monitor for a pressure decrease which would be indicative of a user getting out of the dynamic support apparatus. For example, the controller may monitor for a sudden and sustained pressure drop in all actuators. In some embodiments, analyzing sensor data may include comparing sensor data to previously gathered sensor data in order to determine the dynamic support apparatus is unoccupied. Additionally, in some embodiments, the controller may compare data from a number of different sensors included in a dynamic support apparatus. This may help to ensure that an occupant is fully out of a dynamic support apparatus and may also serve as a cross check for sensor functionality.

In the event that the sensor data analyzed in step 1220 does not indicate that a user has exited the dynamic support apparatus, a predetermined wait period may elapse in step 1222. After this predetermined wait period elapses, the controller may return to step 1220 and analyze new sensor data. Upon determination that the seat is unoccupied, the controller may proceed to both of steps 1224 and 1226 in some embodiments. In alternative embodiments, the controller may wait a predetermine period of time and analyze new sensor data. The controller may then check to ensure that the sensor data is still indicative that the dynamic support apparatus is empty. This may help to ensure that the user is fully out of the dynamic support apparatus before proceeding to later steps.

In step 1224, the controller may enter a maintenance state. In the maintenance state, the controller may periodically replace any fluid which leaks out of actuators in a dynamic support apparatus. This may involve, in some embodiments, taking pressure readings of the actuators on a predetermined schedule and pumping in fluid as is necessary to maintain a predetermined pressure set point. This may be useful in prolonging battery life as the device.

In step 1226, the controller may prompt the user to turn off the dynamic support apparatus. This prompt may be visual, auditory, tactile, or a combination thereof. In one specific embodiment, the controller may beep, light one or more indicator light, and/or display a prompt asking if the user would like to power down the dynamic support apparatus. In step 1228, a user may indicate their desire to power down the device. This may involve a button press, touch gesture on a touch screen, or the like. In some embodiments, the user may have the option of also putting the dynamic support apparatus into a sleep state. This may be desirable in the event that the user will be using the dynamic support apparatus again shortly as it may decrease start up time.

In step 1230, the controller may power down. In an alternative embodiment, steps 1224, 1226, and 1228 may not be included. Instead, in such embodiments, the controller may automatically proceed to step 1230 upon determination that a dynamic support apparatus is empty or otherwise idle.

Figure 58:
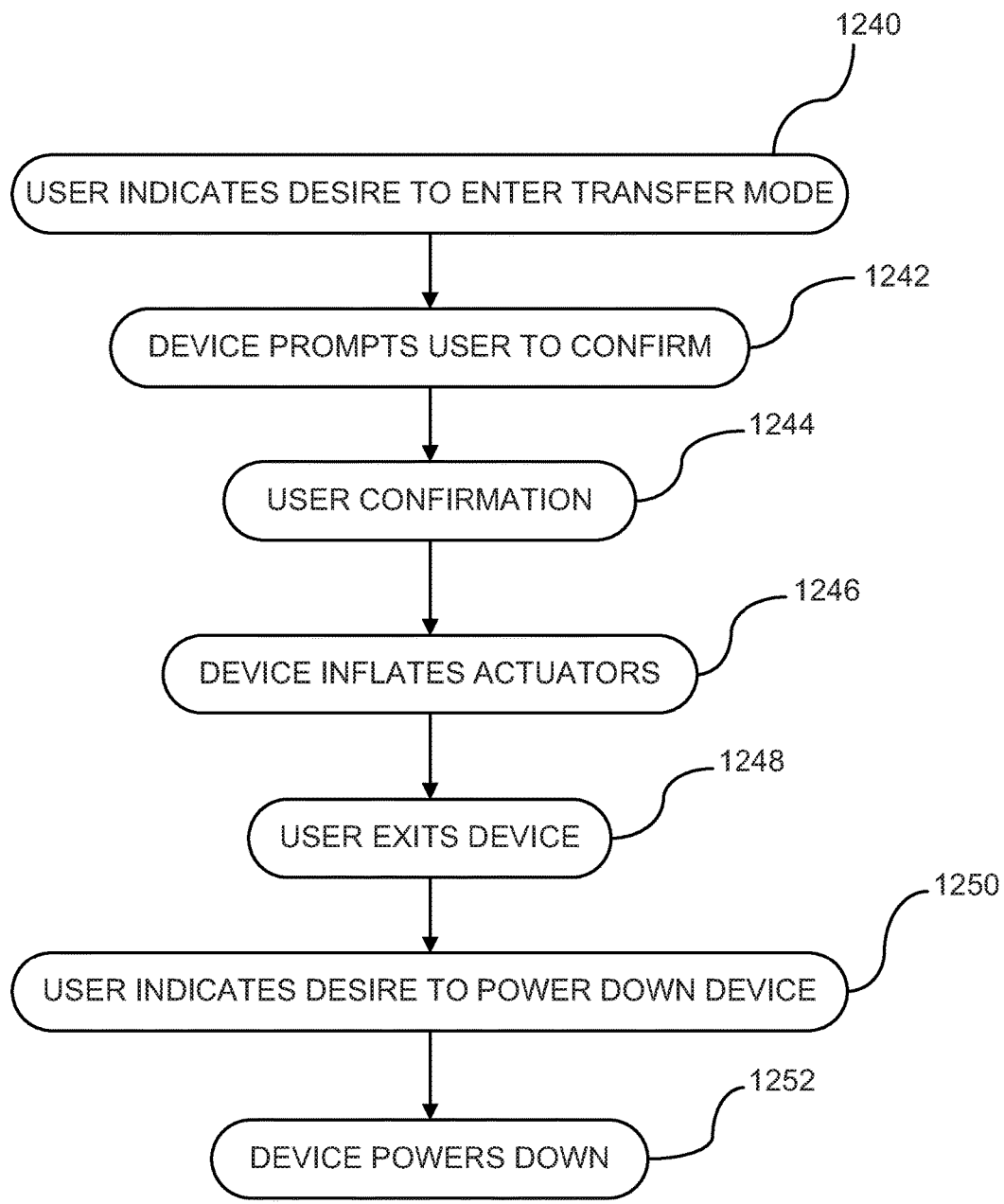
FIG. 58 depicts a flowchart detailing a number of example steps which may be used to enter a transfer mode using a dynamic support apparatus in accordance with one embodiment.

FIG. 58 depicts a flowchart which includes a number of steps which may be used to enter a transfer mode in a dynamic support apparatus. In a transfer mode, the actuators of the dynamic support apparatus may be inflated so as to help lift an occupant out of the dynamic support apparatus. This may make it easier for a user or caretaker to transfer an occupant out of a dynamic support apparatus as the dynamic support apparatus will perform some of the vertical lifting required to transfer the occupant out of the dynamic support apparatus.

As shown, in step 1240 a user may indicate a desire to enter a transfer mode. This may involve a button press, touch gesture on a touch screen, or the like. In some embodiments, this may require a number of different user interactions with a controller. A user may, in some embodiments, need to navigate through a number of menus to reach transfer mode option. A user may need to press a sequence of buttons or a number of buttons simultaneously. In some embodiments, step 1240 may only be completed after a user enters an intermediary mode. This may help to ensure that such a mode is not activated accidentally.

After completion of step 1240, in step 1242 the dynamic support apparatus may prompt a user to confirm that they would like to enter the transfer mode. Such a prompt may be visual, auditory, tactile, or a combination thereof. In one specific embodiment, the controller may beep, light one or more indicator light, and/or display a prompt asking if the user would like to enter the transfer mode. A user may provide suitable confirmation in step 1244. In the event that the user does not confirm (e.g. time out or indicates they do not desire to enter transfer mode) the controller may revert to the mode it was in prior to step 1240.

Once a user has confirmed that they would like to enter transfer mode in step 1244, the controller may inflate the actuators of the dynamic support apparatus in step 1246. In some embodiments, the controller may inflate the actuators of the dynamic support apparatus to the point of turgidity. This may help to lift a user out of a well or depression substantially obviating the need for a user or caretaker to lift the user vertically out of the well. The user may then exit or transfer out of the dynamic support apparatus in step 1248. As the user has already been lifted vertically by the actuators in step 1246, the user may substantially only need to move laterally out of the dynamic support apparatus in step 1248. This may make transferring out of a dynamic support apparatus easier.

After the user has transferred out of the dynamic support apparatus, the user may indicate a desire to power down the dynamic support apparatus in step 1250. The dynamic support apparatus may then power down in step 1252.

Figure 59:
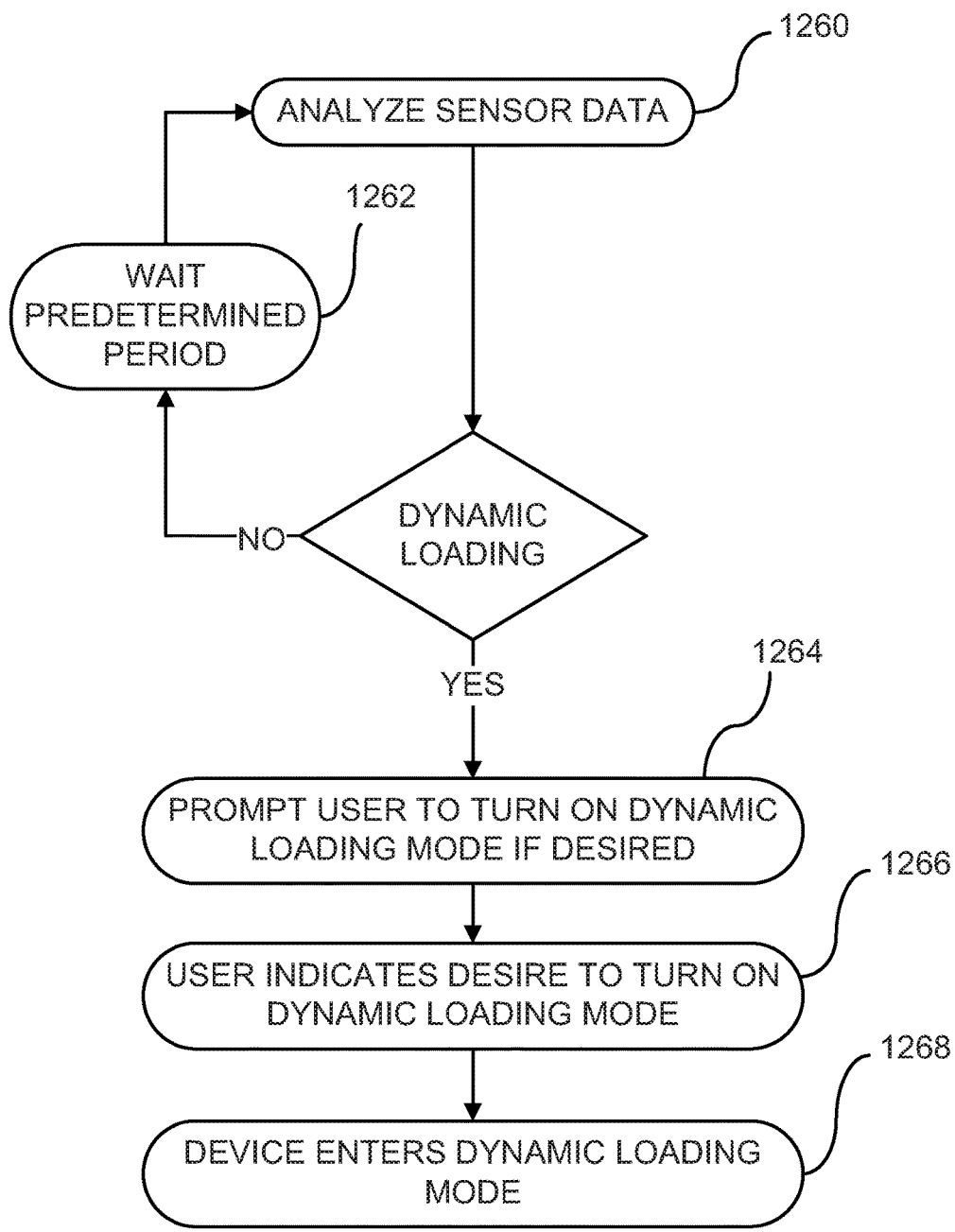
FIG. 59 depicts a flowchart detailing a number of steps which may be used to detect a dynamic loading condition and enter a dynamic loading mode in a dynamic support apparatus in accordance with one embodiment.

FIG. 59 depicts a flowchart detailing a number of steps which may be used by a dynamic support apparatus to determine a dynamic loading condition exists and enter a dynamic loading mode. The flowchart shown in FIG. 59 may begin after the dynamic support apparatus begins a relief regimen. As shown, in step 1260 the controller of the dynamic support apparatus may analyze data from one or more sensors. These sensors may, in various embodiments, be any suitable sensors of the sensors described herein. Using the example of pressure sensors, the controller may monitor for a pressure trend which would be indicative of a dynamic loading condition. Such a condition may, for example, be created as a user rides over uneven surfaces and is jostled about causing pressure in the actuator to spike and fall. In some embodiments, the controller may compare data from a number of different sensors included in a dynamic support apparatus. This may help to increase the accuracy of any determination and may also serve as a cross check for sensor functionality.

In the event that the sensor data analyzed in step 1260 does not indicate that a dynamic loading condition is present, a predetermined wait period may elapse in step 1262. After this predetermined wait period elapses, the controller may return to step 1260 and analyze new sensor data. Upon determination that a dynamic loading condition exists the controller may proceed to step 1264. In alternative embodiments, the controller may wait a predetermine period of time and analyze new sensor data. The controller may then check to ensure that the sensor data is still indicative that the dynamic loading condition exists. This may help to ensure that the controller does not proceed to step 1264 for short-lived dynamic loading scenarios.

In step 1264, the controller may prompt a user to indicate if they would like to turn on a dynamic loading mode. This prompt may be visual, auditory, tactile, or a combination thereof. In one specific embodiment, the controller may beep, light one or more indicator light, and/or display a prompt asking if the user would like to turn on a dynamic loading mode. In step 1266, a user may indicate their desire to enter a dynamic loading mode. This may involve a button press, touch gesture on a touch screen, or the like. The device may then enter the dynamic loading mode in step 1268.

Since a user may be jostled about during a dynamic loading scenario, perfusion in contacting tissues may be stimulated. Such a mode may exploit this by minimizing pump runtime and controller usage to help conserve battery. In some embodiments, a dynamic loading mode may be a mode in which the frequency of relief cycles or duration between steps of a relief cycle is extended in some embodiments. In other embodiments, a dynamic loading mode may be similar to the maintenance mode described above.

Figure 60:
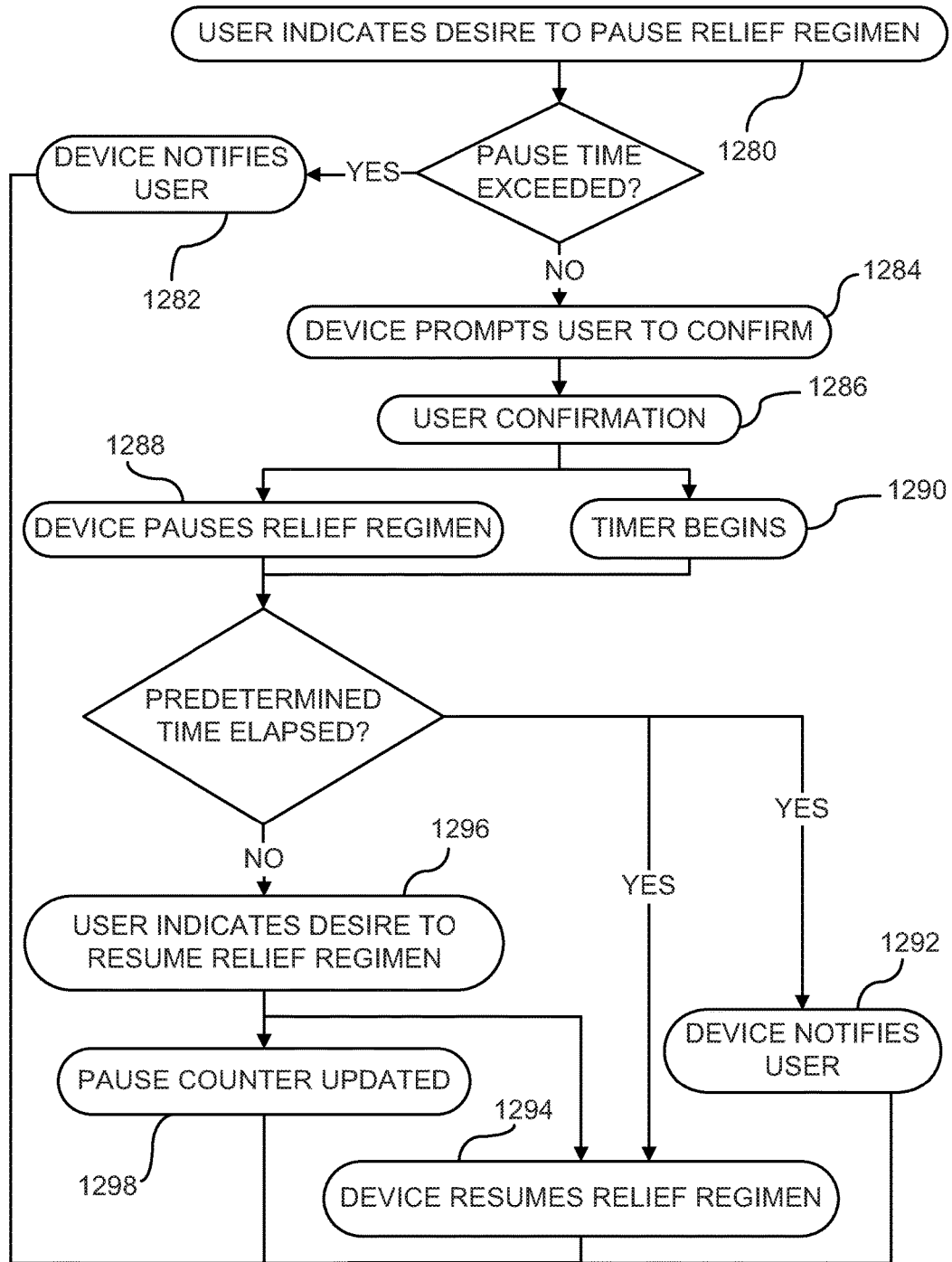
FIG. 60 depicts a flowchart detailing a number of steps which may be used to pause a dynamic support apparatus in accordance with one embodiment.

FIG. 60 depicts a flowchart detailing a number of steps which may be used by a dynamic support apparatus to control pausing of noisy components of such an apparatus. Such components may in various embodiments include pneumatic components of such an apparatus that may making puffing or hissing noises which may be disruptive during various activities (e.g. during a conversation). As shown, the flowchart in FIG. 60 begins after a user has started a relief regimen.

In step 1280, a user may indicate a desire to pause a relief regimen. This may involve a button press, touch gesture on a touch screen, or the like. In some embodiments, a user may pause during other modes of the dynamic support apparatus, such as during a maintenance mode. After a user has performed step 1280, the controller may check to see that a predetermined allotted amount of pause time has not been exceeded. In some embodiments, the allotted pause time may be a predetermined amount or proportion of a predetermined preceding window of time. In the event that the allotted pause time has been exceeded, the dynamic support apparatus may notify the user in step 1282. Alternatively, the dynamic support apparatus may enter a minimally disruptive mode which still conducts relief cycles but minimizes disruption (e.g. by increasing time between cycles or steps of cycles).

In the event that the allotted pause time has not been exceeded, the dynamic support apparatus may prompt the user to confirm that they would like to pause in step 1284. This prompt may be visual, auditory, tactile, or a combination thereof. In one specific embodiment, the controller may beep, light one or more indicator light, and/or display a prompt asking if the user would like to pause. In step 1268, the user may confirm that they would like to pause.

After a user completes step 1268, the dynamic support apparatus may proceed to both step 1228 and 1290. In step 1288, the controller may pause or suspend the pressure relief regimen or other dynamic support apparatus mode. In step 1290 the controller may begin a pause timer.

If the dynamic support apparatus remains paused for more than a predetermined period of time, steps 1292 and 1294 may be performed. The predetermined time may be a predetermined allowable period for a single pause. In some embodiments, the predetermined period of time may be the same as the predetermined period of time checked after step 1280. In some embodiments, the controller may use the shortest of a number of pause time constraints. In some embodiments, the controller may track the amount of pause time over a preceding time window and the amount of time paused during the current pause. When a predetermined limit for either is reached, the controller may perform steps 1292 and 1294.

In step 1292, the controller may notify the user that the predetermined period of pause time has elapsed. In step 1294, the controller may resume the pressure relief regimen. As above, the device may enter a minimally disruptive mode in place of step 1294 in some embodiments.

Before the predetermined period of time has elapsed, a user may perform step 1296. In step 1296, the user may indicate that they would like resume a relief regimen. After completion of step 1296, the controller may proceed to both steps 1294 and 1298. As mentioned, in step 1294, the relief regimen may be resumed by the dynamic support apparatus. In step 1298, the controller may update a pause time counter. This pause time counter may in some embodiments be the pause time counter which is checked after step 1280.

Figure 61:
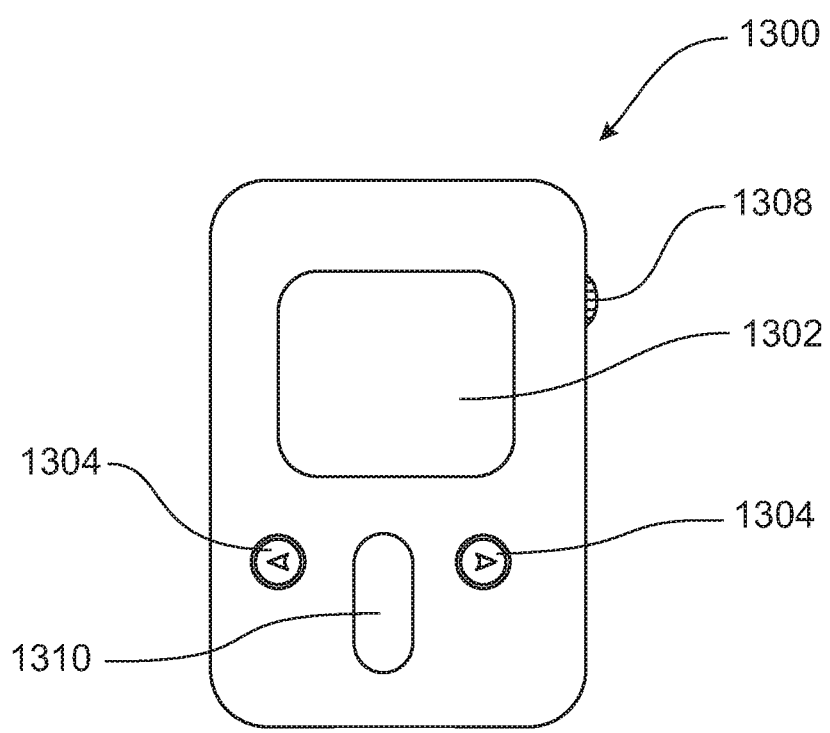
FIG. 61 depicts a remote interface which may be used to control and or configure a dynamic support apparatus in accordance with one embodiment.
Figure 62:
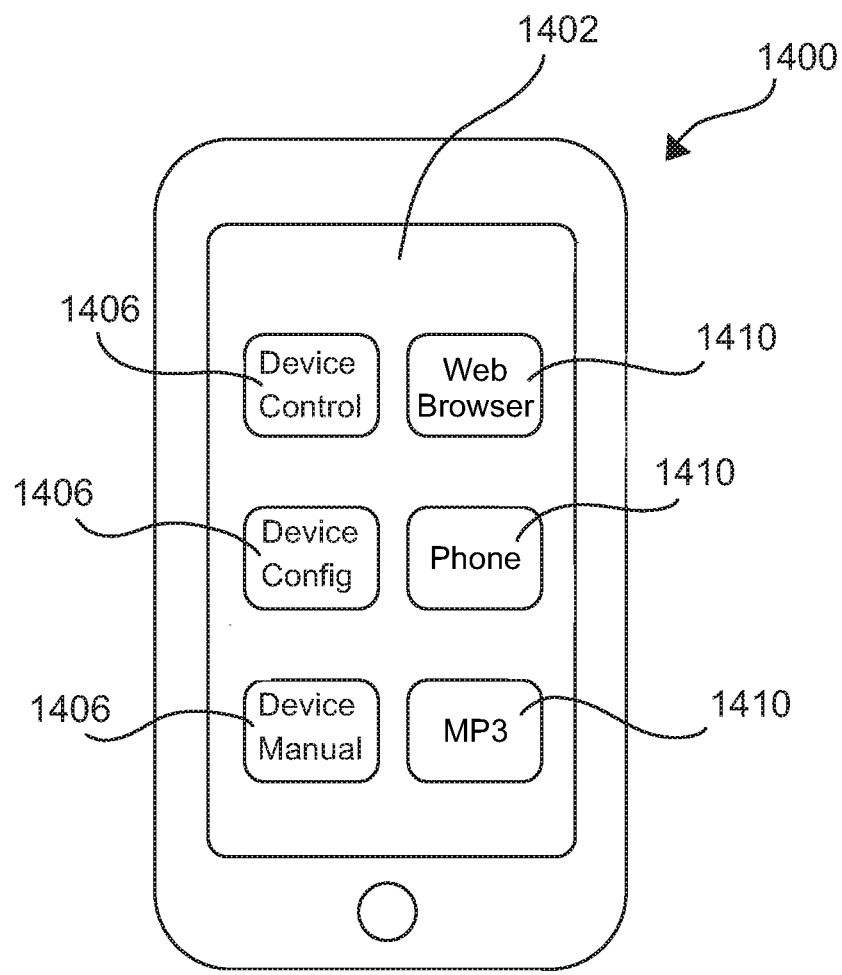
FIG. 62 depicts a remote interface which may be used to control and or configure a dynamic support apparatus in accordance with one embodiment.
Figure 63:
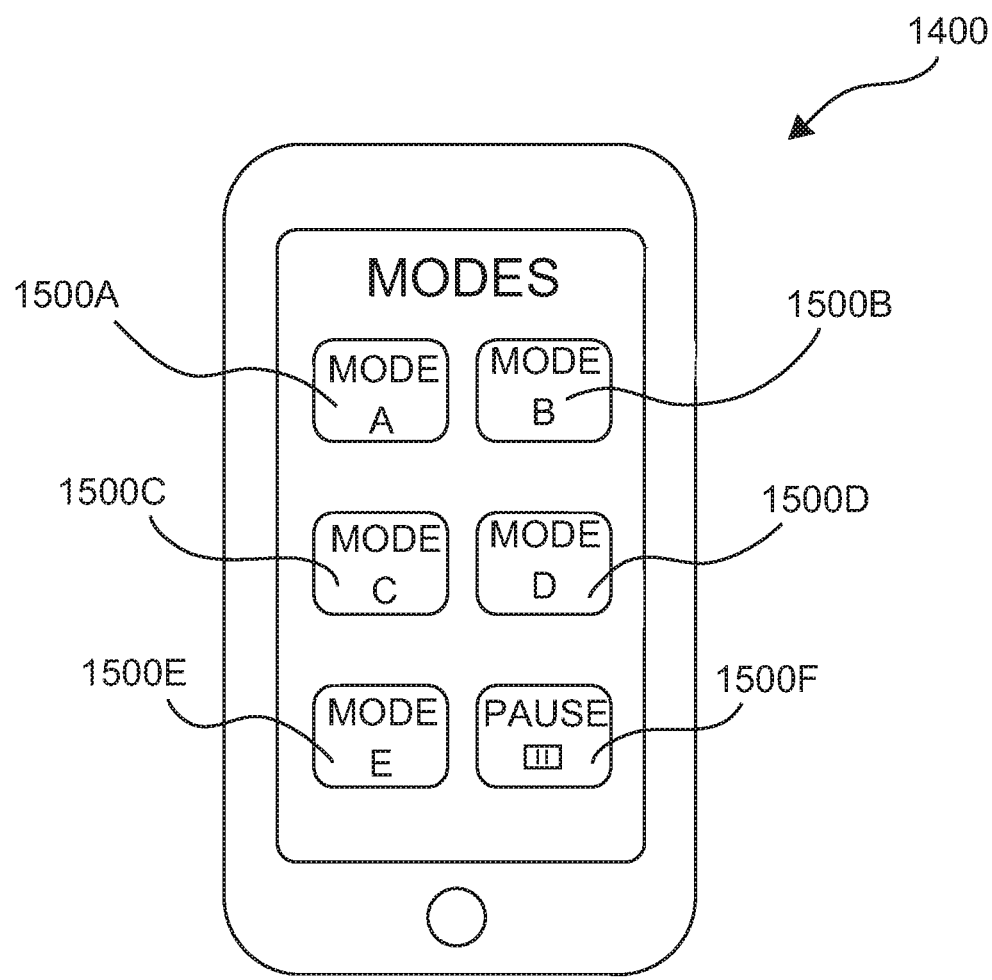
FIG. 63 depicts a remote interface which may be used to control and or configure a dynamic support apparatus in accordance with one embodiment.

Referring now to FIGS. 61-63, in some embodiments the dynamic support apparatus, may be remotely configured and controlled using a remote interface 1300, 1400. When used herein, the term remote interface may refer to any embodiment of a remote interface. A remote interface may be any type of device that is capable of interaction with another device, which may include, but is not limited to, in some embodiments, by way of wireless and/or remote communication. This communication need not be direct. In some embodiments there may be an intermediary component or device which acts as a gateway or relaying component between a remote interface and a device. Additionally, in some embodiments, a device may be configured to be capable of interaction with a number of different remote interfaces. A remote interface may be or may be included as a functionality of, but not limited to, a personal computer, laptop or other portable computer, pda, smartphone, tablet, dedicated remote controller, or the like. Additionally, while some embodiments described herein may be more suitable for particular varieties of remote interfaces, it would be understood by one skilled in the art that such embodiments may be adapted and optimized for use with other varieties of remote interface without departure from the spirit of the disclosure. Likewise, it would be understood by one skilled in the art that the various remote interface screens shown herein may be adapted or optimized for use on an on-board interface for a device such as a dynamic support apparatus.

Two embodiments of remote interfaces are shown in FIGS. 61-63. A remote interface 1300, 1400 may be used to control all, or a portion of, the functionality of a device, which, in some embodiments, may be a dynamic support apparatus such as any of those described herein. In some embodiments a dynamic support apparatus may be configured using a remote interface 1300, 1400. In these embodiments, the dynamic support apparatus may include communications circuitry (not shown) that allows for communication (e.g., wired or wireless) between the dynamic support apparatus or a controller of the dynamic support apparatus and the remote interface 1300, 1400.

Thus, the remote interface 1300, 1400 may be able to remotely control a dynamic support apparatus. Additionally, in some embodiments, the remote interface 1300, 1400 may be able to configure a dynamic support apparatus. In a specific embodiment of the present disclosure, a non-limiting list of possible configurable parameters is shown in Table 1 as follows:

|   | Parameter |
|---|---|
| 1 | Miscellaneous Settings |
| 1.1 | Screen Brightness |
| 1.2 | Screen Dimming |
| 1.3 | Audio Volume |
| 1.4 | Alert Volume |
| 1.5 | Alarm Volume |
| 1.6 | Audio Feedback for Button Presses |
| 1.7 | Vibration On/Off |
| 1.8 | Set Units of Measure |
| 1.9 | Disable/enable Modes or Functionalities |
| 1.10 | Frequency of Pressure Checks in Maintenance State |
| 1.11 | Presentation Type for View Regimen |
| 1.12 | Client/Occupant/User ID |
| 1.13 | Free Text Notes |
| 2 | Configure Regimen |
| 2.1 | Number of Steps Per Cycle |
| 2.2 | Step Duration |
| 2.3 | Number of Actuators |
| 2.4 | Actuator Pressure Set Point(s) |
| 2.5 | Number of Cycles Per Hour |
| 2.6 | Time Waited Between Cycles |
| 2.7 | Time Waited Between Steps |
| 2.8 | Passive or Active Deflate |
| 2.9 | Schedule Regimen? |
| 2.9a | Days of Week for Scheduled Regimen |
| 2.9b | Start Time for Scheduled Regimen |
| 2.9c | End Time for Scheduled Regimen |
| 2.10 | Require Pas scode Before Beginning or Suspending |
| 2.11 | Require Extra Confirmation Before Beginning or Suspending |
| 2.12 | Channel/Port Name/Descriptor |
| 2.13 | Enable/Disable Acutator Channel |
| 2.14 | Actuator Type |
| 2.15 | Actuator Location |
| 2.16 | Order of Step or Inflation |
| 2.17 | Client/Dynamic Support Apparatus Type |
| 2.18 | Repeat Interval/Cycle Duration |
| 2.19 | Step Start Time |
| 2.20 | Step End Time |
| 2.21 | Copy Regimen/Save Regimen as Template |
| 2.22 | Allow Manual Pressure Adjustment During Relief Regimen |
| 2.23 | Swap Settings Between Two Channels |
| 3 | Limits |
| 3.1 | Maximum Pause Length for Individual Pause |
| 3.2 | "X" Pause Time Alloted for "Y" Length Time Window |
| 3.3 | Set Point (e.g. Pressure) High Limit |
| 3.4 | Set Point (e.g. Pressure) Low Limit |
| 3.5 | Time Waited Between Cycles Limit |
| 3.6 | Time Waited Between Steps Limit |
| 3.7 | Step Duration Limit |
| 3.8 | Cycle Duration Limit |

The remote interface 1300, 1400 may in some embodiments include a display assembly 1302, 1402, any of a variety of other output assemblies, at least one input assembly, and communications circuitry (not shown). The at least one input assembly may include, but is not limited to, one or more of the following: an input control device such as jog wheel 1306, slider assembly 1310, touch screen, buttons/switches 1304, or another conventional mode for input into a device. In embodiments having a jog wheel 1306, the jog wheel 1306 may include a wheel, ring, knob, ball, or the like, that may be coupled to a rotary encoder, or other rotation sensor, for providing a control signal based upon, at least in part, movement of the wheel, ring, knob, or the like. In embodiments including a slider 1310, the slider 1310 may be a touch sensitive, capacitive slider. A slider 1310 may be vertically oriented (as shown), horizontal, arcuate, circular, ovoid, etc. In other embodiments, a touch sensitive pad may be used in place of or in addition to a slider 1310.

In some embodiments, the remote interface may include a touch screen. The touch screen may be any suitable variety of touch screen (e.g. a capacitive touch screen). In some exemplary embodiments, as depicted in FIGS. 62 and 63, the display assembly 1402 may be a touch screen and may include one or more icons or touch sensitive buttons 1406, 1410 assigned to functionalities of the remote interface 1400. In some embodiments, one or more of the icons 1406, 1410 may relate to launching applications configured to communicate with a device such as the dynamic support apparatus. In some embodiments, one or more icons 1406 may indicate one or more device(s) which may be controlled via the remote interface. As shown in FIG. 62, in some embodiments, one or more icon 1406 may be assigned to specific individual device applications. For example, an icon 1406 may be assigned to a device controller application, while another may be assigned to a device configuration application, yet another may be assigned to a device user manual application, and so on. Various applications may be opened by a user in response to user input. In the embodiment in FIG. 62, this input may be a touch gesture on the touch screen.

In various embodiments, less than or more than three icons 1406 may be included on the remote interface 1400. Additionally, in some embodiments, certain icons or functionalities may not be included for certain users. In some embodiments, an occupant may only be able to launch a device controller application and view the device manual. A technician or clinician may be able to launch a device configuration application.

In some embodiments, the remote interface 1400 may be a dedicated remote interface. That is, the remote interface 1400 may solely serve as a remote interface for a device such as a dynamic support apparatus. In some embodiments, however, a remote interface 1400 may be a non-dedicated component. In the embodiment in FIG. 62, the remote interface 1400 includes icons 1410 for launching applications related to additional, non-device related, functionalities of the remote interface 1400. In some embodiments, the remote interface 1400 may have an emergency or help functionality. Such a functionality may be used to connect a user to a caregiver or inform a caregiver that the user requires some sort of help or aid. In some embodiments, these additional functionalities may include, but are not limited to, launching a web browser, launching a cell phone or mobile phone functionality and/or launching an audio player or other media player functionality.

In some embodiments, it may be desirable for the user to interact with the remote interface 1400 to "launch" various functions and/or applications of the remote interface 1400. In some embodiments, non-device related functionalities may be dormant and/or may "sleep" until and unless launched. This may be desirable for many reasons, including, but not limited to, extending the battery life, preventing distraction, and/or optimizing performance. In some embodiments, the remote interface 1400 may indicate that an "application" is "minimized" or "hidden" on the display 1402, but application still running or active. In some embodiments, once a device is paired or associated with the remote interface 1400, an application may be automatically launched. Thus, in some embodiments, launching of applications related to a device using an icon 1406 may not be necessary and may instead be automatic once the remote interface 1400 is paired with the device.

Referring to FIG. 63, in some embodiments, a remote interface 1400 may include various buttons on the display assembly that may be used to control behavior of a device such as a dynamic support apparatus. Such a screen may, for example, be navigated to by selecting or tapping one of the icons 1406 shown in FIG. 62. In the embodiments shown in FIG. 63, a number of user selectable modes 1500A-F appear as buttons on the display. These modes may identify specific device behaviors. In some embodiments, a pause button 1500f is shown in addition to buttons for Modes A-E 1500A-E. In some embodiments of the dynamic support apparatus, each mode may be associated with a predefined relief pattern or regimen the dynamic support apparatus may employ. The user may interact with one of the buttons (e.g. with a touch gesture) to indicate that they would like a device to behave as defined by the desired mode.

As mentioned above, the modes available may be defined for a variety of different user activities or activity levels. In some embodiments, there may be modes for one or more of, but not limited to, the following: stationary or no activity, low activity, medium activity, high activity, maintenance mode, transfer mode, dynamic loading mode, etc. Each mode may be individually refined to meet the specific needs of a user. The user may select a mode which best fits anticipated or current activity.

In some embodiments, such a screen may not be used for selecting a device behavior but rather editing and creating relief regimens or behavior modes for the device. In some embodiments, selection of one of the selectable modes, may open the mode for review. In this mode, the user may be able to see the values for the various parameters that define the behavior mode. In some embodiments, the user may also be able to edit parameters of a mode once the mode is open for review.

In various embodiments, a dynamic support apparatus may include the ability to pre-program user profiles, relief regimens, schedules, etc. In some embodiments, this may be accomplished via a remote interface 1400 or other interface. In such embodiments, a user may program one or more specific mode or relief regimen to automatically begin based upon a defined schedule. It may, for instance, be desirable to program a stationary or low activity mode to automatically be employed during a user's normal work hours.

During use, in some embodiments, a remote interface 1300, 1400 may communicate with a dynamic support apparatus using a wireless communication channel. Such a channel may be established between remote interface 1300, 1400 and dynamic support apparatus by a user in some embodiments. The user may use the remote interface 1300, 1400 to program/configure a dynamic support apparatus. In some embodiments, some or all of the communication between remote interface 1300, 1400 and dynamic support apparatus may be encrypted.

In various embodiments of the user interface, the user interface may require user confirmation and/or user input for some or all commands, programming and configuration changes, etc. given and made using the user interface. In some embodiments, the user interface may emphasize ensuring a user knows the effect of various interactions with the dynamic support apparatus. In such embodiments, the device may communicate the result of the user's actions to the user. Such features help to ensure the user understands their actions. One such example may be in the event that a user presses a back button on a screen when changes have been made but not saved or implemented. The user interface may display a confirmation screen which reads "Cancel Changes?". If the user selects "Yes", in various embodiments any pending changes may be discarded, the confirmation screen may be dismissed and the user interface may display the previous screen. When the user selection is "No", on the confirmation screen, the confirmation screen may be dismissed and the user interface may again display the screen with pending change(s). In some embodiments, the pending change(s) may, for example, be highlighted to draw the user's attention. This feature may help mitigate the chance that a user assumes changes have been implemented, when in fact, they have not. This is just one of many examples of the user interface requiring user confirmation and/or input. Similar user confirmation or additional user input may be required on a number of other screens or for a number of other user interactions.

Figure 64:
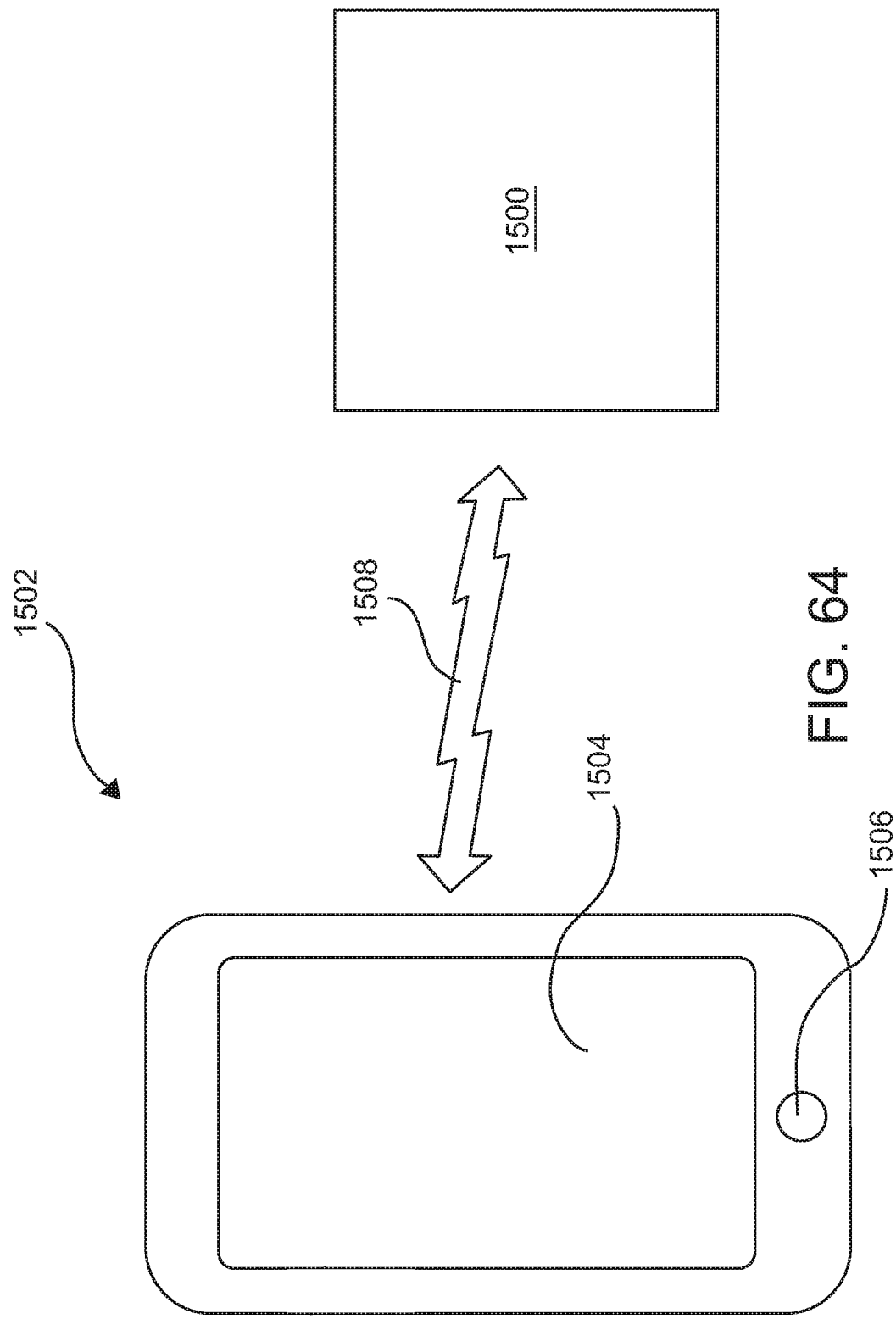
FIG. 64 depicts a remote interface which is in wireless communication with a dynamic support apparatus in accordance with one embodiment.

Additionally and referring also to FIG. 64, in some embodiments of a device such as a dynamic support apparatus 1500 may be configured by a remote interface 1502. In some embodiments, the device 1500 and remote interface 1502 may include communication circuitry (not shown) that allows for communication (e.g., wired or wireless) between the device 1500 and at least one remote interface 1502. Thus, the remote interface 1502 may remotely communicate with the device 1500. The remote interface 1502 may be capable of communicating with the device 1500 and may include, in some embodiments, a display assembly 1504 and at least one input assembly 1506. The input assembly 1506 may include at least one switch assembly in some embodiments. In some embodiments, the input assembly 1506 may be any of one or more of the input assemblies described above.

The remote interface 1502 may include the ability to command the device and/or to receive information from the device. In some embodiments, the remote interface 1502 may include the ability to view history, receive and view alarms, control a device 1500, program configurations (e.g. configure relief regimens), establish user preferences, and/or enable and disable various functionalities for a specific user. In some embodiments, the remote interface 1502 may allow the user to view the status of a device 1500 which may include the power status, alarm status, device 1500 status, and/or any other data that may be communicated from the device 1500 to the remote interface 1502.

In some embodiments, the remote interface 1502 may provide instructions to the device 1500 by way of a communication channel 1508 established between the remote interface 1502 and the device 1500. In some embodiments, the communications channel 1508 is depicted as a wireless communications channel. In other embodiments, the communications channel 1508 may be a wired communications channel. Via the communications channel 1508, a user may use the remote interface 1502 to program/configure the device 1500. Some or all of the communication between remote interface 1502 and the device may be encrypted. Any suitable encryption scheme may be used. Additionally, any suitable communications protocol may be used. Communication between the remote interface 1502 and the device 1500 may be accomplished utilizing a standardized communication protocol. Further, in some embodiments, communication between the various components included in a device 1500 may be accomplished using the same protocol.

In some specific embodiments, the remote interface 1502 and the device 1500 may communicate via RF and may utilize an ISM band such as the 2.4 Ghz band. Any suitable RF communications protocol may be used. In various embodiments, Bluetooth, Zigbee, MiWi, or another suitable RF communications protocol may be used. In some embodiments, each of the remote interface 1502 and the device 1500 may include a processor dedicated to radio communication. Additionally, each of the remote interface 1502 and the device may include one or more additional processor which may perform other processing tasks.

Figure 65:
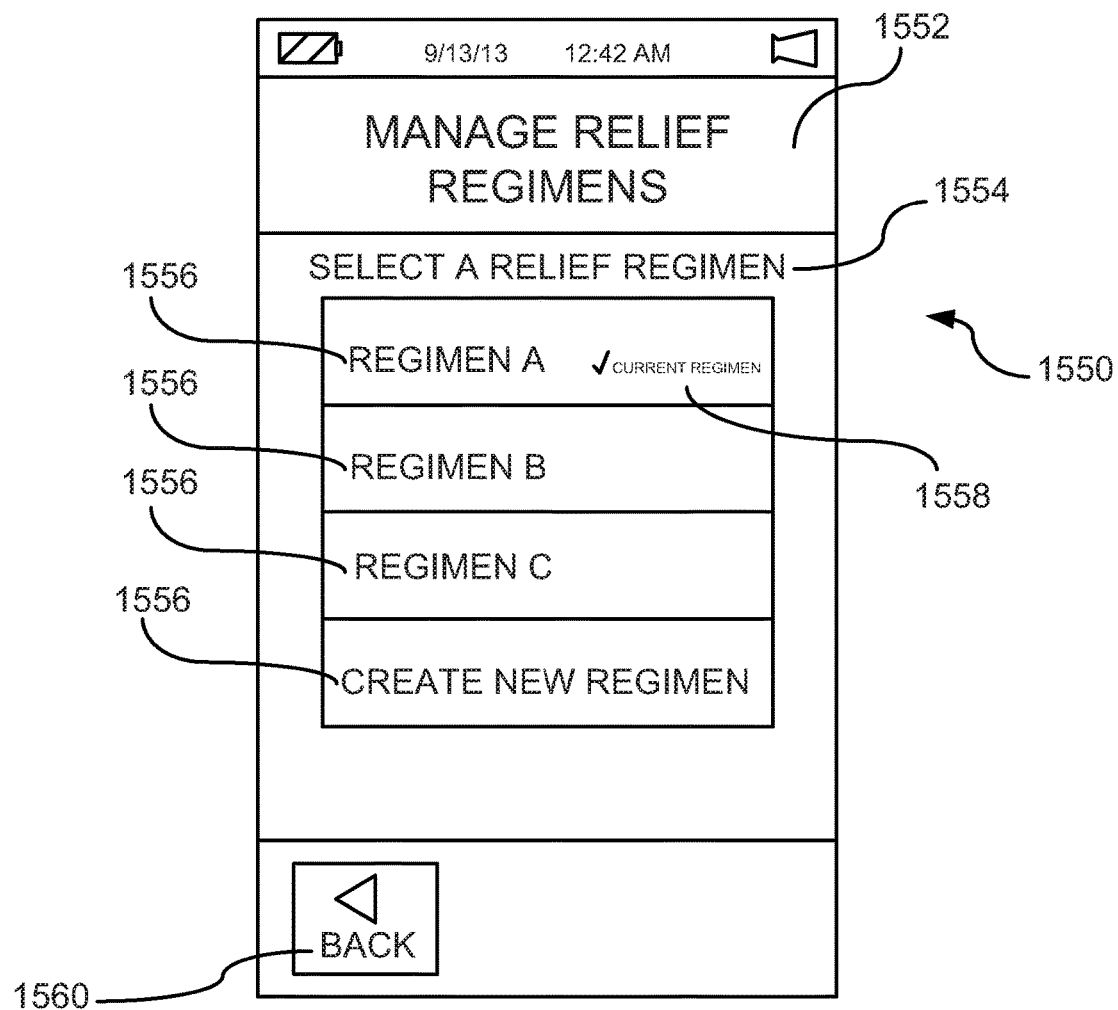
FIG. 65 depicts a screen which may be displayed on a remote interface for a dynamic support apparatus in accordance with one embodiment.

FIG. 65 depicts a screen 1550 which may be displayed on a remote interface. As shown, the screen 1550 may be used by a user to select a relief regimen to be used by a dynamic support apparatus. In various embodiments, such a screen 1550 may be displayed in response to a user selecting or launching a device controller application or selecting a mode such as any of those shown in FIG. 63. Alternatively, such a screen 1550 may be used for editing a relief regimen and may be launched in response to a user selecting a device configuration application or selecting a mode such as any of those shown in FIG. 63.

The screen 1550 may include a heading 1552 which is indicative of the screen's purpose and may indicate what the screen 1550 may be used for. In some embodiments, the heading 1552 reads "Manage Relief Regimens". Additionally, the screen 1550 may include a sub heading 1554 which may provide some instruction to the user on how to interact with the screen 1550. In some embodiments, the sub heading 1554 reads "Select a Relief Regimen". Headings 1552 and sub headings 1554 may be used on various screens of the user interface to make various screens and their usage unambiguous and self explanatory.

A number of boxes 1556 appear on the screen. In FIG. 65, each box 1556 is associated with a relief regimen. In various embodiments, boxes 1556 may not be used. Instead, any other shape or suitable arrangement may be used. The same is true of other embodiments described as having boxes.

As shown in FIG. 65, there are three boxes 1556 labeled regimen, A-C. A user may select the desired relief regimen by an interaction with the user interface. In some embodiments, this interaction may be one or more touch gesture. Once a regimen has been selected, an indicator 1558 may be displayed in association with it. The indicator 1558 may serve to visually convey to the user which of the displayed relief regimens is currently being employed or executed. In some embodiments, as shown, the indicator 1558 in the screen is a checkmark next to the text "Current Regimen". In other embodiments, the active regimen may be displayed in a different color, may be shown in an enlarged box, may be shown in a different or larger font, etc. Additionally, in some embodiments, additional descriptive information may be included and associated with each regimen. Such information may describe the relief regimen or may indicate what type of user activity the regimen would be appropriate for. In alternate embodiments, selecting a relief regimen may open the relief regimen for review and/or editing.

Also shown in the screen in FIG. 65 is a box 1556 which may allow a user to create a new relief regimen. The text in this box 1556 reads "Create new regimen". This box 1556 may be selected by a user interaction with the user interface. In some embodiments, this option or box 1556 may only be included for certain users. For example, such an option may only be available for clinicians. By selecting this option, a user may be able to create a new relief regimen that may be employed by a dynamic support apparatus. A back button 1560 is also included in the screen 1550. This back button 1560 may be used to return to a previous screen.

Figure 66:
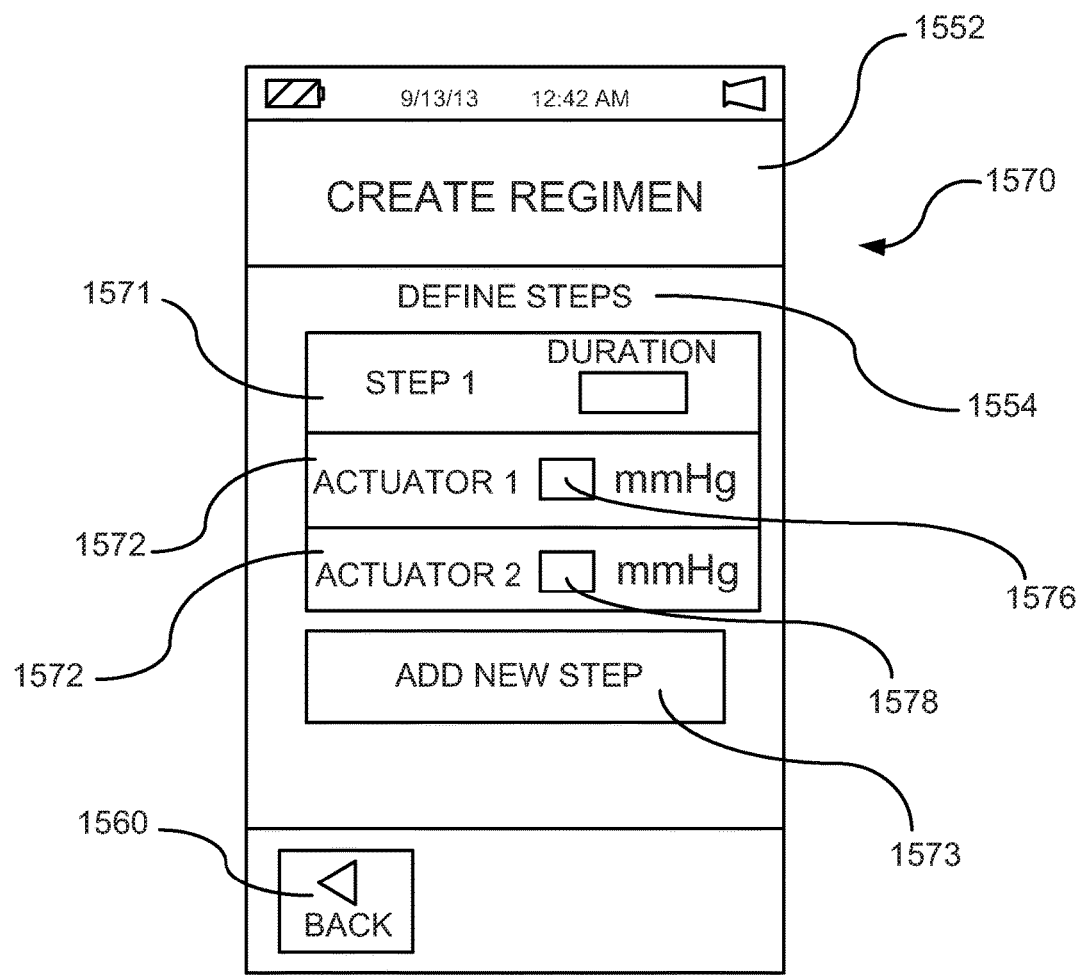
FIG. 66 depicts a screen which may be displayed on a remote interface for a dynamic support apparatus in accordance with one embodiment.

FIG. 66 depicts a screen 1570 which may be displayed on a remote interface. As shown, the screen 1570 may be used by a user to create a relief regimen which may be used by a dynamic support apparatus. In various embodiments, such a screen 1570 may be displayed in response to a user selecting the "Create new regimen" option on the screen 1550 shown in FIG. 65.

As shown, the screen 1570 in FIG. 66 includes a heading and sub heading. The heading 1552 and sub heading 1554 respectively may describe what the screen 1570 may be used for and what the user is required to do on the screen 1570. Additionally, as in FIG. 65, a back button 1560 is included.

As shown, a number of boxes 1571, 1572, 1573 appear on the screen 1570. One box 1571 identifies the step number. The step number may indicate which step of a relief cycle the user is editing. As described elsewhere herein, a relief regimen may consist of a number of different steps which may repeat on a cyclical basis. At each step, a dynamic support apparatus may inflate actuators to different pressures. Additionally, within each step, various actuators included in a dynamic support apparatus may be inflated to different pressures. As shown, the box 1571 identifying the step number includes a parameter field 1574. The parameter field 1574 in some embodiments may be used to define a duration for the step.

To define the set point for the various actuators of the dynamic support apparatus for a desired step, a user may interact with set point boxes 1572 for each of the actuators in the dynamic support apparatus. For each step, the user interface may display corresponding boxes 1572 for each actuator included in a dynamic support apparatus. In some embodiments, the dynamic support apparatus only includes two actuators. In alternate embodiments, a dynamic support apparatus may include any number of actuators.

As shown, the user may enter a value in the parameter field 1576, 1578 associated with each of "Actuator 1" and "Actuator 2". This value may be limited to a predefined unit of measurement, which in some embodiments is mmHg. In some embodiments, the user may be able to select between a number of units of measurement (e.g. psig, mmHg, etc.). It should be noted that the actuator names in the screen 1570 represent one embodiment. In various embodiments, the names may be indicative of the spatial orientation actuators in the dynamic support apparatus and one or more may vary. In some embodiments, the actuator set point boxes 1576, 1578 may identify a "Right Actuator", "Left Actuator", and "Sacral Actuator".

To help minimize confusion, the actuator set point boxes 1572 are connected to the step number box 1571. Other steps or boxes may be separated from boxes associated with an individual step by a space or gap. Additionally, the set point boxes 1572 are indented from the step number box 1571. This may help to further indicate that the set point boxes 1572 are associated with the step number box 1571. In some embodiments, a user may collapse and expand various steps. In some embodiments, when a step is in a collapsed state, only the step number box 1571 for that step may be visible. In expanded state, the set point boxes 1572 may also be displayed. In such embodiments, the step number box 1571 may include an icon or the like (not shown) which a user may interact with to toggle between an expanded and collapsed state. Such a feature may be useful in minimizing clutter and optimizing usage of screen real estate.

Also depicted in the screen shown in FIG. 66 is an "Add New Step" box 1573. As shown, this box 1573 is separated from the boxes 1571, 1572 associated with step 1 by a gap. This may aid in minimizing any possible confusion. This box 1573 may be used to add a step to a relief regimen. When a user interacts with this box 1573, a new set of boxes may appear on the screen. These boxes may include a step number box for the new step and associated actuator set point boxes for the new step. These new boxes may appear beneath the last existing step in a relief regimen. In the event that all steps do not fit on the screen at one time, a user may navigate through the list of steps using a scroll bar, search feature, swipe gesture, etc. A user may add and define the required information for as many steps as is necessary to completely define the desired relief regimen.

In some embodiments, a user may be capable of copying a pre-existing relief regimen when creating a new relief regimen. This may be desirable if the new relief regimen will be similar to a pre-existing relief regimen. In some embodiments, it may be desirable to have a regimen with the same number of steps and actuator set points, but different durations for each step. Thus, copying a pre-existing relief pattern may allow a user to more efficiently create relief regimens. In some embodiments, a copy button or the like may be present for this purpose. In some embodiments, a screen which may be used to create a relief regimen may include a button to save the relief regimen once the relief regimen has been fully defined by the user. Additionally, in some embodiments, a user may create a new relief regimen by opening a pre-existing template relief regimen.

Figure 67:
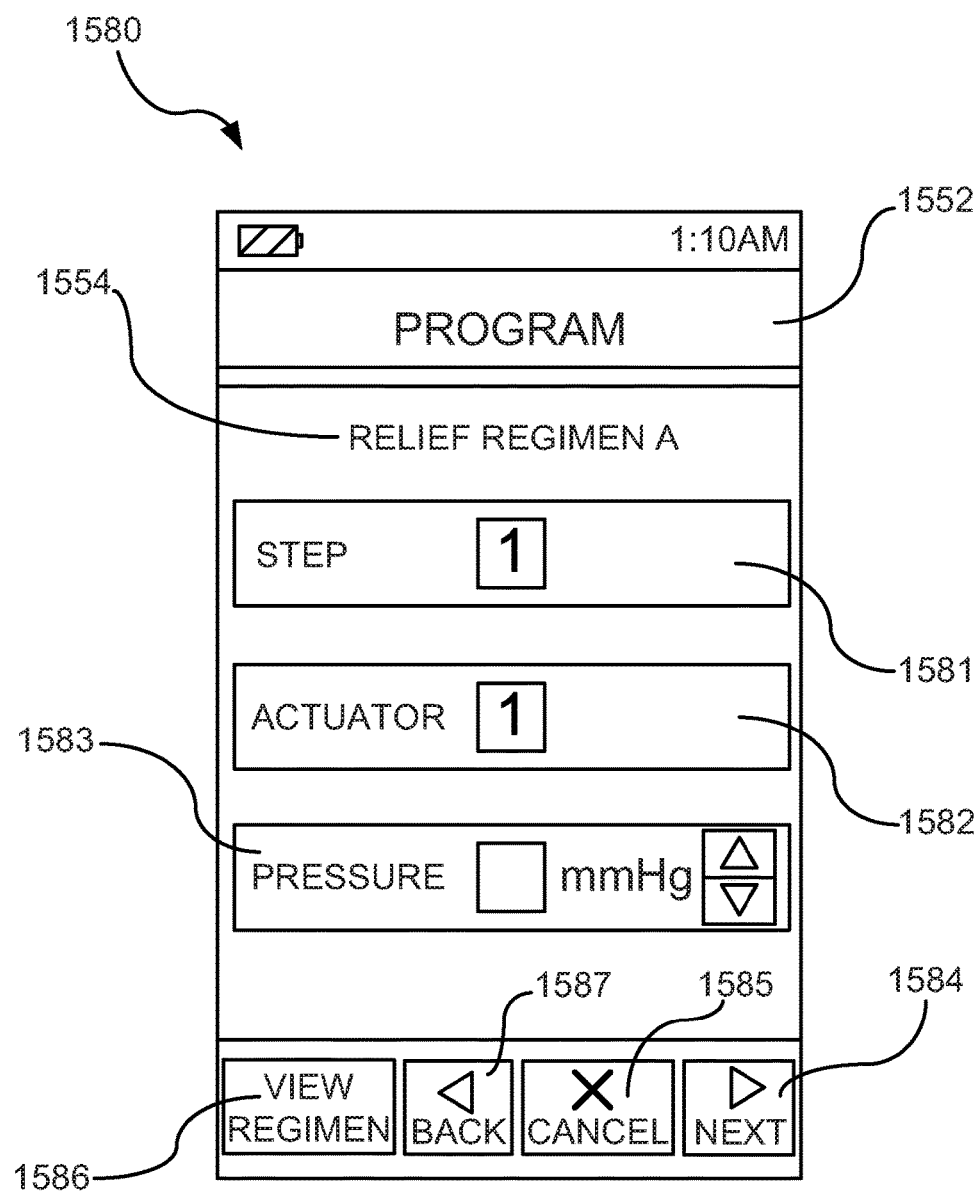
FIG. 67 depicts a screen which may be displayed on a remote interface for a dynamic support apparatus in accordance with one embodiment.

FIG. 67 depicts another screen 1580 which may be displayed on a user interface for a dynamic support apparatus. The screen 1580 may be an alternative screen which may be used to configure a relief regimen. In various embodiments, such a screen 1580 may be displayed in response to a user selecting the "Create new regimen" option on the screen 1550 shown in FIG. 65.

As shown, the screen 1580 includes a heading 1552 and sub heading 1554 which indicate what the screen 1580 is used for. As shown, the screen 1580 includes a number of boxes 1581, 1582, 1583. A step number box 1581 is included in some embodiments. Additionally, an actuator number box 1582 and a pressure box 1583 are included in the screen 1580. A user may use these boxes 1581, 1582, 1583 to define various set points for various actuators for each step in a relief regimen.

Some of the boxes 1581, 1582, 1583 may include an up and down arrow or selector in some embodiments. In the embodiment shown in FIG. 67, the pressure box 1583 includes an up and down arrow. The up and down arrows may be used to define the pressure parameter for an actuator. In some embodiments, once a pressure has been set, a user may interact with a next button 1584. This may cause the user interface to present a new relief regimen configuration screen for the step which may be used to set the pressure set point for the next actuator. If pressure set points for all actuators have been defined for a given step, interaction with a next button 1584 may cause a new step to be added. A new configuration screen allowing a user to configure an actuator set point for that step may then be displayed. The user may continue defining set points for actuators until a desired relief regimen has been completely defined.

In some embodiments, the next button may be disabled or not displayed until all required fields have been defined. Alternatively, if a user attempts to use the next button without defining all required fields, the user interface may draw the user's attention to an incomplete field. In some embodiments, this may involve highlighting or otherwise indicating which fields are incomplete. In other embodiments, the user interface may automatically open the incomplete field for editing.

As shown, a cancel button 1585 is shown in the screen in FIG. 67. The cancel button 1585 may be used to cancel configuration of a new relief regimen. The cancel button 1585 may, in some embodiments, bring a user back to a home screen or other preceding screen. Additionally, a view regimen button 1586 is shown in FIG. 67. This button 1586 may be used to view a visual representation of the relief regimen. Such a visual representation may be a relief regimen graph such as an actuator pressure over time plot. Such a relief regimen graph is further described later in the specification. A back button 1587 is also shown in the screen 1580. A back button 1587 may be used to re-open a previously defined step of a relief regimen for editing. In some embodiments, additional or different buttons may be included. In some embodiments, a "Done" or "Finish" button may be included to indicate that a user has finished defining the desired number of steps for a relief regimen.

Figure 68:
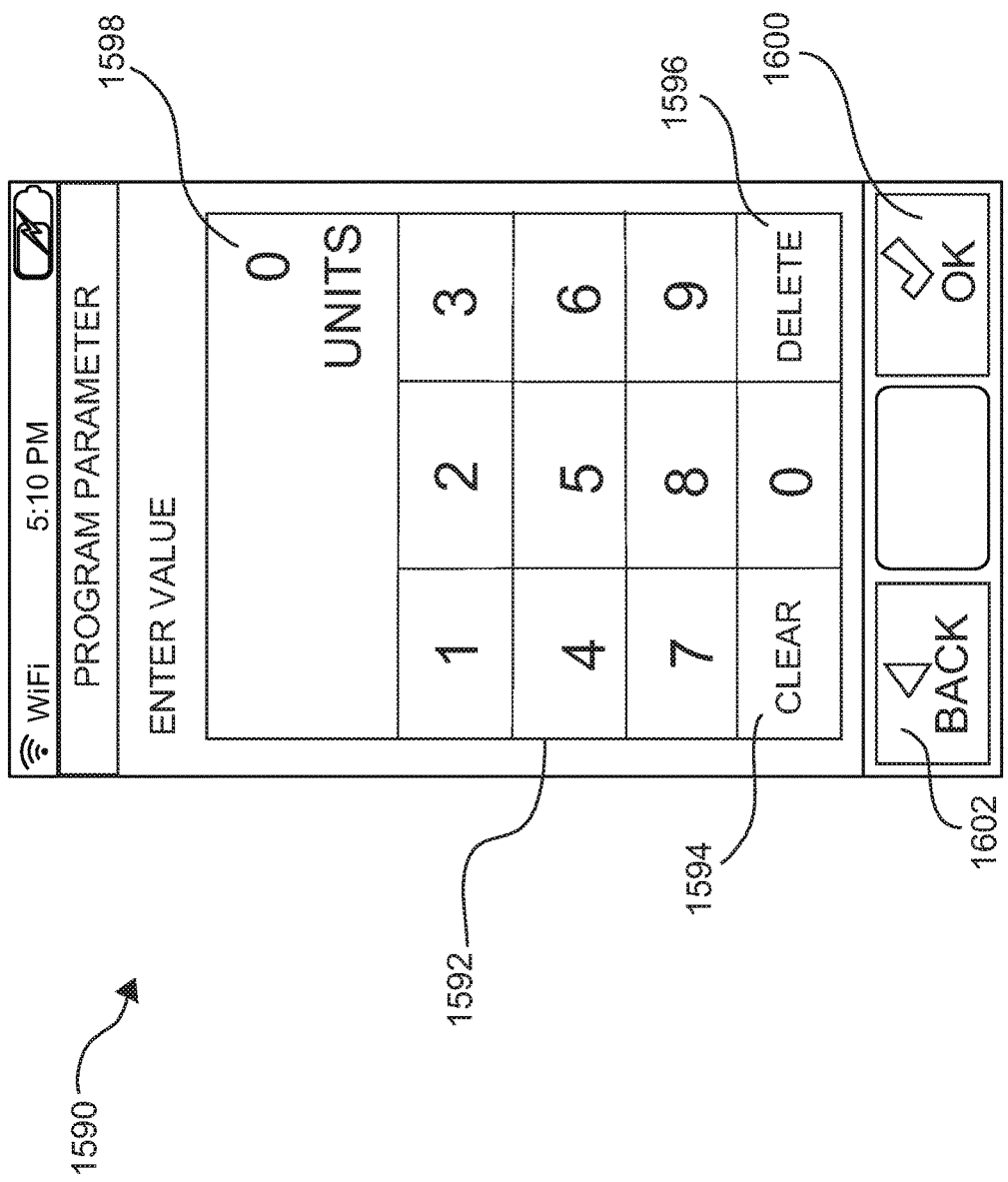
FIG. 68 depicts a screen which may be displayed on a remote interface for a dynamic support apparatus in accordance with one embodiment.

FIG. 68 depicts a screen 1590 which may be used to input a parameter value. As shown, the screen 1590 includes a numeric keypad 1592. The keypad 1592 may be used to select values for the parameter. As shown, the keypad 1592 also includes a clear button 1594 and a delete button 1596. The clear button 1594 may be used to clear any value entered on the screen 1590. The delete button 1596 may be used to delete the previous value entered on such a screen. There may also be a parameter value field 1598 which displays the value entered using the keypad 1592. In some embodiments, this field 1598 is directly above the keypad 1592. Additionally, this field 1598 may include an indication of the units of measure for that value. Once a user has finished entering the desired value, the user may use the OK button 1600 to accept the value and continue editing and creating a relief regimen in some embodiments. If the user desires to abort entering the value, the back button 1602 may be used. In some embodiments, or for some parameter fields (e.g. relief regimen name), an alpha-numeric or alphabetic keyboard may also or instead be displayed. In some embodiments, a user may use one or more other type of input device to enter values. In some embodiments, a keyboard and mouse, for example, may be used.

Figure 69:
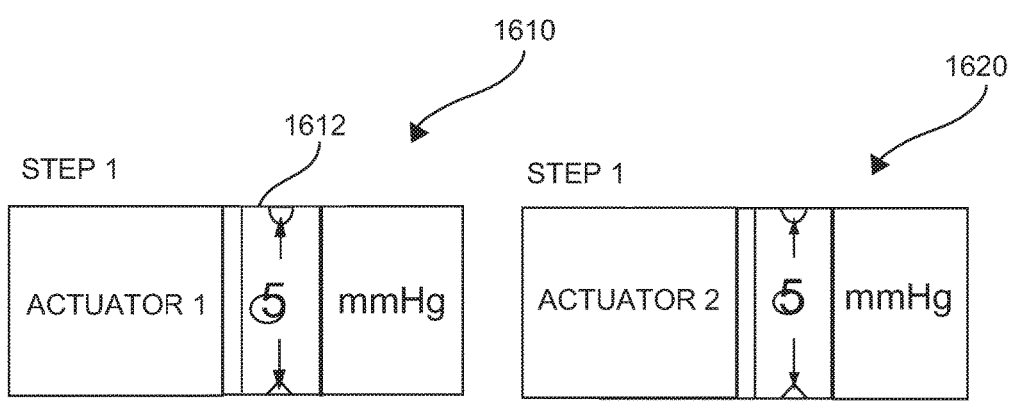
FIG. 69 depicts a screen which may be displayed on a remote interface for a dynamic support apparatus in accordance with one embodiment.

FIG. 69 depicts another user interface screen 1610 which may be used to edit and/or define a relief pattern. As shown, the screen 1610 may include an indication of the current step number. In FIG. 69, the step number shown is step one. The screen 1610 also indicates which actuator the user is editing the set point of. In the screen 1610, the user is editing the set point for actuator 1. As shown, the screen includes a column 1612 in which the user may define the desired actuator set point parameter. The user may define a value for the set point by a vertical or up/down swipe within the bounds of this column 1612.

A downward swipe may cause the value to increase while an upward swipe may cause the value to decrease. In some embodiments, a downward swipe may cause a number to gradually move toward and then off the bottom of the screen (such that it is no long visible) and cause a number to gradually appear from the top of the screen and gradually move toward the bottom of the screen. An upward swipe may cause a number to gradually move toward and then off the top of the screen (such that it is no long visible) and cause a number to gradually appear from the bottom of the screen and gradually move toward the top of the screen. This gradual movement may be incremental or smooth in various embodiments. When a user removes their hand from the screen after making a swiping gesture, the value closest to the center of the screen may become the new value for the parameter.

In the some embodiments, the bounds of the parameter column 1612 are shown on the screen 1610. In other embodiments, the bounds of the column 1612 may not be displayed on the screen 1610. The screen also includes an indication of the unit of measure for the parameter being defined.

Once a user has finished defining an actuator set point the user may continue to define other actuator set points and create other steps. In the example embodiment, this may be accomplished with a horizontal or sideways swipe on the screen. As shown, in some embodiments, the representational hand 1614 is indicated to be swiping to the left of the screen. Such a swipe may cause a new screen to gradually appear from the right of the display, in some embodiments. This may give the impression to the user that the user is dragging or pulling the new screen onto the display. Once the screen has been dragged a predetermined amount onto the display, the values for the previous screen may be saved and the new screen may take the place of the previous screen on the display. In some embodiments, the representative hand 1614 may be provided on the screen to indicate to a user how they may interact with the screen 1610.

Figure 70:
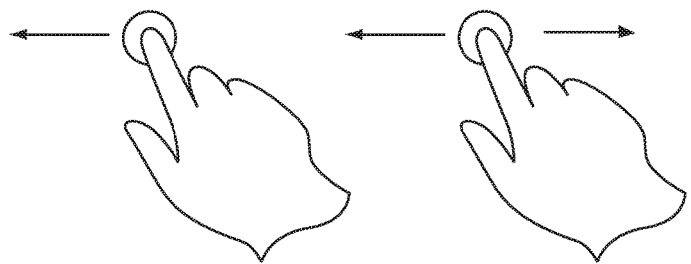
FIG. 70 depicts a screen which may be displayed on a remote interface for a dynamic support apparatus in accordance with one embodiment.

FIG. 70 depicts another user interface screen 1620 which may be used to edit and/or define a relief pattern. This screen 1620 may be the screen which would be dragged onto the display after a user has finished defining the actuator set point in FIG. 69. As shown, this screen 1620 is similar to FIG. 69; however, it allows a user to set the actuator set point for actuator 2 in step 1. In some embodiments, a user may set the set points for all actuators in a given step on a single screen before swiping to the next screen. Once all actuator set points for a given step have been defined, swiping to the left of the display may cause a new step to be added to the relief regimen. The screen which is dragged onto the display may then allow a user to define various set points for the new step.

As shown in FIG. 70, the user may swipe to the left of the screen 1620 as well as the right of the screen 1620. Swiping to the right of the screen 1620 may cause the previous screen to gradually appear from the left of the display in some embodiments. This may give the impression to the user that the user is dragging the previous screen back onto the display. Once the previous screen has been dragged onto the screen a predetermined amount it may replace the current screen on the display. This may allow a user to navigate through various steps and set points when creating a relief regimen.

In some embodiments, if a user attempts to swipe to the next screen without filling out a required field (e.g. actuator set point), the user interface may not allow the new screen to replace the current screen on the display. Additionally, the user's attention may be called to the required field which has not been filled out on the current screen. In some embodiments, there may be a button or the like on the display to indicate that the user is finished creating or editing the desired relief regimen. Alternatively or additionally, a user may define the number of steps they would like to include in the relief regimen before creating the relief regimen. Once a user has swiped through and defined values for each step, the relief regimen may be saved and the relief regimen editor may be exited on the user interface. In some embodiments, a home screen or the like may be displayed after a user has completed the editing a relief regimen.

Figure 71:
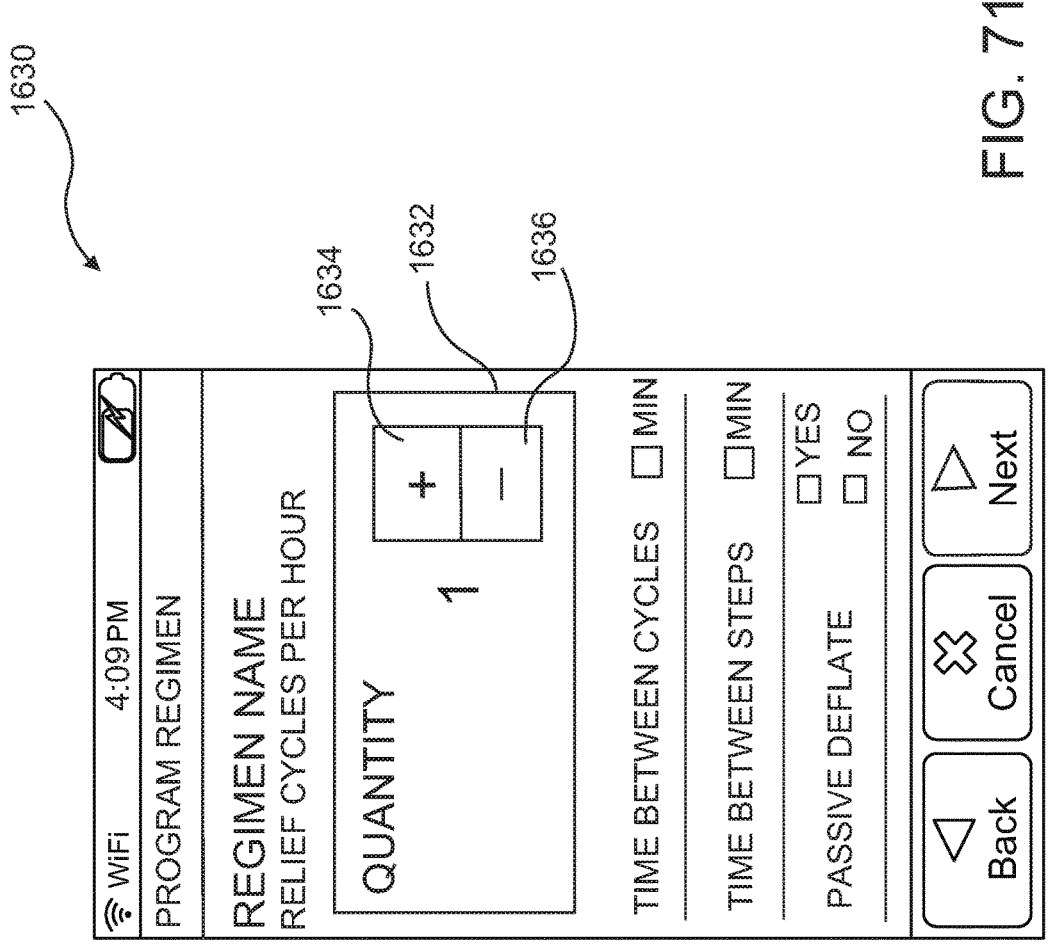
FIG. 71 depicts a screen which may be displayed on a remote interface for a dynamic support apparatus in accordance with one embodiment.

FIG. 71 depicts another screen 1630 which may be displayed on a user interface for a dynamic support apparatus. The screen 1630 may be used to configure a relief regimen. As shown, the screen 1630 may be used to temporally structure a relief regimen. In some embodiment the user may use such a screen 1630 to define the number of relief cycles per hour. In some embodiments, a user may use such a screen 1630 to define a wait period between cycles. In some embodiments, a user may use such a screen 1630 to define a wait period between steps of a cycle. Additionally, in some embodiments, a user may use such a screen 1630 to define whether the relief regimen will actively (e.g. use a pump to pump fluid out of the actuators) or passively deflate actuators.

As shown, in some embodiments when user selects a parameter field for editing, it may enlarge on the screen. In some embodiments, a relief cycles per hour field 1632 has been opened for editing. The relief cycles per hour parameter field 1632 has enlarged and the font size for the parameter value has also increased. Additionally, an up and down button 1634, 1636 to increase and decrease the parameter value appears in the enlarged parameter field.

Figure 72:
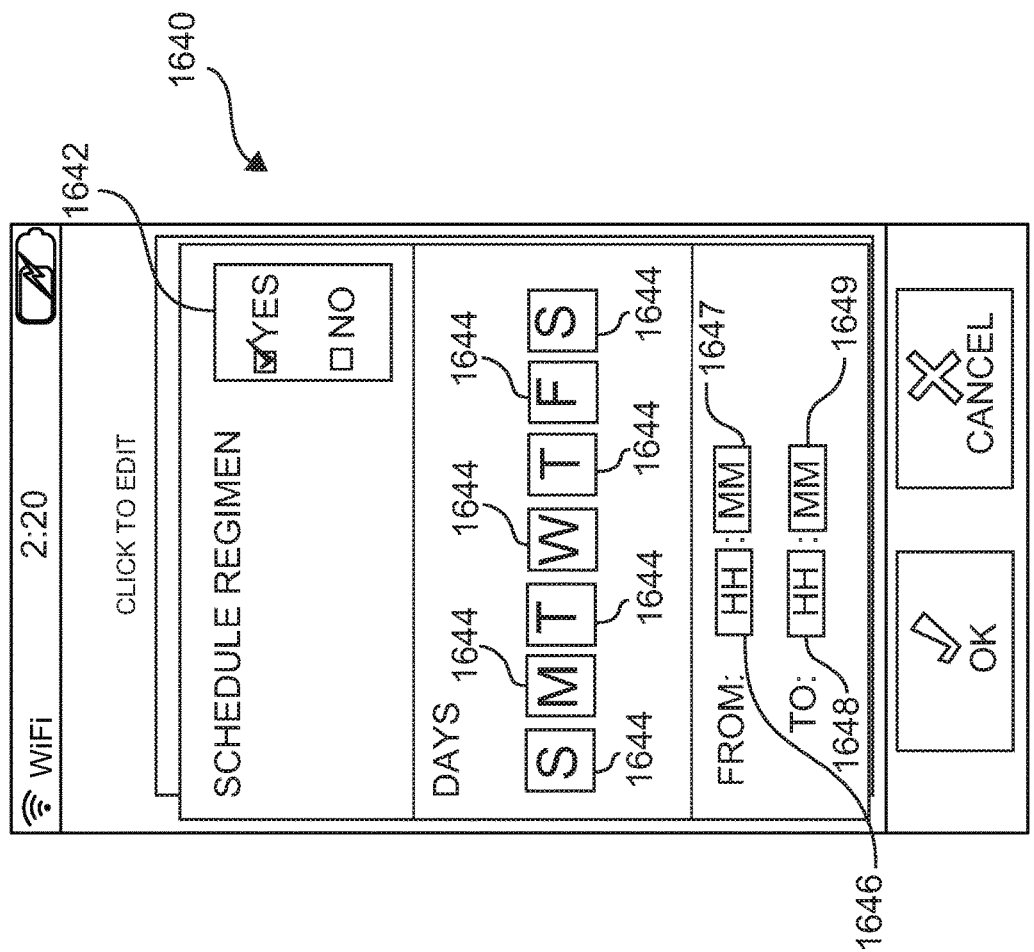
FIG. 72 depicts a screen which may be displayed on a remote interface for a dynamic support apparatus in accordance with one embodiment.

FIG. 72 depicts another screen 1640 which may be displayed on a user interface for a dynamic support apparatus. The screen 1640 may be used to configure a relief regimen. Specifically, the screen 1640 may be used to schedule a regimen. Such scheduling may cause a regimen to automatically begin as defined. In other embodiments, such scheduling may cause the user interface to prompt or remind a user to begin the relief regimen.

As shown, the screen 1640 includes an enable option 1642 which may be selected if a user would like to schedule the regimen. In some embodiments, the enable option 1642 includes "Yes" and "No" checkboxes. In other embodiments, radio buttons or the like may be used. In some embodiments, the screen 1640 also includes selectors 1644 for days of the week which in some embodiments are checkboxes. A user may select the desired days of the week to which they would like the schedule to be applied to. Additionally, the screen 1640 includes fields 1646, 1647, 1648, 1649 in which the user may define a time frame. A user may enter a begin time and an end time for which they would like to schedule the relief regimen. In some embodiments, a user may schedule a regimen to occur while they are at work using the Monday-Friday selectors 1644 and entering the time frame as 9:00 AM to 5:00 PM.

Figure 73:
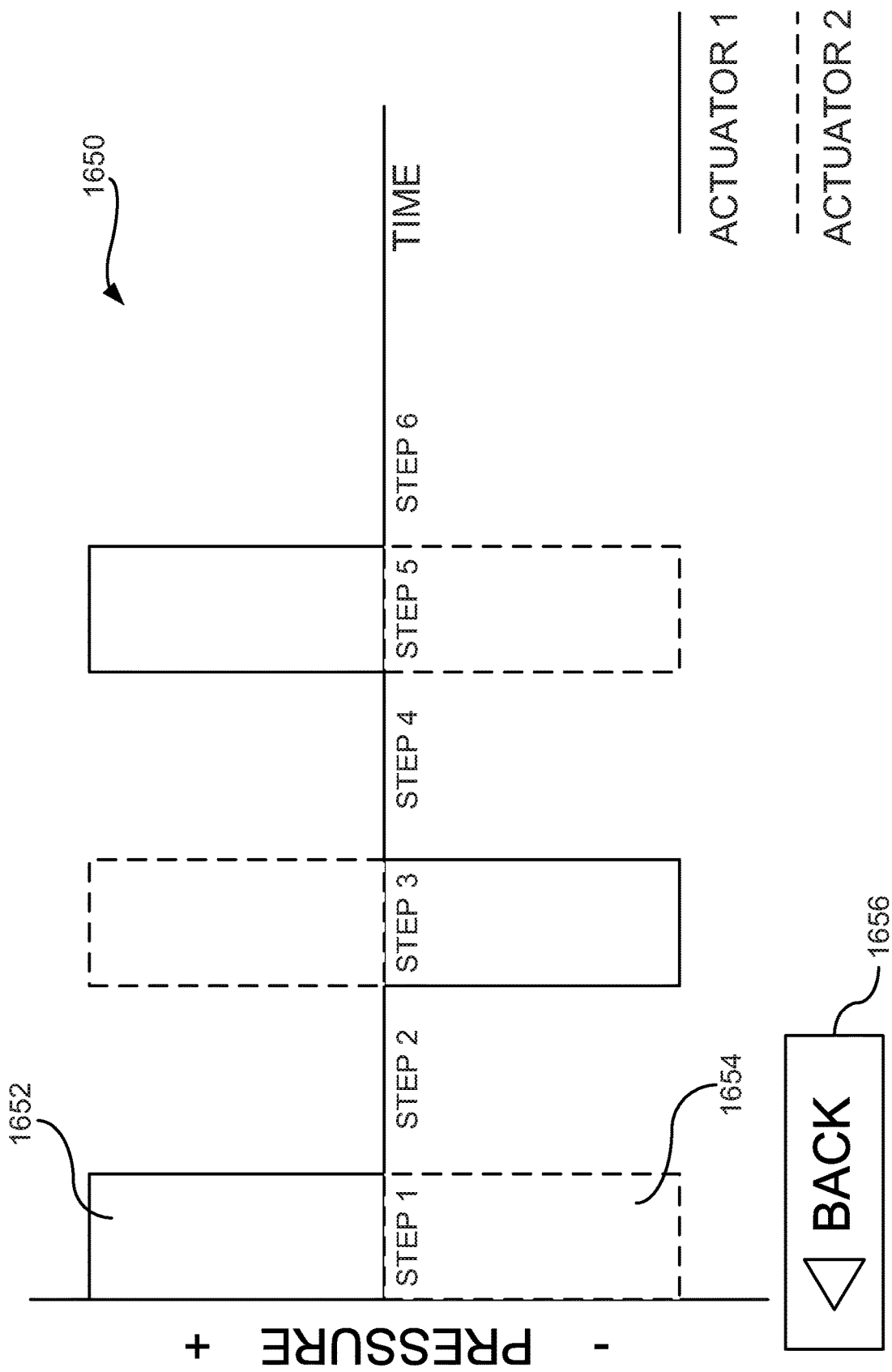
FIG. 73 depicts a graph which may be displayed on a user interface for a dynamic support apparatus in accordance with one embodiment.

In some embodiments, while a user is editing and/or creating a relief regimen, it may be desirable to see a visual representation of the regimen. Such a visual representation may depict the defined relief regimen in a single, easily comprehendible format. In various embodiments, a visual representation may be provided in the form of a graph, specifically an actuator pressure over time graph. An embodiment of such a graph 1650 is depicted in FIG. 73. A user may use a view regimen button, such as that shown in FIG. 67, to view such a graph 1650 in some embodiments.

As shown, the graph 1650 in FIG. 73 depicts a plot 1652, 1654 for each actuator of a dynamic support apparatus. For purposes of illustration, the pressure axis of the graph 1650 is not assigned numeric values rather only an indication of positive and negative. The time axis is also not assigned numeric values. In various embodiments, the time axis may not be assigned time values but rather be divided by step number as shown. A back button 1656 is also included on the graph 1650. A back button 1656 may be used to return to a previous screen once the user is done viewing the graph 1650.

Figure 74:
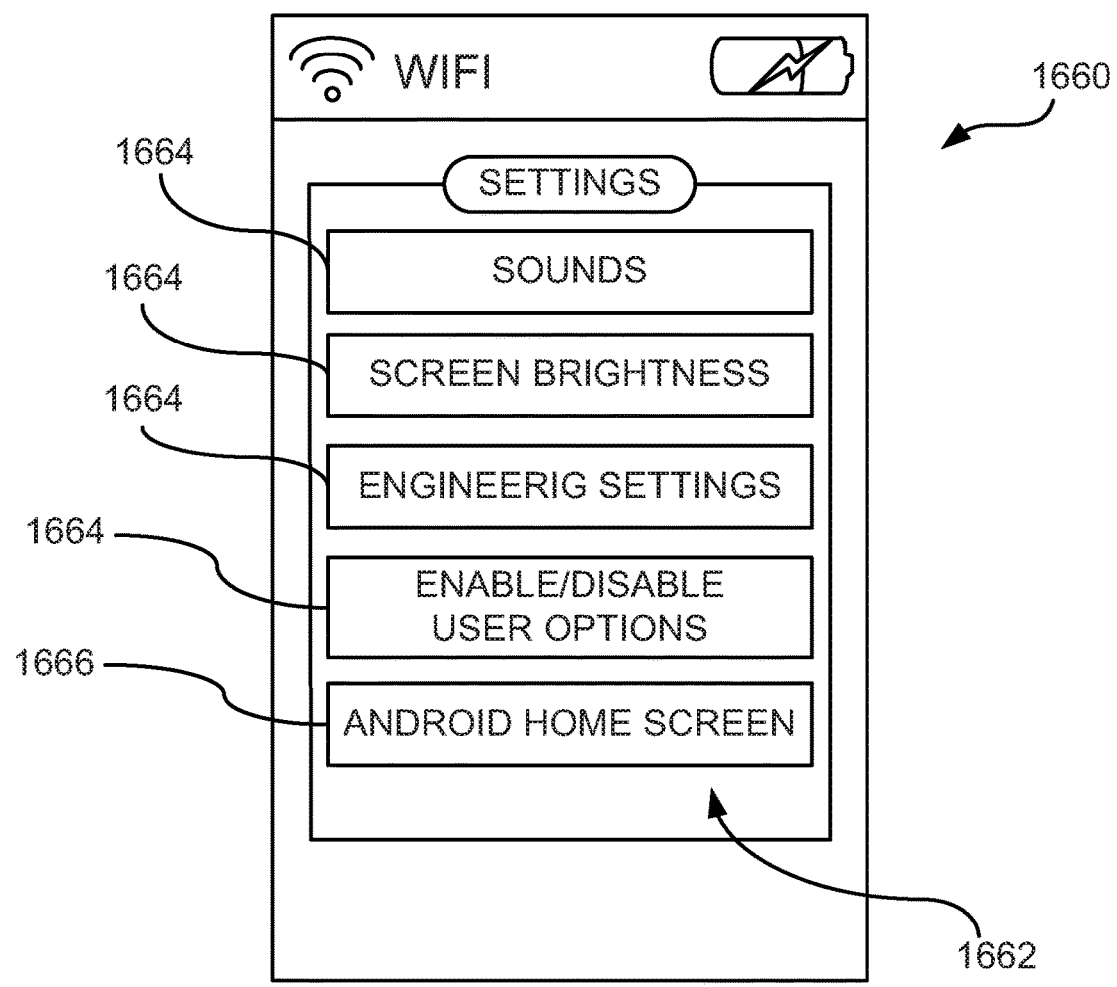
FIG. 74 depicts a screen which may be displayed on a remote interface for a dynamic support apparatus in accordance with one embodiment.

FIG. 74 depicts a screen 1660 which may be displayed on a user interface for a dynamic support apparatus. The screen 1660 includes a menu 1662 which may be used to navigate to various configuration setting of a dynamic support apparatus. As shown, a number of settings categories 1664 are displayed in boxes on the screen 1660. In other embodiments, different settings or a different number of settings may be included. A user may select one of the settings categories 1664 on the screen 1660 to open it for configuration. The screen 1660 also includes an option 1666 to return to a home screen.

Figure 75:
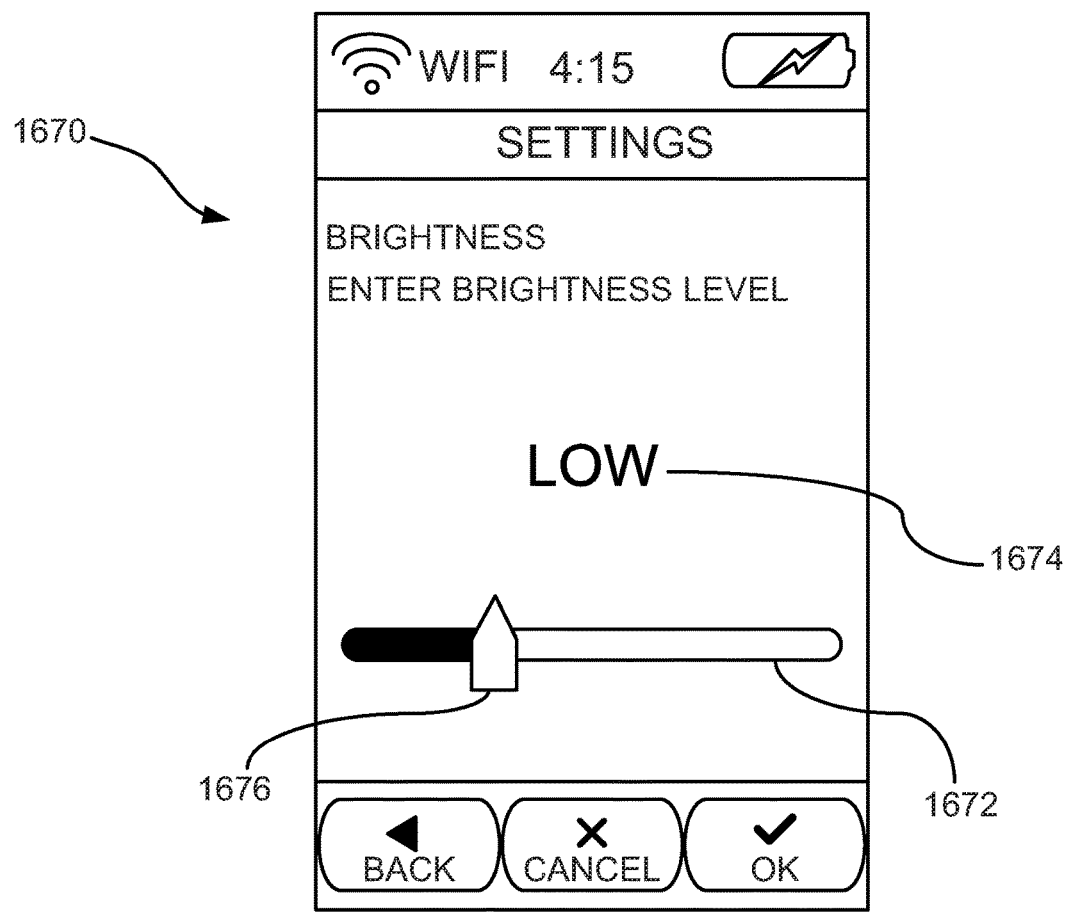
FIG. 75 depicts a screen which may be displayed on a remote interface for a dynamic support apparatus in accordance with one embodiment.

FIG. 75 depicts another screen 1670 which may be displayed on a user interface of a dynamic support apparatus. The screen 1670 shown in FIG. 75 may be one of many screens which may be navigated to by selecting a setting category 1664 in FIG. 74. As shown, the screen 1670 provides an interface which allows a user to adjust screen brightness. As shown, a slider bar 1672 is depicted and may be used by a user to adjust the screen brightness. Slider bars may also be used to allow users to adjust other settings or define parameters in some embodiments. A settings level descriptor 1674 is also shown on the screen 1670. In some embodiments, the settings level descriptor 1674 reads "Low". Other possible values may be "Min.", "Mid", "High", "Max", etc. In various embodiments the settings level descriptor 1674 may be a numeric value. As the slider 1676 of the slider bar 1672 is slid by the user, the settings level descriptor 1674 may change automatically to reflect the slider 1676 position.

Figure 76:
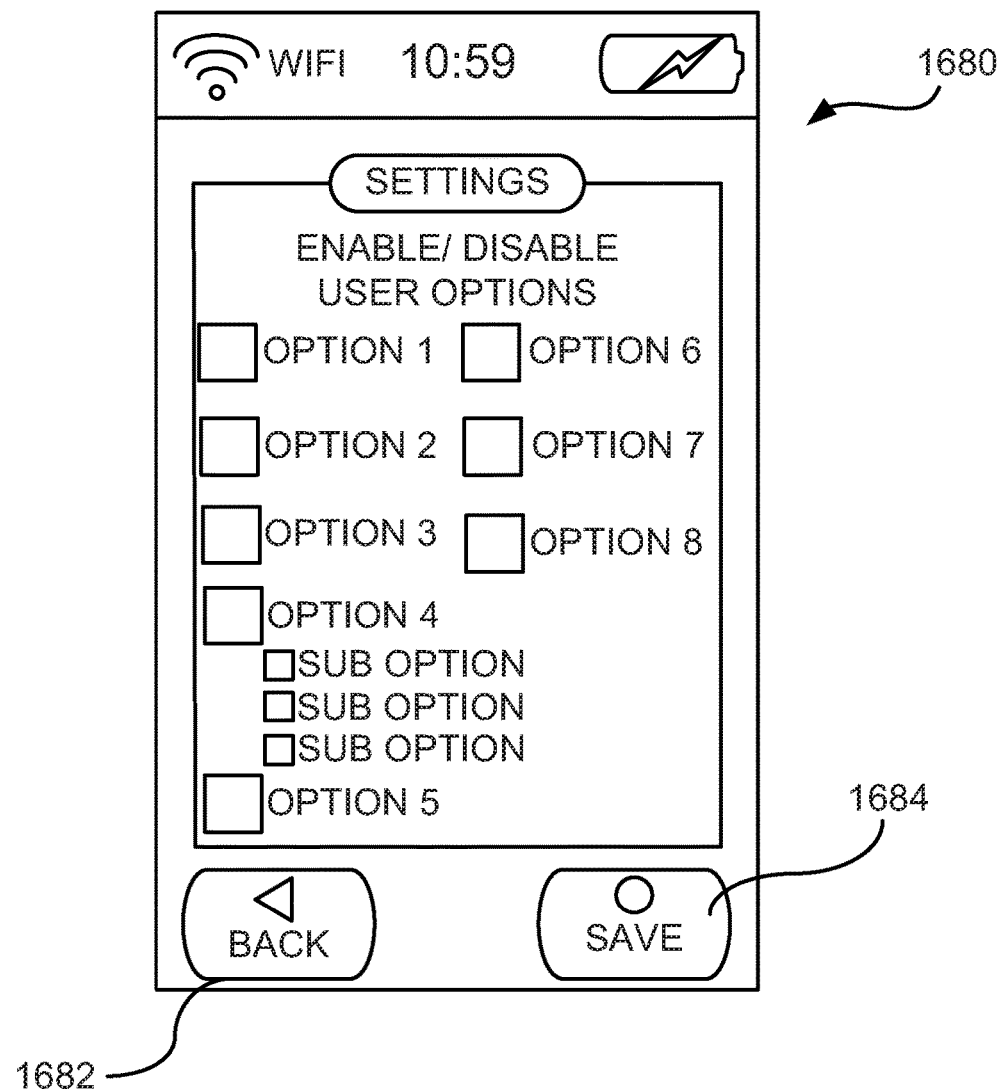
FIG. 76 depicts a screen which may be displayed on a remote interface for a dynamic support apparatus in accordance with one embodiment.

FIG. 76 depicts another screen 1680 which may be displayed on a user interface of a dynamic support apparatus. The screen 1680 shown is a settings screen. In some embodiments, this screen 1680 may be navigated to by selecting the "Enable/Disable User Options" category 1664 in FIG. 74. This screen 1680 may allow a clinician or care giver to configure options and functionalities that may be available for a user. In some embodiments, this screen 1680 may allow a care giver to disable a transfer mode for a user. As shown, eight options are depicted, though in other embodiments, any suitable number of options may be depicted.

As shown, in some embodiments, one or more option may include one or more sub option. In some embodiments, one option may turn a lock functionality on or off. In the event that the lock option is turned on, the sub options may become enabled. The sub options may provide a selection of various varieties of the parent option (e.g. passcode, swipe, biometric, etc.). A user may then select the sub option which is desired. In other embodiments, sub options may present various features of a parent functionality or options. A user may selectively enable and disable such features as desired.

As shown, in some embodiments, one or more option(s) may include one or more parameter field(s) which is/are associated with that option. In some embodiments, if the parent option allows a user to enable or disable a pause option or functionality, the associated parameter field may require a user to enter a limit. The limit may in some embodiments define the maximum pause length. As shown, option 8 is associated with a parameter field on the screen 1680. A back button 1682 and save button 1684 are also included on the screen 1680 shown in FIG. 76.

Figure 77:
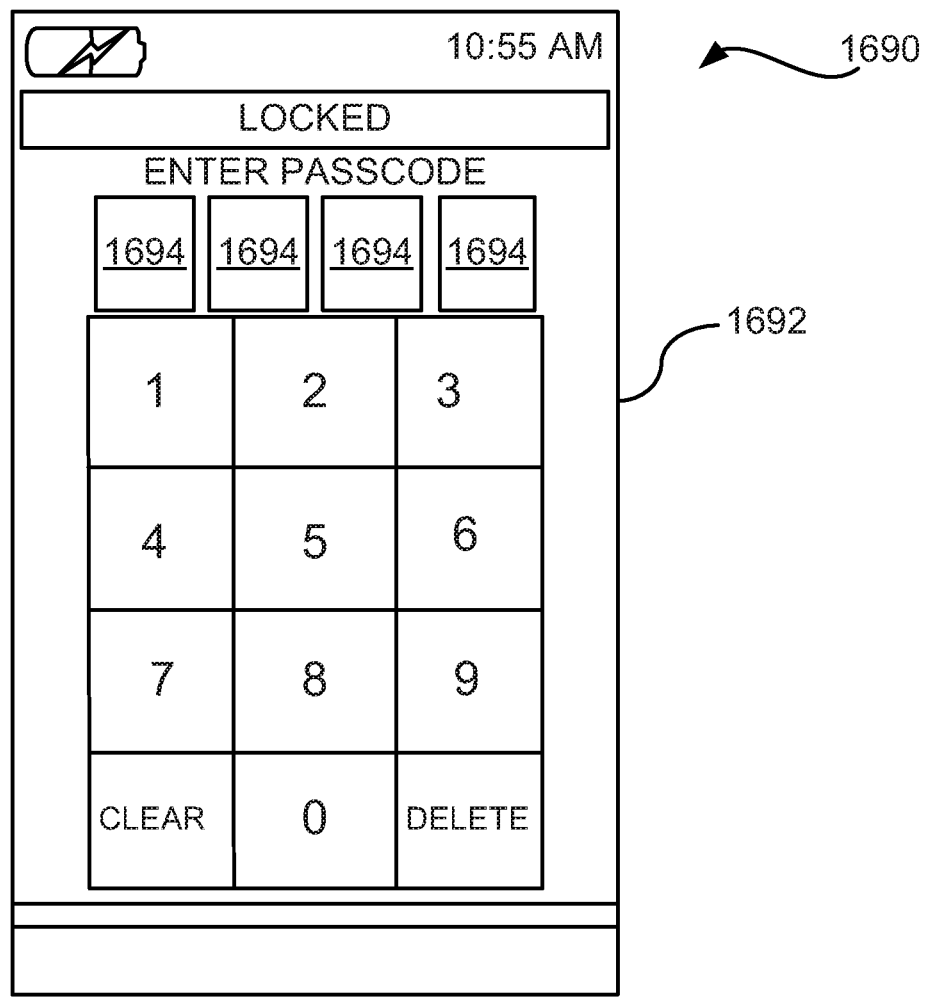
FIG. 77 depicts a screen which may be displayed on a remote interface for a dynamic support apparatus in accordance with one embodiment of the present disclosure.

FIG. 77 depicts an embodiment of a lock or passcode screen 1690. In some embodiments, the lock or passcode screen 1690 may be included to help prevent unauthorized access to a user interface a dynamic support apparatus. In some embodiments, a lock or passcode screen 1690 may be included when a user attempts to access various features on a user interface for a dynamic support apparatus. In some embodiments, a care giver or clinician may define a passcode for various editing features to prevent a user from editing a relief regimen.

As shown, the lock or passcode screen 1690 includes a numeric keypad 1692. The lock or passcode screen 1690 also includes a number of passcode fields 1694 which may be populated as a user enters in a passcode. In some embodiments, the passcode fields 1694 may be populated with the values selected on the keypad 1692. In other embodiments, the passcode fields 1694 may be populated with a generic symbol to indicate a value selection was registered by the user interface.

Figure 78:
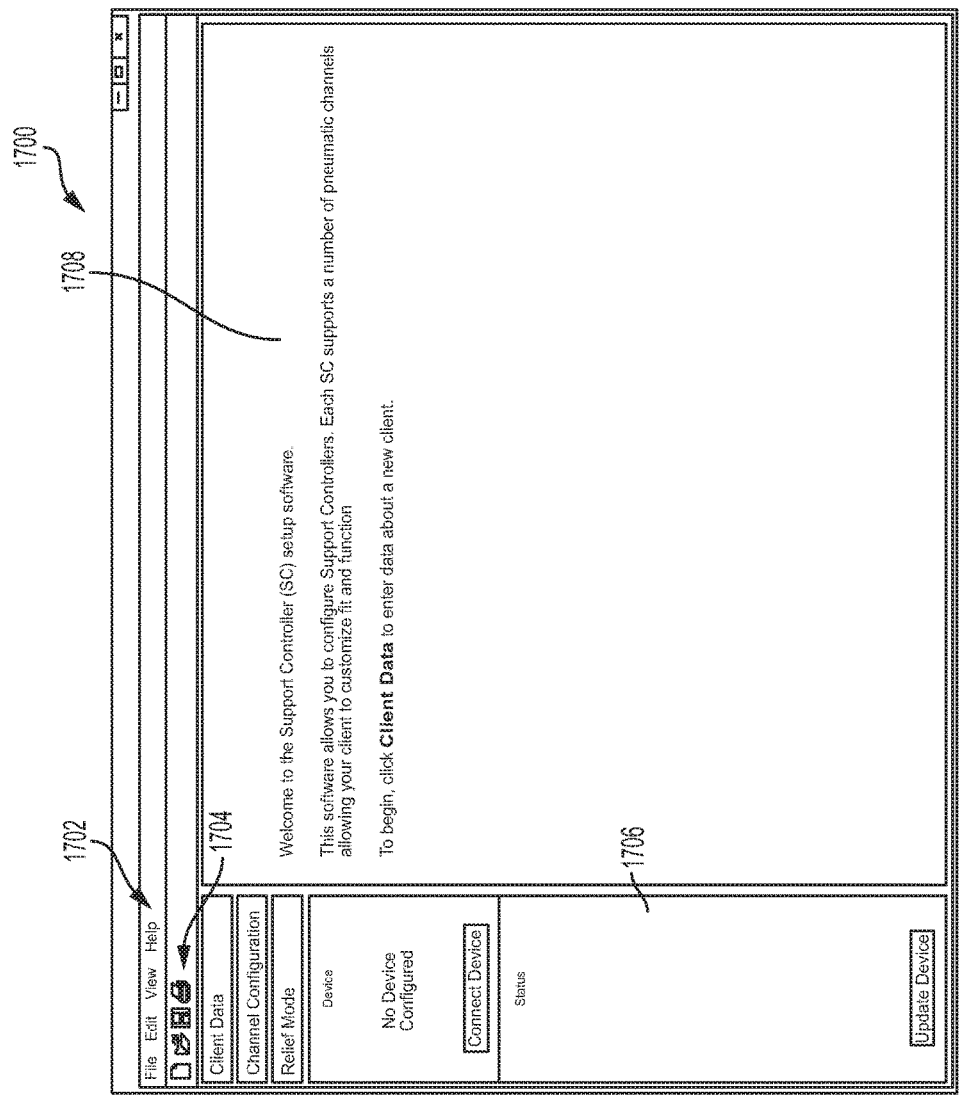
FIG. 78 depicts a screen which may be displayed on a remote interface for a dynamic support apparatus in accordance with one embodiment.

FIG. 78 depicts another screen 1700 which may be displayed on a user interface of a dynamic support apparatus. As shown, the screen 1700 is optimized for a personal computer or laptop. The screen 1700 in FIG. 78 is a welcome screen. The welcome screen describes to the user how the user may begin to use the program. It also may provide information on what the program may be used for.

As shown, the screen includes a window. The window includes a menu bar. The menu bar 1702 may include a number of clickable options. In some embodiments, the menu bar includes a "File" option, an "Edit" option, a "View" option, and a "Help" option.

The "File" option may present a list of choices when clicked. In some embodiments, the "File" option may allow a user to open a previously created relief regimen. The "File" option may allow a user to save a created relief regimen or configuration. The "File" option may allow a user to print a created relief regimen or configuration summary. The "File" option may allow a user to update controller software. The "File" option may also include other choices when clicked. The "Edit" option may also present a list of choices when clicked. In some embodiments, the "Edit" option may present choices to clear all parameters for a created relief regimen or restore all defaults in a regimen. The "View" option may present a number of choices when clicked. In some embodiments, the "View" option may be used to select which of a variety of program functionalities the user would like to use and may open a user interface screen for the desired functionality. The "Help" option may present a number of choices when clicked. In some embodiments, the "Help" option may be used to view a software manual, device manual, readme file, etc. The "Help" option may also provide information about the software release.

The screen 1700 also may include a number of icons 1704 as it does in some embodiments as depicted in FIG. 78. These icons 1704 may, in some embodiments, be skeuomorphic. As shown, a "new configuration" icon is depicted in the form of a blank sheet of paper. An "open previously created configuration" icon is depicted in the form of an open folder. A "save" icon is depicted as a floppy disk. A "print" icon is depicted as a printer. Other icons 1704 may be included in other embodiments. In some embodiments there may be icons 1704 for any of the menu options described above.

In some embodiments, the screen 1700 includes a side bar 1706. The side bar 1706 may be used to select which of a variety of program functionalities the user would like to use. The user interface screen 1700 includes a Client Data functionality, a Channel Configuration functionality, a Relief Mode functionality, a Connect Device functionality, and an Update Device functionality. Other embodiments may include different functionalities or a differing number of functionalities. These functionalities may be navigated as tabs. Clicking on one of the functionalities in the side bar

1706 may cause the user interface to display a screen associated with that functionality. In some embodiments, the side bar 1706 may be present on all user interface screens and be used to navigate from a user interface screen to another user interface screen. In some embodiments, the side bar 1706 may also be used to display status messages.

In some embodiments, before being allowed to configure a relief regimen, a user may be required to connect a device using the Connect Device functionality. This may, in some embodiments, involve physically connecting the controller of a dynamic support apparatus to the remote interface using a data bus cable such as a USB cable. The Connect Device functionality may then cause the remote interface to establish communication with the controller of the dynamic support apparatus.

The screen 1700 also includes a screen-specific portion 1708. In the embodiment shown in FIG. 78, this is the portion of the screen 1700 in which the welcome message is depicted. In some embodiments, the screen-specific portion 1708 of the user interface may change depending on the functionality of the user interface being used. The other portions of the window may remain substantially unchanged.

Figure 79:
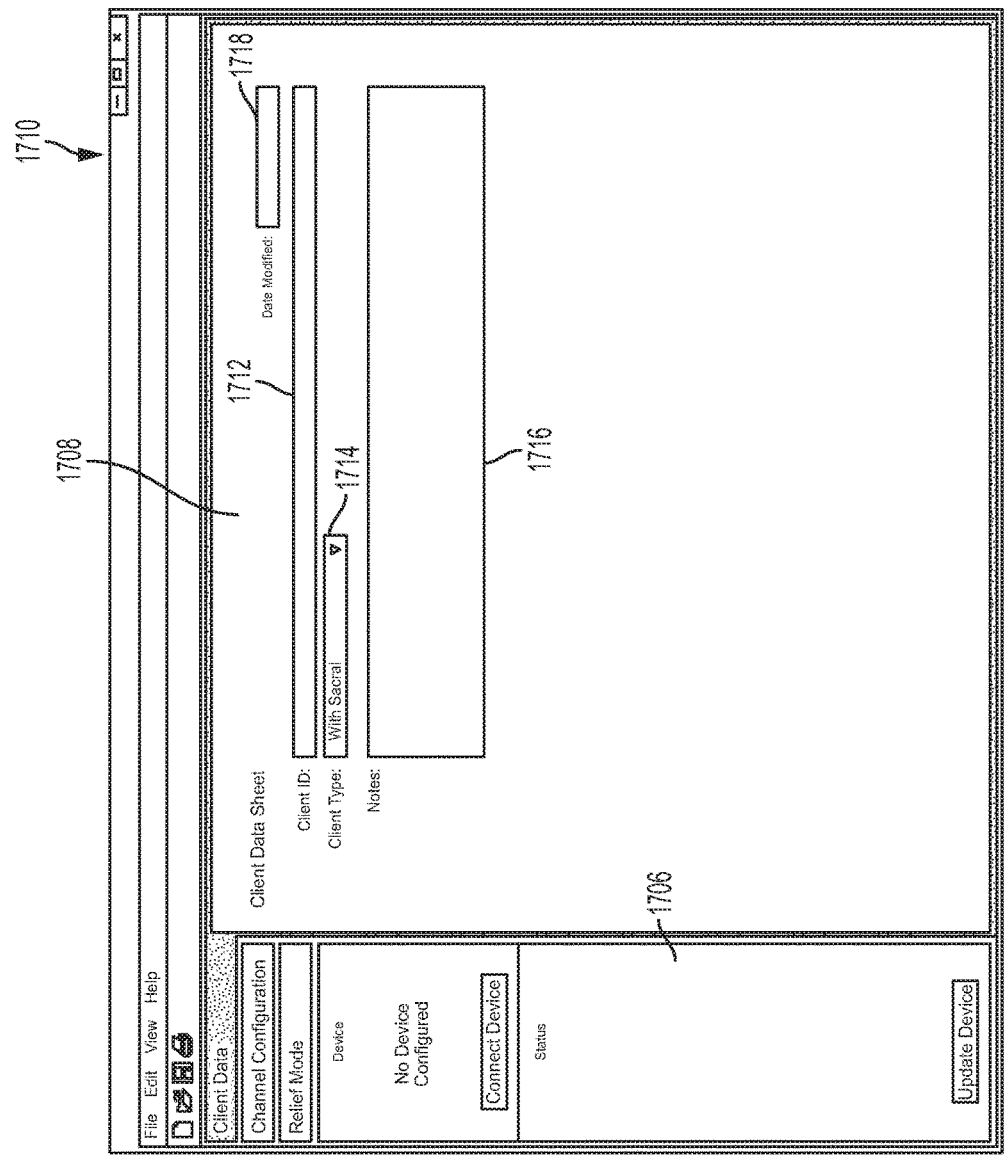
FIG. 79 depicts a screen which may be displayed on a remote interface for a dynamic support apparatus in accordance with one embodiment.

FIG. 79 depicts another screen 1710 which may be displayed on a user interface for a dynamic support apparatus. As shown the screen 1710 allows a user to enter various client data. As shown, the side bar 1706 of the user interface visually indicates that the patient data functionality is in use. Within the screen-specific portion 1708 of the screen 1710 are a number of user definable parameters. A client ID parameter 1712 is included. A user may define this parameter 1712 by entering an identifier for a dynamic support apparatus user. A client type parameter field 1714 is also depicted. This field 1714 may be used to define what type of dynamic support apparatus is being used by the user. In some embodiments, a user may select how many actuators are included in their dynamic support apparatus, what model dynamic support apparatus the user is using, etc. In some embodiments, this parameter field 1714 reads "With Sacral" indicating that the dynamic support apparatus is a model which includes a sacral actuator. Such a model is shown in FIG. 2. A notes parameter field 1716 is also shown in some embodiment. This field 1716 may be used to type in any notes about the dynamic support apparatus user which may be desired. Additionally, a "Date Modified" field 1718 which may be automatically populated is included.

Any editable parameter fields shown may be editable in any number of suitable ways. In some embodiments, some fields may be free text fields. Other fields may be defined by picking a choice via a drop box or slider. Additionally, in some embodiments, a user may define parameters using checkboxes, radio buttons, or any other suitable means.

Figure 80:
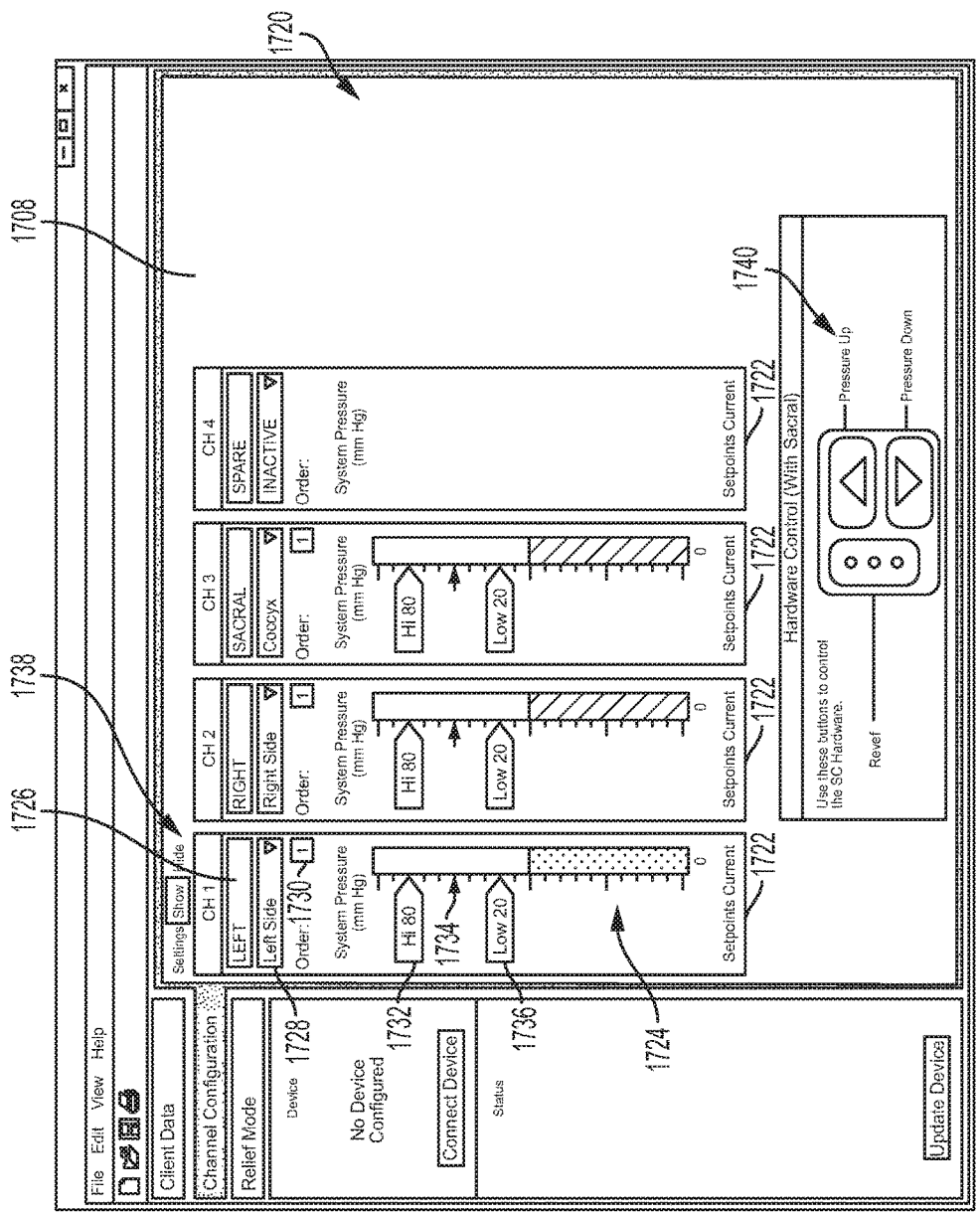
FIG. 80 depicts a screen which may be displayed on a remote interface for a dynamic support apparatus in accordance with one embodiment.

FIG. 80 depicts another screen 1720 which may be displayed on a user interface for a dynamic support apparatus. As shown, the screen 1720 is a channel configuration screen. The channel configuration screen may be used to define various set points for actuators included in a dynamic support apparatus. It may be used to associate various manifold ports or fluid channels with their respective actuators in a dynamic support apparatus. There is also a hardware control interface which may allow a user to remotely control the dynamic support apparatus using the configuration screen.

As shown, the screen-specific portion 1708 of the channel configuration screen may include a number of groups of parameter fields 1722 and user definable settings. Each of the groups 1722 may be modified by the user to configure how the dynamic support apparatus controls an actuator. As shown in FIG. 80, each of the groups 1722 is named with a channel and/or manifold port number. A user may click on a group 1722 in order to access the parameters within that group 1722 for editing. In some embodiments, when a user opens a group 1722 for editing, the group 1722 may visually indicate that it has been opened for editing on the user interface. In some embodiments, the "CH1" group 1722 has been opened for editing. The group 1722 visually indicates that it is open by appearing in a different color than other groups 1722 in the some embodiments. Additionally, hash marks appear on a pressure settings slider bar 1724. The pressure settings slider bar 1724 is further described later in the specification. Additionally, any groups 1722 that are inactive (e.g. no actuator connected to that channel) may be grayed out or not included in some embodiments.

A name parameter field 1726 is included for each of the groups 1722. This field 1726 may, in some embodiments, be a free text field. This field 1726 may be used to define a descriptor or name for the group. This descriptor or name may be chosen to provide, for example, information about which actuator of the dynamic support apparatus the channel is connected to. In the some embodiments, the far left (CH1) group's 1722 name parameter field 1726 reads "LEFT". In other embodiments, this field 1726 may be defined using a dropbox or may not be user definable. Instead, this field 1726 may be fixed and may be used to provide a user with an indication of which actuator of a dynamic support apparatus to connect to each channel. Additionally, in some embodiment, the name parameter field 1726 may be automatically populated if a user has defined a sufficient number of name parameter fields 1726 in other groups 1722. In some embodiments, if there is only a left and right actuator, when a user designates one group 1722 as right, the other group's 1722 name parameter field 1726 may be automatically populated as left.

An actuator type or location parameter field 1728 is also included in the some embodiment. Such a field 1728 may be used to define which actuator of a dynamic support apparatus the channel is connected to. In the embodiment shown in FIG. 80, this field 1728 may be defined using a drop down menu which may present a user with a number of predefined choices. As above, in some embodiments, this field 1728 may be automatically populated after a user has defined a sufficient number of actuator type of location parameter fields 1728 in other groups 1722. In some embodiments, the choices which appear in the drop box may depend upon a previously defined parameter. In some embodiments, a client type parameter field 1714 (see FIG. 79) may determine what choices may be available for the actuator type of location field 1728.

An order parameter field 1730 may also be included. The order parameter field 1730 may be used to define the order in which that channel will be acted on when the regimen is executed by a dynamic support apparatus. In some embodiments, this field 1730 may be selected using a drop box. In some embodiments, this field 1730 may be a free text field.

In some embodiments, where an order parameter field 1730 is a free text field, the user may be restricted to only numeric values. Additionally, in some embodiments, the user may be restricted to only a range of numeric values. In some embodiments, the user may not be able to order a channel to be the fifth channel acted on if only three channels are being used.

A number of user definable pressure settings 1732, 1734, 1736 are also shown on the user interface screen 1720. As described elsewhere herein, in some embodiments, other inflation settings or set points may be used in some embodiments. In some embodiments, there may be a mole of air setting or set point or actuator height setting or set point.

As shown, the pressure settings (or in other embodiments, other inflation settings) may be selected using a slider. The slider in some embodiments is part of a pressure settings slider bar 1724. In other embodiments, each setting may be associated with a user definable parameter field. In some embodiments, there is a maximum pressure limit parameter slider 1732, a minimum pressure limit parameter slider 1736, and an actuator pressure set point parameter slider 1734. These may be dragged by the user along the pressure settings slider bar 1724 to choose the desired set point and limits for each actuator. As shown, the pressure settings slider bar 1724 may also display the current pressure of an actuator or actuator channel in some embodiments. This information may be gathered by sensor data and then processed for display on the screen 1720. The maximum and minimum pressure parameter sliders 1732, 1736 may be used to define the bounds within which a user may deviate (e.g. manually) from a nominal pressure set point while on a dynamic support apparatus. In some embodiments, this may be done by commanding pressure to increase or decrease using an on board interface such as the shown in FIG. 28. In a preferred embodiment, when a limit is defined, other parameters may be restricted from being defined such that they break the limit. In some embodiments, once a high limit has been defined, a user may not define the actuator pressure set point or the minimum pressure set point above that limit.

Inflation information and settings may be displayed in any suitable number of forms in various embodiments. For instance, the fluid pressure may be the basis for the settings on the display with appropriate sets of units (e.g. mmHg) being display with the fluid pressure information. Alternatively in some embodiments, the settings and/or information may be displayed in a unitless form. In some embodiments settings may be a unitless percentage ranging from −100% to +100%. In such embodiments, the percentage could represent the limits of the controller or pump or other factor/clinician defined limitations. In some embodiments, a different variety of scale may be used. In some embodiments, a user may define settings using a scale of −10 to +10.

Other embodiments may include different parameters and/or a different number of parameters. Some embodiments may include different sliders on the pressure settings slider bar 1724. In other embodiments, the pressure settings slider bar 1724 may include sliders for different steps in a relief regimen. In some embodiments, in a relief regimen with four steps, there may be four sliders on the pressure settings slider bar 1724. Each of the sliders may be used to define a pressure set point for one of the steps. In some such embodiments, the sliders may also be labeled with the step number whose step point they may be used to define.

A show/hide option toggle 1738 is also displayed on the user interface screen in FIG. 80. This option toggle 1738 may be used to hide or show a sub set of parameters for each group 1722. As shown by the dark highlight around the "Show" option, the show/hide option toggle 1738 has been toggled to show. In some embodiments, all of the parameters are shown. When toggled to hide, various parameters may be hidden or disappear from the user interface screen 1720. In some embodiments, the actuator name parameters 1726 and actuator type or location parameters 1728 may be hidden.

In some embodiments, an option may be included to swap channels. Such an option may be used to move programming for a channel to another channel (e.g. a channel which is inactive, spare, or not currently being used). In some embodiments, this may be useful in the event that there is an issue with a channel (e.g. there is a bad valve on a channel). A user may use such a swap option to move the existing setting for a channel to another desired channel. Alternatively, in some embodiments, a user may be able to associate a parameter group 1722 with another channel by changing the parameter group's 1722 association via a drop box or the like.

Various embodiments of the hardware control interface 1740, as mentioned above, may be used to remotely control the dynamic support apparatus. In various embodiments, the hardware control interface 1740 may be a virtual representation of the keypad of a dynamic support apparatus controller. The hardware control interface 1740 may be useful/desirable/beneficial for many reasons, including but not limited to, when determining the proper set points for a user of a dynamic support apparatus. The user may be positioned on the dynamic support apparatus and the hardware control interface 1740 may be used to try out various set points for actuators of the dynamic support apparatus. In some embodiments, a pressure mapping mat or the like may also be placed on the dynamic support apparatus. As various actuator set points are tested, data from the pressure mat may be generated. This data may then be reviewed. When suitable actuator set points are determined, the user may then define parameters for each of the groups 1722 on the channel configuration screen. As shown the pressure settings slider bars 1724 may also depict the current pressure of each actuator in a dynamic support apparatus. This may further aid in the development of a suitable pressure regimen.

In some embodiments, a channel configuration screen may include a visual representation of the layout of a dynamic support apparatus. In some embodiments, there may be a representational diagram of the dynamic support apparatus indicating the spatial arrangement of actuators in the dynamic support apparatus. The actuators may be labeled with the channel name to which they are connected in some embodiments.

Figure 81:
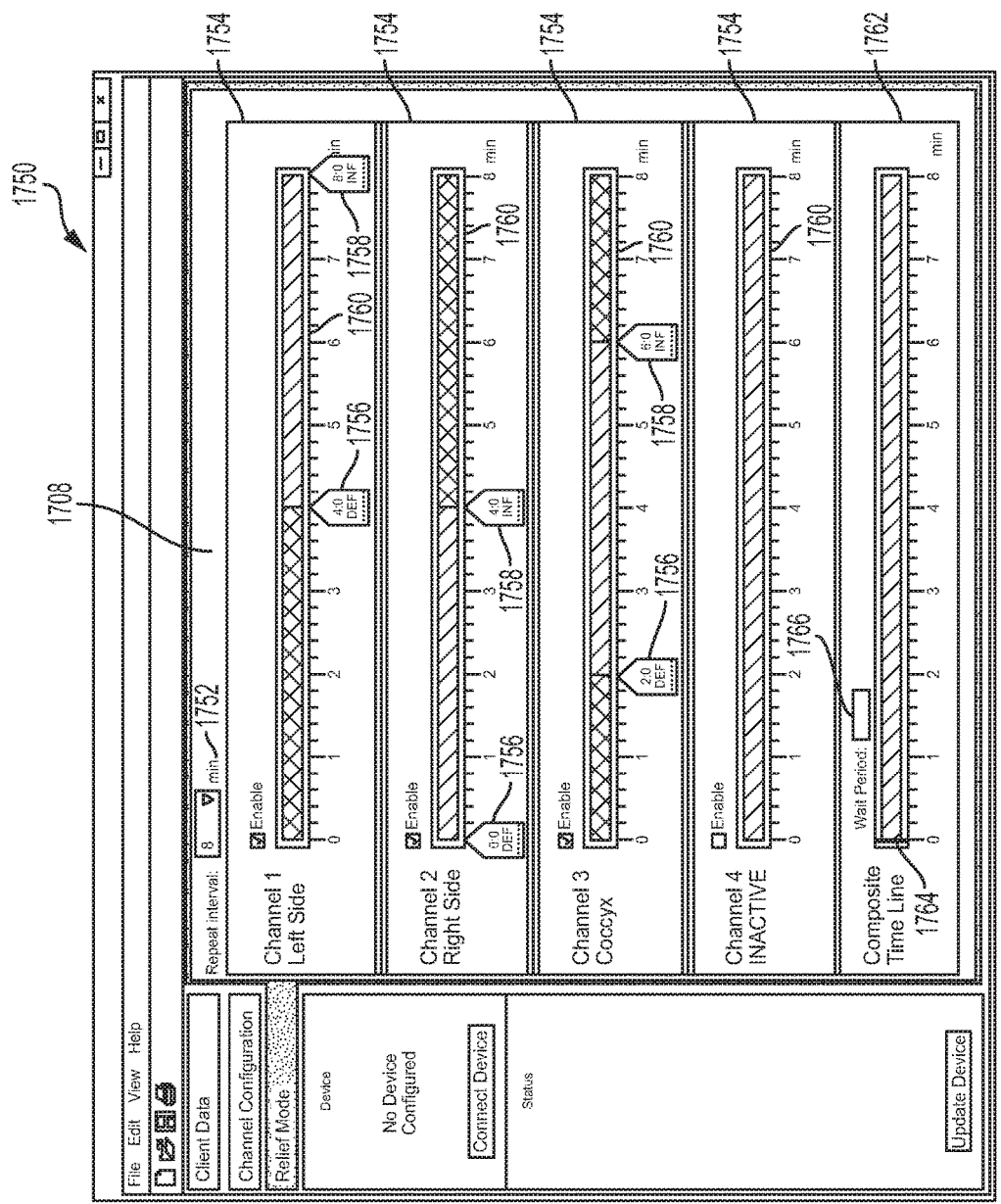
FIG. 81 depicts a screen which may be displayed on a remote interface for a dynamic support apparatus in accordance with one embodiment.

FIG. 81 depicts another screen 1750 which may be displayed on a user interface for a dynamic support apparatus. The screen 1750 shown in FIG. 81 is a relief mode screen. Such a screen 1750 may be used to temporally structure a relief mode. In some embodiments, the relief mode screen may be used to define when specific steps occur and for how long. As shown, the screen specific portion 1708 of the relief mode screen may be used to define any of a number of parameters useful in temporally structuring a relief mode.

In some embodiments, a repeat interval parameter field 1752 is included. As shown, the repeat interval parameter field 1752 may be used to define the length of a relief regimen cycle. That is, the repeat interval parameter field 1752 may define the amount of time in which all steps of a relief regimen cycle will occur once. The repeat interval parameter field 1752 may also define how often a relief regimen cycle will be repeated. In some embodiments, the repeat interval parameter field 1752 is a dropbox. In other embodiments, the repeat interval parameter field 1752 may be defined differently. In some embodiment the repeat interval parameter field 1752 may be defined using a free text field which is restricted to numeric values. As a user defines a value in the repeat interval parameter field 1752, the timelines 1760 may be automatically scaled to the appropriate value.

A group of definable parameters 1754 for each channel is also shown in the user interface screen shown in FIG. 81.

Each group of definable parameters 1754 may be used to specify when each step of a relief regimen cycle for each actuator is to occur. Also as shown, various channels may be enabled and disabled on this screen. In some embodiments, the inactive channel, "Channel 4", is shown as disabled. In some embodiments, channels may be automatically activated depending on previously defined parameters or settings. In some embodiments, if the user has defined which channels are active on a channel configuration screen (see FIG. 80), these channels may automatically be enabled on a relief regimen screen. Likewise, if a channel has been set to inactive, it may be grayed out.

For sake of simplicity, only two steps are included for each actuator, an inflate ("INF") step and a deflate ("DEF"). In other embodiments, there may be any number of steps. As shown, the user may utilize a slider 1756, 1758 on a timeline 1760 to define temporal parameters for each step. In other embodiments, temporal parameters may be defined using a parameter field and a timeline 1760 may not be included. The timeline 1760 may be appropriately divided and numbered based upon a repeat interval parameter 1752 defined by the user. As shown, a user may move the sliders 1756, 1758 along the timeline 1760 to define when each step within the cycle will being and how long the step will last. In some embodiments, for "Channel 2" a user has defined that the actuator connected to channel 2 be deflated at the beginning of each cycle. Additionally, the user has defined that after four minutes, the actuator connected to channel 2 will be re-inflated to its nominal pressure set point. The actuator will remain at that set point until the next cycle begins.

In some embodiments, the time specified for each step may be used by the controller as the time at which the controller begins attempting to reach the set point for that step. In other embodiments, the time specified for each step may be a target time at which the controller aims to have the actuator connected to the channel at the specified set point. Additionally, in some embodiments, the timelines 1760 may provide a visual indication of the time which will nominally be spent to inflate and deflate each channel. In some embodiments, there may be markings (e.g. a timeline 1760 may include cross-hatching or the like) included on the timelines 1760 which indicates how long the inflation and deflation will take.

In some embodiments, once set, a user may also move a group or block of actions along a timeline 1760. In some embodiments, if a user were to set an inflate and deflate step to occur two minutes apart, a user may move this group of steps along the timeline 1760. This may allow a user to more easily and efficiently structure a desired relief configuration or regimen. In some embodiments, a user may also be able to select a plurality of steps to create step groupings or blocks for such movements.

In some embodiments, a composite time line 1762 is also shown on the user interface screen 1750 in FIG. 81. The composite time line 1762 may be used to view a visual summary of the defined relief regimen. In some embodiments, the composite time line 1762 may indicate when the steps of a relief regimen begin and end. In some embodiments, the composite time line 1762 may be a graph similar to that depicted in FIG. 73. In various embodiments, a user may be able to drag groups of steps along the composite timeline 1762 to define the relief regimen or configuration.

In some embodiments, a user may be able command a test of a programmed relief regimen using the relief mode screen. In such embodiments, the composite time line 1762 may have an indicator 1764 which indicates where in the relief cycle the test has progressed to. In some embodiments, the indicator 1764 is at zero because a test has not been initiated.

Some embodiments, as shown in FIG. 81, may include a wait period parameter field 1766. In various embodiments, the wait period parameter field 1766 may be used to define a wait period between cycles or steps. In some embodiments the wait period parameter field 1766 is a free text field. In other embodiments, the wait period parameter field may be a dropbox or the like. Alternatively, the wait period parameter field 1766 may be a delay between the initial inflation (upon start-up) and when the relief regimen or configuration begins.

FIG. 82 depicts another screen 1770 which may be displayed on a user interface for a dynamic support apparatus. The screen 1770 shown in FIG. 82 is a summary screen. The summary screen may display in a single place all or a subset of the parameters and settings defined for a relief regimen. In some embodiments, the settings and parameters are defined in one or more table(s) 1772 although any other suitable presentation form may also be used. Additionally, client related information is shown as a summary heading 1774 on the screen 1770. Such a screen 1770 may, in some embodiments, be used to provide a print out or for review of clinical documentation or a relief regimen/configuration.

The control of the actuators (e.g. inflation, deflation, and maintenance of actuators at set points) may be accomplished in a number of ways. In some embodiments, control of the actuators of a dynamic support apparatus may be similar to one or more of the embodiments described in U.S. patent application Ser. No. 13/461,336, filed May 1, 2012, entitled Dynamic Support Apparatus and System, now U.S. Pat. No. 8,845,754, issued Sep. 30, 2014 which is incorporated by reference herein in its entirety.

Figure 83A:
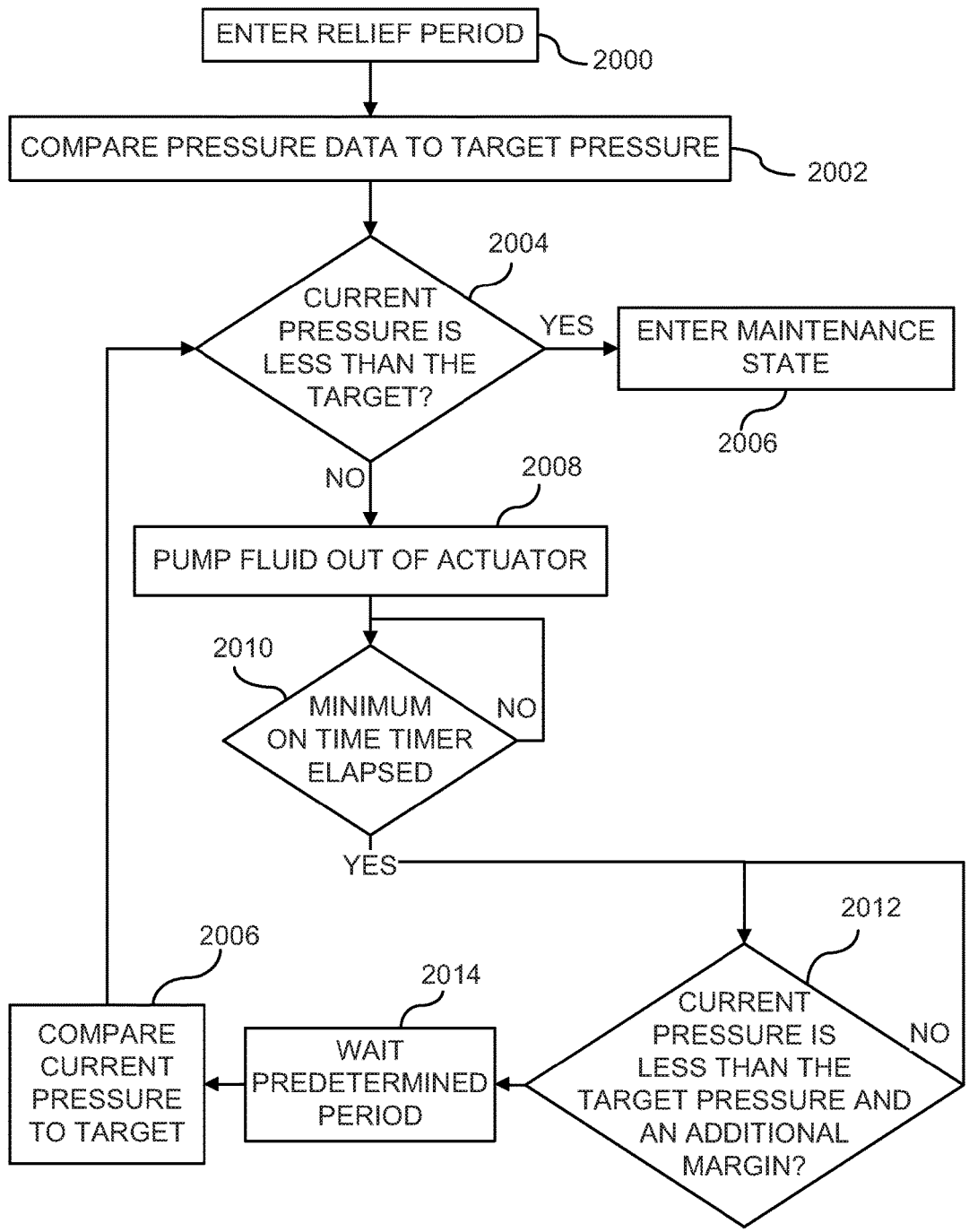
FIG. 83A depicts a flowchart which details a number of example steps that may be used to deflate an actuator based on a pressure set point.

FIG. 83A depicts a flowchart which details a number of example steps that may be used to deflate an actuator based on a pressure set point. In step 2000, a relief period may be entered. A relief period may be entered upon a processor of a dynamic support apparatus registering a button press or other type of interaction with a user interface. Alternatively, a relief period may be entered based on a pre-programmed schedule or after a predetermined amount of time since a previous support or relief period has elapsed. A target pressure may be compared to a current actuator pressure in step 2002. The current actuator pressure may be supplied by one or more pressure sensor associated with the actuator. The one or more pressure sensor may, for example, be located in the actuator itself (e.g. in a sensor assembly attached to the actuator via a stoma) or may read the pressure at a manifold port leading to the actuator. The target pressure may be a preset pressure. If 2004 the processor determines the current pressure is less than the target pressure, the processor may transition into a maintenance state in step 2006. In a maintenance state, the actuator pressure may be monitored by a processor and periodically adjusted to keep it within a range of the target pressure.

If 2004 the current pressure is not less than the target pressure, the processor may command the pump to pump fluid out of the actuator in step 2008. If 2010 a minimum on-time timer has not elapsed, fluid may continue to be pumped out of the actuator. If 2010 the minimum on-time timer has elapsed and if 2012 the current pressure is not below the target pressure (and an additional margin) fluid may continue to be pumped out of the actuator. The additional margin may, for example be at least 2 mmHg, e.g.

between 2-4 mmHg, and may be subtracted from the set point value. In some embodiments, an additional margin may not be included.

If 2010 the minimum on-time timer has elapsed and if 2012 the current pressure is below the target pressure (and the additional margin) the manifold port and actuator may, for example, be isolated from the rest of the system and a wait period may occur in step 2014. The wait period may be a predetermined amount of time. For example, in an embodiment in which the pressure sensors are remote from the actuators (e.g. in manifold ports leading to the actuators) the wait period may be approximately a half second. In an embodiment where a pressure sensor is remote from the target actuator, the wait may be an equalization period during which air flows from the actuator to the location of the pressure sensor. This equalization may cause the actuator pressure to equalize such that the target pressure is substantially reached. The processor may compare the current pressure to the target pressure in step 2016. The method may then return to decision 2004.

Figure 83B:
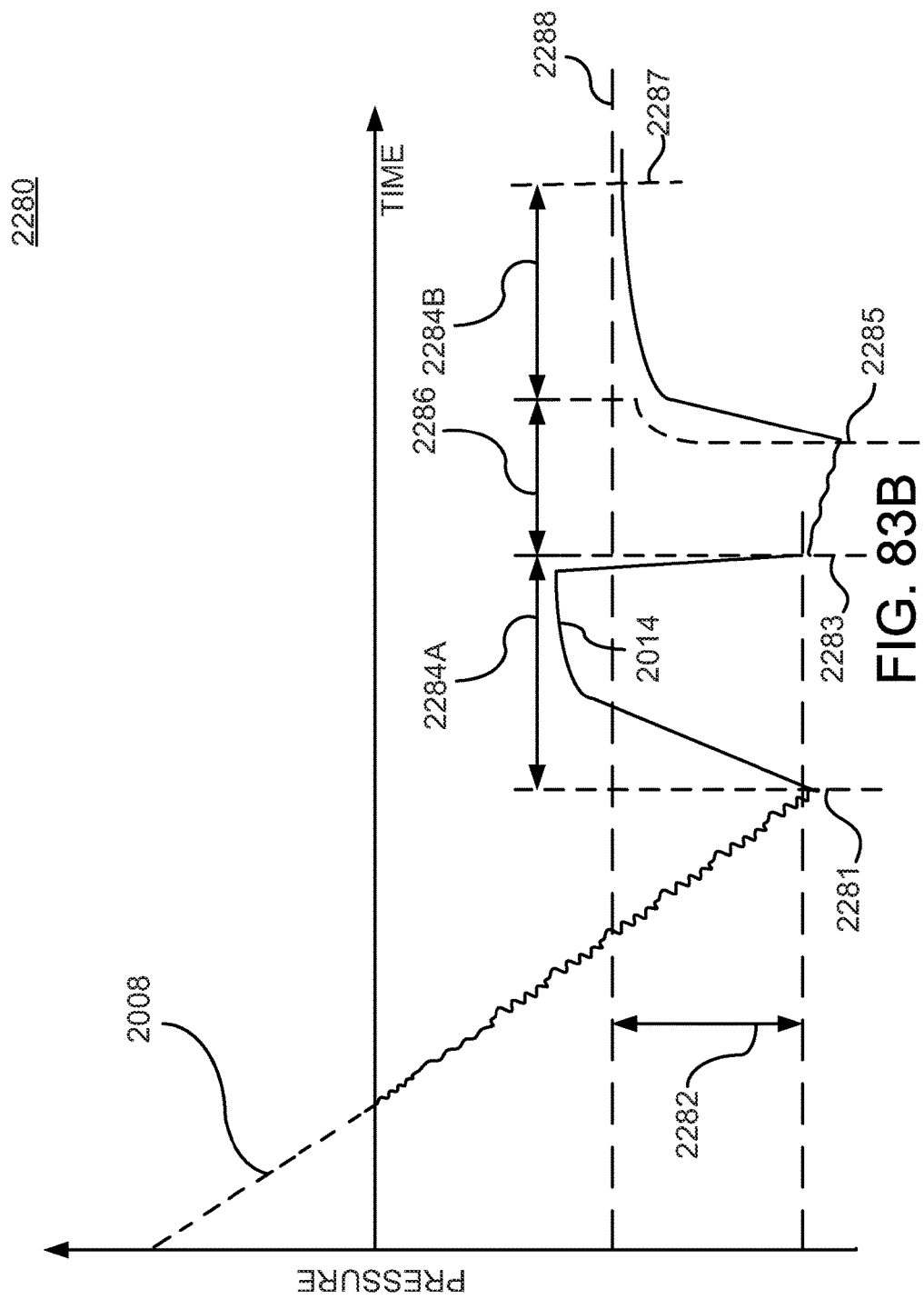
FIG. 83B depicts an example pressure over time plot depicting pressure samples from a pressure sensor monitoring pressure at a manifold port leading to an actuator.

Referring now to FIG. 83B, an example pressure over time plot 2280 depicting pressure samples from a pressure sensor monitoring pressure at a manifold port leading to an actuator is shown. The example plot 2280 is merely exemplary and not drawn to scale. The example plot 2280 depicts pressure while the actuator is being deflated using steps similar to those in FIG. 83A. As shown, the plot 2280 starts with fluid being pumped out of the actuator 2008. Fluid is pumped until (at time 2281) the pressure in the actuator is less than a target pressure 2288, plus an added margin 2282. A predetermined wait period 2284A elapses 2014. During this wait period 2284A the pressure at the manifold port and actuator equalize. Since the equalized pressure is greater than the target pressure 2288, a processor commands a pump to again pump fluid out of the actuator (at time 2283). The processor may keep the pump running for a minimum on time 2286. After the minimum on time 2286 elapses (at time 2285), another wait period 2284B passes. If, after the wait period 2284B elapses (at time 2287), the pressure is below the target pressure 2288 in FIG. 83B, the processor may deem to actuator to be at the desired set point.

Figure 84:
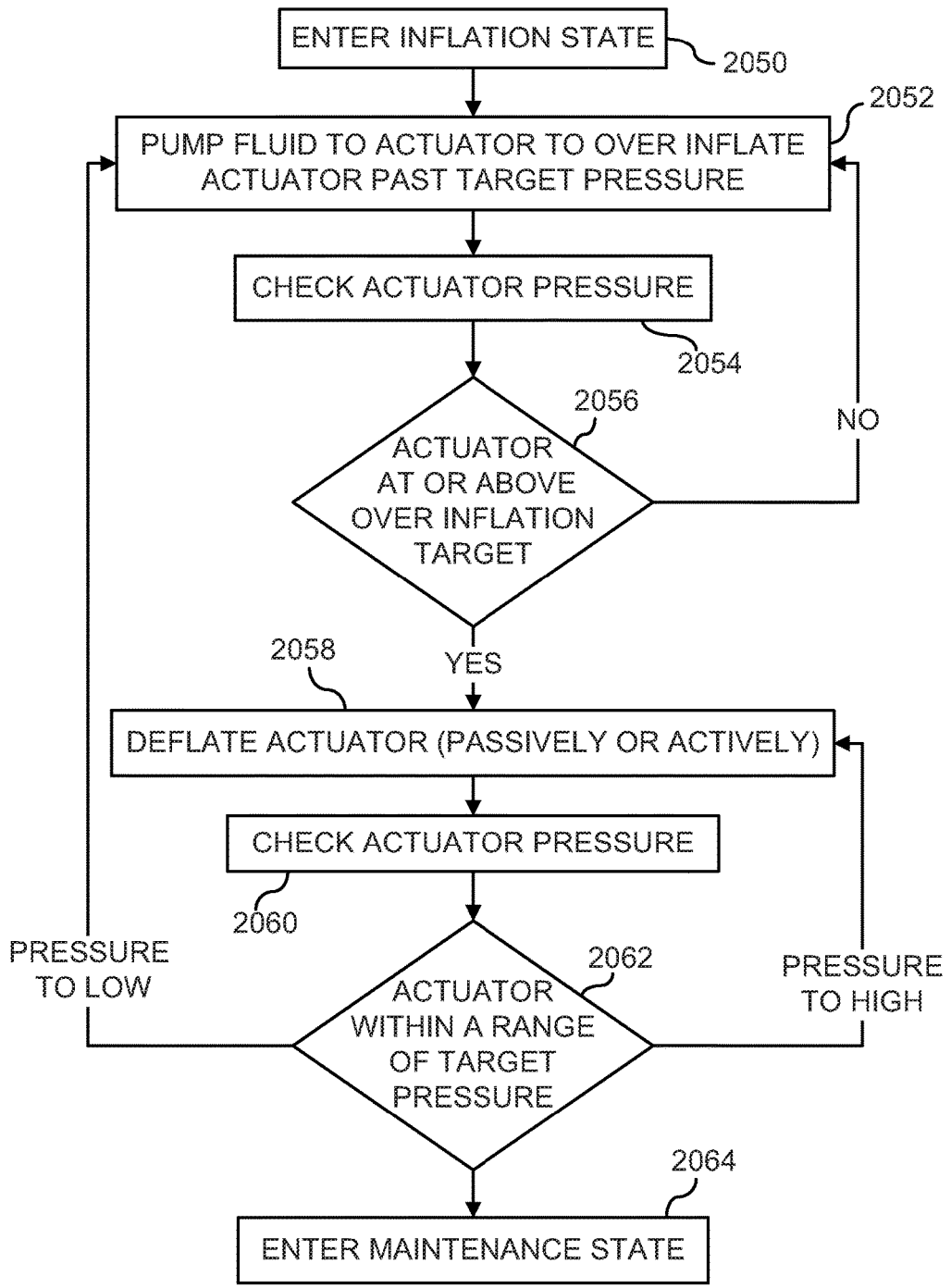
FIG. 84 depicts a flowchart which details a number of example steps that may be used to inflate an actuator based on a pressure set point.

FIG. 84 depicts a flowchart which details a number of example steps that may be used to inflate an actuator based on a pressure set point. During inflation to a set point, a processor may command an actuator be inflated beyond its target pressure and then command fluid to be removed until the actuator is within a range of the target pressure. The processor may also employ a deadband near and/or including the target pressure. Pressure readings outside of this deadband may cause a processor to issue commands to either add or remove fluid from an actuator. In some embodiments, the target pressure may serve as the lower bound of the deadband. Due to characteristics of the correlation between actuator pressure and actuator height (i.e. distance from the load supporting surface of the actuator and an opposing side or face of the actuator in some embodiments) it may be advantageous to overinflate the actuator and subsequently release fluid. This may help to ensure that a user is being supported in a more optimal manner and may help to more uniformly arrive within a tighter range of actuator heights for a given inflation set point.

The processor may enter an inflation state or mode in step 2050. In this mode, the processor may command fluid to be pumped to an actuator to overinflate the actuator past the target pressure (step 2052). The method may also include the processor checking the pressure of the actuator in step 2054. If 2056 the actuator pressure is not at or above the over-inflation target pressure, fluid may continue to be pumped to the actuator. If 2056 the actuator pressure is at or above the over-inflation target pressure, the processor may then command the actuator to be deflated (step 2058). Deflation of the actuator may be done passively (e.g. venting the actuator) or actively (e.g. by pumping fluid out of the actuator). The method may include the processor checking the pressure of the actuator in step 2060. If 2062 the actuator pressure is too low, the method may return to step 2052. If 2062, the actuator pressure is too high, the method may return to step 2058 If 2062 the actuator is within a range of the target pressure, the processor may transition to a maintenance state (step 2064) in which the actuator pressure is maintained by pumping fluid to the actuator as needed. In some embodiments, the range may be defined by the deadband mentioned above.

Figure 85A:
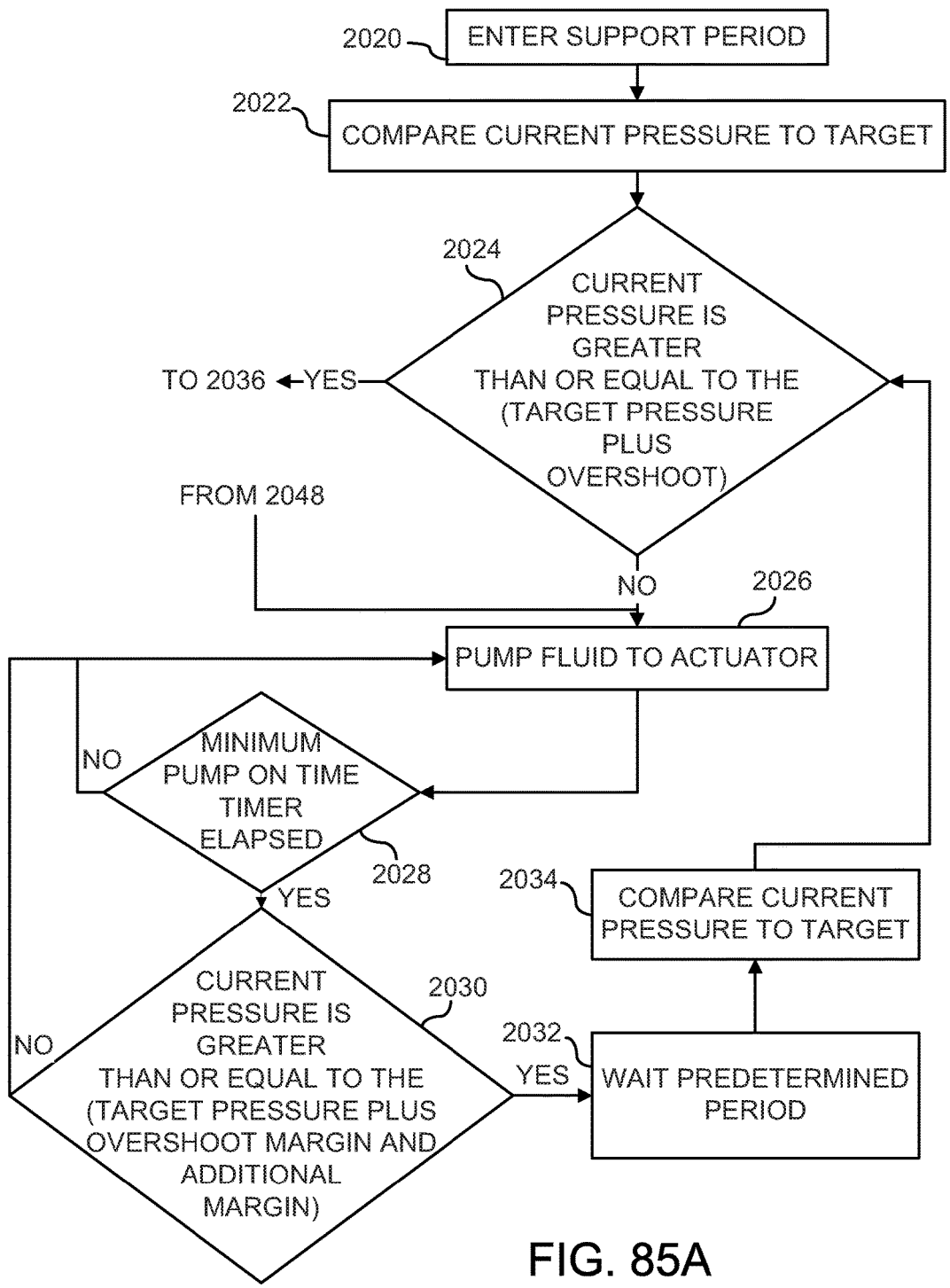
FIGS. 85A-85B depict a flowchart which details a number of example steps that may be used to inflate an actuator based on a pressure set point.
Figure 85B:
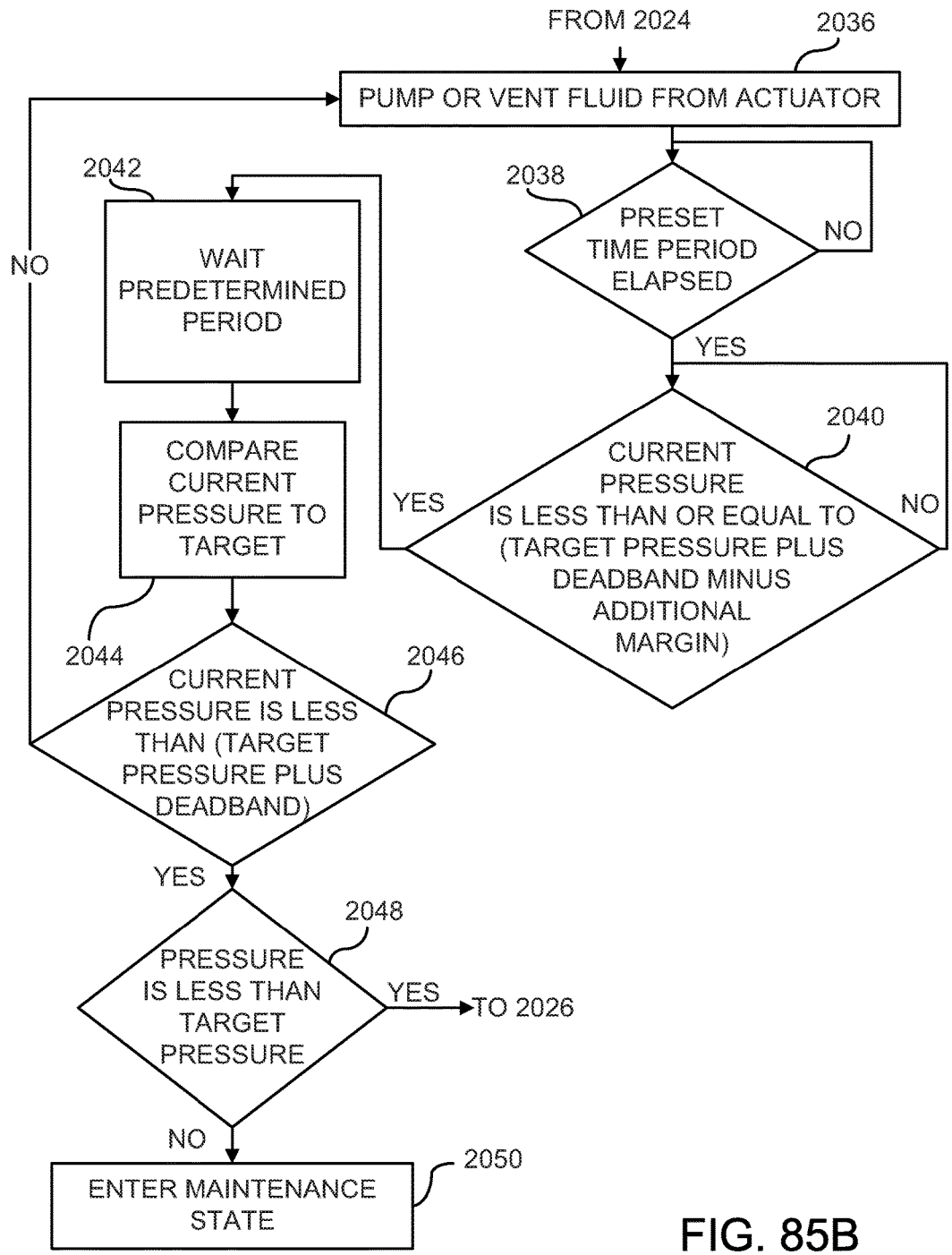

FIGS. 85A and 85B depicts a flowchart which details a number of example steps that may be used to inflate an actuator based on a pressure set point. In step 2020, a support period may be entered. A support period may be entered upon a processor of a dynamic support apparatus registering a button press or other type of interaction with a user interface. Alternatively, a support period may be entered based on a pre-programmed schedule or after a predetermined amount of time since a previous support or relief period has elapsed. A target pressure may be compared to a current actuator pressure in step 2022. The current actuator pressure may be supplied by one or more pressure sensor associated with the actuator. The one or more pressure sensor may, for example, be located in the actuator itself (e.g. in a sensor assembly attached to the actuator via a stoma) or may read the pressure at a manifold port leading to the actuator. The target pressure may be a preset pressure.

If 2024 the processor determines the current pressure is not greater than or equal to the target pressure (and an overshoot), the processor may command a pump to pump fluid to an actuator 2026. If 2028 a minimum on-time timer has not elapsed, fluid may continue to be pumped to the actuator. If 2028 the minimum on-time timer has elapsed and if 2030 the current pressure is not above the target pressure plus the overshoot and an additional margin, fluid may continue to be pumped to the actuator. In some embodiments, the additional margin may, for example, be at least 2 mmHg, e.g. between 2-4 mmHg, and may be added from the set point value. In some embodiments, an additional margin may not be included.

If 2028 the minimum on-time timer has elapsed and if 2030 the current pressure is above the target pressure (and the additional margin) the manifold port and the actuator may, for example, be isolated from the rest of the system and a wait period may occur in step 2032. The wait may be a predetermined amount of time. For example, in an embodiment in which the pressure sensors are remote from the actuators (e.g. in manifold ports leading to the actuators) the wait period may be approximately a half second. In an embodiment where a pressure sensor is remote from the target actuator, the wait may be an equalization period during which air flows from the actuator to the location of the pressure sensor. This equalization may cause the additional margin pressure to equalize out such that the target pressure is substantially reached. The processor may compare the current pressure to the target pressure in step 2034. The method may then return to decision 2024.

If 2024 the current pressure (from step 2022 or 2034) is greater than or equal to the target pressure plus an overshoot pressure and the additional margin, fluid may be pumped from or vented from an actuator in step 2036. If 2038 a preset pump on-time period of time has not elapsed, fluid may continue to be removed from the actuator. If 2038 a preset period of time has elapsed and if 2040 the current pressure is not less than or equal to the target pressure, plus a deadband range, less the additional margin, fluid may continue to be removed from the actuator.

If 2038 a preset period of time has elapsed and if 2040 the current pressure is less than or equal to the target pressure, plus a deadband range, less the additional margin, the manifold port and actuator may, for example, be isolated from the rest of the system and a wait period may elapse in step 2042. The wait period may, for example be a half second in some embodiments. The processor may compare the current pressure to the target pressure in step 2044. If 2046 the current pressure is not less than the target pressure plus the deadband range, the method may return to step 2036 and fluid may be removed (actively or passively) from the actuator.

If 2046 the current pressure is less than the target pressure plus the deadband range, and if 2048 the current pressure is also not less than the target pressure, the processor may enter a maintenance state in step 2050 and the inflation tasked may be deemed done. If 2046 the current pressure is less than the target pressure plus the deadband range, and if 2048 the current pressure is less than the target pressure, the method may return to step 2026 and fluid may be pumped to the actuator.

Figure 85C:
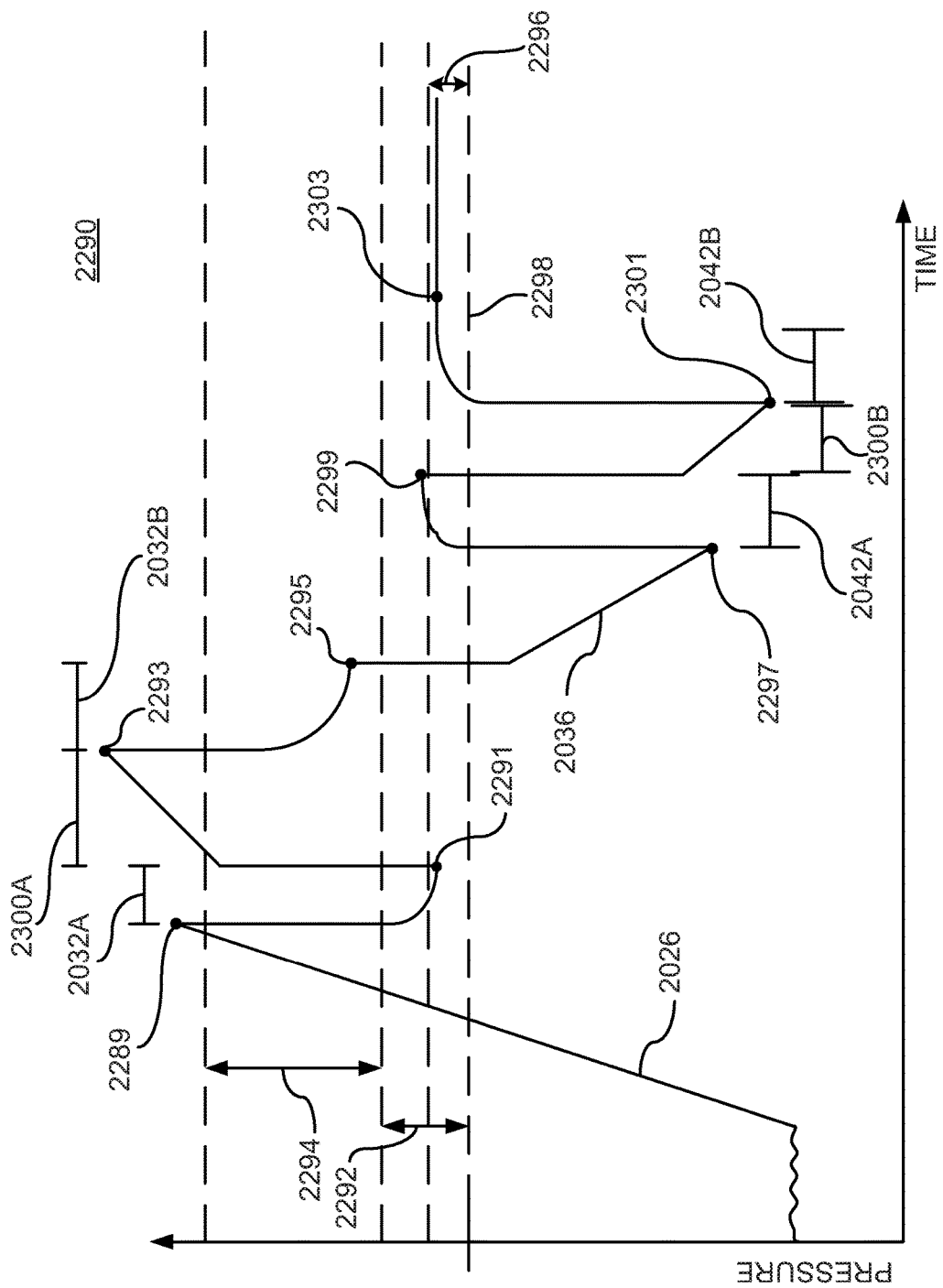
FIG. 85C depicts an example pressure over time plot depicting pressure samples from a pressure sensor monitoring pressure at a manifold port leading to an actuator.

Referring now to FIG. 85C, an example pressure over time plot 2290 depicting pressure samples from a pressure sensor monitoring pressure at a manifold port leading to an actuator is shown. The example plot 2290 is merely exemplary and not drawn to scale. The example plot 2290 depicts pressure while the actuator is being inflated using steps similar to those in FIGS. 85A and 85B. Since the starting pressure is less than the target pressure 2298 plus the overshoot 2292, the plot 2290 begins with fluid being pumped to the actuator 2026. Fluid is pumped until (at time 2289) the pressure in the actuator is greater than or equal to a target pressure 2298 plus an overshoot 2292 and an added margin 2294. A predetermine wait period elapses 2032A. During this wait period 2032A the pressure at the manifold port and actuator equalize. Since the equalized pressure is not greater than the target pressure 2298 plus the overshoot 2292, a processor (at time 2291) commands a pump to again pump fluid to the actuator. The processor may keep the pump running for a minimum on time 2300A. In the example plot 2290, when the pump is turned on, the pressure spikes and follow by a shallower sloped change in pressure over time. The spike indicates the small volume of the manifold quickly being brought to pressure. Once enough of a pressure difference exists between the manifold and the actuator is created, fluid will being to flow from the actuator and the change in pressure may become slower. After the minimum on time 2286 elapses (at time 2293), a wait period 2032B again elapses. Since the pressure is above the target pressure 2298 and overshoot 2292 after the second wait period 2032B and the processor (at time 2295) may deem the over-inflation target for the actuator to have been met.

With the over-inflation target met, the actuator may then be deflated 2036 toward the target pressure 2298. The actuator may be passively or actively deflated. Once (at time 2297) the actuator pressure is less than or equal to the target pressure 2298 plus a deadband pressure range 2296 less the additional margin 2294, a wait period 2042A may elapse. The manifold port and actuator may equalize in pressure over the wait period 2042A. Since (at time 2299) the pressure is greater than the target pressure 2298 plus the deadband pressure range 2296, the processor may again command fluid to be removed from the actuator for a minimum on time 2300B. Another wait period 2042B may elapse (at time 2301). This may continue until (at time 2303) the actuator pressure is less than the target pressure 2298 plus the deadband pressure range 2296, but greater than or equal to the target pressure 2298.

Figure 86:
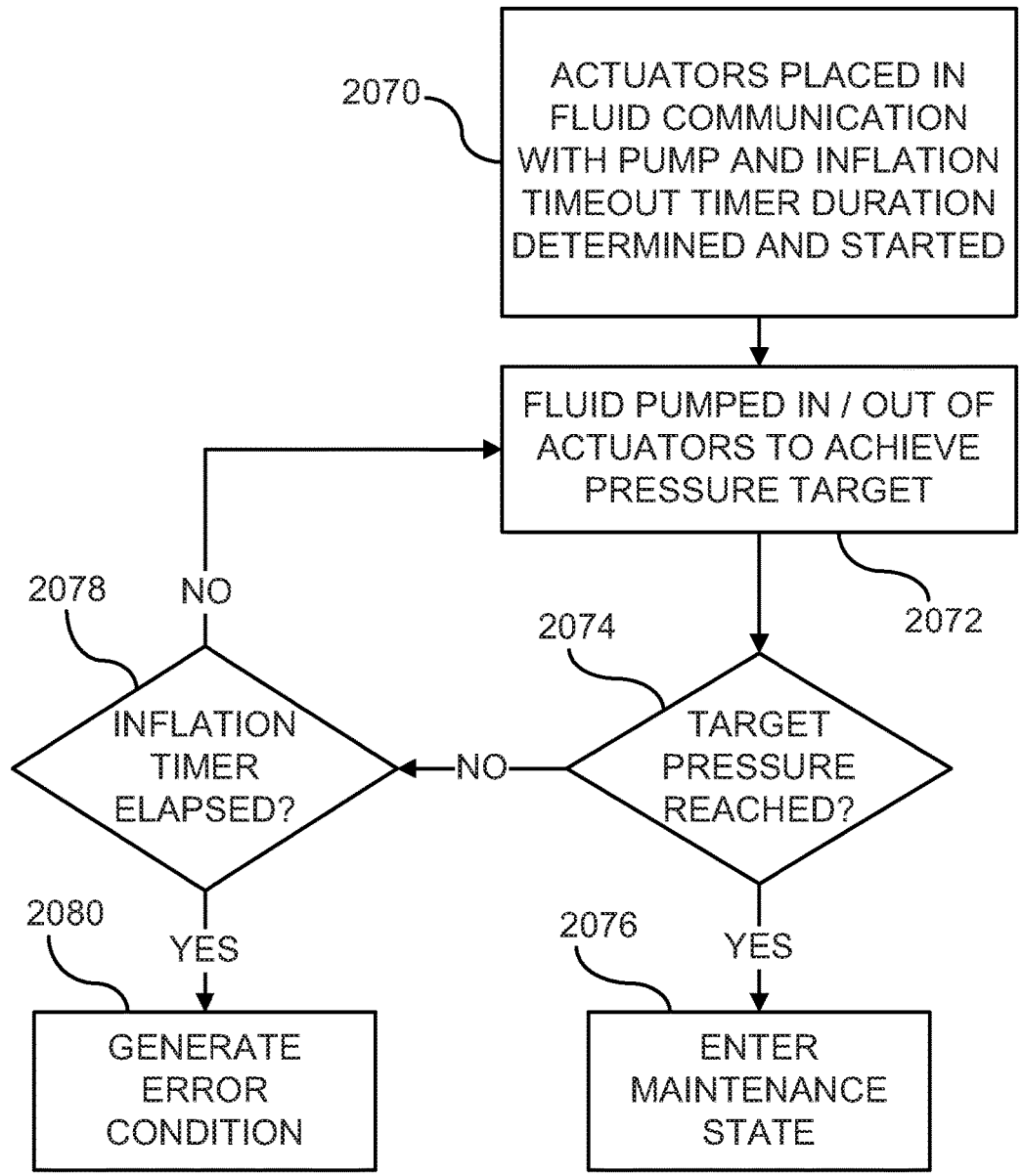
FIG. 86 depicts a flowchart detailing a number of example steps which may be used to detect an error or fault condition when pumping fluid to or from an actuator.

FIG. 86 depicts a flowchart detailing a number of example steps which may be used to detect an error or fault condition when pumping fluid to or from an actuator. A timeout timer may be used to determine if it is taking longer than expected to reach an actuator set point (e.g. a pressure set point) when pumping fluid to or from an actuator. The timeout timer may be a preset period of time in some embodiments. Alternatively, the timeout timer may be calculated at the beginning of a pumping operation. For example, the timeout timer duration may be based on a formula and may depend on the number of actuators being inflated or deflated. In some embodiments, the timeout timer may, for example, be a period of time equal to 120 seconds multiplied by the number of actuators being inflated or deflated.

An actuator or a plurality of actuators may be placed in fluid communication which a pump in step 2070. A processor may command actuation of a valve or number of valves in a manifold, for example, to place an actuator or actuators into communication with a pump in step 2070. A timeout timer may also be started once the actuator(s) have been placed into communication with the pump. In embodiments where the timeout timer is not a fixed preset period, the duration of the timer may be calculated in step 2070 as well. Fluid may be pumped into or out of the actuator(s) to achieve a target pressure for each of the actuator(s) in step 2072. In some embodiments, this may be done as described in relation to FIGS. 83-85B. If 2074 the target pressure is reached, the controller may enter a maintenance state (step 2076) in which a process may monitor pressure of the actuator and add or remove fluid from the actuator as necessary to maintain the actuator at the target pressure. If 2074 the target pressure has not been reached and if 2078 the timeout timer has not elapsed fluid may continue to be pumped in and/or out of the actuator(s). If 2078 the timeout timer has elapsed the processor may generated an error condition in step 2080.

Figure 87:
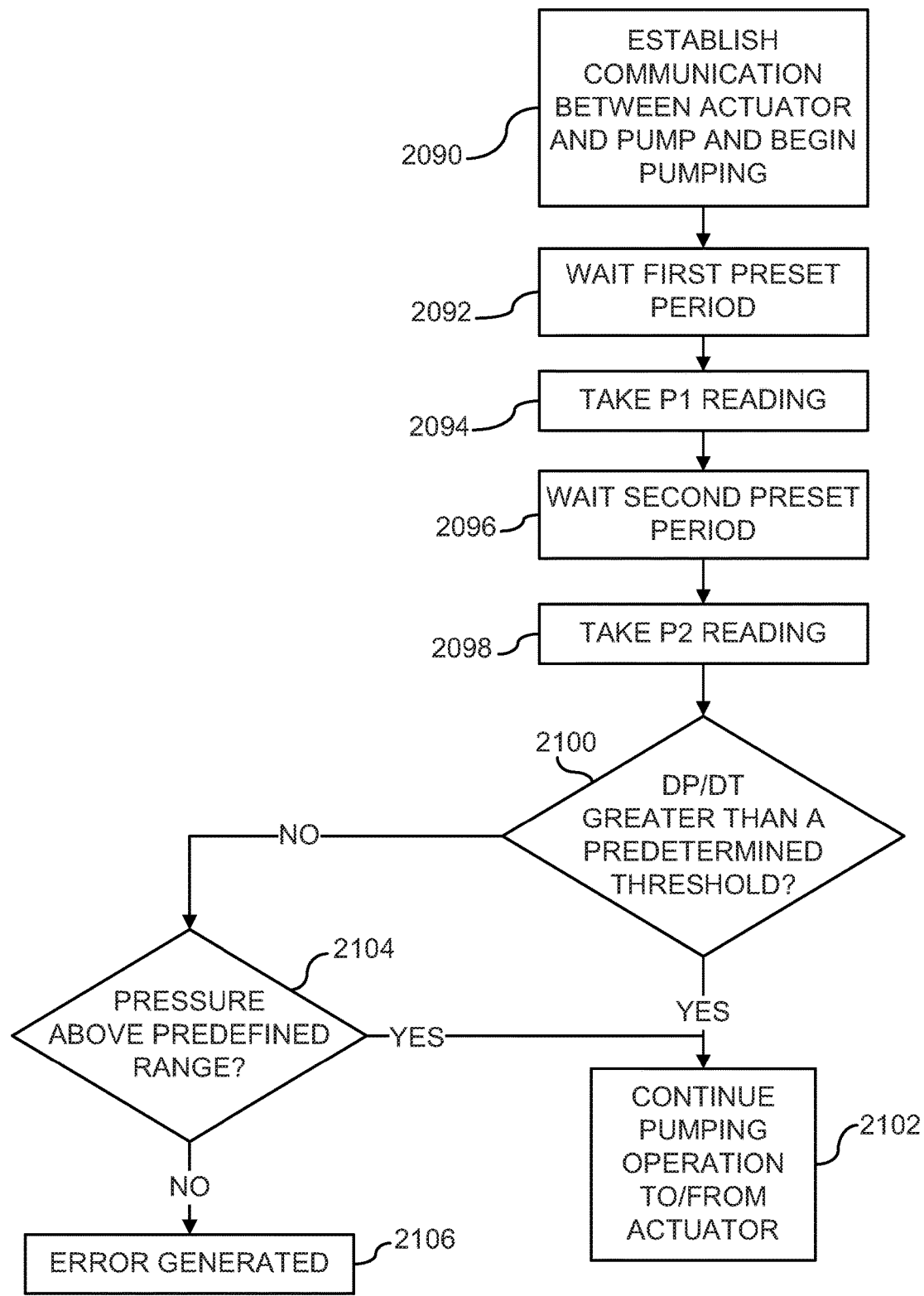
FIG. 87 depicts a flowchart detailing a number of example steps which may be used to detect an error or fault condition when monitoring the pressure of an actuator.

FIG. 87 depicts a flowchart detailing a number of example steps which may be used to detect an error or fault condition when monitoring the pressure of an actuator. If an open channel exists (e.g. the fluid path to or the actuator itself is compromised) the associated actuator's pressure will be near or at zero and will not change over time. Pressure and pressure change over time may be monitored to detect if an open channel condition exists. At least two pressure data samples from a pressure sensor associated with an actuator may be taken at different points in time and compared. If pumping fluid to an actuator during this time, the difference between the two readings may be expected to be greater than some threshold value. If the difference is smaller the threshold, an error may be triggered.

An actuator or plurality of actuators may be placed in fluid communication with a pump and a processor may command the pump to begin pumping fluid to the actuator(s) in step 2090. A processor may command actuation of one or more valve in a manifold to place the desired actuator(s) in communication with the pump in step 2090. While fluid is pumped to or from the actuator(s), a first period of time may then elapse in step 2092. The first period of time may be a predefined period of time and may be between 0.5-2 seconds, in some embodiments approximately 1 second. A pressure data sample, P1, may be taken in step 2094. While fluid is pumped to or from the actuator(s), a second period of time may elapse in step 2096. The second period of time may be a predefined period of time. In some embodiments, the second period of time may be calculated using a formula and not preset. For example, the second period of time may be calculated based on the number of actuators in communication with the pump. In some embodiments, the second wait period may be determined as 12 seconds multiplied by the number of actuators in communication with the pump. The length of the second period of time may depend on the type of pump being used. A second pressure data sample, P2, may be taken in step 2098.

If 2100 the difference in pressure over the second period of time is greater than a predetermined threshold the processor may continue commanding the pump to add or remove fluid from the actuator(s) it is in communication with (step 2102). The absolute value of the pressure change may be required to be above a threshold of 5-10 mmHg, for example 7 mmHg in some embodiments. If 2100 the absolute value of the pressure change is not above the threshold and if 2104 the pressure is outside a predefined range or below a threshold, the processor may generate an error in step 2106. In some embodiments, the threshold may be 10 mmHg-25 mmHg above gauge pressure, for example, 15 mmHg above gauge in some embodiments. The value chosen for the threshold may depend on the type of pump being used. If 2104 the pressure is above the predefined range, the open channel condition may be determined to not exist. The processor may continue commanding the pump to add or remove fluid from the actuator(s) it is in communication with (step 2102).

Figure 88:
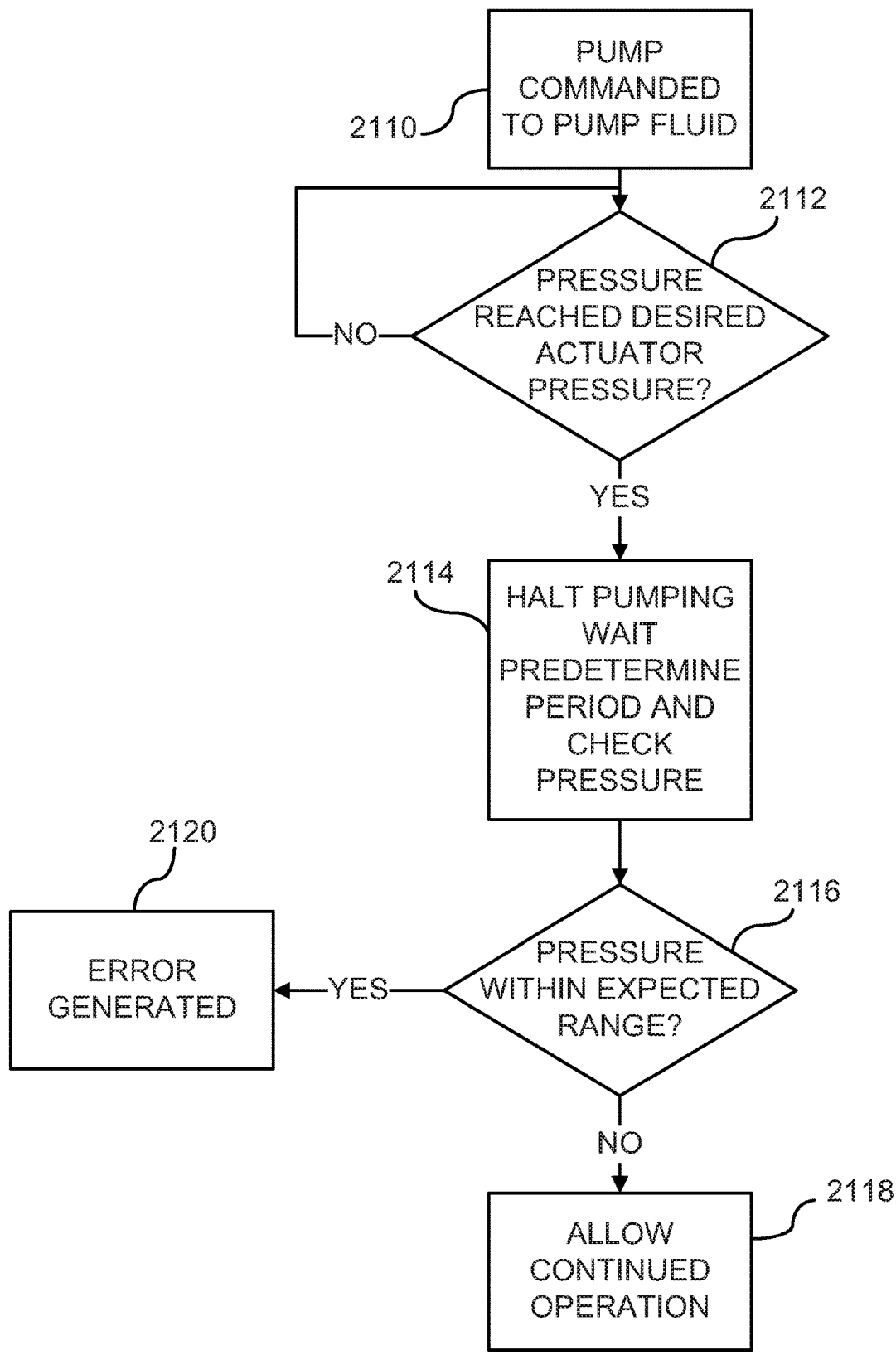
FIG. 88 depicts a flowchart detail a number of example steps which may be used to detected an occlusion in a fluid line extending from a manifold port to an actuator of a dynamic support apparatus.

FIG. 88 depicts a flowchart detail a number of example steps which may be used to detected an occlusion in a fluid line extending from a manifold port to an actuator of a dynamic support apparatus. If an occlusion exists leading from the manifold to an actuator, the pressure in the manifold will spike up or down as the pump respectively attempts to pump fluid to or from the actuator. The pressure at the manifold may be monitored for such spikes to detect a possible occlusion. In some embodiments, when the manifold pressure is checked, it may be compared to an expected range. If the pressure is outside this range, a processor may generate an error to indicate the occlusion.

A processor may command the pump to pump fluid to or from an actuator in step 2110. If 2112 the pressure has not reached the desired actuator pressure, the process may continue commanding the pump to pump fluid. If 2112 the pressure has reached or exceeded the desired actuator pressure, the processor may halt pumping, wait a predetermined period, and check pressure in step 2114. The wait period may be, for example, 0.5 seconds in some embodiments. If 2116 the pressure is within an expected range, the processor may allow continued operation in step 2118 and no error may be generated. If 2116 the pressure is outside of the expected range, an occlusion may be determined to be present and an error may be generated in step 2120. The expected range may vary depending on the type of pump, manifold volume, fluid line conduit volume among other considerations. In some embodiments, the excepted range may be from about −100 mmHg to +100 mmHg.

In alternative embodiments, all pressure readings may be compared to an expected pressure range by a processor. In the event that any of the pressure readings or a number of pressure readings over a predetermined time frame are outside of the expected range pumping may be stopped and a pressure reading may be taken. This reading may be compared to the expected range to determine if an occlusion exists. In other embodiments, in the event that any of the pressure readings or a number of pressure readings over a predetermined time frame are outside of the expected range an occlusion error may be generated.

In embodiments where a pressure sensor is included in an actuator and a pressure sensor is disposed so as to sense pressure at the associated manifold port, the readings from these sensors may be compared. If the pressure of the actuator sensor differs from that of the manifold port sensor by more than a predetermined amount, an occlusion or failure of one or both sensors may be determined to exist and an error may be generated. A number of pressure readings from the actuator and manifold sensors may be required to differ by more than the predetermined amount within a preset time frame for an error to be generated by a processor in some embodiments.

Referring again to FIG. 25, an embodiment of a dynamic support system 2200 is shown. In some embodiments, the dynamic support system 2200 includes both hardware and control components for controlling the hardware. In some embodiments, the hardware may be a dynamic support apparatus 10, which may include, but is not limited to, one or more of the following: at least one control interface 506, actuators 16, actuator channels 520 such as tubing and/or other elements to support integration of the dynamic support apparatus 10. The dynamic support system 2200 therefore may include the control systems 2202 for executing control logic and/or one or more methods for controlling the one or more actuators 16 using, for example, actuator channels 520 such as tubing, and in some embodiments, other hardware elements such as a pump 500.

Figure 89:
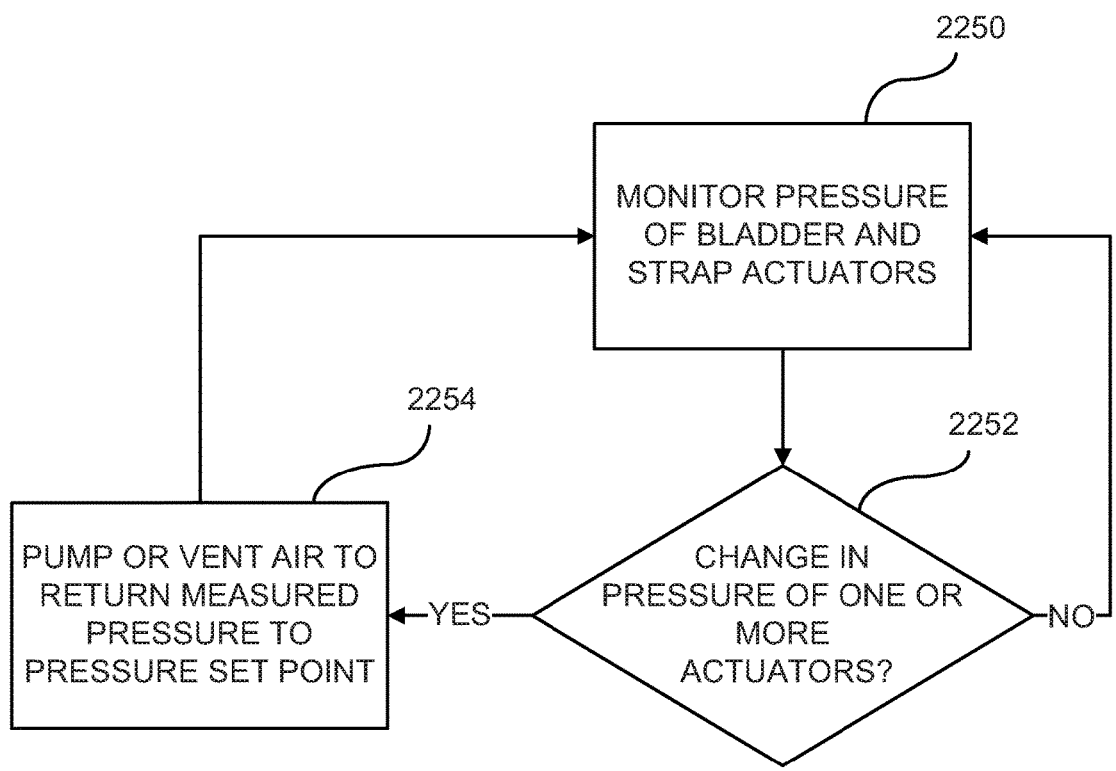
FIG. 89 depicts a flow diagram of one embodiment of the methods for maintaining the baseline pressure of the one or more actuators.

Referring now to FIG. 89, in various embodiments, the leak compensation mode or maintenance mode may include monitoring the pressure of each actuator 16, over time at 2250. For example, in some embodiments the control system 2202, may read the pressure of each actuator 16, at predetermined intervals, e.g., every 0.1 seconds. At 2252, the control system 2202 determines whether there has been a change in the pressure of one or more actuator 16. For example, in some embodiments, the control system 2202 may compare the instantaneous pressure of each actuator 16 to the desired set point pressure or pressure range for that actuator 16 at pre-determined intervals (e.g. in one mere exemplary embodiment, every 60 seconds). Where the sampled instantaneous pressure is lower than the desired set point pressure, at 2254, the control system 2202, shown in FIG. 25, may command the pump 500, shown in FIG. 25, to add or remove air to/from that channel in order to alter the pressure in the actuator 16, (see, e.g., FIG. 25) to the desired set point pressure or pressure range. Conversely, where the sampled instantaneous pressure is in excess of the desired set point pressure, at 2254, the control system 2202, shown in FIG. 25, may open a valve associated with an actuator 16, (see, e.g., FIG. 25) to vent the channel in order to relieve the pressure in the actuator 16, (see, e.g., FIG. 25) to the desired set point pressure or pressure range. In some embodiments, a hysteresis or deadband may be added about the pressure set point to provide a range of acceptable pressures about the pressure set point where no pumping or venting action is required. This hysteresis or deadband may advantageously reduce the amount of work required by the control system 2202, shown in FIG. 25.

While determining actuator pressures changes by comparing the instantaneous pressure to the desired pressure set point or range may be advantageous in some situations for detecting pressure changes at 2252, such as during low activity, in other situations, this control may result in unnecessary air pumping and/or venting. For instance, when the dynamic support apparatus 10 (see, e.g., FIG. 25), is carrying a load, the mechanical forces through the dynamic support apparatus 10 (see, e.g., FIG. 25) to the user will cause the pressure in each channel 520 (see, e.g., FIG. 25) and actuator 16, (see, e.g., FIG. 25) to fluctuate with respect to the set point pressure or range. For example, some actuator 16, (see, e.g., FIG. 25) will undergo compression and have elevated pressures while other actuators will have lower pressures. Thus, if the control system 2202, shown in FIG. 25, controls pumping and/or venting based on the instantaneous pressure in these actuator 16, (see, e.g., FIG. 25) the control system 2202, shown in FIG. 25, is likely to add and/or remove air from the actuator 16, (see, e.g., FIG. 25), unnecessarily.

Therefore, in some embodiments, the control system 2202, shown in FIG. 25, may maintain a constant amount (i.e. mass or moles) of fluid in each actuator channel 520 (see, e.g., FIG. 25), thereby rarely venting and essentially only pumping to replace any lost pressure due to leaking. For example, the control system 2202, shown in FIG. 25, may use the monitored pressure over time in each actuator 16, (see, e.g., FIG. 25) or actuator channel 520 (see, e.g. FIG. 25) as a proxy measurement to estimate the amount of fluid in, or the height of each actuator 16, (see, e.g., FIG. 25). In using the monitored pressure to estimate the amount of fluid in or the height of each actuator 16, (see, e.g., FIG. 25), the assumption is made that, on average, the loading on the actuator 16, (see, e.g., FIG. 25) is constant, which turns out to typically be true, as dynamic loading is generally transient and generally has zero net magnitude.

Therefore, to estimate the amount of fluid in or the height of each actuator 16, (see, e.g., FIG. 25), the control system 2202, shown in FIG. 25, passes the monitored pressure signal through a low-pass filter 2256 (FIG. 90) having a bandwidth sufficiently low to remove most of the pressure transients from the signal. For example, in some exemplary embodiments, the low-pass filter 2256 (FIG. 90) may have a bandwidth of less than or equal to 0.1 Hz. In other exemplary embodiments, the low-pass filter 2256 may have other desired bandwidths. With the pressure transients largely removed from the pressure signal any remaining variations in the filtered pressure signal should be the result of leakage of the actuator channel 520 (see, e.g., FIG. 25) or actuator 16, (see, e.g., FIG. 25) Thus, the control system 2202, shown in FIG. 25, may monitor the low-pass filtered pressure signal at 2252 and, periodically, supply or remove air to/from the actuator 16, (see, e.g., FIG. 25) at 2254 to account for leaks and the like.

In some embodiments, the control system 2202, shown in FIG. 25, may use pulse density modulation control to apply brief pulses of fluid to/from each actuator channel 520 (see, e.g., FIG. 25) to compensate for leakage. Each pulse of air is separated by an idle time between pulses $\Delta t$ in which fluid is not being pumped. As the leak rate from a particular actuator channel 520 (see, e.g., FIG. 25) or actuator 16 (see, e.g., FIG. 25) increases, the time between pulses $\Delta t$ for that channel 520 (see, e.g., FIG. 25) is decreased by the control system 2202, shown in FIG. 25. When the control system 2202, shown in FIG. 25, is in equilibrium, the averaged effect of the air pulses for a particular actuator channel 520 (see, e.g., FIG. 25) or actuator 16 (see, e.g., FIG. 25), in various embodiments, should substantially match the effect of air leakage from that actuator channel 520 (see, e.g., FIG. 25) or actuator 16 (see, e.g., FIG. 25). The control system 2202, shown in FIG. 25, includes control logic for calculating the time between pulses $\Delta t$ for each actuator channel 520 (see, e.g., FIG. 25) or actuator 16 (see, e.g., FIG. 25) based on the low-pass filtered pressure measured in that actuator channel 520 (see, e.g., FIG. 25) or actuator 16 (see, e.g., FIG. 25). In some embodiments, the control logic for determining the time between pulses $\Delta t$ may be a function of an error parameter E, e.g. a measurement of how far from the desired pressure set point or range the actuator 16 (see, e.g., FIG. 25) pressure is. In some embodiments, the function may be exponential and may take the form:

$$\Delta t = f(E) = \Delta t_{max} \cdot \exp(-\alpha \cdot E)$$

where $\alpha = (1/E_{max}) \ln(\Delta t_{max}/\Delta t_{min})$;
$\Delta t_{max}$ is a preset maximum allowable time between pulses;
$\Delta t_{min}$ is a preset minimum allowable time between pulses; and
$E_{max}$ is a preset maximum allowable error.

In this embodiment, when the error parameter E becomes smaller (i.e. approaching zero), the time between pulses $\Delta t$ should grow towards the maximum time $\Delta t_{max}$. Conversely, when the error parameter E becomes larger (i.e. approaching the maximum allowable error $E_{max}$) the time between pulses $\Delta t$ should shrink towards the minimum time $\Delta t_{min}$. When a particular actuator channel 520 (see, e.g., FIG. 25) or actuator 16 (see, e.g., FIG. 25) is being maintained with pulses separated by minimum time $\Delta t_{min}$, the control effort is considered saturated. Although shown as an exponential function, it should be understood by those skilled in the art that the relationship between the time between pulses $\Delta t$ and the error parameter E could take many forms including a linear function, a quadratic function, a cubic function or any other similar polynomial function. For example, a linear relationship may be represented by the equation:

$$\Delta t = f(E) = \Delta t_{max} - (E/E_{max}) \cdot (\Delta t_{max} - \Delta t_{min})$$

Preferably, at the time that the control system 2202, shown in FIG. 25, applies one pulse of air, the control system 2202 shown in FIG. 25, calculates the time between pulses $\Delta t$ to the next pulse and schedules the pulse to occur. Alternatively, at the beginning, during, or at the end of a pulse, a pulse timer may be started. The control system 2202 may continuously calculate $\Delta t$ at every time stamp or every time a predetermined number of time stamps have passed. If a $\Delta t$ calculation is equal to or less than the elapsed time on the pulse timer, the control system 2202 may trigger a pulse. In some embodiments, a number of $\Delta t$ calculations (e.g. a number of Consecutive calculations) may be required to be equal to or less than the elapsed time on the pulse timer in order for a pulse to be triggered. In embodiments where each actuator channel 520 (see, e.g., FIG. 25) or actuators 16 (see, e.g., FIG. 25) operates independently, the calculation of $\Delta t$ may also be performed independently for each channel 520 (see, e.g., FIG. 25) or actuator 16 (see, e.g., FIG. 25) such that the resulting air pulses occur asynchronously.

Figure 90:
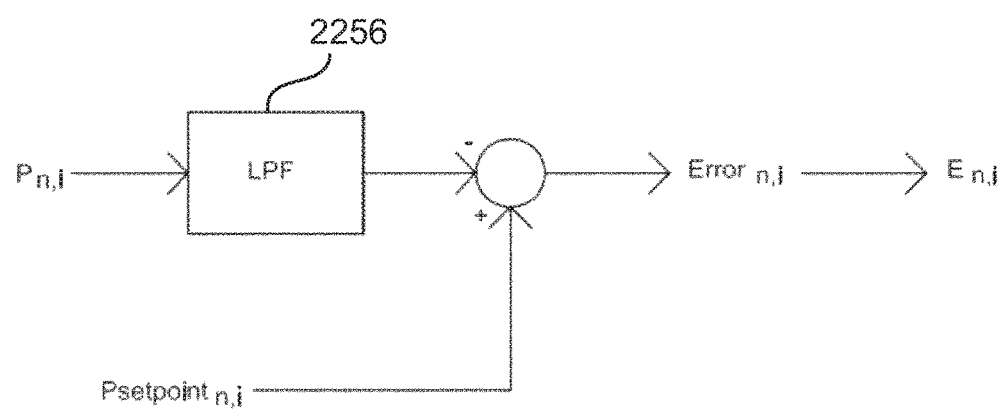
FIG. 90 depicts a schematic view of an embodiment for a leak detection control mode.

The error parameter E may advantageously be determined in a variety of different ways. Referring to FIG. 90, an embodiment, for determining the error parameter E for a particular channel i at time interval n is shown. In this embodiment, the error parameter $E_{n,i}$ equals an $Error_{n,i}$ calculated from the difference between the pressure set point $P_{setpoint\ n,i}$ and the monitored pressure $P_{n,i}$ after passing through the low-pass filter 2256. In this embodiment, when the monitored pressure $P_{n,i}$ passed through the low-pass filter 2256 is lower than the pressure setpoint $P_{setpoint\ n,i}$, e.g. due to air leakage from the channel i, the error parameter $E_{n,i}$ is positive.

Figure 91:
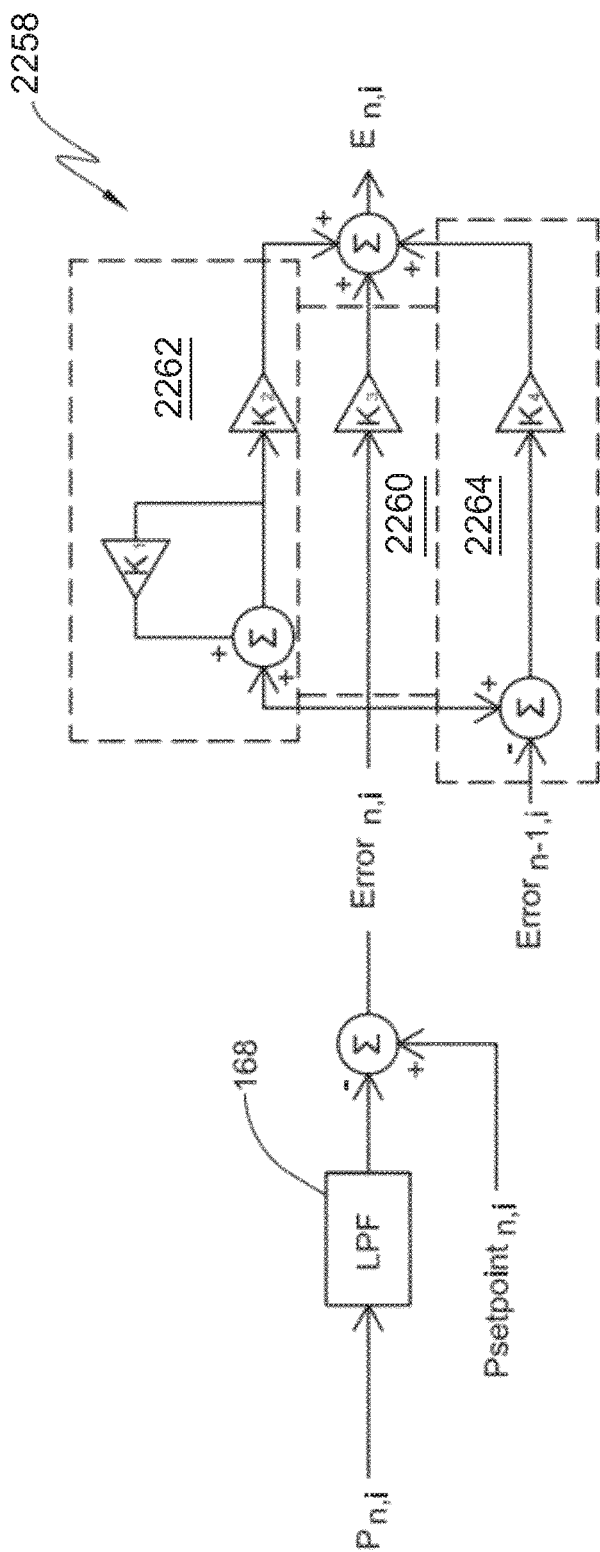
FIG. 91 depicts a schematic view of another embodiment for the leak detection mode; Like reference symbols in the various drawings indicate like elements.

Referring to FIG. 91, in some embodiments, the error parameter E for a particular channel i at a given time interval n may be determined by the control system 2202, shown in FIG. 25, using a proportional-integral-derivative (PID) control unit 2258 having a proportional portion 2260, an integral portion 2262 and a derivative portion 2264. In other embodiments, a derivative portion 2264 may not be included and the control unit 2258 may be a proportional-integral (PI) control unit. In these embodiments, the control system 2202, shown in FIG. 25, first calculates $Error_{n,i}$ from the difference between the pressure set point $P_{setpoint\,n,i}$ and the monitored pressure $P_{n,i}$ after passing through the low-pass filter 2256 in substantially the same manner as that discussed in connection with FIG. 90. The control system 2202, shown in FIG. 25, then processes the signal $Error_{n,i}$ through the PID control unit 2258 and takes a weighted sum of the output signals from the proportional portion 2260, the integral portion 2262 and the derivative portion 2264 to determine $E_{n,i}$. In the proportional portion 2260, $Error_{n,i}$ is multiplied by a gain factor k3, which, in some embodiments, may simply equal 1, to provide a weighted output signal representative of an instantaneous or present error. In the integral portion 2262, the control system 2202, shown in FIG. 25, calculates the integral of the signal $Error_{n,i}$ over time to provide an output signal representative of the accumulation of past error. The integral portion 2262 includes a gain factor k1 that is a leakage factor between 0 and 1 that is applied to the integrated $Error_{n,i}$ with each time step n to prevent the integral output signal from growing without bound. The gain factor k1 may be dependent upon the rate or pressure sampling for the dynamic pressure data. For example, in one exemplary embodiment, provided for mere illustrative purposes, the gain factor k1 may be between 0.93 and 0.99 for a sampling rate of approximately 10 Hz. The output signal from the integral portion 2262 is multiplied by a gain factor k2 to provide the weighted output signal representative of past error. In the derivative portion 2264, the control system 2202, shown in FIG. 89, calculates the derivative of the signal $Error_{n,i}$ by subtracting the $Error_{n-1,i}$ from the previous time step to provide an output signal representative of the rate of change of error, which may provide the control system 2202, shown in FIG. 25, with faster response to transients. The output signal from the derivative portion 2264 is multiplied by a gain factor k4 to provide the weighted output signal representative of the rate of change of error. The control system 2202, shown in FIG. 25, calculates the error parameter $E_{n,i}$ by taking the weighted sum of the output signals from the proportional portion 2260, the integral portion 2262 and the derivative portion 264. The control system 2202, shown in FIG. 25, may use this error parameter $E_{n,i}$ for calculating the time between pulses Δt for each actuator channel i as discussed above.

The control logic discussed above advantageously works in the regime where the error parameter E is between and zero (0) and the maximum allowable error $E_{max}$. However, in some situation, the control system 2202, shown in FIG. 25, may determine that the error parameter E is outside of that regime. For example, the control system 2202, shown in FIG. 25, may determine that the error parameter E exceeds the maximum allowable error $E_{max}$, which would result in the required time between pulses Δt to be shorter than the minimum time $Δt_{min}$. Therefore, in the situation where the error parameter E exceeds the maximum error $E_{max}$, the control system 2202, shown in FIG. 25, turns the pump full-on to restore the pressure to the desired set point pressure or range. Alternatively or additionally, an error or warning may be generated by the processor for display on a user interface.

In some embodiments, when the control system 2202, shown in FIG. 25, implements the control logic discussed above, it is possible that when Δt comes due and a pulse of air should be supplied to a particular actuator 16 (see, e.g., FIG. 25) the instantaneous pressure within the actuator 16 (see, e.g., FIG. 25) may higher than what the pump 500 (see. e.g., FIG. 25) can reasonably supply due to transient external loading. Therefore, if the instantaneous pressure is well above the pressure set point or range, the control system 2202, shown in FIG. 25, may defer the air pulse briefly until the instantaneous pressure returns to a reasonable level in which the pump 500 (see, e.g., FIG. 25), may operate.

In some embodiments, when the control system 2202, shown in FIG. 25, implements the control logic discussed above, the monitored pressure $P_{n,i}$ after passing through the low-pass filter 2256 may be above the target pressure set point or range for a long period of time. This may cause the output signal from the integral portion 2262 of the PID control unit 2258 to become large and negative. To compensate for this, the control system 2202, shown in FIG. 25, may include a pre-defined large and negative threshold for the integral portion that, when surpassed by the output signal, causes the control system 2202, shown in FIG. 25, to provide one or more brief pulses of venting, by opening one or more valves to reduce the pressure in the actuator 16 (see, e.g., FIG. 25) to a level below the target set point pressure or range, which, over time, brings the output signal from the integral portion 2262 back toward zero.

If the E value is negative or less than an $E_{min}$ value, in some embodiments, the control system 2202 may default to $T_{max}$ as the time between pulses. Alternatively, the control system 2202 may suspend pulses until the E value is no longer negative or until the E value is greater than $E_{min}$. In still other embodiments, one or more pulse of venting, e.g., by opening one or more valves connected to the actuator, may be commanded by the control system 2202. The control system 2202 may take different actions in such scenarios depending on the set point of the actuator. For example, if the actuator pressure set point is a negative pressure set point, pulses may be suspended or the time between pulses may be set at $T_{max}$. If the actuator set point is a positive pressure set point, pulses may be suspended or venting pulses may be commanded by the command system 2202. The density of such venting pulses may be determined using a control scheme similar to that described above.

It stands to reason that, when the pressure set point for a particular channel is higher, the leakage rate of a channel 520 (see, e.g., FIG. 25) or actuator 16 (see, e.g., FIG. 25) will be higher than for the same channel 520 (see, e.g., FIG. 25) or actuator 16 (see, e.g., FIG. 25) at a lower pressure set point. Therefore, the leak compensation mode described above may advantageously compensate for higher leakage rates by providing uniform pulses of air more frequently when the pressure set point for a channel is higher than when the pressure set point is lower. Additionally, in some embodiments, the control system 2202, shown in FIG. 25, may vary the pulse duration directly with the operating pressure. Thus, when in a higher operating pressure regime, longer pulses may partially or completely compensate for the higher leakage rates. As should be understood by those skilled in the art, the relationship between set point pressure and pulse width may be linear, exponential, etc.

In some embodiments of the leak compensation mode, the control system 2202, shown in FIG. 25, may advantageously utilize statistics to detect a leaky channel 520 (see, e.g., FIG. 25) or actuator 16 (see, e.g., FIG. 25). For example, the control system 2202, shown in FIG. 25, may keep track of how many pulses performed for each channel 520 (see, e.g., FIG. 25) or actuator 16 (see, e.g., FIG. 25) over a prolonged period of time to determine an average pulse rate for each channel 520 (see, e.g., FIG. 25) or actuator 16 (see, e.g., FIG. 25). The control system 2202, shown in FIG. 25, may then compare the pulse rates to one or more empirically determined pulse rates calculated based on a nominal system. If the pulse rate for a channel 520 (see, e.g., FIG. 25) or actuator 16 (see, e.g., FIG. 25) is significantly above the pulse rate for the nominal system, the control system 2202, shown in FIG. 25, may identify the channel 520 (see, e.g., FIG. 25) or actuator 16 (see, e.g., FIG. 25) as leaky. Additionally or in the alternative, the control system 2202, shown in FIG. 25, may compare the averaged pulse rate of one channel 520 (see, e.g., FIG. 25) or actuator 16 (see, e.g., FIG. 25) to the pulse rates of one or more other peer channels 520 (see, e.g., FIG. 25) or actuators 16 (see, e.g., FIG. 25) to determine whether or not a channel 520 (see, e.g., FIG. 25) or actuator 16 (see, e.g., FIG. 25) is leaky since, a leaky channel 520 (see, e.g., FIG. 25) or actuator 16 (see, e.g., FIG. 25) will require a greater number of pulses compared to its peers over a long period of time to maintain a set point pressure.

By implementing the control logic for the leak detection mode as discussed above, the control system 2202, shown in FIG. 25, is able to advantageously monitor the pressure in actuators 16 (see, e.g., FIG. 25) and to maintain the baseline pressure or the current pressure set point. The leak compensation mode may, in some embodiments, be referred to as a closed-loop system, where monitoring, inflating and deflating may be automatic based on pre-set/pre-determined values, e.g. the baseline pressure, pressure set point or range and/or error threshold. However, in some embodiments, the closed-loop system may be elective by the user and, thus, the user may instead elect to manually inflate/deflate the actuators 16 (see, e.g., FIG. 25) based, e.g., on recommendations from the control system 2202, shown in FIG. 25, and/or based on user desires/requirements.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

A number of embodiments have been described. Nevertheless, it will be understood that various modifications may be made. Accordingly, other embodiments are within the scope of the following claims.

While the principles of the disclosure have been described herein, it is to be understood by those skilled in the art that this description is made only by way of example and not as a limitation as to the scope of the invention. Other embodiments are contemplated within the scope of the present disclosure in addition to the exemplary embodiments shown and described herein. Modifications and substitutions by one of ordinary skill in the art are considered to be within the scope of the present invention.

What is claimed is:

1. A dynamic support apparatus comprising:
a cushion;
at least one actuator wherein the at least one actuator defines an interior volume and wherein the interior volume configured to be at least partially filled with a fluid and the at least one actuator attached to an actuator fluid conduit in communication with the interior volume;
a fluid pump having a pump inlet and a pump outlet;
a rotary valve comprising:
a stationary portion including a pump inlet port, a pump outlet port, an atmosphere port, and an actuator port;
a rotor having a planar body with transversely disposed flow paths recessed into each of a first face and a second face of the rotor, wherein the second face is opposingly situated with respect to the first face, the rotor captured between a first part of the stationary portion and a second part of the stationary portion, the rotor having at least one recessed portion which does not contact the stationary portion, wherein the first face of the rotor includes a plurality of fluid pathways and the second face of the rotor includes a single fluid pathway; and
a motor arranged to impart rotary motion to the rotor to rotate the rotor to at least
a first position in which the pump inlet port is in fluid communication with the atmosphere port through the valve and the pump outlet port is in fluid communication with the actuator port through the valve,
a second position in which the pump inlet port is in communication with the actuator port via the valve and the pump outlet port is in communication with the atmosphere port via the valve, and a third position in which the actuator port is in communication with the atmosphere port via the valve, wherein the rotor comprising a plurality of flow paths on the first face and at least one flow path on the second face extending in a direction perpendicular to at least one of the plurality of flow paths on the first face.

2. The apparatus of claim 1, wherein an outer edge of the motor is teethed.

3. The apparatus of claim 1, wherein the motor is a stepper motor.

4. The apparatus of claim 1, wherein a fastener extend through the first part of the stationary portion and through the rotor to the second part of the stationary portion such that the rotor is held between the first part and second part of the stationary portion.

5. The apparatus of claim 1, wherein the rotor includes four fluid pathways.

6. The apparatus of claim 1, wherein the motor is arranged to impart rotary motion to the rotor in only a single rotational direction.

7. The apparatus of claim 1, wherein the rotary valve is a pneumatic valve.

8. A dynamic support apparatus comprising:
a cushion;
at least one actuator wherein the at least one actuator defines an interior volume and wherein the interior volume configured to be at least partially filled with a fluid and the at least one actuator attached to an actuator fluid conduit in communication with the interior volume;
a fluid pump having a pump inlet and a pump outlet;
a rotary valve comprising:
a stationary portion including a pump inlet port, a pump outlet port, an atmosphere port, and an actuator port;
a rotor having a planar body with transversely disposed flow paths recessed into each of a first face and a second face of the rotor, wherein the second face is opposingly situated with respect to the first face, the rotor captured between a first part of the stationary portion and a second part of the stationary portion, the rotor having at least one recessed portion which does not contact the stationary portion, wherein the first face of the rotor includes a plurality of fluid pathways and the second face of the rotor includes a single fluid pathway; and a motor arranged to impart rotary motion to the rotor to rotate the rotor to at least a first position in which the pump inlet port is in fluid communication with the atmosphere port through the valve and the pump outlet port is in fluid communication with the actuator port through the valve, a second position in which the pump inlet port is in communication with the actuator port via the valve and the pump outlet port is in communication with the atmosphere port via the valve, and a third position in which the actuator port is in communication with the atmosphere port via the valve, wherein the rotor comprising:
at least one flow path on the first face;
at least one flow path on the second face; and
two pass throughs extending from the first face to the second face for each of the at least one flow path on the second face, wherein the pass throughs being in fluid communication with an associated flow path of the at least one flow path on the second face.

9. The apparatus of claim 8, wherein an outer edge of the motor is teethed.

10. The apparatus of claim 8, wherein the motor is a stepper motor.

11. The apparatus of claim 8, wherein a fastener extend through the first part of the stationary portion and through the rotor to the second part of the stationary portion such that the rotor is held between the first part and second part of the stationary portion.

12. The apparatus of claim 8, wherein the rotor includes four fluid pathways.

13. The apparatus of claim 8, wherein the motor is arranged to impart rotary motion to the rotor in only a single rotational direction.

14. The apparatus of claim 8, wherein the rotary valve is a pneumatic valve.

\* \* \* \* \*